(12) United States Patent
Rommens et al.

(10) Patent No.: US 7,619,138 B2
(45) Date of Patent: Nov. 17, 2009

(54) PRECISE BREEDING

(75) Inventors: Caius Rommens, Boise, ID (US); Jingsong Ye, Boise, ID (US); Jaime Menendez-Humara, Boise, ID (US); Hua Yan, Boise, ID (US); Craig Richael, Meridian, ID (US); W. Leigh Brinkerhoff, Meridian, ID (US); Kathy M. M. Swords, Boise, ID (US)

(73) Assignee: J. R. Simplot Company, Boise, ID (US)

( * ) Notice: Subject to any disclaimer, the term of this patent is extended or adjusted under 35 U.S.C. 154(b) by 157 days.

(21) Appl. No.: 11/375,095

(22) Filed: Mar. 15, 2006

(65) Prior Publication Data

US 2006/0156443 A1 Jul. 13, 2006

Related U.S. Application Data

(62) Division of application No. 10/369,324, filed on Feb. 20, 2003, now Pat. No. 7,250,554.

(60) Provisional application No. 60/357,661, filed on Feb. 20, 2002, provisional application No. 60/377,602, filed on May 6, 2002.

(51) Int. Cl.
*C12N 15/84* (2006.01)
*C12N 15/29* (2006.01)

(52) U.S. Cl. ............... 800/294; 800/284; 800/290; 800/320.1; 435/320.1; 435/469; 536/23.6

(58) Field of Classification Search ............... None
See application file for complete search history.

(56) References Cited

U.S. PATENT DOCUMENTS

| | | |
|---|---|---|
| 4,658,082 A | 4/1987 | Simpson et al. |
| 4,693,976 A | 9/1987 | Schilperoort et al. |
| 4,743,548 A | 5/1988 | Crossway et al. |
| 4,940,838 A | 7/1990 | Schilperoort et al. |
| 4,945,050 A | 7/1990 | Sanford et al. |
| 5,149,645 A | 9/1992 | Hoekema et al. |
| 5,221,623 A | 6/1993 | Legocki et al. |
| 5,284,253 A | 2/1994 | Watt et al. |
| 5,302,523 A | 4/1994 | Coffee et al. |
| 5,366,887 A | 11/1994 | Slightom et al. |
| 5,453,367 A | 9/1995 | Paszkowski et al. |
| 5,464,763 A | 11/1995 | Schilperoort et al. |
| 5,482,852 A | 1/1996 | Yoder et al. |
| 5,591,616 A | 1/1997 | Hiei et al. |
| 5,629,183 A | 5/1997 | Saunders et al. |
| 5,731,179 A | 3/1998 | Komari et al. |
| 5,736,369 A | 4/1998 | Bowen et al. |
| 5,767,368 A | 6/1998 | Zhong et al. |
| 5,767,378 A | 6/1998 | Bojsen et al. |
| 5,856,177 A | 1/1999 | Grula et al. |
| 5,886,244 A | 3/1999 | Tomes et al. |
| 5,932,783 A | 8/1999 | Borovkov et al. |
| 5,965,791 A | 10/1999 | Ebinuma et al. |
| 5,981,840 A | 11/1999 | Zhao et al. |
| 5,990,387 A | 11/1999 | Tomes et al. |
| 5,998,701 A | 12/1999 | Kawchuk et al. |
| 6,051,757 A | 4/2000 | Barton et al. |
| 6,066,781 A | 5/2000 | Sutliff et al. |
| 6,096,865 A | 8/2000 | Michaels |
| 6,100,447 A | 8/2000 | Wu et al. |
| 6,103,893 A | 8/2000 | Cooke et al. |
| 6,140,553 A | 10/2000 | D'Halluin |
| 6,143,949 A | 11/2000 | Ozawa et al. |
| 6,153,812 A | 11/2000 | Fry et al. |
| 6,160,204 A | 12/2000 | Steffens |
| 6,174,724 B1 | 1/2001 | Rogers et al. |
| 6,193,988 B1 * | 2/2001 | Stoner et al. ............ 424/405 |
| 6,201,169 B1 | 3/2001 | Paszkowski et al. |
| 6,207,880 B1 | 3/2001 | Kossmann et al. |
| 6,255,561 B1 | 7/2001 | Kossman et al. |
| 6,258,999 B1 | 7/2001 | Tomas et al. |
| 6,265,638 B1 | 7/2001 | Bidney et al. |

(Continued)

FOREIGN PATENT DOCUMENTS

DE    198 46 001    4/2000

(Continued)

OTHER PUBLICATIONS

Hansen et al. pp. 21-57 In: Current Topics in Microbiology and Immunology, vol. 240, Springer-Verlag: Berlin (1999).*

(Continued)

*Primary Examiner*—David T Fox
(74) *Attorney, Agent, or Firm*—Foley & Lardner LLP

(57) ABSTRACT

The present invention relates to a new plant breeding process. The process improves the agronomic performance of crop plants by using genetic material that is also used in classical breeding. Instead of sexually recombining entire genomes at random, as is done in classical breeding, specific genetic elements are rearranged in vitro and inserted back into individual plant cells. Plants obtained through this new plant breeding process do not contain foreign nucleic acid but only contain nucleic acid from the plant species selected for transformation or plants that are sexually compatible with the selected plant species. Plants developed through this new plant breeding process are provided. In particular, potato plants displaying improved tuber storage and health characteristics are provided.

33 Claims, 5 Drawing Sheets

U.S. PATENT DOCUMENTS

| | | | |
|---|---|---|---|
| 6,403,865 | B1 | 6/2002 | Koziel et al. |
| 6,750,379 | B2 | 6/2004 | McElroy et al. |

FOREIGN PATENT DOCUMENTS

| | | | |
|---|---|---|---|
| DE | 198 46 011 A1 | | 4/2000 |
| EP | 0 174 166 | | 3/1986 |
| EP | 0 257 472 | | 3/1988 |
| EP | 0 270 822 | | 6/1988 |
| EP | 0 120 516 | | 10/1991 |
| EP | 0 486 233 | | 7/1995 |
| EP | 0 561 082 | | 2/1999 |
| WO | WO 92/01370 A1 | | 2/1992 |
| WO | WO 92/06205 | | 4/1992 |
| WO | WO 94/03607 A1 | | 2/1994 |
| WO | WO 96/34968 A2 | | 11/1996 |
| WO | WO 97/12046 | * | 4/1997 |
| WO | WO 98/04722 | | 5/1998 |
| WO | WO 98/34471 A1 | | 8/1998 |
| WO | WO 99/01563 | * | 1/1999 |
| WO | WO 99/53050 | | 10/1999 |
| WO | WO 99/60106 A2 | | 11/1999 |
| WO | WO 01/25459 | | 4/2001 |
| WO | WO 01/95702 | | 12/2001 |
| WO | WO 02/10161 A1 | | 2/2002 |
| WO | WO 2004/040999 | | 5/2004 |

OTHER PUBLICATIONS

Stritzker et al. Sequence ID No. 47 in US 2008/0193373 (effective filing date Jul. 2006).*

Mendrick et al. Sequence ID No. 255 in US 2008/0215250 (effective filing date Jul. 2001).*

Doucette-Stamm et al. Sequence ID No. 1017 in US 2008/0194004 (effective filing date Jun. 1998).*

Komari et al., "Vectors Carrying Two Separate T-DNAs for Co-Transformation of Higher Plants Mediated by *Agrobacterium tumefaciens* and Segregation of Transformants Free from Selection Markers", *The Plant Journal*, (1996), pp. 165-174, vol. 10.

Smith et al., "Gene Expression: Total Silencing by Intron-Spliced Hairpin RNAs", *Nature*, (2000), pp. 319-320, vol. 407.

AEOMICA Inc., Accession No. ADC04079, Dec. 18, 2003.

Alber et al., "Nucleotide Sequence of the Triose Phosphate Isomerase Gene of *Saccharomyces cerevisiae*", Journal of Molecular and Applied Genetics, (1982), pp. 419-434, vol. 1.

Dunn et al., Accession No. AZ483608, Oct. 5, 2000.

Hansen et al., "Lessons in Gene Transfer to Plants by a Gifted Microbe", 1999, vol. 240, pp. 21-57, *Curr. Top. Microbiol Immunol.*

Hood et al., "Molecular Farming of Industrial Proteins from Transgenic Maize", Adv. Exp. Med. Biol., 1999, pp. 127-147, vol. 464, Kluwer Academic/Plenum Publishers, N.Y.

Vierling et al., Accession No. AA45318, Nov. 18, 1994; revised Mar. 25, 2003.

Aoki, Seishiro, et al., "Horizontal Gene Transfer and Mutation: Ngrol genes in the genome of *Nicotiana glauca*," PNAS, Nov. 9, 1999, vol. 96, No. 23, pp. 13229-13234.

Apse, Mads P. et al., "Salt Tolerance Conferred by Overexpression of a Vacuolar $Na^+/H^+$ Antiport in Arabidopsis," *Science*, vol. 285, pp. 1256-1258 (1999).

Bailey, T. L. et al., "Combining Evidence Using p-values: Application to Sequence Homology Searches," *Bioinformatics*, vol. 14, No. 1, pp. 48-54 (1998).

Banno, H. et al., "Overexpression of Arabidopsis ESR1 Induces Initiation of Shoot Regeneration," *The Plant Cell*, vol. 13, pp. 2609-2618 (2001).

Beaujean, A. et al., "Engineering Direct Fructose Production in Processed Potato Tubers by Expressing a Bifunctional Alpha-Amylase/Glucose Isomerase Gene Complex," *Biotechnology and Bioengineering*, vol. 70, No. 1, pp. 9-15 (2000).

Bennetzen, Jeffrey L., "Transposable Element Contributions to Plant Gene and Genome Evolution," *Plant Molecular Biology*, vol. 42, pp. 251-269 (2000).

Bevan et al., "The Structure and Transcription Start Site of a Major Potato Tuber Protein Gene," *Nucleic Acids Research*, vol. 14, No. 11, pp. 4624-4637 (1986).

Bird et al., "Starches, Resistant Starches, the Gut Microflora and Human Health," *Curr. Issues Intest. Microbiol.*, vol. 1, No. 1, pp. 25-37 (2000).

Bohner et al., "Characterization of Novel Target Promoters for the Dexamethasone-inducible/tetracycline-repressible Regulator TGV Using Luciferase and Isopentenyl Transferase as Sensitive Reporter Genes," *Mol. Gen Genet*, vol. 264, pp. 860-870 (2001).

Breiteneder et al., "Molecular and Biochemical Classification of Plant-derived Food Allergens," *J. Allergy Clin. Immunol.*, vol. 106, No. 1, pp. 27-36 (2000).

Catterou, M. et al., "Hoc: an Arabidopsis Mutant Overproducing Cytokinins and Expressing High in vitro Organogenic Capacity," *The Plant Journal*, vol. 30, No. 3, pp. 273-287 (2002).

Chiurazzi et al., "Termini and Telomeres in T-DNA Transformation," *Plant Molecular Biology*, vol. 26, pp. 923-934 (1994).

Cornejo et al., "Activity of a Maize Ubiquitin Promoter in Transgenic Rice," *Plant Molecular Biology*, vol. 23, pp. 567-581 (1993).

Dale et al., "Gene Transfer with Subsequent Removal of the Selection Gene from the Host Genome," *Proc. Natl. Acad. Sci. USA*, vol. 88, pp. 10558-10562 (1991).

Dai et al., GBSS gene, STDNAGBSS, X83220, Jan. 11, 1995.

Ellis et al., "The Generation of Plant Disease Resistance Gene Specificities," *Trends in Plant Science*, vol. 5, No. 9, pp. 373-379 (2000).

Fritz et al., "Reduced Steady-state Levels of rbcS mRNA in Plants Kept in the Dark are Due to Differential Degradation," *Proc. Natl. Acad. Sci. USA*, vol. 88, pp. 4458-4462 (1991).

Gao at al., "Fungal Pathogen Protection in Potato by Expression of a Plant Defensin Peptide," *Nat. Biotechnol.*, vol. 18, pp. 1307-1310 (2000).

Garbarino et al., "Isolation of a Polyubiquitin Promoter and Its Expression in Transgenic Potato Plants," *Plant Physiol.*, vol. 109, pp. 1371-1378 (1995).

Gaxiola et al., "Drought and Salt-tolerant Plants Result from Overexpression of the AVP1 $H^+$-pump," *Proc. Natl. Acad. Sci. USA*, vol. 98, No. 20, pp. 11444-11449 (2001).

Gleave et al.; "Selectable marker-free transgenic plants without sexual crossing; transient expression of cre recombinase and use of a conditional lethal dominant gene"; *Plant Molecular Biology*; May 1999; vol. 40, No. 2; pp. 223-235.

Heimovaara-Dijkstra et al., "The Effect of Intracellular pH on the Regulation of the Rab 16A and the ÿ-amylase ⅙-4 Promoter by Abscisic Acid and Gibberellia," *Plant Molecular Biology*, vol. 27, pp. 815-820 (1995).

Hoisington et al., "Plant Genetic Resources: What Can they contribute Toward Increased Crop Productivity," *Proc. Natl. Acad. Sci. USA*, vol. 96, pp. 5937-5943 (1999).

Janzowski et al., "5-Hydroxymethylfurfural: assessment of Mutagenicity, DNA-damaging Potential and Reactivity towards Cellular Glutathione," *Food Chem. Toxicol.*, vol. 38, pp. 801-809 (2000).

Kagan et al., "Ascorbate Is the Primary Reductant of the Phenoxyl Radical of Etoposide in the Presence of Thiols Both in Cell Homogenates and in Model Systems," *Biochemistry*, vol. 33, pp. 9651-9660 (1994).

Kakimoto, Tatsuo, "CKI1, a Histidine Kinase Homolog Implicated in Cytokinin Signal Transduction," *Science*, vol. 274, pp. 982-985 (1996).

Kasuga et al., "Improving Plant Drought, Salt, and Freezing Tolerance by Gene Transfer of a Single Stress-inducible Transcription Factor," *Nature Biotechnology*, vol. 17, pp. 287-291 (1999).

Kirch et al., Structural Organization, Expression and Promoter Activity of a Cold-stress-inducible Gene of Potato (*Solanum tuberosum* L.), *Plant Molecular Biology*, vol. 33, pp. 897-909 (1997).

Klabunde et al., "Crystal Structure of a Plant Catechol Oxidase Containing a Dicopper Center," *Nature Structural Biology*, vol. 5, No. 12, pp. 1084-1090 (1998).

Kononov et al., "Integration of T-DNA Binary Vector 'backbone' Sequences Into the Tobacco Genome: Evidence for Multiple Complex Patterns of Integration," *The Plant Journal*, vol. 11, No. 5, pp. 945-957 (1997).

Koussevitzky et al., "Purification and Properties of a Novel Chloroplast Stromal Peptidase," *The Journal of Biological Chemistry*, vol. 273, No. 42, pp. 27064-27069 (1998).

Krall et al., The Tzs Protein from *Agrobacterium tumefaciens* C58 Produces Zeatin Riboside 5'-phosphate from 4-hydroxy-3-methyl-2-(E)-butenyl Diphosphate and AMP, *FEBS Lett*, vol. 257, pp. 315-318 (2002).

Kuipers et al., "Factors affecting the inhibition by antisense RNA of granule-bound starch synthase gene expression in potato"; *Molecular and General Genetics*; Mar. 1995; vol. 246, No. 6, pp. 745-755.

Kusaba et al., Self-Incompatibility in the Genus Arabidopsis: characterization of the S Locus in the Outcrossing A. Lyrata and Its Autogamous Relative A. Thaliana, *The Plant Cell*, vol. 13, pp. 627-643 (2001).

Loberth et al., "Promoter Elements involved in Environmental and Developmental Control of Potato Proteinase Inhibitor II Expression," *The Plant Journal*, vol. 2, No. 4, pp. 477-486 (1992).

Maganja et al.; "Isolation and sequence analysis of the genomic DNA fragment encoding an aspartic proteinase inhibitor homologue from potato (*Solanum tuberosum* L.)"; *Plant Molecular Biology*; 1992; vol. 20, No. 2; pp. 311-313.

Mogen et al., "Several Distinct Types of Sequence Elements Are Required for Efficient mRNA 3' End Formation in a Pea rbcS Gene," *Molecular and Cellular Biology*, vol. 12, No. 12, pp. 5406-5414 (1992).

Mori et al., "Inducible High-level mRNA Amplification System by Viral Replicase in Transgenic Plants," *The Plant Journal*, vol. 27, No. 1, pp. 79-86 (2001).

Mysore et al., "Role of the *Agrobacterium tumefaciens* VirD2 Protein in T-DNA Transfer and Integration," *Molecular Plant-Microbe Interactions*, vol. 11, No. 7, pp. 668-683 (1998).

Osusky et al., "Transgenic Plants Expressing Cationic Peptide Chimeras Exhibit Broad-spectrum Resistance to Phytopathogens," *Nature Biotechnology*, vol. 18, pp. 1162-1166 (2000).

Otten et al.; "A T-DNA from the *Agrobacterium tumefaciens* Limited-Host-Range Strain AB2/73 Contains a Single Oncogene"; *Molecular Plant-Microbe Interactions*; 1998; vol. 11, No. 5; pp. 335-342.

Oxenboll et al., Pectin Engineering: Modification of Potato Pectin by in vivo Expression of an Endo-1,4-ÿ-D-galactanase, *Proc Natl Acad Sci. USA*, vol. 97, No. 13, pp. 7639-7644 (2000).

Padgette et al., "Bacterial Expression and Isolation of Petunia Hybrida 5-enol-Pyruvylshikimate-3-phosphate Synthase," *Archives of Biochemistry and Biophysics*, vol. 258, No. 2, pp. 564-573 (1987).

Palanichelvam et al., "A Second T-Region of the Soybean-Supervirulent Chrysopine-Type Ti Plasmid pTiChry5, and Construction of a Fully Disarmed vir Helper Plasmid," *Mol. Plant Microbe Interact*, vol. 13, pp. 1081-1091 (2000).

Pokorny J., "Pÿÿrodný Toxické Látky V Potravinách," *Cas Lek Cesk*, vol. 136, pp. 267-270 (1997).

Raboy, V., "Symposium: Plant Breeding: A New Tool for Fighting Micronutrient Malnutrition," *J Nutr.*, vol. 132, pp. 503S-505S (2002).

Rogers, John C., "Two Barley ÿ-Amylase Gene Families Are Regulated Differently in Aleurone Cells," *The Journal of Biological Chemistry*, vol. 260, No. 6, pp. 3731-3738 (1985).

Rohde et al., "Structural and Functional Analysis of Two Waxy Gene Promoters from Potato," *J. Genet & Breed*, vol. 44, pp. 311-315 (1990).

Schneider et al., "Expression Patterns and Promoter Activity of the Cold-Regulated Gene ci21A of Potato," *Plant Physiol.*, vol. 113, pp. 335-345 (1997).

Schwall et al., "Production of Very-high-amylose Potato Starch by Inhibition of SBE A and B," *Nature Biotechnology*, vol. 18, pp. 551-554 (2000).

Shah et al., "Resistance to Diseases and Insects in Transgenic Plants: Progress and Applications to Agriculture," *Trends in Biotechnology*, vol. 13, pp. 362-368 (1995).

Shi et al., "Bone Formation by Human Postnatal Bone Marrow Stromal Stem Cells is Enhanced by Telomerase Expression," *Nature Biotechnology*, vol. 20, pp. 587-591 (2002).

Shibamoto, Takayuki, "Genotoxicity Testing of Maillard Reaction Products," *Prog. Clin. Biol. Res.*, vol. 304, pp. 359-376 (1989).

Shurvinton et al., "A Nuclear Localization Signal and the C-terminal Omega Sequence in the *Agrobacterium tumefaciens* VirD2 Endonuclease are Important for Tumor Formation," *Proc. Natl. Acad. Sci. USA*, vol. 89, pp. 11837-11841 (1992).

Tareke et al., "Analysis of Acrylamide, a Carcinogen Formed in Heated Foodstuffs," *J. Agric. Food Chem.*, vol. 50, pp. 4998-5006 (2002).

Topping et al., "Short-Chain Fatty Acids and Human Colonic Function: Roles of Resistant Starch and Nonstarch Polysacharides," *Physiological Review*, vol. 81, No. 3, pp. 1031-1064 (2001).

Ueda et al., "Level of Expression of the Tomato rbcS-3A Gene Is Modulated by a Far Upstream Promoter Element in a Developmentally Regulated Manner," *The Plant Cell*, vol. 1, pp. 217-227 (1989).

Van Der Leij et al.; "Sequence of the structural gene for granule-bound starch synthase of potato (*Solanum tuberosum* L.) and evidence for a single point deletion in the amf allele"; *Molecular and General Genetics*; 1991; vol. 228, No. 1-2; pp. 240-248.

Van Der Steege et al., "Potato Granule-bound Starch Synthase Promoter-controlled GUS Expression: Regulation of Expression After Transient and Stable Transformation," *Plant Molecular Biology*, vol. 20, pp. 19-30 (1992).

Van Haaren et al., "Mutational Analysis of the Conserved Domains of a T-region Border Repeat of *Agrobacterium tumefaciens*," *Plant Molecular Biology*, vol. 13, pp. 523-531 (1989).

Vikso-Nielsen et al., "Structural, Physicochemical, and Pasting Properties of Starches from Potato Plants with Repressed r1-Gene,3" *Biomacromolecules*, vol. 2, pp. 836-843 (2001).

Wang et al., "N-Nitroso-N-(3-keto-1,2,-butanediol)-3ÿ-nitrotyramine A New Genotoxic Agent Derived from the Reaction of Tyrosine and Glucose in the Presence of Sodium Nitrite," *Arch Toxicol.*, vol. 70, pp. 10-15 (1995).

Waters et al., "Sequence Identity in the Nick Regions of IncP Plasmid Transfer Origins and T-DNA Borders of Agrobacterium Ti Plasmids," *Proc. Natl. Acad. Sci. USA*, vol. 88, pp. 1456-1460 (1991).

Weigel et al., "Activation Tagging in Arabidopsis," *Plant Physiology*, vol. 122, pp. 1003-1013 (2000).

Zuo et al., "Marker-free Transformation: Increasing Transformation Frequency by the use of Regeneration-Promoting Genes," *Current Opinion in Biotechnology*, vol. 13, pp. 173-180 (2002).

Zuo et al., "Chemical-regulated, site-specific DNA Excision in Transgenic Plants," *Nature Biotechnology*, vol. 19, pp. 157-161 (2001).

Düring, "A Plant Transformation Vector with a Minimal T-DNA," *Transgenic Research*, vol. 3, pp. 138-140 (1994).

Greiner et al., "Ectopic Expression of a Tobacco Invertase Inhibitor Homolog Prevents Cold-Induced Sweetening of Potato Tubers," *Nature Biotechnology*, vol. 17, pp. 708-711, (1999).

Lorberth et al. "Inhibition of a Starch-Granule-Bound Protein Leads to Modified Starch and Repression of Cold Sweetening", *Nature Biotechnology*, vol. 16, pp. 473-477, May 1998.

Nielsen, K.M. "Transgenic Organisms—Time for Conceptual Diversification?", *Nature Biotechnology*, vol. 21. Mar. 2003, pp. 227-228.

Rommens, C.M., "All-Native DNA Transformation: A New Approach to Plant Genetic Engineering", *Trends Plant Sci.*, vol. 9, No. 9, pp. 457-464, (Sep. 2004).

Sugita et al., "A Transformation Vector for the Production of Marker-free Transgenic Plants Containing a Single Copy Transgene at High Frequency", *The Plant Journal*, vol. 22, No. 5, pp. 461-469, Jun. 2000.

Rommens, et al., "Plant-Derived Transfer DNAs", *Plant Physiology*, Nov. 2005, vol. 139, pp. 1338-1349.

* cited by examiner

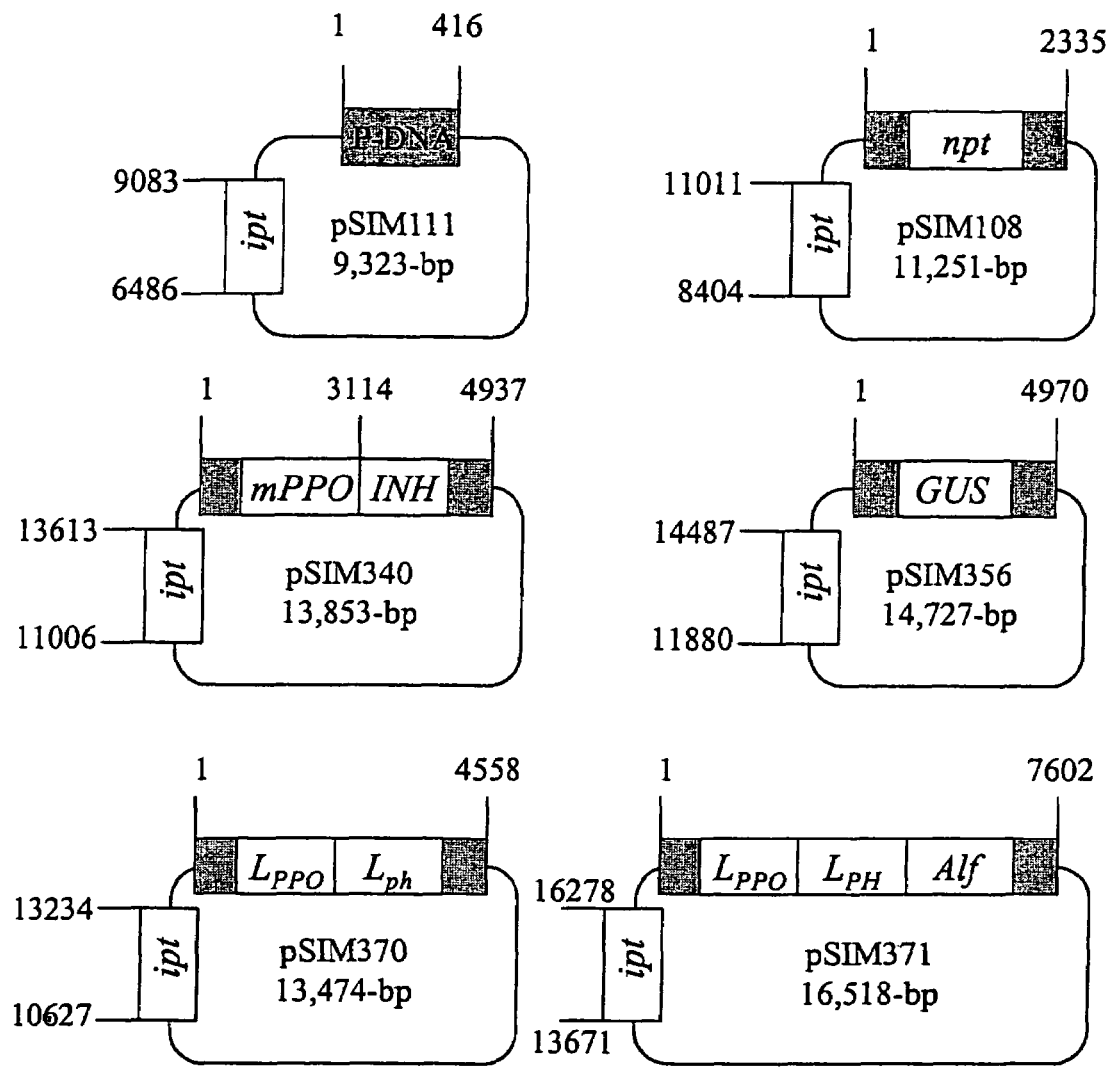
Figure 1. Diagrams for some P-DNA vectors

Figure 2. Alignment of potato and tobacco invertase inhibitor proteins

A.

```
St-inh1    MRNLFPILMLITNLALNNDNNNNNNNNNNYNLIHATCRETPYYSLCLTTLQSGPRSNEVE  60
Nt-inhh    MRNLFPIFMLITNLAFN-DNNNSNN------IINTTCRATTNYPLCLTTLHSDPRTSEAE  53
           *******:*******:* ****.**      :*::*** *. *.******:*.**:.*.*

St-inh1    GGDAITTLGLIMVDAVKSKSIEIMEKIKELEKSNPEWRAPLSQCYVAYNAVLRADVTVAV 120
Nt-inhh    GAD-LTTLGLVMVDAVKLKSIEIMKSIKKLEKSNPELRLPLSQCYIVYYAVLHADVTVAV 112
           *.* :*****:****** ******:.**:*******  * ******:.* ***:******

St-inh1    EALKKGAPKFAEDGMDDVVAEAQTCEYSFNYYNKLDFPISNLSREIIELSKVAKSIIRML 180
Nt-inhh    EALKRGVPKFAENGMVDVAVEAETCEFSFK-YNGLVSPVSDMNKEIIELSSVAKSIIRML 171
           ****:*.*****:** **..**:***:**:  ** *  *:*::..:****** ********

St-inh1    L 181
Nt-inhh    L 172
           *
```

B.

```
St-inh1    MRNLFPILMLITNLALNNDNNNNNNNNNNYNLIHATCRETPYYSLCLTTLQSGPRSNEVE  60
Nt-inh1    MKNLIFLTMFLTILLQTNANN----------LVETTCKNTPNYQLCLKTLLSDKRS--AT  48
           *:**: : *::* * .* **           *:..**::** *.***.** *. **  .

St-inh1    GGDAITTLGLIMVDAVKSKSIEIMEKIKELEKSNP--EWRAPLSQCYVAYNAVLRADVTV 118
Nt-inh1    G--DITTLALIMVDAIKAKANQAAVTISKLRHSNPPAAWKGPLKNCAFSYKVILTASLPE 106
           *   ****.******:*:*: :   .*.:*.:***   *:.**.:* .:*:..:* *.:.

St-inh1    AVEALKKGAPKFAEDGMDDVVAEAQTCEYSFNYYNKLDFPISNLSREIIELSKVAKSIIR 178
Nt-inh1    AIEALTKGDPKFAEDGMVGSSGDAQECE---EYFKGSKSPFSALNIAVHELSDVGRAIVR 163
           *:***.** ********  . :.:** **    :*::     .  *:*  .  :::*:*

St-inh1    MLL 181
Nt-inh1    NLL 166
           **
```

Figure 3. Gene-free expression cassettes

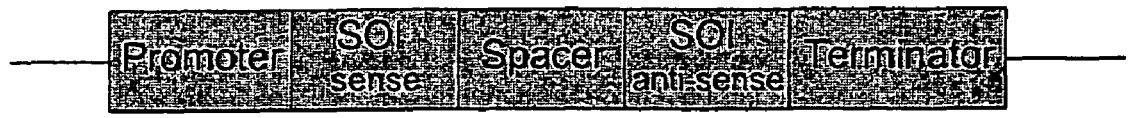

| Promoter | SOI* | Spacer | Total size |
|---|---|---|---|
| P:GBSS-small | Leader a/w** R1 | Ubi intron | 1729-bp |
| P:GBSS-small | Leader a/wR1 | GBSS spacer | 1397-bp |
| P:GBSS-large | Leader a/wR1 | Ubi intron | 2005-bp |
| P:GBSS-large | Leader a/wR1 | GBSS spacer | 1397-bp |
| P:GBSS-small | Trailer a/wR1 | GBSS spacer | 2042-bp |
| P:GBSS-small | Trailer a/wR1 | Ubi intron | 1705-bp |
| P:GBSS-large | Trailer a/wR1 | GBSS spacer | 2313-bp |
| P:GBSS-large | Trailer a/wR1 | Ubi intron | 1981-bp |
| P:GBSS-small | Leader a/wPhosph | GBSS spacer | - |
| P:GBSS-small | Leader a/wPhosph | Ubi intron | - |
| P:GBSS-large | Leader a/wPhosph | GBSS spacer | 1852-bp |
| P:GBSS-large | Leader a/wPhosph | Ubi intron | 2184-bp |
| P:GBSS-large | Leader a/wPPO | Ubi intron | 1958-bp |
| P:GBSS-large | Leader a/wPPO | GBSS spacer | 1626-bp |
| P:GBSS-small | Leader a/wPPO | Ubi intron | - |
| P:GBSS-small | Leader a/wPPO | GBSS spacer | - |

*: sequence-of-interest; **: "associated with"

Figure 4. Alignment of the 3'-end of tuber-expressed PPO genes and trailers associated with these genes.

```
P-PPO3       CTGGCGATAACGGAACTGTTGGAGGATATTGGTTTGGAAGATGAAGATACTATTGCGGTG  60
PPOM-41      CTGGCGATAACGGAACTGTTGGAGGATATTGGATTGGAAGATGAAGATACTATTGCGGTA  60
PPOM-44      CTGGCGATAACGGAACTGTTGGAGGATAATGGATTGGAAGATGAAGGTACTATNGCGGTA  60

P-PPO3       ACTCTGGTGCCAAAGAGAGGTGGTGAAGGTATCTCCATTGAAAGTGCGACGATCAGTCTT  120
PPOM-41      ACTTTGGTTCCAAAAGTAGGTGGTGAAGGTGTATCCATTGAAAGTGTGGAGATCAAGCTT  120
PPOM-44      ACTTTGGTTCCAAAAGTTGGTGGTGAAGGTGTATCCATTGAAAGTGCGGAGATCAAGCTT  120

P-PPO3       GCAGATTGTTAATTAGTCTCTA-TTGA-ATCTGCTG----AGATTACAC-TTTGATGGAT  173
PPOM-41      GAGGATTGTTAAGTCCTCATGAGTTGGTGGCTACGGTACCAAATTTTATGTTTAATTAGT  180
PPOM-44      GAGGATTGTTAAGTCCTCATGAGTTGGTGGCTATGGTACCAAATTNTATGTTTAATTAGT  180

P-PPO3       GATGCTCTGTT--TTTGTTTTCTTGTTCTGTTTTTCCTC-TGTTGAAATCAGCTTTGTT   230
PPOM-41      ATTAATGTGTGTATGTGTTTGATTATGTTTCGGTTAAAATGTATCAGCTGGATAGCTGAT  240
PPOM-44      ATTAATGTGTG----TGTTTGATTATGTTTCGGTTAAAATGTATCANCTGGATAGCTGAT  236

P-PPO3       -GCTTGATTTC---ATTGAAGTTGTTATTCAAGAA-TAAATCAGTTA-CAATT------  277
PPOM-41      TACTAGCCTTGCCAGTTGTTAATGCTATGTATGAAATAAATAAATAAATGGTTGTCTTCT  300
PPOM-44      TACTAGCCTTCCCAGTTGTTAATGCTATGTATGAAATACATAAATAAATGGTTGTCTTCC  296
```

Figure 5. Diagrams for some LifeSupport vectors
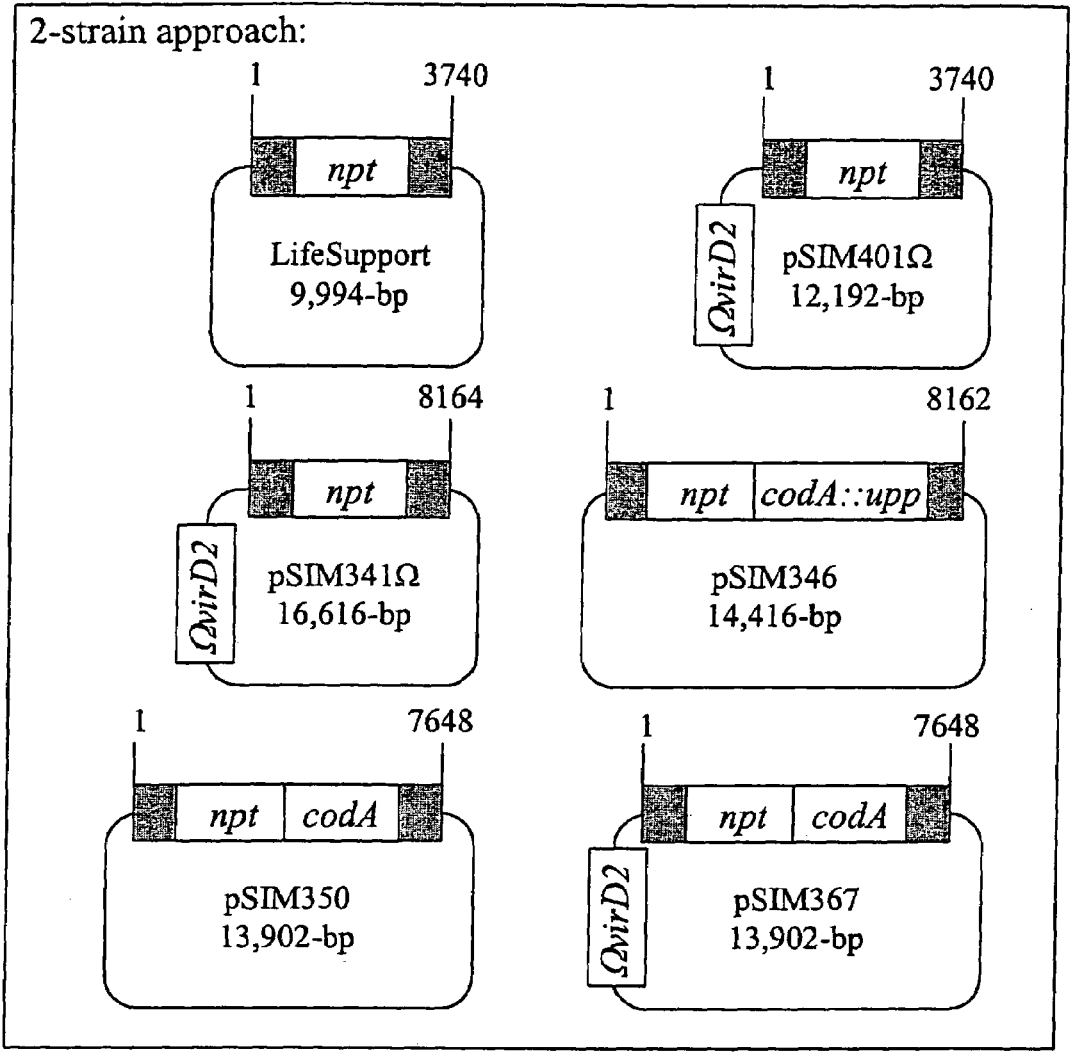
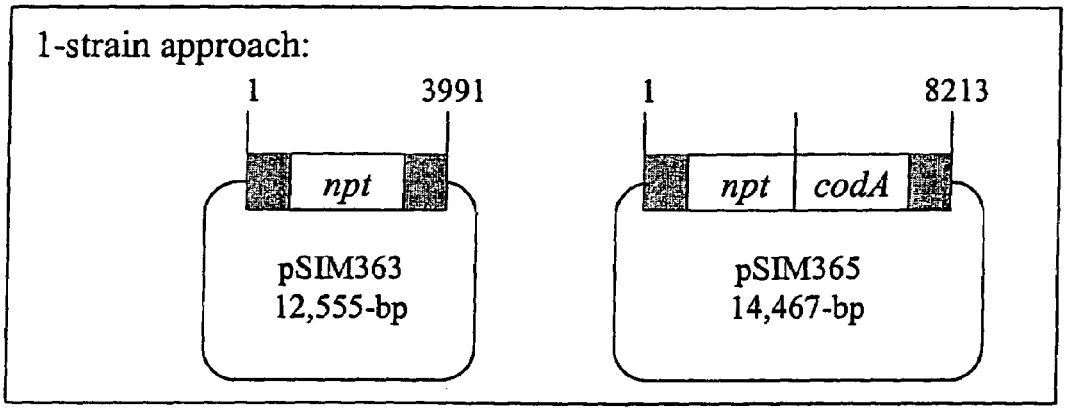

PRECISE BREEDING

FIELD OF THE INVENTION

This application is a divisional application of U.S. Ser. No. 10/369,324, filed on Feb. 20, 2003, and which granted as U.S. Pat. No. 7,250,554 on Jul. 31, 2007, which claims priority to U.S. provisional application Ser. Nos. 60/357,661, filed on Feb. 20, 2002 and 60/377,602, filed on May 6, 2002, which are all incorporated herein by reference. The present invention relates to methods for improving the nutritional, health, and agronomic characteristics of a plant by modifying specific, well-characterized DNA in the plant's genome. As opposed to classical plant breeding, the inventive process does not introduce unknown or potentially toxic genes into the plant genetic make-up. Furthermore, the inventive method, unlike conventional genetic engineering strategies, does not incorporate nucleic acids from foreign species, i.e., species that are not inter-fertile with the plant to be modified by genetic engineering, into the plant genome. Plants developed though the inventive plant breeding process display improved agronomic characteristics. Particularly preferred plants of the present invention include potatoes that exhibit unproved health and tuber storage characteristics, and turfgrasses that exhibit improved disease and drought tolerance.

BACKGROUND

The agronomic performance of plants has typically been improved by either classical plant breeding or genetic engineering. Classical breeding typically results in the transfer of unknown nucleic acids from one plant to another. Genetic engineering techniques introduce foreign nucleic acids into the plant genome, i.e., DNA that is not from a plant or that is not from a plant that is naturally interfertile with the plant to be modified by genetic engineering. For example, genetic engineering introduces non-plant nucleic acids into a plant genome. Both classical breeding and genetic engineering strategies create plant genomes that contain undesirable and unwanted genetic material, and the resultant cross-bred or transgenic plants can exhibit unfavorable traits. The inadequacies of both strategies can prove harmful to the transgenic plants, as well as to the animals and humans who consume such products.

Conventional Breeding Relies on the Transfer of Unknown DNA

Plant breeding typically relies on the random recombination of plant chromosomes to create varieties that have new and improved characteristics. Thus, by screening large populations of progeny that result from plant crosses, breeders can identify those plants that display a desired trait, such as an increase in yield, improved vigor, enhanced resistance to diseases and insects, or greater ability to survive under drought conditions. However, classical breeding methods are laborious and time-consuming, and new varieties typically display only relatively modest improvements.

Furthermore, classical plant breeding typically results in the transfer of hundreds of unknown genes into a plant genome. It is likely that some of those transferred genes encode potentially harmful allergens, such as patatin, lectins, chitinases, proteases, thaumatin-like proteins, lipid transfer proteins, amylases, trypsin inhibitors, and seed storage proteins (Breiteneder et al., *J Allergy Clin Immunol* 106: 27-36).

Similarly, introgressed genes can be involved in the biosynthesis of toxins including lathyrogens, hydrazines, glucosinolates and goitrogens, cumarins, saponins, alkaloids, glycoalkaloids, biogenic amines, enzyme inhibitors, such as lectins (haemagglutinins), trypsin inhibitors, chelating substances such as phytates and oxalates, ribotoxins, antimicrobial peptides, amino acids such as beta-N-oxalylamino-L-alanine, atractyloside, oleandrine, taxol, and isoquinoline (Pokorny, *Cas Lek Cesk* 136: 267-70, 1997). The risk of inadvertently introducing such poisons into human and animal food supplies is further increased through efforts to "untap" the genetic diversity of wild crop relatives that have not been used before for food consumption (Hoisington et al., *Proc Natl Acad Sci USA* 96: 5937-43, 1999).

Although classical plant breeding can easily introduce genes involved in undesirable anti-nutritional compounds into food crops and plants, it cannot easily remove them. For instance, it took about 15 years to reduce harmful phytate levels in corn and rice by inactivating Lpa genes (Raboy, *J Nutr* 132: 503S-505S, 2002). The long timeframe for realizing positive results is not practical, especially since there is an urgent need for methods that more effectively and efficiently improve the quality of food crops. One example of a gene that only recently was found to be associated with the synthesis of anti-nutritional compounds is the polyphenol oxidase (PPO) gene, which oxidizes certain phenolic compounds to produce mutagenic, carcinogenic and cytotoxic agents like phenoxyl radicals and quinoid derivatives (Kagan et al., *Biochemistry* 33: 9651-60, 1994). The presence of multiple copies of this gene in the genome of plants such as potato makes it particularly difficult to reduce PPO activity through breeding.

Even more time is needed for the removal of anti-nutritional compounds if little or nothing is known about their genetic basis. For instance, no genes have been linked to the accumulation of high concentrations of acrylamide, a potent neurotoxin and mutagen, in some potatoes that are heated to 160° C. or higher (Tareke et al., *J Agric Food Chem.* 50: 4998-5006, 2002). It is therefore very difficult to efficiently develop new potato varieties that produce less acrylamide during processing using conventional breeding. Thus, there is a need to grow potatoes and other carbohydrate-rich foods, such as wheat, with reduced levels of such dangerous compounds, but without the use of unknown or foreign nucleic acids.

Other anti-nutritional compounds that can accumulate during processing and are difficult to minimize or eliminate through breeding include the Maillard-reaction products N-Nitroso-N-(3-keto-1,2-butanediol)-3'-nitrotyramine (Wang et al., *Arch Toxicol* 70: 10-5, 1995), and 5-hydroxymethyl-2-furfural (Janzowski et al., *Food Chem Toxicol* 38: 801-9, 2000). Additional Maillard reaction products that have not been well characterized are also known to display mutagenic properties (Shibamoto, *Prog Clin Biol Res* 304: 359-76, 1989).

It can be equally difficult to rapidly increase levels of positive nutritional compounds in food crops due to the inherent imprecision of conventional plant breeding. For instance, it would be desirable to increase levels of "resistant starch" (Topping et al., *Physiol Rev* 81: 1031-64, 2001) in a variety of crops. Such starch is ultimately responsible for promoting immune responses, suppressing potential pathogens, and reducing the incidence of diseases including colorectal cancer (Bird et al., *Curr Issues Intest Microbiol* 1: 25-37, 2000). However, the only available plants with increased levels of resistant starch are low-yielding varieties like maize mutants "amylose extender", "dull", and "sugary-2." Creation of new high resistant starch sources, such as potato, would enable broader dietary incorporation of this health-promoting component.

The inability to safely manipulate the genotypes of plants often leads to the use of external chemicals to induce a desired phenotype. Despite numerous breeding programs to delay tuber sprouting, for example, no potato varieties are available commercially that can be stored for months without treatment with sprout inhibitors. The latter, such as isopropyl-N-chlorophenyl-carbamate (CIPC), is linked to acute toxicity and tumor development, and can be present in processed potato foods at concentrations between 1 mg/kg and 5 mg/kg.

Genetic Engineering Relies on the Transfer of Foreign DNA

Genetic engineering can be used to modify, produce, or remove certain traits from plants. While there has been limited progress in improving the nutritional value and health characteristics of plants, most improvements target plant traits that promote ease of crop cultivation. Thus, certain plants are resistant to the glyphosate herbicide because they contain the bacterial gene 5-enolpyruvylshikimate-3-phosphate synthase (Padgette et al., Arch Biochem Biophys. 258: 564-73, 1987). Similarly, genetic engineering has produced insect-, viral-, and fungal-resistant plant varieties (Shah et al., Trends in Biotechnology 13: 362-368, 1995; Gao et al., Nat Biotechnol. 18: 1307-10, 2000; Osusky et al., Nat Biotechnol. 18: 1162-6, 2000), but few with enhanced nutrition or health benefits.

According to standard, well-known techniques, genetic "expression cassettes," comprising genes and regulatory elements, are inserted within the borders of Agrobacterium-isolated transfer DNAs ("T-DNAs") and integrated into plant genomes. Thus, Agrobacterium-mediated transfer of T-DNA material typically comprises the following standard procedures: (1) in vitro recombination of genetic elements, at least one of which is of foreign origin, to produce an expression cassette for selection of transformation, (2) insertion of this expression cassette, often together with at least one other expression cassette containing foreign DNA, into a T-DNA region of a binary vector, which usually consists of several hundreds of basepairs of Agrobacterium DNA flanked by T-DNA border sequences, (3) transfer of the sequences located between the T-DNA borders, often accompanied with some or all of the additional binary vector sequences from Agrobacterium to the plant cell, and (4) selection of stably transformed plant cells. See, e.g., U.S. Pat. Nos. 4,658,082, 6,051,757, 6,258,999, 5,453,367, 5,767,368, 6,403,865, 5,629,183, 5,464,763, 6,201,169, 5,990,387, 4,693,976, 5,886,244, 5,221,623, 5,736,369, 4,940,838, 6,153,812, 6,100,447, 6,140,553, 6,051,757, 5,731,179, 5,149,645 and EP 0 120,516, EP 0 257,472, EP 0 561,082, 1,009,842A1, 0 853,675A1, 0 486,233B1, 0 554,273A1, 0 270,822A1, 0 174, 166A1, and WO 01/25459.

Thus, genetic engineering methods rely on the introduction of foreign nucleic acids into the food supply. Those techniques transfer complex fusions of a few to more than 20 genetic elements isolated from viruses, bacteria, and plants, that are not indigenous to the transformed plant species. Such foreign elements include regulatory elements such as promoters and terminators, and genes that are involved in the expression of a new trait or function as markers to identify or select for transformation events. Despite the testing of foods containing foreign DNA for safety prior to regulatory approval, many consumers are concerned about the long-term effects of eating foods that express foreign proteins, which are produced by genes obtained from other, non-plant species.

One commonly used regulatory element is the 35S "super" promoter of cauliflower mosaic virus (CaMV), which is typically used in plant engineering to induce high levels of expression of transgenes to which it is directly linked. However, the 35S promoter also can enhance the expression of native genes in its vicinity (Weigel et al., Plant Physiol., 122: 1003-13, 2000). Such promoters may thus induce unpredictable alterations in the expression of endogenous genes, possibly resulting in undesirable effects such as increased alkaloid production. Preferred "strong" promoters are generally those isolated from viruses, such as rice tungro bacilliform virus, maize streak virus, cassava vein virus, mirabilis virus, peanut chlorotic streak caulimovirus, figwort mosaic virus and chlorella virus. Other frequently used promoters are cloned from bacterial species and include the promoters of the nopaline synthase and octopine synthase gene.

To obtain appropriate termination of gene translation, terminator sequences are fused to the 3'-end of transgenes and include genetic elements from the nopaline synthase and octopine synthase genes from Agrobacterium. Other genetic elements may be used to further enhance gene expression or target the expressed protein to certain cell compartments. These elements include introns to boost transgene expression and signal peptide sequences to target the foreign gene to certain cellular compartments, often derived from foreign plant species.

Certain genes involved in expression of a new trait are most frequently derived from foreign sources. If native genes are used, they are often inverted to silence the expression of that gene in transgenic plants and co-transformed with foreign DNA such as a selectable marker. The main disadvantage of this "antisense" technology is that the inverted DNA usually contains new and uncharacterized open reading frames inserted between a promoter and terminator. Thus, potato plants that were genetically modified with antisense constructs derived from the starch related gene R1 (Kossmann et al., U.S. Pat. No. 6,207,880), the L- and H-type glucan phosphorylase genes (Kawchuk et al., U.S. Pat. No. 5,998,701, 1999), the polyphenol oxidase gene (Steffens, U.S. Pat. No. 6,160,204, 2000), and genes for starch branching enzymes I and II (Schwall et al., Nature Biotechnology 18: 551-554, 2000) all potentially express new peptides consisting of at least 50 amino acids (Table 1). These new peptides may interfere with plant development and/or reduce the nutritional value of potato, and are therefore undesirable.

Conventional marker genes are incorporated into genetic constructs and used to select for transformation events. They confer either antibiotic or herbicide resistance (U.S. Pat. No. 6,174,724), a metabolic advantage (U.S. Pat. No. 5,767,378), or a morphologically abnormal phenotype (U.S. Pat. No. 5,965,791) to the transformed plant. Such markers are typically derived from bacterial sources.

Furthermore, because of the infidelity of T-DNA transfer, about 75% of transformation events in plants such as tomato, tobacco, and potato contain plasmid "backbone" sequences in addition to the T-DNA (Kononov et al., Plant J. 11: 945-57, 1997). The presence of such backbone sequences is undesirable because they are foreign and typically contain origins of replication and antibiotic resistance gene markers.

There do exist various methods for removing elements like foreign marker genes, but few are easily applicable to plant genetic engineering. According to one such method, the marker gene and desired gene or nucleotide sequence are placed on different vectors. The infection of plants with either a single Agrobacterium strain carrying both vectors (U.S. Pat. No. 6,265,638) or two Agrobacterium strains each of which carries one of the vectors can occasionally result in unlinked integration events, which may be separated genetically through outbreeding. The main disadvantage of this method is that the genetic separation of loci can be very laborious and time-consuming, especially if T-DNA integration events are linked. Furthermore, this method is not widely applicable in apomictic plants, which reproduce asexually, such as Kentucky bluegrass, or vegetatively propagated crops such as potato, which cannot be readily bred due to inbreeding depression, high levels of heterozygosity, and low fertility levels.

Another method for removing foreign genetic elements relies on inserting the foreign gene, like the selectable marker, into a transposable element. The modified transposable element may then be spliced out from the genome at low frequencies. Traditional crosses with untransformed plants must then be performed to separate the transposed element from the host (U.S. Pat. No. 5,482,852). As described for the previous method, this alternative method cannot be used for vegetatively propagated or apomictic plant systems.

A third method of removing a marker gene uses the Cre/lox site-specific recombination system of bacteriophage P1 (Dale & Ow, *Proc. Natl. Acad. Sci. USA*, 88: 10558-62, 1991). Insertion of a marker gene together with the Cre recombinase gene and a chimeric gene involved in induction of Cre (both with their own promoters and terminators) between two lox sites leads to excision of the region delineated by the lox sites during the regeneration process (Zuo et al., *Nat. Biotechnol.*, 19: 157-61, 2001). This complicated process is inefficient and not reliable, and may cause genome instability.

Recent studies report that some plant genes themselves may be used as transformation markers. Examples of such plant markers include Pga22 (Zuo et al., *Curr Opin Biotechnol.* 13: 173-80, 2002), Cki1 (Kakimoto, *Science* 274: 982-985, 1996) and Esr1 (Banno et al., *Plant Cell* 13: 2609-18, 2001). All of the genes, however, trigger cytokinin responses, which confer an undesirable phenotype to the transformed plant. Furthermore, such plant markers would still need to be removed upon transformation by any of the methods described above.

Alternative methods to transform plants are also based on the in vitro recombination of foreign genetic elements, and rely on bacterial plasmid sequences for maintenance in *E. coli*, parts of which are co-integrated during the transformation process. Examples of such methods to transform plants with foreign DNA are described in U.S. Pat. Nos. 5,591,616, 6,051,757, 4,945,050, 6,143,949, 4,743,548, 5,302,523, and 5,284,253.

Marker-free transgenic plants may also be obtained by omitting any selection procedures prior to regeneration. A disadvantage of this method is that most events generated through this method will represent untransformed or chimeric plants because they will usually not be derived from single transformed plant cells. It is extremely difficult and laborious to use a marker-free procedure for the identification of transgenic plants that contain the same DNA insertion(s) in all their cells.

Thus, there is a very important need to improve plants beyond that which can be accomplished through the classical breeding crosses and conventional genetic engineering techniques, and which does not rely on the insertion of unknown or foreign nucleic acid into a plant genome. Accordingly, the present invention provides methods and compositions for precisely modifying a plant's own genetic material. Thus, the inventive "precise breeding" strategy does not induce undesirable phenotypes and does not introduce unknown or foreign nucleic acid into a plant genome.

SUMMARY

The present invention provides methods of genetically enhancing the nutritional value and agronomic performance of a plant without the permanent or stable incorporation of either unknown or foreign DNA into the genome of that plant. According to the methods of the present invention, specific, well-characterized nucleic acids, gene elements, and genes are isolated from a desired plant species or from a plant species that is sexually compatible with the desired plant, modified, and then reinserted back into the genome of the desired plant species. The modification may entail mutating the isolated nucleic acid sequence, deleting parts of the isolated nucleic acid, or simply joining the isolated nucleic acid to another polynucleotide, such as subcloning the isolated nucleic acid into a plasmid vector.

Accordingly, transgenic plants produced by the inventive methodology do not possess genomes that comprise any foreign species' nucleic acids. Thus, the methods of the present invention produces a transgenic plant whose genome does not comprise a non-plant species promoter, does not comprise a non-plant species terminator, does not comprise a non-plant species 5'-untranslated region, does not comprise a non-plant species 3'-untranslated region, does not comprise a non-plant species marker gene, does not comprise a non-plant species regulatory element, does not comprise a non-plant species gene, and does not comprise any other polynucleotide that is obtained from a non-plant species genome.

Thus, the present invention provides a method for producing a stable transgenic plant that exhibits a modified phenotype that is not exhibited by the non-transformed plant, comprising (a) transforming plant cells with a desired polynucleotide; (b) growing plants from the transformed cells; and (c) selecting a plant stably transformed with said desired polynucleotide which exhibits a new phenotype that is not exhibited by plants grown from the corresponding non-transformed plant cells. Preferably, the desired polynucleotide consists essentially of (i) nucleic acid sequences that are isolated from and/or native to the genome of the plant cells, or to other plants of the same species, or are isolated from and/or native to the genome of a plant species that is sexually compatible with the plant from which the plant cells were isolated; and (ii) at least one DNA sequence that is a border-like sequence that has a sequence that is native to the genome of said plant cells or is native to the genome of plant cells of the same species, or is native to a plant that is sexually compatible with the plant from which the plant cells were isolated, and wherein the border-like sequence is capable of stably integrating the desired polynucleotide into the genome of said plant cells.

A preferred method of the present invention entails producing a transgenic plant that exhibits a modified phenotype that is not exhibited by the non-transformed plant, comprising (a) infecting explants with *Agrobacterium* carrying (i) a "P-DNA" vector, which contains a desired polynucleotide that is native to the transgenic plant, and (ii) a "LifeSupport" vector that contains an expression cassette containing a selectable marker gene; (b) selecting for transient expression of the selectable marker gene, preferably for 1-10 days, for 3-7 days, or for 4-5 days; (c) transferring explants to regeneration media to allow shoot formation; (d) screening populations of shoots to determine which comprise at least one copy of the desired polynucleotide in their genomes and, of those, which shoots do not contain any foreign nucleic acids, such as the selectable marker gene, in their genomes; and (e) allowing shoots which contain the desired polynucleotide in their genomes but not any marker gene DNA, to develop into whole plants, wherein the resultant whole plants exhibit a modified phenotype that is not exhibited by plants grown from non-transformed plant cells of the same species.

According to such a method, the desired polynucleotide (i) consists essentially of only elements that are isolated from and/or native to the genome of the plant cell species or sexually compatible species thereof; (ii) comprises at least one border element that has a sequence that is isolated from, or native to, the genome of the plant cell species or sexually compatible species thereof, and is capable of stably integrating the desired polynucleotide into the genome of a plant cell exposed to the vector; and (iii) is stably integrated into the genome of the transformed plant; wherein the method does not integrate non-plant species or foreign DNA into the genome of the transformed plant.

Furthermore, any selectable marker gene may be used as an indicator of successful transformation. For instance, a "neomycin phosphotransferase" marker gene, or an "hpt" marker gene may be used to confer resistance to the aminoglycoside antibiotics, kanamycin and hygromycin respectively. Other marker genes include the "bar" marker gene, which confers resistance to herbicide phosphinothricin; the "DHFR" marker gene, which confers resistance to methotrexate; and the "ESPS" marker gene, which confers resistance to Round-up herbicide. It is well known in the art how to follow expression of such marker genes to determine whether or not the marker gene has been stably expressed into the genome of a transformed plant cell. Accordingly, the skilled artisan knows how to follow expression of the marker gene to determine that the marker gene is only transiently expressed in the transformed plant cell.

In another aspect of the invention, there is provided a method of making a stably transformed plant comprising the steps of: (1) identifying a target gene; (2) isolating a leader or trailer DNA sequence associated with said target gene; (3) optionally modifying said isolated leader or trailer DNA; (4) operably linking said leader or trailer DNA to native regulatory elements to form an expression cassette; (5) inserting said expression cassette into a P-DNA that is located on a binary vector, wherein the binary vector also carries an operable cytokinin gene such that the inadvertent insertion of additional binary vector sequences, which are of foreign origin, are detected by expression of the cytokinin gene; (6) introducing the modified binary vector into *Agrobacterium*; (7) stably integrating the rearranged native DNA into the genomes of plant cells using LifeSupport-mediated transformation; (8) regenerating plant cells that contain the rearranged native DNA; (9) discarding plants that display a cytokinin-overproducing phenotype and do not fully regenerate; and (10) maintaining for further analysis the desirable plants that are indistinguishable from untransformed plants.

In another aspect of the instant invention, a method of modifying the expression of a trait in a selected plant species is provided. In one embodiment, the method comprises (1) identifying the trait to be modified; (2) constructing a recombinant DNA molecule consisting essentially of genetic elements isolated from, or native to, the selected plant species, wherein the recombinant DNA molecule, when integrated into the genome of the selected plant species, modifies the expression of the trait in the transformed plant species; (3) stably integrating the recombinant DNA molecule into cells of the selected plant species using LifeSupport-mediated transformation; and (4) identifying transformed plants exhibiting modified expression of the trait.

In a preferred embodiment, polynucleotide that is native to a desired plant is inserted into the desired plant's genome by infecting explants with two different *Agrobacterium* strains. A first *Agrobacterium* strain is capable of transferring the native DNA from P-DNA vectors to plant cells; a second strain can transfer a T-DNA carrying an expression cassette for a selectable marker gene to plant cells. Examples of the latter vector include the so-called, "LifeSupport" vectors described herein. By preferably selecting plants that transiently express the marker gene for 1-10 days, for 3-7 days, or for 4-5 days, and subsequently transferring explants to regeneration media, a population of events is obtained, part of which represents plants that contain at least one copy of the polynucleotide, but which lack any copies of the T-DNA or marker gene.

In another embodiment, a single *Agrobacterium* strain is used that carries both a P-DNA vector, which houses the desired, native gene of interest or polynucleotide between P-DNA border-like sequences, and a LifeSupport vector, which contains a marker gene. The marker gene may, or may not, be inserted between P-DNA border-like sequences, T-DNA border sequences, or other T-DNA-like border sequences.

Thus, in another preferred embodiment, the P-DNA vector contains at least two expression cassettes, one of which comprises a native screenable or selectable marker gene driven by a native promoter and followed by a native terminator.

By preferably selecting for at least 2 days and more preferably for at least 5 days for native marker gene expression and subsequently transferring explants to regeneration media, a population of events is obtained that represent plants containing at least one copy of the introduced DNA stably integrated into their genomes. In preferred embodiments, the plant-derived marker gene encodes a mutant 5-enolpyruvul-3-phosphoshikimic acid synthase or tryptophan decarboxylase. In a more preferred embodiment, the selectable marker encodes for salt tolerance. In a most preferred embodiment, the salt tolerance gene has the nucleotide sequence shown in SEQ ID NO: 35 and is used to select for transformation events in potato.

In yet another embodiment, the modified expression of the trait is characterized by an increase in expression, a decrease in expression, or in undetectable expression.

In another aspect of the instant invention, a plant made by the method of (1) identifying the trait to be modified; (2) constructing a recombinant DNA molecule consisting essentially of genetic elements isolated from the selected plant species, wherein the recombinant DNA molecule when integrated into the genome of the selected plant species modifies the expression of the trait in the transformed plant species; (3) stably integrating the recombinant DNA molecule into cells of the selected plant species through LifeSupport-mediated transformation; and (4) identifying transformed plants exhibiting modified expression of the trait, is provided.

In a further aspect, a method of modifying expression of a trait in a selected plant species is provided. This method comprises (1) identifying the trait to be modified; (2) constructing a recombinant DNA molecule consisting essentially of (a) genetic elements isolated from the selected plant species, wherein the genetic elements when integrated into the genome of the selected plant species modifies the expression of the trait in the transformed plant species; and (b) a selectable marker gene that is isolated from the same plant species; (3) stably integrating the recombinant DNA molecule into cells of the selected plant species through LifeSupport-mediated transformation; (4) detecting the selectable marker gene; and (5) identifying transformed plants exhibiting modified expression of the trait.

In yet one other aspect, a plant exhibiting a modified expression of a trait is provided. In one embodiment, the plant has stably integrated into its genome a recombinant DNA molecule consisting essentially of genetic elements isolated from a plant of the same species, or from a plant that is sexually compatible with that species, wherein the recombinant DNA molecule modifies the expression of the trait.

In another aspect of the present invention, an isolated nucleotide sequence referred to as "plant-DNA" ("P-DNA") is provided. In a preferred embodiment, the P-DNA itself lacks any genes or parts thereof and is delineated by terminal, T-DNA "border-like" sequences that share at least 50%, at least 75%, at least 90% or at least 95% sequence identity with the nucleotide sequence of the T-DNA borders of any virulent *Agrobacterium* strain, and which support an efficient transfer of the entire P-DNA from *Agrobacterium* to plant cells.

In a preferred embodiment a "border-like" sequence promotes and facilitates the integration of a polynucleotide to which it is linked. In another preferred embodiment, each terminal sequence of the modified P-DNA is between 5-100 bp in length, 10-80 bp in length, 15-75 bp in length, 15-60 bp in length, 15-50 bp in length, 15-40 bp in length, 15-30 bp in length, 16-30 bp in length, 20-30 bp in length, 21-30 bp in length, 22-30 bp in length, 23-30 bp in length, 24-30 bp in length, 25-30 bp in length, or 26-30 bp in length. More preferably, the border-like sequence is between 20 and 28 nucleotides in length.

In a preferred embodiment, the P-DNA left and right border sequences of the present invention are isolated from and/or are native to the genome of a plant that is to be modified and are not identical in nucleotide sequence to any known *Agrobacterium*-derived T-DNA border sequence. Thus, in one embodiment, a P-DNA border sequence may possess 1, 2, 3, 4, 5, 6, 7, 8, 9, 10, 11, 12, 13, 14, 15, 16, 17, 18, 19, 20, or more nucleotides that are different from a T-DNA border sequence from an *Agrobacterium* species, such as *Agrobacterium tumefaciens* or *Agrobacterium rhizogenes*. Alternatively, in another embodiment, a P-DNA border, or a border-like sequence of the present invention has at least 95%, at least 90%, at least 80%, at least 75%, at least 70%, at least 60% or at least 50% sequence identity with a T-DNA border sequence from an *Agrobacterium* species, such as *Agrobacterium tumefaciens* or *Agrobacterium rhizogenes*. More preferably, a native plant P-DNA border sequence that shares greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% nucleotide sequence identity with an *Agrobacterium* T-DNA border sequence.

In another preferred embodiment, a border-like sequence can be isolated from a plant genome and then modified or mutated to change the efficiency by which they are capable of integrating a nucleotide sequence into another nucleotide sequence. In another embodiment, other polynucleotide sequences may be added to or incorporated within a border-like sequence of the present invention. Thus, in yet another embodiment, a P-DNA left border or a P-DNA right border may be modified so as to possess 5'- and 3'-multiple cloning sites, or additional restriction sites. In a further embodiment, a P-DNA border sequence may be modified to increase the likelihood that backbone DNA from the accompanying vector is not integrated into the plant genome.

In an even more preferred embodiment, the P-DNAs are isolated from any plant by using degenerate primers in a polymerase chain reaction. In one preferred embodiment, the P-DNA is derived from potato, is delineated by 25-bp termini with 80 and 88% identity to conventional T-DNA borders, respectively, and has the nucleotide sequence shown in SEQ ID NO. 1. In another most preferred embodiment, the P-DNA is derived from wheat, is delineated by 25-bp termini with 72% and 92% identity with conventional T-DNA borders, respectively, and contains the nucleotide sequence shown in SEQ ID NOs. 94 or 95.

Such a P-DNA may be modified so as to comprise other polynucleotides positioned between the border-like sequences. In a preferred embodiment, the modified P-DNA consists essentially of, in the 5'- to 3'-direction, a first border-like sequence that promotes DNA transfer, a promoter, a desired polynucleotide that is operably linked to the promoter, a terminator and a second border-like sequence that also promotes DNA transfer. In one other embodiment, the desired polynucleotide represents one or several copies of a leader, a trailer or a gene in sense and/or antisense orientations. In a more preferred embodiment, the modified P-DNA contains expression cassettes for both a mutant PPO gene and an invertase inhibitor gene.

Thus, in a preferred embodiment, the desired polynucleotide comprises a sense and antisense sequence of a leader sequence. In a more preferred embodiment, the leader sequence is associated with a gene that is endogenous to a cell of the selected plant species. In yet a more preferred embodiment, the leader is associated with a gene that is selected from the group consisting of a PPO gene, an R1 gene, a type L or H alpha glucan phosphorylase gene, an UDP glucose glucosyltransferase gene, a HOS1 gene, a S-adenosylhomocysteine hydrolase gene, a class II cinnamate 4-hydroxylase gene, a cinnamoyl-coenzyme A reductase gene, a cinnamoyl alcohol dehydrogenase gene, a caffeoyl coenzyme A O-methyltransferase gene, an actin depolymerizing factor gene, a Nin88 gene, a Lol p 5 gene, an allergen gene, a P450 hydroxylase gene, an ADP-glucose pyrophosphorylase gene, a proline dehydrogenase gene, an endo-1,4-beta-glucanase gene, a zeaxanthin epoxidase gene, and a 1-aminocyclopropane-1-carboxylate synthase gene.

In yet another preferred embodiment, the desired polynucleotide sequence comprises a sense and antisense sequence of a trailer sequence. In a preferred embodiment, the trailer sequence is associated with a gene selected from the group consisting of a PPO gene, an R1 gene, a type L or H alpha glucan phosphorylase gene, an UDP glucose glucosyltransferase gene, a HOS1 gene, a S-adenosylhomocysteine hydrolase gene, a class II cinnamate 4-hydroxylase gene, a cinnamoyl-coenzyme A reductase gene, a cinnamoyl alcohol dehydrogenase gene, a caffeoyl coenzyme A O-methyltransferase gene, an actin depolymerizing factor gene, a Nin88 gene, a Lol p 5 gene, an allergen gene, a P450 hydroxylase gene, an ADP-glucose pyrophosphorylase gene, a proline dehydrogenase gene, an endo-1,4-beta-glucanase gene, a zeaxanthin epoxidase gene, and a 1-aminocyclopropane-1-carboxylate synthase gene.

In a preferred embodiment, the desired polynucleotide, such as a gene, is isolated from, and/or is native to the plant that is to be transformed. In another preferred embodiment, the desired polynucleotide is modified or mutated. In one embodiment, a mutation to the isolated polynucleotide may render the desired nucleotide greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% dissimilar to its unmutated form.

In a preferred embodiment of the present invention, the promoter of an expression cassette located within a P-DNA is a constitutive promoter. In a more preferred embodiment the constitutive promoter is the promoter of the Ubiquitin-3 gene of potato. In an even more preferred embodiment the constitutive promoter is the promoter of the Ubiquitin-7 gene of potato.

In another embodiment, the promoter of an expression cassette located within a P-DNA is a regulatable promoter. In a more preferred embodiment, the regulatable promoter is sensitive to temperature. In an even more preferred embodiment, the regulatable promoter is a ci21A promoter or a C17 promoter, each isolated from potato (Schneider et al., *Plant Physiol.* 113: 335-45, 1997; Kirch et al., *Plant Mol Biol* 33: 897-909, 1997).

In another embodiment, the promoter of an expression cassette located within a P-DNA can be regulated in a temporal fashion. In a preferred embodiment, the promoter is an rbcS promoter (Ueda et al., *Plant Cell* 1: 217-27, 1989).

In yet another embodiment, the promoter of an expression cassette located within a P-DNA is regulated by any one of abscisic acid, wounding, methyl jasmonate or gibberellic acid. In a further embodiment, this promoter is a promoter selected from either a Rab 16A gene promoter, an α-amylase gene promoter or a pin2 gene promoter.

In another embodiment, the promoter of an expression cassette located within a P-DNA is a tissue-specific promoter. In a particularly preferred embodiment, this promoter is a GBSS promoter isolated from *S. tuberosum*.

In one embodiment, the present invention provides a P-DNA vector that is capable of replication in both *E. coli* and *Agrobacterium*, and contains either a P-DNA or a modified P-DNA. In a preferred embodiment, this vector also contains an expression cassette for a cytokinin gene in its backbone to enable the selection against backbone integration events.

In another preferred embodiment, the desired nucleotide sequence further comprises a spacer element. In a more preferred embodiment, the spacer element is a Ubi intron sequence or a GBSS spacer sequence.

In another preferred embodiment, the desired nucleotide sequence comprises a mutated native gene encoding a functionally inactive protein, which reduces the overall activity of that protein if expressed in transgenic plants. In yet a more preferred embodiment, this mutated gene encodes a functionally inactive polyphenol oxidase lacking a copper binding domain.

In another preferred embodiment, the desired nucleotide sequence comprises a native gene encoding a functionally active protein. In yet a more preferred embodiment, this gene encodes for a protein with homology to the tobacco vacuolar invertase inhibitor.

In another embodiment, the terminator of an expression cassette located within a P-DNA is a Ubi3 terminator sequence or a 3'-untranslated region of a gene of a selected plant species.

In another aspect of the instant invention, a method for modifying a target plant cell is provided. In one embodiment, the method comprises: (1) inserting a modified P-DNA into the genome of at least one cell in the target plant cell using LifeSupport-mediated transformation; and (2) observing if there is a phenotypic change in the target plant cell; wherein the promoter in the modified P-DNA transcribes the sense and/or antisense untranslated sequences associated with a native gene to reduce expression of that native gene, thereby modifying the target plant cell. In another preferred embodiment, the promoter in the modified P-DNA transcribes a gene to overexpress that gene in the target plant cell.

In yet another aspect, there is provided a method of making a transgenic plant cell of a selected plant species that contains a modified P-DNA. The method comprises co-transfecting a plant cell of the selected plant species with a P-DNA vector and a LifeSupport vector that comprises a marker gene flanked by a T-DNA left border and a T-DNA right border and a mutant virD2 gene inserted into the vector backbone, and selecting for a plant cell that transiently expresses the marker gene, and isolating a plant cell that contains the modified P-DNA integrated into its genome but does not contain any nucleotides from the LifeSupport vector. In a preferred embodiment, the marker gene confers resistance to kanamycin. In a most preferred embodiment the yeast ADH terminator follows the kanamycin resistance gene.

In a preferred embodiment, the plant cell of the selected plant species targeted for transformation is in culture. In another preferred embodiment, the plant cell of the selected plant species targeted for transformation is within a plant.

The present invention also provides a plant of the selected species that comprises at least one cell with a genome that contains a modified P-DNA. In a preferred embodiment, the modified P-DNA consists essentially of, in the 5'- to 3'-direction, a first terminus that functions like a T-DNA border followed by P-DNA sequences, a promoter, a desired nucleotide sequence operably linked to both a promoter, a terminator and additional P-DNA sequences delineated by a second terminus. In another embodiment, the desired polynucleotide represents one or several copies of a leader, a trailer and a gene in the sense and/or antisense orientation.

In another embodiment, a plant that comprises at least one cell with a genome that contains a modified P-DNA is envisioned.

In another aspect of the invention, a method for reducing the expression of a gene in a selected plant species is provided. The method comprises the LifeSupport-mediated transformation of a plant cell from a selected plant species with a P-DNA vector, wherein the modified P-DNA of this vector is stably integrated into the genome of the plant cell. In another aspect of the invention, the modified P-DNA comprises a desired polynucleotide that reduces expression of an endogenous gene from the selected plant species.

In another aspect of the instant invention, a gene native to the selected plant species may be mutated and reintroduced into the plant using the inventive methods. Preferably, the mutated gene, for instance a mutated PPO gene, is integrated into the plant cell genome using a P-DNA vector.

The present invention also provides a method for reducing the undesirable expression of the polyphenol oxidase gene in a selected plant species. In a preferred embodiment, the method comprises integrating into a genome of a selected plant species a modified P-DNA comprised only of nucleotide sequences isolated from the selected plant species or from a plant that is sexually compatible with the selected plant species, consisting essentially of, in the 5'- to 3'-direction, a first P-DNA terminus that functions like a T-DNA border followed by flanking P-DNA sequences; a promoter; a desired nucleotide which is a sense-oriented trailer nucleotide sequence associated with a specific PPO gene; an antisense-oriented sequence of the trailer nucleotide sequence from the specific PPO gene; a termination sequence, and additional P-DNA sequences delineated by a second terminus that functions like a T-DNA border, wherein the promoter produces a double-stranded RNA molecule that reduces the expression of the specific PPO gene, thereby reducing black spot bruising in specific tissues of the plant. In another embodiment, the sense- and antisense-oriented nucleotide sequences from the leader nucleotide sequences are obtained from the 5'-untranslated region preceding the specific PPO gene. In a further embodiment, the sense- and antisense-oriented leader or trailer sequence associated with the PPO gene may be separated by another polynucleotide sequence, referred to herein, as either an intron or a "spacer." In a preferred embodiment, the leader or trailer sequence is associated with a potato PPO gene. In a more preferred embodiment, the leader or trailer sequence is associated with a potato PPO gene that is expressed in potato tubers. In a most preferred embodiment, the leader or trailer sequence is associated with a potato PPO gene that is expressed in all parts of the potato tuber except for the epidermis.

The present invention also provides a method for reducing acrylamide production, sprout-induction during storage, phosphate accumulation, and/or cold-induced sweetening in tubers of a selected plant species.

In a preferred embodiment, the method comprises the Life-Support-mediated transformation of a selected plant species with a modified P-DNA comprised only of nucleotide sequences isolated from the selected plant species, or from plants that are sexually compatible with the selected plant species, consisting essentially of, in the 5'- to 3'-direction, a first P-DNA with a left border-like sequence, a promoter, a desired nucleotide sequence, which is a sense-oriented nucleotide sequence from the leader sequence associated with the R1 gene, an antisense-oriented sequence from this leader sequence, a termination sequence, and a right border-like sequence. Upon expression, a leader-RNA duplex is produced that reduces expression of the R1 gene, thereby reducing cold-induced sweetening in the plant. In another embodiment, the desired sense- and antisense-oriented nucleotide sequences represent the trailer associated with the R1 gene. In a further embodiment, the sense- and antisense-oriented leader or trailer associated with R1 may be separated by another polynucleotide sequence, referred to herein, as either an intron or a "spacer."

In another preferred embodiment, the method comprises the LifeSupport-mediated transformation of a selected plant species with a modified P-DNA that is similar to the one described above but contains a leader- or trailer sequence associated with an alpha glucan phosphorylase gene.

In yet another preferred embodiment, the method comprises the LifeSupport-mediated transformation of a selected plant species with a modified P-DNA that contains an invertase inhibitor gene.

In another embodiment, the modified P-DNA described in the preceding paragraphs are used to reduce the accumulation of additional undesirable products of the Maillard reaction, which occurs during the heating of carbohydrate-rich foods such as potato tubers. These undesirable products include advanced glycation end products (AGEs) that have been associated with various pathologies.

The present invention also provides a method for increasing resistant starch levels in the storage organs of plants and food crops.

In a preferred embodiment, the method comprises the Life-Support-mediated transformation of a selected plant species with a modified P-DNA that contains an expression cassette for a fusion of the trailer sequences associated with the starch branching enzyme I and II genes.

The present invention also provides isolated nucleotide sequences comprising the promoters of the potato GBSS gene and the potato proteinase inhibitor gene, which are predominantly expressed in tubers. The isolated promoters have the nucleotide sequence shown in SEQ ID NO.: 6 and SEQ ID NO.:40, respectively.

In one aspect, the present invention provides a method of modifying a trait of a selected plant comprising:
 a. stably transforming cells from the selected plant with a desired polynucleotide, wherein the desired polynucleotide consists essentially of a nucleic acid sequence that is native to the selected plant, native to a plant from the same species, or is native to a plant that is sexually interfertile with the selected plant,
 b. obtaining a stably transformed plant from the transformed plant cells wherein the transformed plant contains the desired polynucleotide stably integrated into the genome and wherein the desired polynucleotide modifies the trait.

In a preferred embodiment, the method further comprises co-transfecting the plant cells with a selectable marker gene that is transiently expressed in the plant cells, and identifying transformed plant cells, and transformed plants obtained from the transformed plant cells, wherein the selectable marker gene is not stably integrated and the desired polynucleotide is stably integrated into the genome.

In a preferred embodiment, the desired polynucleotide comprises a P-DNA, GBSS promoter, Ubi7 promoter, Ubi3 promoter, PIP promoter, modified PPO gene, invertase inhibitor gene, salt tolerance gene, R1-associated leader, phosphorylase-associated leader, R1-associated trailer, SBE-associated trailers, Ubi-intron, GBSS spacer, UbiT.

In another preferred embodiment, a "plant" of the present invention is a monocotyledenous plant, selected from the group consisting of wheat, turf, turf grass, cereal, maize, rice, oat, wheat, barley, sorghum, orchid, iris, lily, onion, banana, sugarcane, sorghum, and palm.

In yet another embodiment, a "plant" of the present invention is a dicotyledenous plant, selected from the group consisting of avacado, potato, tobacco, tomato, sugarbeet, broccoli, cassava, sweet potato, pepper, cotton, poinsetta, legumes, alfalfa, soybean, carrot, strawberry, lettuce, oak, maple, walnut, rose, mint, squash, daisy, and cactus.

In yet another embodiment, plants and plant cells of the present inventive methods are transformed via *Agrobacterium*-mediated transformation. Preferably, the *Agrobacterium*-mediated transformation relies on the use of at least one binary vector. In yet another embodiment, the *Agrobacterium*-mediated transformation method uses a first binary vector and a second binary vector. In a preferred embodiment the first binary vector contains the desired polynucleotide and the second binary vector contains a selectable marker gene, wherein the selectable marker gene is operably linked to a promoter and a terminator.

According to the present methods, the trait that is modified is selected from the group consisting of enhanced health and nutritional characteristics, improved storage, enhanced yield, enhanced salt tolerance, enhanced heavy metal tolerance, increased drought tolerance, increased disease tolerance, increased insect tolerance, increased water-stress tolerance, enhanced cold and frost tolerance, enhanced color, enhanced sweetness, improved vigor, improved taste, improved texture, decreased phosphate content, increased germination, increased micronutrient uptake, improved starch composition, improved flower longevity.

The present invention also encompasses a plant made by the present methods.

In another aspect, the present invention provides a method of modifying a trait in a selected plant comprising:
 (a) identifying the trait to be modified;
 (b) constructing a first polynucleotide consisting essentially of native genetic elements isolated from the selected plant, a plant from the same species, or a plant that is sexually interfertile with the selected plant, wherein the native genetic elements are capable of modifying the expression of a gene that controls the trait (c) constructing a second polynucleotide comprising a selectable marker gene that is operably linked to a promoter and a terminator;

(d) co-transfecting plant cells from the selected plant with the first and second polynucleotides;

(e) selecting for the transient expression of the selectable marker gene;

(f) screening for plant cells stably transformed with the first polynucleotide but do not contain the second DNA molecule integrated into the genome; and (g) obtaining a stably transformed plant from the transformed plant cells that exhibit a modified expression of the trait.

In one embodiment, the genetic elements comprise at least one of a promoter, sequence of interest, terminator, enhancer, intron, spacer, or regulatory elements. In another embodiment, method of claim 4, wherein the plant cells are transfected with the first polynucleotide before the second polynucleotide or vice versa.

In one embodiment, the sequence of interest is a gene. In another embodiment, the gene is a mutated or wild-type polyphenol oxidase gene or a mutated or wild-type R1 gene. In one other embodiment, the sequence of interest is a leader or trailer sequence, wherein the leader or trailer sequence represents a sequence upstream or downstream of a gene that is native to the plant cell. In yet another embodiment, the sequence of interest comprises a sense-oriented leader sequence operably linked to an antisense leader sequence. In another embodiment, the sequence of interest comprises a sense-oriented trailer sequence operably linked to an antisense trailer sequence. In another embodiment, the promoter is an inducible promoter. In another embodiment, the terminator is a yeast ADH terminator sequence.

According to the present invention, a leader construct comprises in 5'- to 3'-direction, a promoter, a sense-oriented leader sequence, the antisense sequence of the leader, and a terminator, wherein expression of the leader construct produces a double-stranded RNA molecule that facilitates the down-regulation of expression of the gene to which it is associated. In one other embodiment, the leader sequence is associated with, and located upstream of, the coding region of the PPO gene, the R1 gene, an L-type phosphorylase gene, or an alpha glucan phosphorylase gene.

In another embodiment, the trailer construct comprises in 5'- to 3'-direction, a promoter, a sense-oriented trailer sequence, the antisense sequence of the trailer, and a terminator, wherein expression of the trailer construct produces a double-stranded RNA molecule that facilitates the down-regulation of expression of the gene to which it is associated. In a preferred embodiment, the trailer sequence is associated with, and located downstream of, the coding region of the PPO gene, the R1 gene, an L-type phosphorylase gene, or an alpha glucan phosphorylase gene.

The method further comprises exposing the plant cell to a second vector that comprises a marker element, wherein the marker is transiently expressed in the transformed plant and is not stably integrated into the genome of the transformed plant. In one embodiment, the marker is a herbicide resistance gene, an antibiotic resistance gene, or NPTII.

Preferably, the plant cells are transformed via *Agrobacterium*-mediated transformation. In one embodiment, the *Agrobacterium*-mediated transformation relies on the use of at least one binary vector. In yet another embodiment, the *Agrobacterium*-mediated transformation method uses a first binary vector and a second binary vector. In one other embodiment, the first binary vector carries the first polynucleotide and the second binary vector carries the second polynucleotide.

The present invention provides another method of modifying the expression of a gene in a selected plant comprising:

(a) identifying the functional gene;

(b) constructing a first polynucleotide consisting essentially of native genetic elements isolated from the selected plant, a plant of the same species as the selected plant, or a plant that is sexually interfertile with the selected plant, wherein the native genetic elements are capable of modifying the expression of the gene;

(c) constructing a second polynucleotide comprising a functional selectable marker gene;

(d) co-transfecting plant cells from the selected plant with the first and second polynucleotides;

(e) selecting for the transient expression of the selectable marker gene;

(f) screening for plant cells stably transformed with the first polynucleotide but do not contain the second polynucleotide integrated into the genome; and (g) obtaining a transformed plant from the transformed plant cells that exhibit modified expression of the gene.

Preferably, the plant cells are transformed via *Agrobacterium*-mediated transformation. In one embodiment, the *Agrobacterium*-mediated transformation relies on the use of at least one binary vector. In yet another embodiment, the *Agrobacterium*-mediated transformation method uses a first binary vector and a second binary vector. In one other embodiment, the first binary vector carries the first polynucleotide and the second binary vector carries the second polynucleotide.

In another embodiment, the first polynucleotide comprises at least one of a P-DNA, GBSS promoter, Ubi7 promoter, Ubi3 promoter, PIP promoter, modified PPO gene, invertase inhibitor gene, salt tolerance gene, R1-associated leader, phosphorylase-associated leader, R1-associated trailer, SBE-associated trailers, Ubi-BSS spacer, UbiT.

In another embodiment, the second polynucleotide comprises at least one of a selectable marker gene, an omega-mutated virD2 polynucleotide, a codA polynucleotide, and a codA::upp fusion polynucleotide.

The present invention also encompasses a plant made by such method.

In one other embodiment, a transgenic plant is provided which exhibits a modified expression of a trait compared to the non-transgenic plant from which it was derived, wherein the transgenic plant is stably transformed with a desired polynucleotide consisting essentially of native genetic elements isolated from the plant, a plant in the same species, or a plant that is sexually interfertile with the plant, and wherein the polynucleotide modifies the expression of the trait.

In another preferred embodiment, the "plant" of the present invention is a monocotyledenous plant, selected from the group consisting of wheat, turf, turf grass, cereal, maize, rice, oat, wheat, barley, sorghum, orchid, iris, lily, onion, banana, sugarcane, sorghum, and palm.

In yet another embodiment, the "plant" of the present invention is a dicotyledenous plant, selected from the group consisting of avacado, potato, tobacco, tomato, sugarbeet, broccoli, cassava, sweet potato, pepper, cotton, poinsetta, legumes, alfalfa, soybean, carrot, strawberry, lettuce, oak, maple, walnut, rose, mint, squash, daisy, and cactus.

In another embodiment, the trait is selected from the group consisting of enhanced health and nutritional characteristics, improved storage, enhanced yield, enhanced salt tolerance, enhanced heavy metal tolerance, increased drought tolerance, increased disease tolerance, increased insect tolerance, increased water-stress tolerance, enhanced cold and frost tolerance, enhanced color, enhanced sweetness, improved vigor, improved taste, improved texture, decreased phosphate content, increased germination, increased micronutrient uptake, improved starch composition, improved flower longevity.

In another embodiment, the desired polynucleotide comprises at least one of a P-DNA, GBSS promoter, Ubi7 promoter, Ubi3 promoter, PIP promoter, modified PPO gene, invertase inhibitor gene, salt tolerance gene, R1-associated leader, phosphorylase-associated leader, R1-associated trailer, SBE-associated trailers, Ubi-intron, GBSS spacer, UbiT.

The present invention also encompasses an isolated, border-like nucleotide sequence ranging in size from 20 to 100 bp that shares between 52% and 96% sequence identity with a T-DNA border sequence from *Agrobacterium tumafaciens*. In a preferred embodiment, the isolated nucleotide sequence is isolated from a monocotyledenous plant, selected from the group consisting of wheat, turf, turf grass, cereal, maize, rice, oat, wheat, barley, sorghum, orchid, iris, lily, onion, banana, sugarcane, sorghum, and palm. In another embodiment, the nucleotide sequence is isolated from a dicotyledenous plant selected from the group consisting of potato, tobacco, tomato, sugarbeet, broccoli, cassava, sweet potato, pepper, cotton, poinsetta, legumes, alfalfa, soybean, carrot, strawberry, lettuce, oak, maple, walnut, rose, mint, squash, daisy, and cactus.

In yet another embodiment, the isolated nucleotide sequence is isolated from potato, and has a nucleotide sequence shown in SEQ ID NOs. 1, 54, or 55. In a preferred embodiment, the isolated nucleotide sequence shares 52% sequence identity with a T-DNA border sequence from *Agrobacterium tumafaciens*. The present invention encompasses a vector that comprises such nucleotide sequences.

The present invention also provides method of making a plant stably transformed with a desired polynucleotide comprising:

(a) isolating a P-DNA that is flanked by border-like sequences from the plant wherein the border-like sequences share between 52% and 96% sequence identity with an *Agrobacterium tumafaciens* T-DNA border sequence;

(b) inserting the desired polynucleotide between the P-DNA border-like sequences to form a P-DNA construct; and (c) transforming aa plant cell from the plant with the P-DNA construct; and (d) recovering a plant from the transformed plant cell stably transformed with the P-DNA construct.

In one embodiment, the P-DNA construct is carried on a vector comprised of a backbone integration marker gene and transformed plant cells are selected that do not contain the backbone integration marker gene. In another embodiment, the backbone integration marker gene is a cytokinin gene. In another embodiment, plant shoots are not selected that exhibit a cytokinin-overproducing phenotype. In yet another embodiment, the backbone integration marker gene is the IPT gene, and plant shoots are not selected that exhibit an abnormal phenotype or cannot develop roots.

In one other embodiment, the plant cells are from a monocotyledenous plant selected from the group consisting of wheat, turf, turf grass, cereal, maize, rice, oat, wheat, barley, sorghum, orchid, iris, lily, onion, banana, sugarcane, sorghum, and palm.

In another embodiment, the plant cells are from a dicotyledenous plant selected from the group consisting of potato, tobacco, tomato, sugarbeet, broccoli, cassava, sweet potato, pepper, cotton, poinsetta, legumes, alfalfa, soybean, carrot, strawberry, lettuce, oak, maple, walnut, rose, mint, squash, daisy, and cactus.

Preferably, the plant cells are transformed via *Agrobacterium*-mediated transformation. In one embodiment, the *Agrobacterium*-mediated transformation relies on the use of at least one binary vector. In yet another embodiment, the *Agrobacterium*-mediated transformation method uses a first binary vector and a second binary vector. In one other embodiment, the first binary vector carries the first polynucleotide and the second binary vector carries the second polynucleotide. In one further embodiment, the second binary vector comprises at least one of a negative selectable marker gene and an omega-mutated virD2 gene, wherein the negative selectable marker gene is positioned within the right T-DNA border and the left T-DNA border, and wherein the omega-mutated virD2 gene is positioned within the backbone of the second binary vector. In a preferred embodiment, the second binary vector comprises both a negative selectable marker gene positioned within the right T-DNA border and the left T-DNA border, and an omega-mutated virD2 gene positioned within the backbone of the second binary vector.

The present invention also provides a P-DNA consisting essentially of, in the 5'- to 3'-direction, a first T-DNA border-like sequence, a promoter, a desired polynucleotide sequence operably linked to the promoter, a terminator, and a second T-DNA border-like sequence, wherein the border-like sequences have less than 100% sequence identity with T-DNA border sequences In a preferred embodiment, the T-DNA border-like sequences, the promoter, the desired polynucleotide, and the terminator, are all isolated from the same plant, the same plant species, or plants that are sexually interfertile.

In another embodiment, the P-DNA further consists essentially of a selectable marker gene.

In yet another embodiment, the T-DNA border-like sequences, the promoter, the desired polynucleotide, the terminator and the selectable marker gene, are all isolated from the same plant, the same plant species, or plants that are sexually interfertile.

In yet another embodiment, the desired polynucleotide sequence in the P-DNA is a sequence upstream or downstream of the coding region of a gene, wherein the upstream sequence is a leader sequence, and wherein the downstream sequence is a trailer sequence. In this embodiment, the T-DNA border-like sequences, the promoter, the leader sequence, the trailer sequence, the terminator and the selectable marker gene are all isolated from the same plant, the same plant species, or plants that are sexually interfertile.

In another embodiment, vectors comprising such P-DNA constructs are provided by the present invention.

In another embodiment, the promoter is a regulatable promoter. In yet another embodiment, the regulatable promoter is sensitive to temperature. In a preferred embodiment, the regulatable promoter is a wheat wcs120 promoter. In another embodiment, the promoter is under temporal regulation. In yet another embodiment, the promoter is a carboxylase promoter. In a further embodiment, the carboxylase promoter is a maize carboxylase promoter.

The promoter may be regulated by any one of abscisic acid, wounding, methyljasmonate or gibberellic acid. In another embodiment, the promoter is a promoter selected from either a Rab 16A gene promoter, an α-amylase gene promoter or a pin2 gene promoter. In yet another embodiment, the promoter is a tissue-specific promoter.

In one other embodiment, the leader sequence is a part of a 5'-untranslated region of a gene that is endogenous to a cell of the selected plant species. In another embodiment, the 5'-untranslated region is upstream of a start codon of a gene that is selected from the group consisting of a PPO gene, an R1 gene, a HOS1 gene, a S-adenosylhomocysteine hydrolase gene, a class II cinnamate 4-hydroxylase gene, a cinnamoyl-coenzyme A reductase gene, a cinnamoyl alcohol dehydrogenase gene, a caffeoyl coenzyme A O-methyltransferase gene, an actin depolymerizing factor gene, a Nin88 gene, a Lol p 5 gene, an allergen gene, a P450 hydroxylase gene, an ADP-glucose pyrophosphorylase gene, a proline dehydrogenase gene, an endo-1,4-beta-glucanase gene, a zeaxanthin epoxidase gene, and a 1-aminocyclopropane-1-carboxylate synthase gene.

In another embodiment, the trailer sequence is a part of the 3'-untranslated region of a gene that is downstream of a termination codon of a gene selected from the group consisting of a PPO gene, an R1 gene, a HOS1 gene, a S-adenosylhomocysteine hydrolase gene, a class II cinnamate 4-hydroxylase gene, a cinnamoyl-coenzyme A reductase gene, a cinnamoyl alcohol dehydrogenase gene, a caffeoyl coenzyme A O-methyltransferase gene, an actin depolymerizing factor gene, a Nin88 gene, a Lol p 5 gene, an allergen gene, a P450 hydroxylase gene, an ADP-glucose pyrophosphorylase gene, a proline dehydrogenase gene, an endo-1,4-beta-glucanase gene, a zeaxanthin epoxidase gene, and a 1-aminocyclopropane-1-carboxylate synthase gene.

The present vector may further comprise a spacer element that is either an Ubi intron sequence or a GBSS spacer sequence. In another embodiment, the vector comprises a terminator that is a Ubi3 terminator sequence or a 3'-untranslated region of an endogenous plant gene.

In another embodiment, the vector comprises a selectable marker gene operably linked to a constitutive promoter and a Cre gene operably linked to an inducible promoter, wherein the selectable marker gene and the Cre gene are flanked by a first recombinase recognition site and a second recombinase recognition site. In another embodiment, the first recombinase recognition site and the second recombinase recognition site are lox sites.

In another embodiment, the inducible promoter is a temperature-sensitive promoter, a chemically-induced promoter, or a temporal promoter. In yet another embodiment, the inducible promoter is a Ha hsp17.7 G4 promoter, a wheat wcs120 promoter, a Rab 16A gene promoter, an α-amylase gene promoter, a pin2 gene promoter, a carboxylase promoter. In yet another preferred embodiment, further comprises a plant-derived marker gene. In another preferred embodiment, the plant-derived marker gene is an enolpyruvul-3-phosphoshikimic acid synthase gene.

In another aspect of the present invention, a method for modifying a plant cell is provided, comprising integrating a P-DNA sequence into the genome of a plant cell, wherein the P-DNA consists essentially of, in the 5'- to 3'-direction, a first T-DNA border-like sequence, a promoter, a desired polynucleotide sequence operably linked to the promoter, a terminator, and a second T-DNA border-like sequence, wherein the border-like sequences have less than 100% sequence identity with T-DNA border sequences, and wherein the T-DNA border-like sequences, the promoter, the desired polynucleotide, and terminator, are all isolated from or native to the genome of the plant cell, wherein the desired polynucleotide comprises sense and antisense sequences of a leader sequence or trailer sequence that are associated with the upstream or downstream non-coding regions of a gene in the plant, and wherein expression of the desired polynucleotide produces a double-stranded RNA transcript that targets the gene associated with the desired polynucleotide, thereby modifying the plant cell.

The present invention also encompasses a method for modifying a plant, comprising:
(i) transfecting at least one cell in the plant with the vector of the present invention;
(ii) selecting a cell expressing the functional selectable marker;
(iii) isolating the cell expressing the functional selectable marker;
(iii) inducing the expression of the functional Cre gene in the isolated cell;
(iv) culturing the isolated cell; and
(ii) observing the phenotype of cultured cells;

wherein a phenotype that is different to an untransfected plant cell indicates that the target plant cell has been modified.

In a preferred embodiment the selecting step of this and other methods of the present invention is performed by identifying which cells are resistant to an antibiotic.

In another aspect, a method for identifying a target plant cell whose genome contains a P-DNA, comprises co-transfecting a plant target cell with the vector of the present invention and a second *Agrobacterium*-derived vector that comprises a marker gene flanked by a T-DNA left border and a T-DNA right border and a omega-mutated virD2 gene, wherein the P-DNA is integrated into the genome of the plant target cell, and wherein no part of the second *Agrobacterium*-derived vector is integrated into the genome of the plant target cell. In a preferred embodiment, the marker in the second *Agrobacterium*-derived vector is a neomycin phosphotransferase gene.

In another aspect, the method for identifying a target plant cell whose genome contains at least a part of an integration cassette is provided, further comprises selecting cells that survive temporary growth on a kanamycin-containing media, wherein the genomes of the selected cells contain only the integration cassette. In one embodiment, the target plant cell is within a plant. A plant comprising at least one cell whose genome comprises such a P-DNA is also encompassed by the present invention.

The present invention also encompasses a plant comprising at least one cell whose genome is artificially manipulated to contain only plant-derived nucleic acids, wherein no cells of the plant contain foreign nucleic acids integrated into the cell genome.

The present invention also encompasses a polynucleotide comprising the polynucleotide sequence of SEQ ID NO. 93, wherein the polynucleotide is between 20 and 80 nucleotides in length. In one embodiment, the polynucleotide is between 21 and 70 nucleotides in length, between 22 and 50 nucleotides in length, between 23 and 40 nucleotides in length, or between 24 and 30 nucleotides in length.

In another aspect, the invention encompasses a tuber-specific promoter as shown in SEQ ID NO. 40.

The present invention also encompasses an *Agrobacterium*-based method of making transgenic plant cells that do not contain a selectable marker gene stably integrated in nuclear DNA comprising:
a. constructing a first binary vector comprised of a polynucleotide consisting essentially of a desired functional gene operably linked to T-DNA borders or T-DNA border-like sequences at the 5' and 3' ends of the desired functional gene;
b. constructing a second binary vector comprised of a functional selectable marker gene operably linked to T-DNA borders or T-DNA border-like sequences at the 5' and 3' ends of the functional selectable marker gene;

c. incubating plants cells with:

i. an *Agrobacterium* strain carrying the first and the second binary vectors; or a first *Agrobacterium* strain carrying the first binary vector and a second *Agrobacterium* strain carrying the second binary vector;

d. selecting plant cells wherein the desired functional gene is integrated into plant nuclear DNA without integration of the selectable marker gene into plant nuclear DNA following incubation for an appropriate time period on a medium containing an appropriate selection agent.

In a preferred embodiment, the selectable marker gene is a herbicide resistance gene or an antibiotic resistance gene. In another preferred embodiment, the antibiotic resistance gene is the nNPTII gene. In another embodiment, the antibiotic resistance gene is the npt II structural gene operably linked to the promoter from the Ubiquitin-7 gene and the terminator from yeast alcohol dehydrogenase 1 (ADH1) gene. According to this method, the plant cells are first incubated with the first *Agrobacterium* strain and then subsequently incubated with the second *Agrobacterium* strain or vice versa.

In a preferred embodiment, the first binary vector further comprises a binary integration marker gene that can be used to detect plant cells stably transformed with binary vector backbone sequences. In another embodiment, the binary vector integration marker gene is selected from the group consisting of herbicide resistance gene, antibiotic resistance gene, or NPTII. In yet another embodiment, the second binary vector further comprises a gene fusion between the bacterial cytosine deaminase (codA) and uracil phophoribsyltransferase (upp) genes, which is inserted between the T-DNA or T-DNA border-like sequences, and plant cells are exposed to 5-fluorocytosine following incubation with the first and second *Agrobacterium* strains in order to select against those plant cells transformed with the second binary vector.

In yet another embodiment, the secondary binary vector further comprises a gene that reduces the probability of backbone integration. In one embodiment, such a gene is the omega-mutated virD2 gene, wherein the omega-mutated virD2 gene reduces the frequency of integration of the selectable marker gene into the plant nuclear DNA.

The present invention also encompasses an isolated nucleotide sequence comprising the GBSS promoter isolated from *S. tuberosum*. In a preferred embodiment, this isolated nucleotide sequence has the nucleotide sequence that is SEQ ID NO. 6 or 13.

BRIEF DESCRIPTION OF THE DRAWINGS

FIG. 1. Schematic illustrations of P-DNA vectors used in the present invention. P-DNA region is indicated as grey box. "ipt"=expression cassette for the ipt gene; "npt"=expression cassette for the nptII gene; "mPPO"=expression cassette for a modified PPO gene; "INH"=expression cassette for an invertase inhibitor gene; "GUS"=expression cassette for the GUS gene; "LPPO"=expression cassette for a sense and antisense copy of the leader associated with a PPO gene; "$L_{PH}$"=expression cassette for a sense and antisense copy of the leader associated with a phosphorylase gene; "Alf"=expression cassette for a potato Alfin homolog. See text for details.

FIGS. 2A-2B. Alignment of potato and tobacco invertase inhibitor proteins. "St"=*Solanum tuberosum* (potato); "Nt"=*Nicotiana tabacum* (tobacco) (SEQ ID NOS 115-116 in FIG. 2A, and SEQ ID NOS 117-118 in FIG. 2B respectively, in order of appearance).

FIG. 3. Gene expression cassettes

FIG. 4. Alignment of trailers associated with various PPO genes (SEQ ID NOS 119-121, respectively, in order of appearance).

FIG. 5. Schematic illustrations of LifeSupport vectors used in the present invention. "codA" is an expression cassette for the coda gene; "codA::upp" is an expression cassette for the codA gene fused to upp; "ΩvirD2" is an expression for the ΩvirD2 gene.

DETAILED DESCRIPTION OF THE PREFERRED EMBODIMENTS

The "precise breeding" strategy of the present invention improves the agronomic performance, nutritional value, and health characteristics of plants and crops without introducing unknown nucleic acid, or nucleic acid from a foreign species into a plant species genome, and without producing undesirable phenotypes or harmful side-effects.

Thus, the present invention provides a transgenic plant, and methods for making such a plant that do not integrate nucleic acid from non-plant species into that plant's genome. Nucleic acids, promoters, regulatory elements, other non-coding gene sequences, markers, polynucleotides, and genes that are integrated into the selected plant genome are all preferably isolated from the plant that is to be transformed, plants of the same species to be transformed, or plants that are sexually interfertile with the plant to be transformed. Such "native" nucleic acids can be mutated, modified or cojoined with other native nucleic acids in an expression cassette and reintegrated into the selected plant genome, according to the methods described herein. Accordingly, the genotype and phenotype of the transgenic plant is altered using only that selected plant's own nucleic acid, or using nucleic acid from a plant that is sexually compatible with the selected plant.

To facilitate the production of such transgenic plants, the present invention makes use of the fact that not all T-DNA vectors used in *Agrobacterium*-mediated transformation are actually integrated into the plant genome; i.e., while a vector may be taken up by the plant cell, an actual integration event may not occur. According to the present invention, one may use such a vector to carry a selectable marker gene into a plant cell. Plant cells can then be screened to determine whether the marker has been stably integrated into the plant genome by determining for how long the marker gene is expressed. Accordingly, plant cells that only transiently express the selectable marker gene are desired because they represent cells that took up, but did not integrate into their genomes, the selectable marker gene.

Thus, by co-transforming a plant with such a "marker vector" and also with another vector that contains the desired native gene or polynucleotide, one can select plant cells that took up both vectors and, from those, determine which cells possess genomes that contain only the desired gene or polynucleotide. The "marker vector" can be modified to further reduce the possibility that the marker will be integrated into the plant genome. The present invention provides such "marker vectors" in the form of "LifeSupport" vectors.

Unless defined otherwise, all technical and scientific terms used herein have the same meaning as commonly understood by one of ordinary skill in the art to which this invention belongs. Generally, the nomenclature used herein, and the laboratory procedures in cell culture, molecular genetics, and nucleic acid chemistry and hybridization described herein, are those well known and commonly employed in the art.

Standard techniques are used for recombinant nucleic acid methods, polynucleotide synthesis, microbial culture, cell culture, tissue culture, transformation, transfection, transduction, analytical chemistry, organic synthetic chemistry, chemical syntheses, chemical analysis, and pharmaceutical formulation and delivery. Generally, enzymatic reactions and purification and/or isolation steps are performed according to the manufacturers' specifications. The techniques and procedures are generally performed according to conventional methodology disclosed, for example, in *Molecular cloning a laboratory manual*, 2d ed., Cold Spring Harbor Laboratory Press, Cold Spring Harbor, N.Y. (1989), and *Current protocols in molecular biology*, John Wiley & Sons, Baltimore, Md. (1989).

Amino acid sequence: as used herein, includes an oligopeptide, peptide, polypeptide, or protein and fragments thereof, that are isolated from, native to, or naturally occurring in a plant, or are synthetically made but comprise the nucleic acid sequence of the endogenous counterpart.

Artificially manipulated: as used herein, "artificially manipulated" means to move, arrange, operate or control by the hands or by mechanical means or recombinant means, such as by genetic engineering techniques, a plant or plant cell, so as to produce a plant or plant cell that has a different biological, biochemical, morphological, or physiological phenotype and/or genotype in comparison to unmanipulated, naturally-occurring counterpart.

Asexual propagation: producing progeny by generating an entire plant from leaf cuttings, stem cuttings, root cuttings, tuber eyes, stolons, single plant cells protoplasts, callus and the like, that does not involve fusion of gametes.

Backbone: nucleic acid sequence of a binary vector that excludes the T-DNA or P-DNA sequence intended for transfer.

Border and Border-like sequences: "border sequences" are specific *Agrobacterium*-derived sequences. Typically, a left border sequence and a right border sequence flank a T-DNA and they both function as recognition sites for virD2-catalyzed nicking reactions. Such activity releases nucleic acid that is positioned between such borders. See Table 2 below for examples of border sequences. The released nucleic acid, complexed with virD2 and virE2, is targeted to plant cell nuclei where nucleic acid is often integrated into the genome of the plant cell. Usually, two border sequences, a left-border and a right-border, are used to integrate a nucleotide sequence that is located between them into another nucleotide sequence. It is also possible to use only one border, or more than two borders, to accomplish integration of a desired nucleic acid in such fashion.

According to the present invention, a "border-like" sequence is isolated from the selected plant species that is to be modified, or from a plant that is sexually-compatible with the plant species to be modified, and functions like the border sequences of *Agrobacterium*. That is, a border-like sequence of the present invention promotes and facilitates the integration of a polynucleotide to which it is linked. A plant-DNA, i.e., P-DNA, of the present invention preferably contains border-like sequences.

A border-like sequence of a P-DNA is between 5-100 bp in length, 10-80 bp in length, 15-75 bp in length, 15-60 bp in length, 15-50 bp in length, 15-40 bp in length, 15-30 bp in length, 16-30 bp in length, 20-30 bp in length, 21-30 bp in length, 22-30 bp in length, 23-30 bp in length, 24-30 bp in length, 25-30 bp in length, or 26-30 bp in length.

The border-like sequences of the present invention can be isolated from any plant, such as from potato and wheat. See SEQ ID NO. 1 and SEQ ID NO. 34, for sequences which contain, at either end, the border-like sequences isolated from potato and wheat respectively. Thus, a P-DNA left and right border sequences of use for the present invention are isolated from and/or native to the genome of a plant that is to be modified. A P-DNA border-like sequence is not identical in nucleotide sequence to any known *Agrobacterium*-derived T-DNA border sequence. Thus, a P-DNA border-like sequence may possess 1, 2, 3, 4, 5, 6, 7, 8, 9, 10, 11, 12, 13, 14, 15, 16, 17, 18, 19, 20, or more nucleotides that are different from a T-DNA border sequence from an *Agrobacterium* species, such as *Agrobacterium tumefaciens* or *Agrobacterium rhizogenes*. That is, a P-DNA border, or a border-like sequence of the present invention has at least 95%, at least 90%, at least 80%, at least 75%, at least 70%, at least 60% or at least 50% sequence identity with a T-DNA border sequence from an *Agrobacterium* species, such as *Agrobacterium tumefaciens* or *Agrobacterium rhizogenes*, but not 100% sequence identity. As used herein, the descriptive terms "P-DNA border" and "P-DNA border-like" are exchangeable.

A native P-DNA border sequence is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51% or 50% similar in nucleotide sequence to a *Agrobacterium* a T-DNA border sequence. A border-like sequence can, therefore, be isolated from a plant genome and be modified or mutated to change the efficiency by which they are capable of integrating a nucleotide sequence into another nucleotide sequence. Other polynucleotide sequences may be added to or incorporated within a border-like sequence of the present invention. Thus, a P-DNA left border or a P-DNA right border may be modified so as to possess 5'- and 3'-multiple cloning sites, or additional restriction sites. A P-DNA border sequence may be modified to increase the likelihood that backbone DNA from the accompanying vector is not integrated into the plant genome.

Table 2 below depicts the sequences of known T-DNA border sequences and sequences identified herein as border-like sequences. None of the sequences identified as "border-like" in Table 2 have been identified previously as having a T-DNA border-like structure. The potato border-like sequences were isolated by the present inventive methods using degenerate primers in polymerase chain reactions from potato genomic DNA. The present invention encompasses the use of any P-DNA border-like sequence for transferring a cojoined polynucleotide into the genome of a plant cell.

Indeed, the present invention encompasses any border-like sequence that has the nucleic acid sequence structure of SEQ ID NO. 93: ANGATNTATN$_6$GT (SEQ ID NO. 93), where "N" is any nucleotide, such as those represented by "A," "G," "C," or "T." This sequence represents the consensus sequence of border-like nucleic acids identified by the present invention.

TABLE 2

"Border" and "Border-Like" sequences

| Agrobacterium T-DNA borders | |
| --- | --- |
| TGACAGGATATATTGGCGGGTAAAC (SEQ ID NO. 41) | *Agrobacterium nopaline* strains (RB) |
| TGGCAGGATATATTGTGGTGTAAAC (SEQ ID NO. 42) | *Agrobacterium nopaline* strains (LB) |

TABLE 2-continued

"Border" and "Border-Like" sequences

| Sequence | Description |
|---|---|
| TGGCAGGATATATACCGTTGTAATT (SEQ ID NO. 43) | Agrobacterium octopine strains (RB) |
| CGGCAGGATATATTCAATTGTAATT (SEQ ID NO. 44) | Agrobacterium octopine strains (LB) |
| TGGTAGGATATATACCGTTGTAATT (SEQ ID NO. 45) | LB mutant |
| TGGCAGGATATATGGTACTGTAATT (SEQ ID NO. 46) | LB mutant |
| YGRYAGGATATATWSNVBKGTAAWY (SEQ ID NO. 47) | Border motif |

Border-like sequences

| Sequence | Description |
|---|---|
| CGGCAGGATATATCCTGATGTAAAT (SEQ ID NO. 48) | R. leguminosarum |
| TGGCAGGAGTTATTCGAGGGTAAAC (SEQ ID NO. 49) | T. tengcongensis |
| TGACAGGATATATCGTGATGTCAAC (SEQ ID NO. 50) | Arabidopsis thaliana |
| GGGAAGTACATATTGGCGGGTAAAC (SEQ ID NO. 51) | A. thaliana CHR1v07142002 |
| TTACAGGATATATTAATATGTATGA (SEQ ID NO. 52) | Oryza sativa AC078894 |
| TAACATGATATATTCCCTTGTAAAT (SEQ ID NO. 53) | Homo sapiens clone HQ0089 |
| TGACAGGATATATGGTAATGTAAAC (SEQ ID NO. 54) | potato (left border sequence)* |
| TGGCAGGATATATACCGATGTAAAC (SEQ ID NO. 55) | potato (right border sequence)* |

Y = C or T; R = A or G; K = G or T; M = A or C; W = A or T; S = C or G; V = A, C, or G; B = C, G, or T. The accession numbers for the border-like sequences are: Oryza sativa chromosome 10 BAC OSJNBa0096G08 genomic sequence (AC078894.11); Arabidopsis thaliana chromosome 3 (NM_114337.1); Arabidopsis thaliana chromosome 1 (NM_105664.1); T. tengcongensis strain MB4T, section 118 of 244 of the complete genome (AE013091.1); Homo sapiens clone HQ0089 (AF090888.1); Rhizobium Clone: rhiz98e12.qlk.
*potato left and right border sequences were obtained and isolated according to the presently-described inventive methods.

Carrier DNA: a "carrier DNA" is a DNA segment that is used to carry certain genetic elements and deliver them into a plant cell. In conventional foreign DNA transfer, this carrier DNA is often the T-DNA of *Agrobacterium*, delineated by border sequences. The carrier DNA described here is obtained from the selected plant species to be modified and contains ends that may be structurally and functionally different from T-DNA borders but shares with such T-DNAs the ability to support both DNA transfer from *Agrobacterium* to the nuclei of plant cells or certain other eukaryotes and the subsequent integration of this DNA into the genomes of such eukaryotes.

Consisting essentially of: a composition "consisting essentially of" certain elements is limited to the inclusion of those elements, as well as to those elements that do not materially affect the basic and novel characteristics of the inventive composition. Thus, so long as the composition does not affect the basic and novel characteristics of the instant invention, that is, does not contain foreign DNA that is not from the selected plant species or a plant that is sexually compatible with the selected plant species, then that composition may be considered a component of an inventive composition that is characterized by "consisting essentially of" language.

Degenerate primer: a "degenerate primer" is an oligonucleotide that contains sufficient nucleotide variations that it can accommodate base mismatches when hybridized to sequences of similar, but not exact, homology.

Dicotyledon (dicot): a flowering plant whose embryos have two seed leaves or cotyledons. Examples of dicots include, but are not limited to, tobacco, tomato, potato, sweet potato, cassava, legumes including alfalfa and soybean, carrot, strawberry, lettuce, oak, maple, walnut, rose, mint, squash, daisy, and cactus.

Regulatory sequences: refers to those sequences which are standard and known to those in the art, that may be included in the expression vectors to increase and/or maximize transcription of a gene of interest or translation of the resulting RNA in a plant system. These include, but are not limited to, promoters, peptide export signal sequences, introns, polyadenylation, and transcription termination sites. Methods of modifying nucleic acid constructs to increase expression levels in plants are also generally known in the art (see, e.g. Rogers et al., 260 *J. Biol. Chem.* 3731-38, 1985; Comejo et al., 23 *Plant Mol. Biol.* 567: 81, 1993). In engineering a plant system to affect the rate of transcription of a protein, various factors known in the art, including regulatory sequences such as positively or negatively acting sequences, enhancers and silencers, as well as chromatin structure may have an impact. The present invention provides that at least one of these factors may be utilized in engineering plants to express a protein of interest. The regulatory sequences of the present invention are native genetic elements, i.e., are isolated from the selected plant species to be modified.

Foreign: "foreign," with respect to a nucleic acid, means that that nucleic acid is derived from non-plant organisms, or derived from a plant that is not the same species as the plant to be transformed or is not derived from a plant that is not interfertile with the plant to be transformed, does not belong to the species of the target plant. According to the present invention, foreign DNA or RNA represents nucleic acids that are naturally occurring in the genetic makeup of fungi, bacteria, viruses, mammals, fish or birds, but are not naturally occurring in the plant that is to be transformed. Thus, a foreign nucleic acid is one that encodes, for instance, a polypeptide that is not naturally produced by the transformed plant. A foreign nucleic acid does not have to encode a protein product. According to the present invention, a desired transgenic plant is one that does not contain any foreign nucleic acids integrated into its genome.

Native genetic elements, on the other hand, can be incorporated and integrated into a selected plant species genome according to the present invention. Native genetic elements are isolated from plants that belong to the selected plant species or from plants that are sexually compatible with the selected plant species. For instance, native DNA incorporated into cultivated potato (*Solanum tuberosum*) can be derived from any genotype of *S. tuberosum* or any genotype of a wild potato species that is sexually compatible with *S. tuberosum* (e.g., *S. demissum*).

Gene: "gene" refers to the coding region and does not include nucleotide sequences that are 5'- or 3'- to that region. A functional gene is the coding region operably linked to a promoter or terminator.

Genetic rearrangement: refers to the reassociation of genetic elements that can occur spontaneously in vivo as well as in vitro which introduce a new organization of genetic material. For instance, the splicing together of polynucleotides at different chromosomal loci, can occur spontaneously in vivo during both plant development and sexual recombination. Accordingly, recombination of genetic elements by non-natural genetic modification techniques in vitro is akin to recombination events that also can occur through sexual recombination in vivo.

In frame: nucleotide triplets (codons) are translated into a nascent amino acid sequence of the desired recombinant protein in a plant cell. Specifically, the present invention contemplates a first nucleic acid linked in reading frame to a second nucleic acid, wherein the first nucleotide sequence is a gene and the second nucleotide is a promoter or similar regulatory element.

Integrate: refers to the insertion of a nucleic acid sequence from a selected plant species, or from a plant that is from the same species as the selected plant, or from a plant that is sexually compatible with the selected plant species, into the genome of a cell of a selected plant species. "Integration" refers to the incorporation of only native genetic elements into a plant cell genome. In order to integrate a native genetic element, such as by homologous recombination, the present invention may "use" non-native DNA as a step in such a process. Thus, the present invention distinguishes between the "use of" a particular DNA molecule and the "integration" of a particular DNA molecule into a plant cell genome.

Introduction: as used herein, refers to the insertion of a nucleic acid sequence into a cell, by methods including infection, transfection, transformation or transduction.

Isolated: "isolated" refers to any nucleic acid or compound that is physically separated from its normal, native environment. The isolated material may be maintained in a suitable solution containing, for instance, a solvent, a buffer, an ion, or other component, and may be in purified, or unpurified, form.

Leader: Transcribed but not translated sequence preceding (or 5' to) a gene.

LifeSupport Vector: a LifeSupport vector is a construct that contains an expressible selectable marker gene, such as a neomycin phosphotransferase marker, that is positioned between T-DNA or T-DNA-like borders. The LifeSupport vector may be modified to limit integration of such a marker, as well as other polynucleotides, that are situated between the border or border-like sequences, into a plant genome. For instance, a LifeSupport vector may comprise a mutated virD2, codA::upp fusion, or any combination of such genetic elements. Thus, a modified virD2 protein will still support T-DNA transfer to plant nuclei but will limit the efficiency of a subsequent genomic integration of T-DNAs (Shurvinton et al., *Proc Natl Acad Sci USA*, 89:11837-11841, 1992; Mysore et al., *Mol Plant Microbe Interact*, 11: 668-683, 1998). Alternatively, codA::upp gene fusion can be used as negative selectable marker prior to regeneration. In one preferred construct, the LifeSupport vector comprises the npt marker operably linked to the yeast ADH terminator element.

Monocotyledon (monocot): a flowering plant whose embryos have one cotyledon or seed leaf. Examples of monocots include, but are not limited to turf grass, maize, rice, oat, wheat, barley, sorghum, orchid, iris, lily, onion, and palm.

Native: a "native" genetic element refers to a nucleic acid that naturally exists in, orginates from, or belongs to the genome of a plant that is to be transformed. Thus, any nucleic acid, gene, polynucleotide, DNA, RNA, mRNA, or cDNA molecule that is isolated either from the genome of a plant or plant species that is to be transformed or is isolated from a plant or species that is sexually compatible or interfertile with the plant species that is to be transformed, is "native" to, i.e., indigenous to, the plant species. In other words, a native genetic element represents all genetic material that is accessible to plant breeders for the improvement of plants through classical plant breeding. Any variants of a native nucleic acid also are considered "native" in accordance with the present invention. In this respect, a "native" nucleic acid may also be isolated from a plant or sexually compatible species thereof and modified or mutated so that the resultant variant is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in nucleotide sequence to the unmodified, native nucleic acid isolated from a plant. A native nucleic acid variant may also be less than about 60%, less than about 55%, or less than about 50% similar in nucleotide sequence.

A "native" nucleic acid isolated from a plant may also encode a variant of the naturally occurring protein product transcribed and translated from that nucleic acid. Thus, a native nucleic acid may encode a protein that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in amino acid sequence to the unmodified, native protein expressed in the plant from which the nucleic acid was isolated.

Naturally occurring nucleic acid: this phrase means that the nucleic acid is found within the genome of a selected plant species and may be a DNA molecule or an RNA molecule. The sequence of a restriction site that is normally present in the genome of a plant species can be engineered into an exogenous DNA molecule, such as a vector or oligonucleotide, even though that restriction site was not physically isolated from that genome. Thus, the present invention permits the synthetic creation of a nucleotide sequence, such as a restriction enzyme recognition sequence, so long as that sequence is naturally occurring in the genome of the selected plant species or in a plant that is sexually compatible with the selected plant species that is to be transformed.

Operably linked: combining two or more molecules in such a fashion that in combination they function properly in a plant cell. For instance, a promoter is operably linked to a structural gene when the promoter controls transcription of the structural gene.

P-DNA: according to the present invention, P-DNA ("plant-DNA") is isolated from a plant genome and comprises at each end, or at only one end, a T-DNA border-like sequence. The border-like sequence preferably shares at least 50%, at least 60%, at least 70%, at least 75%, at least 80%, at least 90% or at least 95%, but less than 100% sequence identity, with a T-DNA border sequence from an *Agrobacterium* species, such as *Agrobacterium tumefaciens* or *Agrobacterium rhizogenes*. Thus, P-DNAs can be used instead of T-DNAs to transfer a nucleotide sequence from *Agrobacterium* to another polynucleotide sequence. The P-DNA may be modified to facilitate cloning and should preferably not naturally encode proteins or parts of proteins. The P-DNA is characterized in that it contains, at each end, at least one border sequence, referred to as either a "P-DNA border sequence" or "P-DNA border-like sequence," which are interexchangeable terms. See the definition of a "border sequence" and "border-like" above. A P-DNA may also be regarded as a "T-DNA-like" sequence, see definition below.

Plant: includes angiosperms and gymnosperms such as potato, tomato, tobacco, alfalfa, lettuce, carrot, strawberry, sugarbeet, cassava, sweet potato, soybean, maize, turf grass, wheat, rice, barley, sorghum, oat, oak, eucalyptus, walnut, and palm. Thus, a plant may be a monocot or a dicot. The word "plant," as used herein, also encompasses plant cells, seed, plant progeny, propagule whether generated sexually or asexually, and descendents of any of these, such as cuttings or seed. Plant cells include suspension cultures, callus, embryos, meristematic regions, callus tissue, leaves, roots, shoots, gametophytes, sporophytes, pollen, seeds and microspores. Plants may be at various stages of maturity and may be grown in liquid or solid culture, or in soil or suitable media in pots, greenhouses or fields. Expression of an introduced leader, trailer or gene sequences in plants may be transient or permanent. A "selected plant species" may be, but is not limited to, a species of any one of these "plants."

Precise breeding: refers to the improvement of plants by stable introduction of nucleic acids, such as native genes and regulatory elements isolated from the selected plant species, or from another plant in the same species as the selected plant, or from species that are sexually compatible with the selected plant species, into individual plant cells, and subsequent regeneration of these genetically modified plant cells into whole plants. Since no unknown or foreign nucleic acid is permanently incorporated into the plant genome, the inventive technology makes use of the same genetic material that is also accessible through conventional plant breeding.

Plant species: the group of plants belonging to various officially named plant species that display at least some sexual compatibility.

Plant transformation and cell culture: broadly refers to the process by which plant cells are genetically modified and transferred to an appropriate plant culture medium for maintenance, further growth, and/or further development.

Recombinant: as used herein, broadly describes various technologies whereby genes can be cloned, DNA can be sequenced, and protein products can be produced. As used herein, the term also describes proteins that have been produced following the transfer of genes into the cells of plant host systems.

Selectable marker: a "selectable marker" is typically a gene that codes for a protein that confers some kind of resistance to an antibiotic, herbicide or toxic compound, and is used to identify transformation events. Examples of selectable markers include the streptomycin phosphotransferase (spt) gene encoding streptomycin resistance, the phosphomannose isomerase (pmi) gene that converts mannose-6-phosphate into fructose-6 phosphate; the neomycin phosphotransferase (nptII) gene encoding kanamycin and geneticin resistance, the hygromycin phosphotransferase (hpt or aphiv) gene encoding resistance to hygromycin, acetolactate synthase (als) genes encoding resistance to sulfonylurea-type herbicides, genes coding for resistance to herbicides which act to inhibit the action of glutamine synthase such as phosphinothricin or basta (e.g., the bar gene), or other similar genes known in the art.

Sense suppression: reduction in expression of an endogenous gene by expression of one or more an additional copies of all or part of that gene in transgenic plants.

T-DNA-Like: a "T-DNA-like" sequence is a nucleic acid that is isolated from a selected plant species, or from a plant that is sexually compatible with the selected plant species, and which shares at least 75%, 80%, 85%, 90%, or 95%, but not 100%, sequence identity with *Agrobacterium* species T-DNA. The T-DNA-like sequence may contain one or more border or border-like sequences that are each capable of integrating a nucleotide sequence into another polynucleotide. A "P-DNA," as used herein, is an example of a T-DNA-like sequence.

Trailer: Transcribed but not translated sequence following (or 3' to) a gene.

Transcribed DNA: DNA comprising both a gene and the untranslated leader and trailer sequence that are associated with that gene, which is transcribed as a single mRNA by the action of the preceding promoter.

Transcription and translation terminators: the expression vectors of the present invention typically have a transcription termination region at the opposite end from the transcription initiation regulatory region. The transcription termination region may be selected, for stability of the mRNA to enhance expression and/or for the addition of polyadenylation tails added to the gene transcription product (Alber & Kawasaki, *Mol. & Appl. Genetics* 4: 19-34, 1982). Illustrative transcription termination regions include the E9 sequence of the pea RBCS gene (Mogen et al., *Mol. Cell Biol.,* 12: 5406-14, 1992) and the termination signals of various ubiquitin genes.

Transformation of plant cells: a process by which DNA is stably integrated into the genome of a plant cell. "Stably" refers to the permanent, or non-transient retention and/or expression of a polynucleotide in and by a cell genome. Thus, a stably integrated polynucleotide is one that is a fixture within a transformed cell genome and can be replicated and propagated through successive progeny of the cell or resultant transformed plant. Transformation may occur under natural or artificial conditions using various methods well known in the art. Transformation may rely on any known method for the insertion of nucleic acid sequences into a prokaryotic or eukaryotic host cell, including *Agrobacterium*-mediated transformation protocols, viral infection, whiskers, electroporation, heat shock, lipofection, polyethylene glycol treatment, micro-injection, and particle bombardment.

Transgene: a gene that will be inserted into a host genome, comprising a protein coding region. In the context of the instant invention, the elements comprising the transgene are isolated from the host genome.

Transgenic plant: a genetically modified plant which contains at least one transgene.

Using/Use of: The present invention envisions the use of nucleic acid from species other than that of the selected plant species to be transformed to facilitate the integration of native genetic elements into a selected plant genome, so long as such foreign nucleic acid is not stably integrated into the same host plant genome. For instance, the plasmid, vector or cloning construct into which native genetic elements are cloned, positioned or manipulated may be derived from a species different to that from which the native genetic elements were derived.

Variant: a "variant," as used herein, is understood to mean a nucleotide or amino acid sequence that deviates from the standard, or given, nucleotide or amino acid sequence of a particular gene or protein. The terms, "isoform," "isotype," and "analog" also refer to "variant" forms of a nucleotide or an amino acid sequence. An amino acid sequence that is altered by the addition, removal or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software.

It is understood that the present invention is not limited to the particular methodology, protocols, vectors, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a gene" is a reference to one or more genes and includes equivalents thereof known to those skilled in the art and so forth. Indeed, one skilled in the art can use the methods described herein to express any native gene (known presently or subsequently) in plant host systems.

P-DNA Vectors

*Agrobacterium*-mediated transformation methods are the preferred means of incorporating recombined DNA into plant cells. According to the present invention, a binary vector was developed to produce genetically modified potato plants that contain only native potato nucleic acids. Such a vector is different from conventional, *Agrobacterium*-mediated transformation vectors in three ways: (1) instead of an *Agrobacterium*-derived T-DNA sequence delineated by T-DNA borders, the present vector contains a native plant DNA (P-DNA) fragment that is flanked by border-like sequences, which support P-DNA transfer from *Agrobacterium* to plant cells although they are structurally and functionally different from T-DNA borders, (2) the backbone of the present vector may contain a marker that, if integrated into the plant cell's genome, prevents these cells from developing into mature plants, and (3) the present vector does not contain a foreign selectable marker gene between P-DNA termini.

The present invention demonstrates, surprisingly, that P-DNA fragments flanked by border-like sequences support DNA transfer from *Agrobacterium* into plant cells. P-DNA can be isolated from the genome of any plant by using primers that are designed on the basis of homology between the termini of a potato P-DNA and conventional T-DNA borders. Such fragments can then be tested and, if efficacious, used to transform that plant with native DNA exclusively. It is also possible to search plant genomic databases for DNA fragments with regions that show homology with T-DNA borders by using programs such as 'blastn' (Altschul et al., *J Mol Biol* 215: 403-10, 1990). The identified P-DNAs may then be modified to increase their utility. For instance, internal fragments of the isolated P-DNAs may be deleted and restriction sites may be added to facilitate cloning. It may also be efficacious to introduce point mutations at the terminal sequences to render the P-DNA more effective in transferring DNA.

Any gene expression cassette can be inserted between P-DNA border-like sequences. For potato transformations, such an expression cassette could consist of a potato promoter, operably linked to a potato gene and/or a leader or trailer sequence associated with that gene, and followed by a potato terminator. The expression cassette may contain additional potato genetic elements such as a signal peptide sequence fused in frame to the 5'-end of the gene, and a potato intron that could, for instance, be placed between promoter and gene-of-interest to enhance expression. For transformation of wheat with a modified P-DNA, all genetic elements that are inserted on the wheat P-DNA, including the P-DNA itself would be derived from wheat or plant species that are sexually compatible with wheat.

Another way to isolate P-DNAs is by generating a library of *Agrobacterium* strains that contain random plant DNA fragments instead of a T-DNA flanking a selectable marker gene. Explants infected with this library can be placed on proliferation medium that contains an appropriate selectable agent to identify P-DNAs that support the transfer of the marker gene from the vector in *Agrobacterium* to the plant cell.

It is possible that not just the native modified P-DNA, but also additional plasmid sequences are co-transferred from *Agrobacterium* to the plant cell during the transformation process. For the purposes of the present invention, this is an undesirable process because such plasmid "backbone" sequences represent non-plant, foreign DNA, such as bacterial DNA. The present invention prevents transformed plant cells that contain backbone sequences from developing into mature plants. Thus, the present invention makes it possible to distinguish backbone-containing and backbone-free transformation events during the regenerated shoot phase.

The method to select or screen against backbone integration events relies on the presence of an expression cassette for a marker, such as the isopentenyl phosphotransferase (IPT) gene, in the vector backbone, outside of the P-DNA. Upon backbone integration, the accumulation of IPT-induced cytokinin will alter the shape or transformed shoots, and prevent these shoots to develop roots. Instead of the IPT gene, any other gene that alters the shape, texture or color of the transformed plant's leaves, roots, stem, height or some other morphological feature can be used to screen and/or select against backbone integration events. Such a gene is referred to herein as a "backbone integration marker." Thus, the transformed plant that exhibits an altered morphological feature attributable to the expression of the backbone integration marker gene is known to, contain in its genome foreign DNA in addition to the desired P-DNA. Accordingly, plants that exhibit a phenotype associated with the backbone integration marker are not desired.

The present invention is not limited to the use of only an IPT gene as a backbone integration marker; other genes can be used in such fashion. For example, a backbone integration marker may be an *Agrobacterium transzeatine* synthase (TZS) gene (Krall et al., *FEBS Lett* 527: 315-8, 2002) or a recessive *Arabidopsis* gene hoc1 (Catterou et al., *Plant J* 30: 273-87, 2002). This method can be more easily applied for use in the present invention than some methods that insert toxic genes in vector backbone sequences. See, for instance, EP 1 009,842.

By positioning a backbone integration marker gene, such as a functional cytokinin gene upstream or downstream of the P-DNA, it is straightforward to distinguish between transformation events. Transformed plants that exhibit an altered morphological feature are discarded because they contain non-native DNA sequences integrated into the genome.

Another strategy for identifying plants that are stably transformed with only native DNA, is to employ the polymerase chain reaction. By using primers that are specifically designed to detect backbone sequences, plants can be identified and discarded that contain foreign backbone sequences in addition to the P-DNA. Other primer sets can subsequently be used to confirm the intact transfer of the P-DNA. Thus, by either using the expression of a gene to change a morphological feature of a plant, or by screening for stably integrated foreign DNA in a transformed plant, plants stably transformed with only native DNA sequences can be identified and selected.

Genetic elements from a particular host plant can be inserted into the P-DNA sequence of a binary vector capable of replication in both *E. coli* and *Agrobacterium*. Introduction of the resulting vectors into disarmed *Agrobacterium* strains such as LBA4404 can be accomplished through electroporation, triparental mating or heat-shock treatment of chemically competent cells. The new strains can then be used to transform individual plant cells through infection of whole plants or explants.

Genetic elements from a particular host plant can be inserted into the P-DNA sequence of a binary vector capable of replication in both *E. coli* and *Agrobacterium*. Introduction of the resulting vectors into *Agrobacterium* strains such as LBA4404 can be accomplished through electroporation, tri-parental mating or heat-shock treatment of chemically competent cells. The new strains can then be used to transform individual plant cells through infection of whole plants or explants. LBA4404 contains the disarmed Ti-plasmid pAL4404, which carries the virulence functions and a streptomycin resistance gene.

LifeSupport Vectors

Although the stable integration of bacterial marker genes into the genomes of plant cells facilitates the identification of transformation events, such modifications of plant genomes are undesirable because marker genes represent foreign DNA. Use of a foreign marker gene can be avoided by developing new *Agrobacterium*-based transformation methods.

One preferred embodiment is a novel method that relies on the use of two *Agrobacterium* strains: one strain containing a binary vector with a selectable marker gene intended for transient expression in plant nuclei, and another strain carrying the P-DNA with the actual sequences of interest intended for stable integration in plant genome (see Example 7).

Upon co-infection with the *Agrobacterium* strains, some plant cells will receive both a T-DNA with the marker gene and a P-DNA with the sequences of interest. Instead of subsequently selecting for stable integration of the marker gene by subjecting the infected explants for a long period of time to the appropriate antibiotic, explants are only briefly exposed to the antibiotic. In this way, all plant cells that transiently express the marker gene will survive. Because T-DNAs will in most cases degrade due to endogenous nuclease activities rather than stably integrate into their host's genome, the majority of plant cells that survived the transient selection are shown here to develop into shoots lacking a marker gene. The present invention, furthermore, demonstrates that a significant proportion of these marker-free shoots contain stably integrated P-DNAs.

There are various tools to enhance the efficiency of marker-free transformation. First, the present invention demonstrates that this frequency can be increased by sequentially infecting explants with two *Agrobacterium* strains carrying the T-DNA/marker and P-DNA/sequences-of-interest, respectively. Explants are first infected with the P-DNA strain, and after about 4 to 6 hours with the T-DNA strain.

Second, the T-DNA strain can be modified to express an omega-mutated virD2 gene. The modified virD2 protein will still support T-DNA transfer to plant nuclei but limit the efficiency of a subsequent genomic integration of T-DNAs (Shurvinton et al., *Proc Natl Acad Sci USA*, 89: 11837-11841, 1992; Mysore et al., *Mol Plant Microbe Interact*, 11: 668-683, 1998). The most preferred method of expressing a modified virD2 gene is by inserting an omega-mutated virD2 gene driven by the virD promoter in the backbone of the T-DNA vector.

Third, stable T-DNA integration can be further impaired by inserting telomere sequences close to the left- and right-border sequences of the T-DNA (Chiurazzi & Signer, Plant Mol. Biol., 26: 923-934, 1994).

Fourth, the size of the T-DNA region carrying the marker gene can be increased to enhance the frequency of T-DNAs and P-DNAs moving together into the plant cell nucleus, and to reduce the frequency of genomic integration of the T-DNA.

Fifth, the frequency of T-DNAs and P-DNAs moving together into the plant cell nucleus can also be enhanced by using a single *Agrobacterium* strain carrying two compatible binary vectors with the T-DNA and P-DNA, respectively. An example of two compatible binary vectors are a pSIM 1301-derived vector and a pBI121-derived vector.

Because the transiently expressed marker gene will usually not integrate into the plant genome, it is not necessary that both this gene and its regulatory sequences represent native DNA. In fact, it may be advantageous to use foreign regulatory sequences to promote high levels of transient gene expression in infected plant cells. A surprising discovery of the present invention is that an expression cassette containing the GUS gene followed by the terminator of the yeast alcohol dehydrogenase 1 (ADH1) was transiently expressed at high levels in potato cells. A similar construct with the yeast CYC1 terminator, however, did not function adequately. It may also be possible to enhance transient expression levels by operably linking a marker gene to a non-native promoter. Examples of such promoters are, e.g., synthetic promoters such as glucocorticoid-inducible promoters (Mori et al., Plant J., 27: 79-86, 2001; Bohner et al., Mol. Gen. Genet., 264: 860-70 2001), and non-native promoters such as the 35S promoters of cauliflower mosaic virus and figwort mosaic virus, and fungal promoters.

As an alternative to the two-strain *Agrobacterium*-mediated transformation approach described above, plants may also be transformed with a single strain that contains a P-DNA with both a native marker gene and the actual sequences of interest. The present invention demonstrates that it is possible to use salt tolerance genes as native markers for transformation. Such salt tolerance genes include crop homologs of the *Arabidopsis* genes SOS1 (Shi et al., *Nat Biotechnol*. 2002), AtNHX1 (Apse et al., *Science*. 285: 1256-8, 1999), Avp1 (Gaxiola et al., *Proc Natl Acad Sci USA*. 98: 11444-9, 2001), and CBF3 (Kasuga et al., *Nat Biotechnol*. 17: 287-91, 1999).

The rearrangements of genetic elements accomplished through the inventive Precise Breeding methodology could also occur spontaneously through the process of genetic recombination. For instance, all plants contain elements that can transpose from one to another chromosomal location. By inserting into promoters or genes, such transposable elements can enhance, alter, and/or reduce gene expression. For instance, the AMu4 insertion of the maize Mutator element in the promoter of the transcriptional regulator gene P-wr causes stripy red pericarps. Insertion of the same element in the promoter of the leaf-specific MADS-box gene ZMM19 resulted in expression of this gene in the inflorescences of maize, causing a foliaceous elongation of the glumes and other changes in male and female inflorescences, resulting in the famous phenotype of pod corn. Because of its bizarre tassels and ears, pod corn was of religious significance for certain native American tribes. Many genes are also rearranged through other transposon-induced modifications such as inversions, deletions, additions, and ectopic recombinations (Bennetzen, *Plant Mol Biol* 42: 251-69, 2000). Furthermore, plant DNA rearrangements frequently occur through the process of intragenic recombination. For instance, by recombining genes involved in resistance against specific pathogens, plants are able to develop resistance genes with new specificities and, thus, co-evolve with their pathogens (Ellis et al., *Trends Plant Sci* 5: 373-9, 2000). Another example of intragenic recombination relates to how plants reproduce: plants transition from cross-fertilizing to self-fertilizing by recombining genes involved in self-incompatibility (Kusaba et al., Plant Cell 13: 627-43, 2001). Other processes that promote genome evolution include, for instance, chromosome breakage and interchromosomal recombination.

Enhancing the Nutritional Value of Plants and Food Crops

To modify negative traits such as acrylamide accumulation during processing, glycoalkaloid accumulation, accumulation of undesirable advanced glycation products, CIPC accumulation, low levels of resistant starch, bruise susceptibility, cold-induced sweetening, disease susceptibility, low yield and low quality in crop plants through precise breeding, at least one specific expression cassette is incorporated into a host genome. Three different methods are used to eliminate negative traits: (1) overexpression of genes that prevent the occurrence of negative traits, (2) overexpression of mutated versions of genes associated with negative traits in order to titrate out the wild-type gene products with non-functional proteins, and (3) silencing specific genes that are associated with a negative trait by expressing at least one copy of a leader or trailer fragment associated with that gene in the sense and/or antisense orientation.

One example of an endogenous gene that is associated with a negative trait in potato and can be modified in vitro so that it encodes a non-functional protein is the polyphenol oxidase (PPO) gene. Upon impact injury, the PPO gene product is released from the plastid into the cytoplasm (Koussevitzky et al., J. Biol. Chem., 273: 27064-9, 1998), where it will mediate the oxidation of phenols to create a variety of phenoxyl radicals and quinoid derivatives, which are toxic and/or ultimately form undesirable polymers that leave dark discolorations, or "black spots" in the crop.

Overexpressing a mutant PPO gene that contains a non-functional copper-binding domain can lower the activity of all PPO genes that are mainly expressed in tubers and associated organs such as sprouts. The mutations render the polyphenol oxidase protein inactive because it is unable to bind copper. The skilled artisan would know where to make point mutations that would, in this case, compromise the function of a gene product. The applicants identified the copper binding domain in potato PPO by aligning the potato PPO protein sequence with a sweet potato PPO protein sequence (Klabunde et al., Nat Struct. Biol., 5:1084-90, 1998). Areas of conservation, particularly those containing conserved histidine residues in copper-binding sites, were targets for inactivating the transgene product. Because the almost complete absence of PPO activity in such organs may negatively impact the plant's ability to resist pathogens, the present invention also describes an improved method of only lowering a specific PPO gene that is predominantly expressed in all parts of the mature tuber except for the epidermis. Silencing of this specific PPO gene by using a trailer sequence associated with that gene does not reduce PPO expression in the tuber epidermis, the part of the tuber that is most directly exposed to pathogens attempting to infect.

Enzymatic browning induced by the PPO gene not only reduces the quality of potato tubers; it also negatively affects crop foods such as wheat, avocado, banana, lettuce, apple, and pears.

Other genes that are associated with negative traits and can be silenced by using the leader or trailer sequences associated with those genes include the potato R1 gene and L-type phosphorylase genes. Both genes are involved in the degradation of starch to reducing sugars, such as glucose and fructose, which upon heating participate in the Maillard reaction to produce toxic products such as acrylamide. The present invention demonstrates that a reduction of cold-induced sweetening by lowering R1 or phosphorylase activity leads to a reduction of both non-enzymatic browning and acrylamide accumulation during the frying process of potatoes.

The invention also demonstrates the utility of overexpressing certain native genes in genetically modified crops. Levels of Maillard-reaction products such as acrylamide were reduced significantly by lowering the conversion of sucrose to reducing sugars through overexpression of a newly isolated vacuolar invertase inhibitor gene in potato.

The present invention also predicts that potato tubers displaying either an increased level of invertase inhibitor expression or a reduced level of R1 or phosphorylase expression will not require the intensive treatment with chemical sprout inhibitors such as CIPC prior to storage because their lowered levels of reducing sugars will (1) delay sprouting, and (2) allow storage at lower temperatures, thus further delaying sprouting. The highly reduced CIPC-residue levels, or the absence thereof, further enhances the nutritional value of processed foods derived from plants containing certain modified P-DNAs described here.

Thus, French fries or chips derived from tubers that contain the modified P-DNA will contain strongly reduced CIPC residue levels, further boosting their nutritional value.

The effect of simultaneously downregulating the expression of the PPO and either R1 or phosphorylase genes in potato tubers is synergistic because reducing sugars are not only required for non-enzymatic browning through the Maillard reaction but also for browning mediated by the PPO enzyme. Decreased levels of reducing sugars in transgenic potato tubers will, therefore, also limit PPO activity and black spot bruise susceptibility. Thus, PPO, R1, and phosphorylase genes, and/or the leader or trailer sequences that are associated with these genes, represent DNA segments of interest that can be isolated, modified and reintroduced back into the plant to down-regulate the expression of these genes.

Apart from developing bruise resistance and reduced cold-induced sweetening, there are many other traits that can be introduced through Precise Breeding without using foreign DNA. For instance, disease resistance genes can be isolated from wild potato species and inserted into the genomes of disease susceptible varieties.

The Environmental Benefits of Modified Plants and Crops

As described above, reduced levels of either R1 or phosphorylase result in a reduced phosphorylation of starch. This reduction in starch phosphorylation results in a 90% decrease in phosphate content of potato tubers (Vikso-Nielsen, Biomacromolecules, 2: 836-43, 2001). This will result in a reduction in phosphate levels in wastewaters from potato processing plants, which are currently about 25-40 mg/L. Thus, the use of low-phosphate tubers will reduce the release of phosphates into the environment and help to protect important ecosystems. Furthermore, low-phosphate potatoes may require less phosphate fertilization for optimal growth and yield, which would support a more sustainable agriculture by delaying the depletion of available phosphate resources.

Enhancing the Agricultural Performance of Plants and Food Crops

Apart from reduced bruise susceptibility and reduced cold-sweetening, which are two important processing traits, the present invention also provides salt tolerance, an increasingly important input trait. Some of the modified P-DNA constructs described in the present invention contain a salt tolerance gene as native marker for transformation. Importantly, the utility of this gene is not limited to a screening step in the transformation procedure. Overexpression of the salt tolerance gene in potato plants reduces stress symptoms induced by high salinity soil levels, and will make it possible to grow new varieties containing a modified P-DNA on a growing percentage of agricultural lands that contain salinity levels exceeding the maximum 2 millimhos/cm electrical conductivity levels that are optimal for growing conventional varieties.

Using Regulatory Elements Isolated from a Selected Plant Species or from a Species Sexually Compatible with the Selected Plant Species Once the leader, gene or trailer has been isolated from the plant species of interest, and optionally modified, it can be operably linked to a plant promoter or similar regulatory element for appropriate expression in plants. Regulatory elements such as these serve to express untranslated sequences associated with a gene of interest in specific tissues or at certain levels or at particular times.

Dependent on the strategy involved in modifying the trait, it may be necessary to limit silencing to a particular region of the plant. The promoter normally driving the expression of the endogenous gene may not be suitable for tissue-specific expression. As described in the section above, stable integration of bacterial or viral regulatory components, such as the cauliflower mosaic virus 35S "super" promoter, can result in unpredictable and undesirable events. Thus, one aspect of the present invention uses promoters that are isolated from the selected host plant species.

In a preferred embodiment of the instant invention, for use in *S. tuberosum*, the leader or trailer sequences associated with R1, phosphorylase, and PPO genes are operably linked to the granule-bound starch synthase gene promoter (Rohde et al., *J Gen & Breed*, 44, 311-315, 1990). This promoter has been used frequently by others to drive gene expression and is particularly active in potato tubers (van der Steege et al., *Plant Mol Biol*, 20: 19-30, 1992; Beaujean et al., *Biotechnol. Bioeng*, 70: 9-16, 2000; Oxenboll et al., *Proc Natl Acad Sci USA*, 9: 7639-44, 2000). This promoter may also be used, in a preferred embodiment, for expression of the modified leader or trailer sequences of R1, phosphorylase, and PPO genes.

Alternatively, other potato promoters can be operably linked to sequences of interest from potato. Such promoters include the patatin gene promoter (Bevan et al., *Nucleic Acids Res*, 14: 4625-38, 1986), or a fragment thereof, that promotes expression in potato tubers, the potato UDP-glucose pyrophosphorylase gene promoter (U.S. Pat. No. 5,932,783) and the promoter of the ubiquitin gene (Garbarino et al., *Plant Physiol*, 109: 1371-8, 1995).

The transcription of leaders and/or trailers can also be regulated by using inducible promoters and regulatory regions that are operably linked in a construct to a polynucleotide of interest. Examples of inducible promoters include those that are sensitive to temperature, such as heat or cold shock promoters. For instance, the potato ci21A-, and C17-promoters are cold-inducible (Kirch et al., *Plant Mol. Biol*, 33: 897-909, 1997; Schneider et al., *Plant Physiol*, 113: 335-45, 1997).

Other inducible promoters may be used that are responsive to certain substrates like antibiotics, other chemical substances, or pH. For instance, abscisic acid and gibberellic acid are known to affect the intracellular pH of plant cells and in so doing, regulate the Rab 16A gene and the alpha-amylase 1/6-4 promoter (Heimovaara-Dijkstra et al., *Plant Mol Biol*, 4 815-20, 1995). Abscisic acid, wounding and methyl jasmonate are also known to induce the potato pin2 promoter (Lorberth et al., *Plant J*, 2: 477-86, 1992).

In another example, some nucleotide sequences are under temporal regulation and are activated to express a downstream sequence only during a certain developmental stage of the plant or during certain hours of the day. For instance, the potato promoter of the small subunit of ribulose-1,5-bisphosphate carboxylase (rbcS) gene can direct cell-specific, light-regulated expression (Fritz et al., *Proc Natl Acad Sci USA*, 88: 4458-62, 1991). The skilled artisan is well versed in these exemplary forms of inducible promoters and regulatory sequences.

The use of certain polyadenylation signals may also be useful in regulating expression, by varying the stability of the mRNA transcript. In particular, some polyadenylation signals when operably linked to the '3 end of a polynucleotide cause the mRNA transcript to become accessible to degradation.

Thus, it is possible to regulate expression of a gene by operably linking it with one or more of such promoters, regulatory sequences, 3' polyadenylation signals, 3' untranslated regions, signal peptides and the like. According to the instant invention, DNA sequences and regulatory elements such as those described herein, and which will ultimately be integrated into a plant genome, are obtained from DNA of the selected plant species to be modified by the Precise Breeding process of the present invention. That is, DNA sequences and regulatory elements that are derived, isolated and cloned from other species, such as from bacteria, viruses, microorganisms, mammals, birds, reptiles and sexually incompatible plant species are not integrated into the genome of the transformed plant. DNA foreign to the selected plant species genome may be used in the present invention to create a transformation construct, so long as that foreign DNA is not integrated into a plant genome.

Not only does the present invention provide a method for transforming a plant species by integrating DNA obtained from the selected plant species, or from a plant that is sexually-compatible with the selected plant species, it also provides a means by which the expression of that DNA can be regulated. Accordingly, it is possible to optimize the expression of a certain sequence, either by tissue-specific or some other strategy, as previously described.

Using 3' Terminator Sequences Isolated from a Selected Plant Species

In addition to regulatory elements that initiate transcription, the native expression cassette also requires elements that terminate transcription at the 3'-end from the transcription initiation regulatory region. The transcription termination region and the transcription initiation region may be obtained from the same gene or from different genes. The transcription termination region may be selected, particularly for stability of the mRNA to enhance expression.

This particular element, the so-called "3'-untranslated region" is important in transporting, stabilizing, localizing and terminating the gene transcript. In this respect, it is well known to those in the art, that the 3'-untranslated region can form certain hairpin loop. Accordingly, the present invention envisions the possibility of operably linking a 3' untranslated region to the 3' end of a cloned polynucleotide such that the resultant mRNA transcript may be exposed to factors which act upon sequences and structures conferred by the 3' untranslated region.

A 3' sequence of the ubiquitin gene can be subcloned from the plant species from which the promoter and transgene were isolated and inserted downstream from a transgene to ensure appropriate termination of transcription. Both exemplary transgenes can be fused to the terminator sequence of the potato Ubiquitin gene (Ubi3) regardless of which promoter is used to drive their expression.

EXAMPLES

Example 1

Cloning of P-DNAs

This example demonstrates that T-DNA borders are specific to *Agrobacterium*. It also shows that plants contain T-DNA border-like sequences, and it provides the sequence of DNA fragments isolated from potato and wheat that are delineated by such border-like sequences.

Conventional transformation systems use *Agrobacterium*-derived T-DNAs as vehicles for the transfer of foreign DNA from *Agrobacterium* to plant cells (Schilperoort et al., U.S. Pat. No. 4,940,838, 1990). Although T-DNAs usually comprise several hundreds of basepairs, delineated by a left-border (LB) and right-border (RB) repeat, they can also merely consist of such borders. The T-DNA borders play an essential role in the DNA transfer process because they function as specific recognition sites for virD2-catalyzed nicking reaction. The released single stranded DNA, complexed with Agrobacterial virD2 and virE2, is transferred to plant cell nuclei where it often integrates successfully into the plant genome. All T-DNA borders that have been used for foreign DNA transfer are derived from nopaline and octopine strains of *Agrobacterium tumefaciens* and *A. rhizogenes* (Table 2). These borders and often some flanking *Agrobacterium* DNA are present in thousands of binary vectors including, for example, pPAM (AY027531), pJawohl (AF408413), pYL156 (AF406991), pINDEX (AF294982), pC1300 (AF294978), pBI121 (AF485783), pLH9000 (AF458478), pAC161 (AJ315956), BinHygTOp (Z37515), pHELLSGATE (AJ311874), pBAR-35S (AJ251014), pGreen (AJ007829), pBIN19 (X77672), pCAMBIA (AF354046), pX6-GFP (AF330636), pER8 (AF309825), pBI101 (U12639), pSKI074 (AF218466), pAJ1 (AC138659), pAC161 (AJ315956), pSLJ8313 (Y18556), and pGV4939 (AY147202). Recently, two homologs of T-DNA borders were identified in the chrysopine-type Ti plasmid pTiChry5 (Palanichelvam et al., *Mol Plant Microbe Interact* 13: 1081-91, 2000). The left border homolog is identical to an inactive border homolog located in the middle of the T-DNA of pTi15955. The right border homolog is unusually divergent from the sequence of functional T-DNA borders. It is therefore unlikely that these homologs are functionally active in supporting DNA transfer from pTiChry5 to plant cells.

Development of a new method that makes it possible to transform plants with only native DNA requires, in the first place, a replacement of the T-DNA including LB and RB. Unfortunately, advanced BLAST searches of public databases including those maintained by The National Center For Biotechnology Information, The Institute for Genomic Research, and SANGER failed to identify any border sequences in plants. It was therefore necessary to consider plant DNA sequences that are similar but not identical to T-DNA borders, designated here as "border-like" (border-like). Examples of plant border-like sequences that were identified in public databases are shown in Table 2. The challenge in trying to replace T-DNA borders with border-like sequences is that border sequences are highly conserved (see Table 2). A large part of these sequences is also highly conserved in the nick regions of other bacterial DNA transfer systems such as that of IncP, PC194, and φX174, indicating that these sequences are essential for conjugative-like DNA transfer (Waters et al., *Proc Natl Acad Sci* 88: 1456-60, 1991). Because there are no reliable data on border sequence requirements, the entire border seems therefore important in the nicking process. A single study that attempted to address this issue by testing the efficacy of border mutants in supporting DNA transfer is unreliable because negative controls did not appear to function appropriately (van Haaren et al., *Plant Mol Biol* 13: 523-531, 1989). Furthermore, none of the results of this study were confirmed molecularly. Despite these concerns, two possibly effective border mutants are shown in Table 2 as well.

Based on the homology among border sequences, a T-DNA border motif was identified (Table 2). Although this motif comprises 13,824 variants, many of which may not function—or may be inadequate—in transferring DNA, it represents the broadest possible definition of what a T-DNA border sequence is or may be. This border motif was then used to search publicly available DNA databases for homologs using the "Motif Alignment and Search Tool" (Bailey and Gribskov, *Bioinformatics* 14: 48-54, 1998) and "advanced BLASTN" ("penalty for nucleotide mismatch"=−1; "expect"=$10^5$; Altschul et al., *Nucleic Acids Res* 25: 3389-3402, 1997). Again, these searches did not identify any identical matches in organisms other than *Agrobacterium*.

To try and increase the chance of isolating a potato DNA fragment containing border-like sequences that correspond to the border motif, DNA was isolated from 100 genetically diverse accessions (the so-called "core collection," provided by the US Potato Genebank, WI). This DNA was pooled and used as template for polymerase chain reactions using a variety of oligonucleotides designed to anneal to borders or border-like sequences. Amplified fragments were sequence analyzed, and the sequence was then confirmed using inverse PCR with nested primers. One of the potato DNA fragments that was of particular interest contains a novel sequence without any major open reading frames that is delineated by border-like sequences (Table 2). One of the border-like sequences of this fragment contains at least 5 mismatches with T-DNA borders; the other border-like sequence contains at least 2 mismatches. Although both sequences contain one mismatch with the border motif, they were tested for their ability to support DNA transfer. For that purpose, the fragment was first reduced in size to 0.4-kilo basepairs by carrying out an internal deletion (SEQ ID NO.: 1). The resulting fragment was designated "P-DNA" (plant DNA) to distinguish it from the *Agrobacterium*-derived T-DNA. A similar fragment was isolated from the genome of the potato variety Russet Ranger, but has not been used for any further experiments.

Based on the divergence between P-DNA and T-DNA borders, the elongase amplification system (Life Technologies) was used with the following degenerate primers to isolate a P-DNA from wheat: 5'-GTTTACANHNBNATATATCCT-GYCA-3' (Bor-F) (SEQ ID NO. 124), and 5'-TGRCAG-GATATATNVNDNTGTAAAC-3' (Bor-R) (SEQ ID NO. 57). The resulting 825-bp fragment is shown in SEQ ID NO.: 2, and was used to replace the T-DNA of a conventional binary vector. The efficacy of this construct can be tested by inserting an expression cassette for the GUS gene between P-DNA termini, and infecting wheat with an *Agrobacterium* strain carrying the resulting vector.

Example 2

Tobacco Transformation with P-DNA Vectors

This Example demonstrates that, despite structural (sequence divergence) and functional (transformation frequencies) differences between P-DNA termini and T-DNA borders, a P-DNA can be used in a similar way as a T-DNA to transfer DNA from *Agrobacterium* to tobacco cells.

A T-DNA-free vector that can be maintained in both *E. coli* and *A. tumefaciens* was obtained by removing the entire T-DNA region of the conventional binary vector pCAMBIA1301 (Cambia, AU). This was accomplished by simultaneously ligating a 5.9 kb SacII-SphI fragment of pSIM1301 with 2 fragments amplified from pCAMBIA1301 using the oligonucleotides pairs: 5'-CCGCGGTGATCACAGGCAG-CAAC-3' (SEQ ID NO. 58) and 5'-AAGCTTCCAGCCAGC-CAACAGCTCCCCGAC-3' (SEQ ID NO. 59), and 5'-AAGCTTGGCTACTAGTGC-GAGATCTCTAAGAGAAAAGAGCGTTTA-3' (SEQ ID NO. 60), and 5'-GCATGCTCGAGATAGGTGACCACATA-CAAATGGACGAACGG-3' (SEQ ID NO. 61), respectively.

To make it possible to screen against backbone integration events, an expression cassette comprising the *Agrobacterium* isopentenyl transferase (IPT) gene driven by the Ubi3 promoter and followed by the Ubi3 terminator (SEQ ID NO.: 3) was inserted as 2.6 kbp SacII fragment into the backbone of the T-DNA-free vector described above, yielding pSIM100-OD-IPT. Transformed plant cells expressing the IPT gene are expected to accumulate cytokinins and grow into abnormal shoots that cannot develop roots.

The 0.4 kb P-DNA fragment described in Example 1 was inserted into pSIM100-OD-IPT to generate pSIM111 (FIG. 1; SEQ ID NO.: 4).

To test whether pSIM111 can be used to obtain transformed plants carrying P-DNAs (including any sequences located between P-DNA termini) without the additional vector backbone, a neomycin phosphotransferase (NPTII) gene expression cassette was inserted into the P-DNA of pSIM111 to create pSIM108 (FIG. 1).

The efficacy of P-DNA termini in supporting DNA transfer was tested by comparing transformation frequencies between pSIM108 and a control vector that contained a modified P-DNA with conventional T-DNA borders. This control vector, designated pSIM109, was generated by amplification of the entire P-DNA containing the NPTII gene expression cassette with the oligonucleotide pairs: 5'-ACTAGTGTTTAC-CCGCCAATATATCCTGTCAGAG-3' (SEQ ID NO. 62), and 5'-AAGCTTTGGCAGGATATATTGTGGTG-TAAACGAAG-3' (SEQ ID NO. 63). A second control vector that was used for these experiments is the conventional binary vector pBI121 (Genbank accession number AF485783), which contains the same NPTII expression cassette inserted on a regular T-DNA. The binary vectors were introduced into *Agrobacterium tumefaciens* LBA4404 cells as follows. Competent LB4404 cells (50 uL) were incubated for 5 minutes at 37° C. in the presence of 1 µg of vector DNA, frozen for about 15 seconds in liquid nitrogen (about −196° C.), and incubated again at 37° C. for 5 minutes. After adding 1 mL of liquid broth (LB), the treated cells were grown for 3 hours at 28° C. and plated on LB/agar containing streptomycin (100 mg/L) and kanamycin (100 mg/L). The vector DNAs were then isolated from overnight cultures of individual LBA4404 colonies and examined by restriction analysis to confirm the presence of intact plasmid DNA.

Test transformations of the model plant tobacco were carried out by growing a 10-fold dilution of overnight-grown LBA4404::pSIM108 cells for 5-6 hours, precipitating the cells for 15 minutes at 2,800 RPM, washing them with MS liquid medium (Phytotechnology) supplemented with sucrose (3%, pH 5.7) and resuspending the cells in the same medium to an $OD_{600\ nm}$ of 0.2. The suspension was then used to infect leaf explants of 4-week-old in vitro grown *Nicotiana tabacum* plants. Infected tobacco explants were incubated for 2 days on co-culture medium (1/10 MS salts, 3% sucrose, pH 5.7) containing 6 g/L agar at 25° C. in a Percival growth chamber (16 hrs light) and subsequently transferred to M401/agar medium containing timentine (150 mg/L) and kanamycin (100 mg/L). The number of calli per explant that developed within the next 4 weeks is shown in Table 3. Our data demonstrate that P-DNAs delineated by either native termini or conventional T-DNA borders are about 50% more effective in transforming tobacco than T-DNAs. The increased efficiency of P-DNA transfer may be due to either its different CG content or other unknown structural features of the P-DNA.

Example 3

Potato Transformation with P-DNA Vectors

This Example demonstrates that a P-DNA can be used in a similar way as a T-DNA to transfer DNA from *Agrobacterium* to potato cells.

Potato transformations were carried out by infecting stem explants of 4-week-old in vitro grown Russet Ranger plantlets with *Agrobacterium* strains according to the following procedure. Ten-fold dilutions of overnight-grown cultures were grown for 5-6 hours, precipitated for 15 minutes at 2,800 RPM, washed with MS liquid medium (Phytotechnology) supplemented with sucrose (3%, pH 5.7), and resuspended in the same medium to an $OD_{600\ nm}$ of 0.2. The resuspended cells were then used to infect 0.4-0.6 mm internodal potato segments. Infected stems were incubated for 2 days on co-culture medium (1/10 MS salts, 3% sucrose, pH 5.7) containing 6 g/L agar at 22° C. in a Percival growth chamber (16 hrs light) and subsequently transferred to callus induction medium (CIM, MS medium supplemented with 3% sucrose 3, 2.5 mg/L of zeatin riboside, 0.1 mg/L of naphthalene acetic acid, and 6 g/L of agar) containing timentine (150 mg/L) and kanamycin (100 mg/L). After 1 month of culture on CIM, explants were transferred to shoot induction medium (SIM, MS medium supplemented with 3% sucrose, 2.5 mg/L of zeatin riboside, 0.3 mg/L of giberelic acid GA3, and 6 g/L of agar) containing timentine and kanamycin (150 and 100 mg/L respectively). After 3-4 weeks, the number of explants developing transgenic calli and/or shooting was counted. As shown in tobacco, the number of stem explants infected with pSIM108 that showed calli was higher than those in control experiments with the conventional binary vector pBI121 (Table 3). Shoots that subsequently arose from these calli could be grouped into two different classes. The first class of shoots was phenotypically indistinguishable from control shoots transformed with LBA::pBI121. The second class of shoots displayed an IPT phenotype. Shoots of the latter class were stunted in growth, contained only very small leaves, displayed a light-green to yellow color, and were unable to root upon transfer to hormone-free media. To confirm that shoots with an IPT phenotype contained the IPT gene stably integrated in their genomes, all shoots were transferred to Magenta boxes containing MS medium supplemented with 3% sucrose and timentine 150 mg/L, allowed to grow for 3 to 4 additional weeks, and used to isolate DNA. This plant DNA served as template in PCR reactions with an oligonucleotide pair designed to anneal to the IPT gene: 5'-GTC CAA CTT GCA CAG GAA AGA C-3' (SEQ ID NO: 122), and 5'-CAT GGA TGA AAT ACT CCT GAG C-3' (SEQ ID NO: 123). As shown in Table 4, the PCR experiment confirmed a strict correlation between IPT phenotype and presence of the IPT gene. The presence of backbone DNA was also examined in plants obtained from a transformation with pBI121. This was done by performing PCR reactions on DNA isolated from the transformation events with the 'pBI121 backbone primers': 5'-CGGTGTAAGTGAACTGCAGTTGCCATG-3' (SEQ ID NO. 64), and 5'-CATCGGCCTCACTCATGAGCAGATTG-3' (SEQ ID NO. 65). Amplification of a 0.7 kbp band is indicative for backbone integration. By comparing the data presented in Table 4, it can be concluded that backbone integration frequencies are similar for P-DNA vectors and T-DNA vectors.

A second PCR experiment was carried out to test whether IPT-free plants did not contain any other backbone sequences. Because the IPT expression cassette is positioned close to the left border-like sequences, the oligonucleotide pair for this experiment was designed to anneal to backbone sequences close to the right border-like sequence: 5'-CACGCTAAGT-GCCGGCCGTCCGAG-3' (SEQ ID NO. 66), and 5'-TC-CTAATCGACGGCGCACCGGCTG-3' (SEQ ID NO. 67). Data from this experiment confirm that plants that are positive for the IPT gene are also positive for this other part of the backbone.

Similar experiments were carried out with the potato variety Russet Burbank. Based on an assessment of IPT phenotypes, the backbone integration frequencies for pSIM108 and pSIM109 were shown to be comparable to those in Russet Ranger (see Tables 4 and 5).

Example 4

Potato Invertase Inhibitor Gene

Using conventional transformation methods, this Example demonstrates that overexpressing a novel potato invertase inhibitor gene enhances the processing and health characteristics of potato tubers.

The following primers were designed to amplify a new potato homolog of the tobacco vacuolar invertase inhibitor Nt-inhh1 (Greiner et al., Nature Biotechnology, 17, 708-711, 1999): 5'-AAAGTTGAATTCAAATGAGAAATTTATTC-3' (SEQ ID NO. 68), and 5'-TTTTAAGCTTTCATAATAACAT-TCTAAT-3' (SEQ ID NO. 69). The amplification reaction was performed by mixing the following components: 4 µl plant DNA, 2 µl forward primer (10 pM/ml), 2 µl reverse primer, 25 µl Hot Start Master Mix (Qiagen Catalog Nr. 203443), and 17 µl water. This reaction mix was subjected to the following polymerase chain reaction (PCR) conditions using a PTC-100 thermocycler (MJ Research): (1) 5 minutes at 95° C. (I cycle), (2) 1 minute at 94° C., 1 minute at 45° C. and 4 minutes at 72° C. (35 cycles), and (3) 10 minutes at 72° C. (1 cycle). The total product was loaded on a 0.8% agarose gel, and a 540 base pair band was purified from gel using QIAquick Gel Extraction Kit (Qiagen, CA). This purified fragment was then ligated into pGEM-T Easy (Promega, WI) and transformed into E. coli DH5-alpha using Max Efficiency Competent Cells (GibcoBRL, MD). Sequence analysis of recombinant plasmid DNA isolated from transformed DH5-alpha revealed the presence of a single open reading frame consisting of 543 base pairs that encodes for a putative 181-amino acid protein (SEQ ID NO.: 5); clustal-alignment revealed 70% homology to Nt-inhh (FIG. 2). This high level of homology extends to the 15-amino acid N-terminal domain, indicating that the potato homolog is targeted to the vacuole. Interestingly, the potato invertase inhibitor homolog, designated St-inh1, shares only 43% homology with the patented tobacco cell wall invertase inhibitor designated Nt-inh1 (Patent WO98/04722; FIG. 2).

Although the St-inh1 gene is present in unmodified potato tubers, its expression level is inadequate for full inhibition of invertase and reduced cold-induced sweetening. To increase the storage characteristics of potato, the St-inh1 gene was fused to a new tuber-enhanced promoter of the granule-bound starch synthase (GBSS) gene, which is known to promote high levels of gene expression in tubers. The GBSS promoter was isolated from the potato cultivar Russet Ranger by carrying out a PCR reaction using the forward primer 5'-GAAC-CATGCATCTCAATC-3' (SEQ ID NO. 70) and the reverse primer 5'-GTCAGGATCCCTACCAAGCTACAGAT-GAAC-3' (SEQ ID NO. 71). Sequence analysis of the amplified product cloned in pGEM-T demonstrated that this new promoter contains 658 basepairs (SEQ ID NO.: 6). The resulting promoter/gene fusion was then ligated to the 3' regulatory sequence of the potato ubiquitin gene (UbiT; SEQ ID NO.: 7), thus ensuring appropriate termination of transcription of the invertase inhibitor gene.

This expression cassette was inserted between T-DNA borders of a binary vector, and the resulting vector pSIM320 was used to transform Russet Ranger as described above. Three cuttings of nine independent transgenic lines were planted in soil and grown for four weeks in a growth chamber (11 hrs light; 20° C.). At least 3 minitubers were then harvested from each line and transferred to a refrigerator set at 4° C. to induce cold-sweetening. After 4 weeks, the glucose levels in these cold-stored minitubers were determined by using either an Accu-Chek meter and test strips (Roche Diagnostics, IN) or a glucose oxidase/peroxidase reagent (Megazyme, Ireland). These levels were compared with the average glucose levels in both 6 untransformed lines and 6 "vector control" lines transformed with a pSIM110-derived vector lacking the invertase inhibitor gene. As shown in Table 6, three transgenic lines accumulated less than 40% of the glucose in "vector control" lines demonstrating that the potato invertase inhibitor homolog is functionally active.

The following experiment showed that the amount of reducing sugars present in tubers correlates with acrylamide production during tuber processing. Russet Ranger potato tubers were freshly harvested from the field and stored at 4° C. to induce cold-sweetening; control tubers were stored at 18° C. After 4 weeks, glucose levels were determined in both groups of tubers. Subsequently, tubers were washed, blanched for either 8 minutes or 12 minutes at 165° F., cut into 0.290×0.290 shoestring strips, dipped in a 1% sodium acid pyrophosphate solution at 160° F., dried at 160° F. until 14±2% dryer weight loss is achieved, fried at 390° F. for 40 seconds to attain 64±2% first fry moisture, and frozen for 20 minutes at −15° F., shaking the tray 2-3 times in the first 6 minutes. The resulting French fries were then analyzed for acrylamide levels by Covance laboratory (WI). As shown in Table 7, the glucose levels in tubers stored at 18° C. were below the detection level of 0.1 mg/g whereas cold-stored tubers contained on average 3.4 mg/g glucose. This table also shows that fries produced from the latter potatoes contain about 10-fold higher levels of acrylamide than fries produced from potatoes stored at 18° C. Even by using a shorter blanch time for 18° C.-stored potatoes than for 4° C.-stored potatoes to produce fries with a similar color (color ids of 78 and 71, respectively), a 5-fold difference in acrylamide accumulation was obtained (Table 7). Thus, there appears to be a straight correlation between the amount of reducing sugars such as glucose in tubers and the accumulation of acrylamide in fries derived from these tubers.

To determine whether the reduced glucose levels in pSIM320 lines would limit the processing-induced accumulation of acrylamide, cold-stored pSIM320 minitubers were processed by cutting into wedges, blanching for 8 minutes, dipping in 0.5% SAPP for 30 seconds, drying for 4.5 minutes at 160° F., frying for 40 seconds at 380° F., freezing for 15 minutes at −15° F., and finally drying for 3 minutes and 10 seconds at 160° F. The processed material was then shipped to Covance laboratory for acrylamide determinations. As shown in Table 6, French fries obtained from minitubers with the lowest amounts of glucose accumulated the lowest levels of acrylamide. A 40% reduction in glucose levels in lines "320-2" and "320-4" is associated with a 5-fold reduction in acrylamide levels.

Example 5

Leader and Trailer Sequences Associated with the Potato R1 Gene

Using conventional transformation methods, this Example demonstrates that a novel leader sequence associated with the potato R1 gene can be used effectively to enhance the processing and health characteristics of potato tubers. It also predicts that a novel trailer associated with that same gene can be exploited in the same way.

As an alternative to overexpressing the invertase inhibitor gene, methods were developed to limit acrylamide production without using any actual gene sequences. One such method is based on silencing the tuber-expressed R1 gene. Previously, it was shown that this starch-related gene can be silenced through antisense expression of a 1.9-kb gene fragment derived from that gene (Kossmann et al., U.S. Pat. No. 6,207,880). However, the antisense expression of large DNA fragments is undesirable because such fragments contain new open reading frames (Table 1). As a safer approach to the one described above, a small leader sequence associated with the R1 gene was isolated from potato. This leader was obtained by performing a rapid amplification of cDNA ends with the 5' RACE kit supplied by GIBCO BRL on total RNA from the tubers of Russet Ranger potato plants. Sequence analysis demonstrated that the R1-associated leader consists of 179 basepairs (SEQ ID NO.: 8). Both a sense and antisense copy of this leader sequence, separated by the potato Ubiquitin intron (SEQ ID NO.: 9), were placed between the GBSS promoter and UbiT. The resulting expression cassette for the leader sequence associated with R1 is shown in FIG. 3 (SEQ ID NO.: 10). A similar cassette containing a spacer derived from the GBSS promoter (SEQ ID NO.: 11)—instead of the Ubi intron—separating the sense and antisense copies of the R1 trailer is shown in (FIG. 3; SEQ ID NOs.: 12). Additional variants with a longer version of the GBSS promoter (SEQ ID NO.: 13) are shown in FIG. 3 (SEQ ID NOs.: 14-15).

To test the efficacy of the R1-associated leader in limiting acrylamide production, the expression cassette shown in FIG. 3 was inserted as KpnI-XbaI fragment between T-DNA borders of a binary vector. An *Agrobacterium* LBA4404 strain carrying the resulting vector pSIM332 was used to transform Russet Ranger potato. To induce tuber formation, 25 shoots representing independent transformation events were transferred to soil and placed in a growth chamber (11 hours light, 25° C.). After three weeks, at least 3 minitubers/line were stored for 4 weeks at 4° C. to induce starch mobilization. The glucose levels in these cold-stored minitubers were subsequently determined as described in Example 4, and compared with the average glucose levels in untransformed plants and vector controls. As shown in Table 8, minitubers derived from all 25 lines displayed reduced levels of glucose after cold-storage. An approximate 2-fold reduction in acrylamide levels in expected in French fries derived from minitubers displaying reduced R1 expression levels compared to controls. Much stronger effects of down-regulating R1 gene expression are anticipated in mature tubers.

As an alternative to the leader-based approach, expression cassettes that contained both a sense and antisense copy of the trailer sequence associated with R1 were generated. This trailer was obtained by performing a reverse transcription polymerase chain reaction (RT-PCR) on total RNA isolated from microtubers of the potato cultivar Russet Ranger. Complementary DNA was generated using the Omniscript RT Kit (Qiagen, CA) and then used as a template for a PCR reaction with Hot start DNA polymerase (Qiagen, CA) with the gene-specific reverse primer R1-1 (5'-GTTCAGACAA-GACCACAGATGTGA-3' SEQ ID NO: 114). Sequence analysis of the amplified DNA fragment, cloned in pGEM-T demonstrated that the trailer associated with R1 consists of 333 basepairs (SEQ ID NO.: 16). The sense and antisense copies of the trailer were separated by either the Ubi intron or the GBSS spacer- and sandwiched between GBSS promoter and Ubi3 terminator (FIG. 3; SEQ ID NOs.: 17-18). Similar versions with the larger GBSS promoter are shown in FIG. 3 (SEQ ID NOs.: 19-20).

Glucose and acrylamide levels can be determined as described above. Tubers displaying about 50% or greater reductions in glucose concentrations are expected to also accumulate about 50% less acrylamide during the frying process. The improved health and storage characteristics of modified plants can be confirmed in mature field-grown tubers.

Phosphate levels in potato tubers can be determined by using AOAC Method 995.11 Phosphorus (Total) in Foods (45.1.33 Official Methods of Analysis of AOAC International, 17th Edition). Samples are prepared by dry ashing in a muffle furnace followed with an acid digestion. The dissolved samples are then neutralized and treated with a molybdate-ascorbic acid solution and compared to a series of phosphorus standards (treated similarly). A dual beam spectrophotometer would be used for the calorimetric analysis at 823 nanometers. A significant decrease in phosphate content, which is beneficial for the environment, is expected.

Example 6

Leader Sequence Associated with the L-Alpha Glucan Phosphorylase Gene

Using conventional transformation methods, this Example demonstrates that a novel leader sequence associated with the potato L-alpha glucan phosphorylase gene can be used to effectively enhance the processing and health characteristics of potato tubers.

Previously, it was shown that cold-induced sweetening can be reduced through antisense expression of 0.9-kb fragments derived from alpha glucan phosphorylase genes (Kawchuk et al., U.S. Pat. No. 5,998,701, 1999). However, the antisense expression of these relatively large DNA fragments is undesirable because they contain new and uncharacterized open reading frames that may impact the nutritional quality of foods if expressed in transgenic plants (Table 1).

As a safer approach to the one described above, small leader and trailer sequences that are associated with a L-type glucan phosphorylase gene were isolated from RNA of mature tubers. The primer pair used for this purpose is: 5'-GGATCCGAGTGTGGGTAAGTAATTAAG-3' (SEQ ID NO. 72), and 5'-GAATTCTGTGCTCTCTATG-CAAATCTAGC-3' (SEQ ID NO. 73). The resultant leader sequence of 273 bp was amplified and is shown in SEQ ID NO.: 21. Similarly, the "direct" primer, 5'-GGAACAT-TGAAGCTGTGG-3' (SEQ ID NO. 74), was used with an oligo-dT primer to amplify a 158 bp "trailer sequence" that is associated with the L-type phosphorylase gene (SEQ ID NO.: 22).

Expression cassettes were then designed using these trailer or leader sequences to modify the expression of L-type phosphorylase gene and, in so doing, lowering acrylamide levels in fried products by limiting starch mobilization. These cassettes were constructed in a similar way as described in Example 5, and are depicted in FIG. 3 (SEQ ID Nos.: 23-26). An *Agrobacterium* strain containing a binary vector with this expression cassette, designated pSIM216, was used to infect potato stems, and generate 25 transgenic plants. Minitubers derived from these plants were stored for 4 weeks at 4° C. to induce cold-sweetening. The cold-stored minitubers were then analyzed for glucose levels. As shown in Table 9, minitubers from all transgenic lines displayed reduced glucose levels.

Four lines that displayed at least 50% reduced glucose concentrations (lines 216-2, 216-5, 216-10, and 216-21) were used to assess processing-induced acrylamide levels. Although acrylamide levels in fried tubers derived from the first three lines were similar to those of controls, French fries that were derived from line 216-21 accumulated only 45% of the wild-type acrylamide levels (136 vs. 305 parts per billion). These results confirm the experiments described in Example 4 for tubers overexpressing the potato invertase inhibitor gene, in that relatively large reductions in glucose (and fructose) concentrations are needed to limit the heating-induced acrylamide accumulation in cold-stored minitubers. Because silencing of the phosphorylase gene is expected to be more effective in mature "216" tubers, reductions in acrylamide levels are also anticipated to be more pronounced in the French fries produced from such tubers. The improved health and storage characteristics of modified plants can be confirmed in mature tubers.

Example 7

Modified Polyphenol Oxidase Gene

Using conventional transformation methods, this Example demonstrates that a modified polyphenol oxidase gene lacking a functional copper-binding site can be used effectively to reduce bruise susceptibility in tubers.

Previously, it was shown that black spot bruise susceptibility can be reduced through antisense expression of the 1.8-kb PPO gene (Steffens, U.S. Pat. No. 6,160,204, 2000). However, expression of the reverse complement of this large gene is undesirable because it contains new and uncharacterized open reading frames encoding peptides consisting of more than 100 amino acids, which may potentially impact the nutritional quality of foods (Table 1). As a safer approach to the one described above, the PPO gene was modified to encode a non-functional protein.

The wild-type potato PPO gene was isolated from Russet Ranger by using a polymerase chain reaction (PCR) method. First, genomic DNA was isolated from sprouts of Russet Ranger. The potato PPO gene was then amplified from the potato genomic DNA using DNA polymerase and oligonucleotide primers: 5': CGAATTCATGGCAAGCTTGTG-CAATAG-3' (PPO-F) (SEQ ID NO. 75), and 5'-CGAATTCT-TAACAATCTGCAAGACTGATCG-3' (PPO-R) (SEQ ID NO. 76). These were designed to complement the 5'- and 3'-ends of the potato PPO gene. The amplified 1.6 kb fragment was cloned into a pGEM-T EASY vector (Promega) and confirmed to represent a functional PPO gene by sequence analysis (SEQ ID NO.: 27).

The copper binding domain in potato PPO was identified by aligning this protein with a sweet potato PPO protein that was shown to contain conserved Cysteine (Cys) residue at position 92, Glutamine residue (Glu) at position 236, and Histidine (His) residues at positions 88, 109, 118, 240, 244 and 274 coordinating the two active site coppers (Kiabunde et al., Nature Structural Biol., 5: 1084-1090, 1998). These Cys, Glu, and His residues are also present in potato PPO.

The inactive PPO gene was created by using a PCR mutation replacement approach. Three fragments were amplified by Proof Start Taq DNA Polymerase (Qiagen) using 3 pairs of primers and wild-type Russet Ranger PPO as a template. The sequences of the first pair, designated P1-F and P2-R, respectively, are: 5'-GAGAGATCTTGATAAGACACAACC-3' (SEQ ID NO. 77), and 5'-CATTACC[1]ATAAGCC[2]CAC[3]TGTATATTAGCTTGTT GC-3' (SEQ ID NO. 78) (1: "A" to "C" mutation, resulting in Cysteine to Glycine substitution at position 186; 2: "A" to "C" mutation, resulting in Cysteine to Tryptophan substitution at position 183; 3: "A" to "C" mutation, resulting in Histine to Glutamine substitution at position 182). The sequences of the second pair, designated P3-F and P4-R, respectively, are 5'-GTGCTTATAGAATTGGTGGC-3' (SEQ ID NO. 79), and 5'-TAGTTCCCGGGAGTTCAGTG-3' (SEQ ID NO. 80). The sequences of the third pair, designated P5-F and P6-R, respectively, are 5'-CTCCGGGAACTATAGG[4]AAACATTCCTCT[5]CGG TCCTGTCCACATCTGGTC-3' (SEQ ID NO. 81) and 5'-GTGTGATATCTGTTCTTTTCC-3' (SEQ ID NO. 82) (4: "A" to "G" mutation, resulting in Glutamine to Glycine substitution at position 326; 5: "A" to "T" mutation, resulting in Histine to Leucine substitution at position 330).

An 80 bp fragment was amplified using primer P1-F and P2-R and digested with BglII. This fragment contains one sticky end (BglII) and one blunt end, and carries three mutations in copper binding site I. A 0.4 kb fragment amplified using primer P3-F and P4-R and digested with XmaI contains one blunt end and one sticky end (XmaI). A 0.2 Kb fragment was amplified using primer P5-F and P6-R and digested with XmaI and EcoRV. This third fragment with a sticky end (XmaI) and a blunt end (EcoRV) has two mutations in copper binding site II. The BglII and EcoRV fragment from cloned wild-type potato PPO was then replaced with the above three ligated PCR amplified fragments. The presence of a total of 5 point mutations in the modified PPO gene was confirmed by sequence analysis (SEQ ID NO.: 28). To create an expression cassette for modified PPO (mPPO), the following four fragments were simultaneously ligated together: (1) a BamHI-HindIII fragment containing the GBSS promoter, (2) a HindIII-SacI fragment containing mutant PPO, (3) a SacI-KpnI fragment containing the Ubi-3 terminator, and (4) plasmid pBluescript, digested with KpnI and BamHI. This expression cassette was then inserted between borders of a binary vector to create pSIM314.

The efficacy of the mPPO gene expression cassette was assessed by transforming Russet Ranger stem explants with pSIM314. Nodal cuttings of transgenic plants containing this expression cassette were placed on MS medium supplemented with 7% sucrose. After a 5-week incubation period in the dark at 18° C., microtubers were isolated and assayed for PPO activity. For this purpose, 1 g of potato tubers was pulverized in liquid nitrogen. This powder was then added to 5 ml of 50 mM MOPS (3-(N-morpholino) propane-sulfonic acid) buffer (pH 6.5) containing 50 mM catechol, and incubated at room temperature with rotation for about 1 hour. The solid fraction was then precipitated, and the supernatant transferred to another tube to determine PPO activity by measuring the change of OD-410 over time. As shown in Table 10, microtubers isolated from some of the transgenic lines displayed a significantly reduced polyphenol oxidase activity compared to either untransformed controls or controls transformed with a construct not containing the mutant PPO gene. The strongest reduction in PPO activity was observed in lines "314-9", "314-17", and "314-29". To test whether expression of the mutant PPO gene also reduced PPO activity in minitubers, rooted plantlets of transgenic lines were planted in soil and incubated in a growth chamber for 4 weeks. A PPO assay on isolated minitubers demonstrated that reduced PPO activity in microtubers correlated in most cases with reduced activities in minitubers (Table 10). Transgenic lines displaying a reduced PPO activity can be propagated and tested both in the greenhouse and the field to confirm the "low bruise" phenotype in mature tubers. Because micro- and minitubers express a variety of polyphenol oxidases, some of which share only limited sequence homology with the targeted polyphenol oxidase that is predominantly expressed in mature tubers, an even more profound reduction of PPO activity may be anticipated in the mature tubers of lines such as "314-9" and "314-17". The data indicate that overexpression of a functionally inactive PPO gene can result in reduced bruise susceptibility. The improved health and storage characteristics of modified plants can also be confirmed in mature field-grown tubers.

Example 8

Trailer Sequence of a Polyphenol Oxidase Gene that is Specific for the Non-Epidermal Tissues of Potato Tubers Using conventional transformation methods, this Example demonstrates that a novel trailer sequence associated with the potato PPO gene can be used effectively to reduce bruise susceptibility in tubers.

Reverse transcription PCR was used to also isolate the trailer sequence associated with the PPO gene expressed in potato tubers. The primers for the first PCR reaction were PPO-1 (5'-GAATGAGCTTGACAAGGCGGAG-3', (SEQ ID NO. 83)) and oligo-dT; primers for a second nested PCR reaction were PPO-2 (5'-CTGGCGATAACGGAACTGTTG-3', (SEQ ID NO. 84)) and oligo-dT. Sequence analysis of the amplified DNA fragments cloned into pGEM-T revealed the presence of a 154-bp trailer (SEQ ID NO.: 29). A sense and antisense copy of this trailer, separated by the Ubi intron, was then fused to the GBSS promoter and Ubi3 terminator as described above to generate an expression cassette shown in FIG. 3 (SEQ ID NO.: 30). An alternative construct containing the trailer segments separated by a GBSS spacer is shown in FIG. 3 (SEQ ID NO.: 31). Similar versions with the larger GBSS promoter are shown in FIG. 3 (SEQ ID NOs.: 32-33). Interestingly, the trailer of the PPO gene that is predominantly expressed in mature tubers (indicated with P-PPO3 in FIG. 4) is different from the trailer of PPO genes that are predominantly expressed in other tissues including microtubers (indicated with PPOM-41 and PPOM-44 in FIG. 4). Because of the low homology between trailers associated with different PPO genes, the use of the P-PPO3 trailer will result in a silencing of the mature tuber-specific PPO gene only. This very specific gene silencing would be difficult to accomplish with sequences derived from the PPO gene itself, thus demonstrating the advantage of using non-coding sequences for gene silencing. To visualize the extend of PPO activity, 0.5 mL of 50 mM catechol was pipetted on the cut surfaces of sliced genetically modified minitubers. Compared to controls, visual browning of the tuber regions was about 5 to 10-fold reduced. Interestingly, though, no reduced browning was observed in the potato skin. It appears that the trailer sequence used specifically silenced the PPO gene that is predominantly expressed in cortex and pith but not in the epidermal skin. This unexpected finding may be beneficial for tubers to protect themselves against some pathogens attempting to infect through the skin because the PPO gene may play some role in certain defense responses. To quantitatively determine PPO activity, an assay was performed as described in Example 7. Table 11 shows up to 80% reduction of PPO activity in transformed minitubers compared to untransformed controls. The level of reduction is expected to be even greater in mature tubers because these tubers express the targeted PPO gene more predominantly than mini- and microtubers. The improved characteristics of lines such as "217-7" and "217-26" can be confirmed in mature tubers.

Example 9

An Expression Cassette to Increase Levels of Resistant Starch

Increasing the amylose/amylopectin ratios in tubers can further enhance the nutritional value of potato products. One method that makes it possible to increase amylose content is based on the antisense expression of genes encoding for the starch branching enzyme (SBE) I and II (Schwall et al., *Nature Biotechnology* 18: 551-554, 2000). The disadvantages of this method are that (1) the efficiency of simultaneously silencing two different genes through exploitation of antisense technologies is very low, (2) the antisense expression of the relatively large SBE-I and SBE-II gene sequences results in the undesirable expression of open reading frames (Table 1) (3) corresponding constructs that harbor the two antisense expression cassettes are unnecessarily large and complex, thus, increasing chances of recombination and lowering transformation frequencies.

Our approach to increase amylose content in potato is based on the expression of the trailer sequences that are associated with both genes. These trailers (SEQ ID No.:34 and 35) were isolated with the primer pairs 5'-GTCCATGATGTCTTCAGGGTGGTA-3' (SEQ ID NO. 85), and 5'-CTAATATTTGATATATGTGATTGT-3' (SEQ ID NO. 86), and 5'-ACGAACTTGTGATCGCGTTGAAAG-3' (SEQ ID NO. 87), and 5'-ACTAAGCAAAACCTGCTGAAGCCC-3' (SEQ ID NO. 88). A single promoter drives expression of a sense and antisense fusion of both trailers, separated by the Ubiquitin-7 intron, and followed by the Ubiquitin-3 terminator. The size of the entire expression cassette is only 2.5-kb.

Example 10

Development of Marker-Free Transformation Methods

This Example demonstrates that plants can be transformed effectively without to need for stable integration of selectable marker genes.

This method is the first to take advantage of the phenomenon that DNAs targeted to the nuclei of plant cells often fails to subsequently integrate into the plant cell's genome. The inventors made the surprising discovery that it is possible to select for cells that temporarily express a non-integrating T-DNA containing a selectable marker gene by placing infected explants for 5 days on a plant medium with the appropriate selective agent. A second phenomenon that was applied to develop the current method is that T-DNAs from different binary vectors often target the same plant cell nucleus. By using two different binary vectors, one containing the selectable marker on a T-DNA, and the other one carrying a T-DNA or P-DNA with the actual sequences of interest, it was possible to apply a transient selection system and obtain populations of calli, shoots or plants, a significant portion of which represents marker-free transformation events.

A conventional binary vector designated pSIM011 was used to represent the vector with the "sequence of interest", which is, in this test case, an expression cassette for the beta glucuronidase (GUS) gene located on a conventional T-DNA. The second binary vector that was used for these experiments contains an expression cassette comprising the neomycin phosphotransferase (NPTII) gene driven by the strong promoter of the Ubiquitin-7 gene and followed by the terminator sequences of the nopaline synthase (nos) gene between the borders of the T-DNA of a pSIM011-derivative.

Surprisingly, a strong level of transient NPTII gene expression levels could also be obtained by replacing the nos terminator with the terminator of the yeast alcohol dehydrogenase 1 (ADH1) gene (Genbank accession number V01292, SEQ ID NO. 56). This finding is interesting because the yeast ADH1 terminator does not share homology with any plant terminator. Importantly, it should be noted here that many yeast terminators do not function adequately in plants. For instance, almost no GUS gene expression was observed in a similar experiment as described above with the GUS gene followed by the yeast iso-1-cytochrome c (CYC1) terminator (Genbank accession number SCCYT1). An improved vector carrying the selectable marker gene NPTII was generated by replacing the nos terminator with the yeast ADH1 terminator. The binary vector containing a selectable marker gene for transient transformation is designated "LifeSupport" (FIG. 5).

Potato stem explants were simultaneously infected with two *A. tumefaciens* LBA4404 strains containing pSIM011 and LifeSupport, respectively. A 1/10 dilution of overnight-grown cultures of each strain were grown for 5-6 hours before they were precipitated, washed and resuspended an $OD_{600\,nm}$ of 0.4 as described in Example 3. The resuspended cells were then used to infect 0.4-0.6 cm internodal potato segments at a final density of each bacteria of 0.2 ($OD_{600\,nm}$). Infected stems were treated as in Example 3 with a main difference: the selection with kanamycin was limited to the first 5 days of culture on callus induction medium. Then, explants were allowed to further develop in fresh CIM and SIM containing only timentine 150 mg/L but no selective antibiotic. Within about 3 months from the infection day leaves from shoots derived from calli developed in 40-60% of the infected stems were both tested for GUS expression and PCR analyzed to identify events that contained the sequences of interest but no marker gene. As shown in Table 12, 11% of shoots represented marker-free transformation events.

The two-strain approach described above was also used to transform tobacco. Shoots that developed within about 2 months were GUS assayed and PCR analyzed. The high frequency of marker-free transformation events identified (18%) implies that the developed method is applicable to plant species other than potato (Table 12).

Importantly, sequential rather than simultaneous infection with the two different *Agrobacterium* strains resulted in an increase in the efficiency of marker-free transformation. The surprising effect of sequential infections was discovered by infecting potato stem explants with the *Agrobacterium* strain containing pSIM011, placing the infected explants on co-cultivation plates for 4 hours, and then re-infecting them with the LifeSupport vector. The doubly infected explants were treated as previously described in this example. As shown in Table 13, the lag time of 4 hours between the two different infections resulted in a 2-fold increased frequency of marker-free transformation events in potato.

Example 11

Precise Breeding with pSIM340

This Example demonstrates the efficacy of precise breeding. The health and agronomic characteristics of potato plants are enhanced by inserting potato genetic elements (see Examples 1, 4, and 7) into potato, using marker-free transformation (Example 10).

A binary vector containing two expression cassettes for the invertase inhibitor and mutant polyphenol oxidase genes inserted between P-DNA termini, designated pSIM340 (FIG. 1), was created by inserting both expression cassettes of mutant PPO and invertase inhibitor into a binary vector pSIM112'. Potato stem explants were infected simultaneously with pSIM340 and a further improved LifeSupport vector. The infected explants were then co-cultivated, subjected to transient selection, and induced to proliferate and develop shoots as discussed earlier. After 3 months, small shoots were transferred to new media and allowed to grow for 3 additional weeks. Shoots were then phenotypically analyzed, and leaf material was collected for molecular analyses to determine the presence of backbone, marker gene and P-DNA with the sequences of interest, as described in Examples 2 and 3. As shown in Table 14, 1.2% of events represented a plant that contained the modified P-DNA of pSIM340 without LifeSupport. This frequency of maker-free transformation is lower than found for a T-DNA, again revealing a functional difference between P-DNA and T-DNA.

Example 12

Selecting Against Stable Integration of LifeSupport T-DNAs

This Example demonstrates that the efficiency of precise breeding methods can be increased by selecting against stable integration of LifeSupport T-DNAs using the bacterial cytosine deaminase gene.

The previous example demonstrates that the efficiency of marker-free transformation is several-fold lower with a modified P-DNA than with a conventional T-DNA. To improve the efficiency of generating shoots only containing a modified P-DNA, an expression cassette for a suicide gene fusion comprising the bacterial cytosine deaminase (codA) and uracil phosphoribosyltransferase (upp) genes (InvivoGen, CA) was inserted between T-DNA borders of the LifeSupport vector, generating pSIM346 (FIG. 5). Potato stem explants were infected with one strain carrying pSIM340 and the other carrying pSIM346, and subsequently placed on the following media: (1) co-cultivation media for 2 days, (2) CIMTK media to select for transient marker gene expression for 5 days, (3) CIMT media to allow proliferation of plant cells that transiently expressed the marker gene for 30 days, (4) SIMT media with 500 mg/L of non-toxic 5-fluorocytosine (5-FC), which will be converted by plant cells expressing codA::upp into the toxic toxic 5-fluorouracil (5-FU), to select against stable integration of the LifeSupport TDNA. Callus gave rise to shoots on SIMT within 4 weeks. These shoots were transferred to MS media with timentin and allowed to grow until sufficient tissue was available for PCR analysis. DNA was then extracted from 100 shoots and used to determine the presence of P-DNA, LifeSupport and backbone. As shown in Table 15, none of the shoots analyzed contained a LifeSupport T-DNA, indicating, for the first time, that the codA::upp gene fusion can be used as negative selectable marker prior to regeneration. More importantly, our results demonstrate that a negative selection against LifeSupport T-DNA integration increases the frequency of shoots that only contain a modified P-DNA. By coupling a positive selection for transient marker gene expression with a negative selection against stable integration of the codA::upp gene fusion, the frequency of shoots only containing a modified P-DNA is about 5-fold higher than by only employing the positive selection for transient marker gene expression (Table 15).

An even greater increase in the efficiency of marker-free transformation was obtained by using the LifeSupport vector pSIM350 (FIG. 5), which is similar to pSIM346 but contains the codA gene instead of the codA::upp gene fuision. Potato stem explants simultaneously infected with pSIM340 and pSIM350 were treated as described above, and 51 resulting shoots were molecularly tested for the occurrence of events only containing the T-DNA region from pSIM340. Interestingly, this PCR analysis revealed that some shoots contained the codA gene (Table 15). This finding demonstrates that coda is not as tight a negative selectable marker as codA::upp in plants. More importantly, a large number of shoots (29%) were shown to represent marker-free transformation events.

Efficiencies can be further increased by not infecting explants simultaneously with pSIM340 and pSIM350 but sequentially. By infecting the explants with pSIM340 and re-infecting them with pSIM350 after 4 hours, marker-free transformation frequencies are expected to be approximately 30-40%.

Example 13

Impairing Integration of LifeSupport T-DNAs

This Example demonstrates that the efficiency of precise breeding methods can be increased by impairing integration of the LifeSupport T-DNA into the plant genome using an omega-mutated virD2 gene.

It has been shown that the omega domain of the *Agrobacterium* protein virD2 is important for the ability of that protein to support T-DNA integration into plant genomes (Mysore et al., *Mol Plant Microbe Interact* 11: 668-83, 1998). Based on this observation, modified LifeSupport vectors were created that contain an expression cassette for an omega-mutated virD2 protein inserted into the SacII site in their backbone sequences. The expression cassette was obtained by amplifying a 2.2-kb DNA fragment from plasmid pCS45 (courtesy of Dr. Walt Ream—Oregon State University, OR, USA-, SEQ ID NO.: 36). A LifeSupport-derivative carrying this expression cassette, designated pSIM401Ω (FIG. 5), was used to support the transformation of potato plants with the modified P-DNA of pSIM340. After transient selection and shoot induction, 100 shoots were molecularly tested for the presence of transgenes. As shown in Table 15, 4.4% of shoots only contained the modified P-DNA, indicating that the use of omega-virD2 increases the efficiency of marker-free transformation about 4-fold (Table 15).

Efficiencies are further improved by increasing the size of the LifeSupport T-DNA from 3.7 kb (in pSIM401Ω) to 8.1 kb (in the pSIM401Ω-derivative designated pSIM341Ω; FIG. 5). By regenerating shoots from potato stem explants simultaneously infected with pSIM340 and pSIM341Ω, 7 of 81 analyzed events (7%) were shown to represent marker-free transformation events (Table 15).

A further improvement can be obtained by infecting explants sequentially rather than simultaneously with pSIM340 and LifeSupport. In a similar way as described in Example 10, the frequency of plants that only contain a modified P-DNA can be about doubled by infecting the explants with pSIM340 and re-infecting them with LifeSupport after 4 hours.

Example 14

Development of a 1-Strain Approach

This Example demonstrates that high frequencies of marker-free transformation can also be obtained by using a single *Agrobacterium* strain that contains both the P-DNA vector and LifeSupport Two compatible binary vectors were created that can be maintained simultaneously in *Agrobacterium*. Instead of using this system to stably integrate two T-DNAs carrying the DNA-of-interest and a marker gene, respectively (Komari et al. U.S. Pat. No. 5,731,179, 1998), it is intended for integration of only the modified P-DNA.

The first vector, designated pSIM356, contains an expression cassette comprising the GUS gene driven by the Ubi7 promoter and followed by UbiT inserted between P-DNA termini. The backbone portion of this vector contains bacterial origins of replication from pVS1 and pBR322, a spectinomycin resistance gene for bacterial selection, and an expression cassette for the IPT gene to enable selection against backbone integration in plants (FIG. 1). The second vector, designated pSIM363, contains an expression cassette comprising the NPTII gene driven by the Ubi7 promoter and followed by the yeast ADH1 terminator inserted between conventional T-DNA borders (FIG. 5). The backbone portion of this vector contains bacterial origins of replication from ColE1 (Genbank number V00268) and ori V (Genbank number M20134), and a kanamycin resistance gene for bacterial selection.

The concept of increasing marker-free transformation frequencies using pSIM356 and pSIM363 was tested in 100 tobacco shoots. As shown in Table 16, about 19% of regenerated shoots contained the DNA of interest without marker gene. An increase in marker-free transformation efficiency was also found by applying this 1-strain approach to potato.

Nine of 60 independent shoots tested (15%) contained the pSIM340 T-DNA and lacked the LifeSupport T-DNA (Table 16).

The 1-strain approach can be combined with the method described in Example 12 to couple a positive selection for transient marker gene expression with a negative selection against stable integration of the codA gene. For this purpose, the LifeSupport vector pSIM365 was developed (FIG. 5). An *Agrobacterium* strain carrying this vector together with a P-DNA vector can be used to efficiently develop plants that only contain an expression cassette-of-interest located within a P-DNA stably integrated in their genomes.

Example 15

Precise Breeding Method Relying on a Native Marker

Apart from transforming crop plants with P-DNAs that only contain the desirable sequences to introduce beneficial traits, the present invention also provides a method of transforming such plants with P-DNAs that contain an additional native marker gene. Our novel and native marker genes of choice are potato homologs of the *Arabidopsis* vacuolar Na+/H+ antiporter gene and alfalfa alfin-1 gene. Expression of these genes do not only allow the identification of transformation events, but also provides salt tolerance to transformed plants. High salinity levels in an increasing acreage of agricultural land will therefore less affect potato plants containing the salt tolerance marker.

Two versions of a vacuolar Na+/H+ antiporter homolog, designated Pst (Potato salt tolerance) were amplified from cDNA of a late blight resistant variety obtained from the US Potato Genbank (WI), designated "LBR4", using the oligonucleotide pair 5'-CCCGGGATGGCTTCTGTGCTGGCT-3' (SEQ ID NO. 89) and 5'-GGTACCTCATGGACCCTGT-TCCGT-3' (SEQ ID NO. 90). Their sequences are shown in SEQ ID NO.:37 and 38. A third gene (SEQ ID NO.:39) with homology to alfin-1 was amplified from LBR4 potato DNA using the primers 5'-CCCGGGTATGGAAAATTCGGTAC-CCAGGACTG-3' (SEQ ID NO. 91) and 5'-ACTAGT-TAAACTCTAGCTCTCTTGC-3' (SEQ ID NO. 92). The efficacy of the Pst genes to function as transformation marker was assessed by inserting a fusion with the Ubi7 promoter between conventional T-DNA borders of a modified pSIM341 vector. After a transient selection period, kanamycin-resistant cells are allowed to proliferate and develop shoots. These shoots are then transferred to media that contain 100-150 mM sodium chloride. Salt-tolerant shoots represent transformation events that contain the T-DNA of the modified pSIM341.

Example 16

Tuber-Specific Promoter

A newly isolated tuber-specific promoter can replace the GBSS promoter used to develop the expression cassettes described in previous examples. This promoter was isolated from the genome of Russet Burbank potato plants by using the inverse polymerase chain reaction with primers specific for a potato proteinase inhibitor gene (Genbank Accession D17332) (SEQ ID NO. 39). The efficacy of the PIP promoter was tested by creating a binary vector that contains the GUS gene driven by this promoter and an expression cassette for the NPTII marker gene. A similar construct with the PIP promoter replaced by the GBSS promoter was used as control. Transformed shoots were obtained by infecting stem explants with *Agrobacterium* strains carrying the binary vectors, co-cultivation for 2 days, and selection on CIMTK medium for 2 months. These shoots were transferred to new media to induce root formation, and then planted into soil. Tubers can be assayed for GUS expression after a 3-month growth period in the green house.

Example 17

Preferred Constructs and Transformation Methods for Precise Breeding

Apart from pSIM340, many other vectors can be used to improve potato plants by transforming them with modified P-DNAs. Two of such vectors contain an expression cassette for a sense and antisense copy of the trailer associated with a PPO gene that is expressed in all tuber tissues except for the epidermis (see Example 8). Vector pSIM370 contains an additional expression cassette for a sense and antisense copy of the leader associated with phosphorylase gene (see Example 6). Vector pSIM371 contains a third expression cassette for the potato alfin-1 homolog (FIG. 1).

A third alternative vector, designated pSIM372, contains both an expression cassette for the potato alfin-1 homolog, and an expression cassette for a sense and antisense copy of a fusion of the PPO-associated trailer, R1-associated leader, and phosphorylase-associated leader.

The preferred LifeSupport vector for a 1-strain approach is pSIM365. For a 2-strain approach, the preferred vector is pSIM367, which contains expression cassettes for both NPTII and codA between T-DNA borders, and an additional expression cassette for omega virD2 in the plasmid backbone (FIG. 5).

Potato stem explants are infected with 1 strain carrying both pSIM365 and any of the vectors pSIM370, 371, and 372, or sequentially with 2 strains carrying pSIM366 and any of the preferred vectors-of-interest, respectively. After a 2-day co-cultivation and a 5-day transient selection period, the explants are transferred to media for proliferation/regeneration and elimination of *Agrobacterium*. Thirty days later, explants are transferred again to the same media but now also containing 5-FU to eliminate events containing LifeSupport T-DNAs. Shoots that subsequently arise on calli are transferred to regeneration media that may contain 100-200 mM salt to screen for salt tolerant events. The IPT-negative shoots are allowed to root and develop into mature plants. A large proportion of these plants (10%-100%) are predicted to represent marker-free and backbone-free plants containing a P-DNA with nucleotide sequences of interest stably integrated into their genomes.

TABLE 1

Potentially expressed uncharacterized peptides in antisense potato lines

| Gene (size of fragment used) | Predicted peptides encoded by ORFs in reverse-complemented DNA |
|---|---|
| RI (1.9-kb) | MSSTSNVGQD CLAEVTISYQ WVGRVINYNF FLLIHWYTVV EASTGITFQI FPIGIRSEDD RSFYEKADRF |
| | AWVT |
| | MSSESTFSKT PNGRATDVGI PTEEGTFPFR YAILRDLAPT ISLVNSSADI A |

TABLE 1-continued

Potentially expressed uncharacterized peptides in antisense potato lines

| Gene (size of fragment used) | Predicted peptides encoded by ORFs in reverse-complemented DNA |
|---|---|
|  | MSEGVGFKSK ILPSFAWRSA NILGSKHVAK QTFPFLARTE TCERTSGMSG VIRATAPSGI SSSPLTDFAT |
|  | KIVGFS |
| GLTP (1-kb) | VCSPALKADK SKSADGTCVD HSRRLIVVLV LYPGMGTSYA TAFISSPPIQ YLFPSDPVET FP |
|  | MLGSLVLPKS PENRKQAVPN PHFQEQHLVP EKPHFLDCGQ GFSKLPQMHQ |
|  | MVNFLTQGIV DMETAFGSPK MGGFGKEQFG ACVSRSEMDE SGIGAVMVEQ VCSICSRHFV LSMQI |
| GHTP (0.9-kb) | MLEGSMWPWN QESMKRAFLN HHFLMLHLFP AQRPPQAADP VCLKHQHMHC GCLSFQLHLS KLAPGDTPLI |
|  | SSMFALD |
|  | MKLCSSIILS IIKQKQVEIL RACFGFPETK TISVFSSVSW NWHIICKSL |
|  | MTKKPDRKDN IMPYNFPGTK FLQPIFRNFF LPSLCDKLLK KSISVPQAIT PCWKVQCGHG IKKA |
| PPO (1.8-kb) | TILKLDLHTF NGHFFTASFW NQSHRNSIFI FQSNILQQFS YRQLESNTGN MISITSMNM RQASITPCKL |
|  | RLIKLICIHS LVHVQKHIEP YIVPIIIRYF IECQYLLLLI FLLCCP |
|  | MKGKEKPREM NLQFFTTNFV STVAISTMNI SLLFKAKRVK GVFIKFPHST RSQLILGYVL LIRRMSRGAD |
|  | AEFSHRRELV VRNTIDLIGY RRATTVYYIN TFFYMGSTTR LEIRRWYRCS SR |
|  | MEWALARNRI PFFYCPNSLR TSHGKGYDFH RRKRIQSSTN LYLLNPFFSR QLISIHSTSC PHWHGGSKKS |
|  | DLNRVSRNYP CLHRFFDEVC HRSRCEPEYE GCFQ |
| SBE A (1.2-kb) | MNNITHSPIL IPFLEQLNPF ISNCHMQPIV KANTPILNGN TKCRHSANIF TNGNCIWEKP MNKIVDQHQI |
|  | HNSIHISCES KVFLVVPSES HR |
|  | MKFRYPSPPN PIVTSLIILC NAIPRSINDV DGLSRAIKSY ISLSISQNAI VLSPTRA |
| SBE B (2.6-kb) | MVNIMTSSSM ATKFPSITVQ CNSVLPWQVT SNFIPFVCVL WVEVEYKYQV TTFKHNNLII IIHAAYYLFS |
|  | MAKLVTHEIE VPLSSQGHCE KMDHLVKRNS SINNRRSICQ ARHARIHLFV H |
|  | MFETKLNSGV VWNDWLTVNI RNSNTPNTKL VLLHHVVRTV PSIEIANNFV FLSSRSPFTI DYATIFPVES |
|  | KF |

TABLE 1-continued

Potentially expressed uncharacterized peptides in antisense potato lines

| Gene (size of fragment used) | Predicted peptides encoded by ORFs in reverse-complemented DNA |
|---|---|
|  | MLYTSLYISY LSNSMLLPSW TNLHHSYSLN NLSTYLGLPL PGGNQNQFLP QKQAGQGPAY QKHLRQ |

TABLE 3

Transformation efficiency

| Binary vector | Calli/tobacco leaf explant ± SE | Calli/potato stem explant ± SE |
|---|---|---|
| pBI121 | 7.8 ± 0.6 | 0.31 ± 0.10 |
| pSIM108 | 10.2 ± 0.6 | 0.59 ± 0.07 |
| pSIM109 | 12.8 ± 0.6 | 0.47 ± 0.05 |

TABLE 4

Backbone integration resulting from Russet Ranger transformation

| Binary vector | Total Nr. | IPT phenotype | PCR+ for IPT | PCR+ for 0.6 kb backbone fragment |
|---|---|---|---|---|
| pBI121 | 98 | NA | NA | 54 (55%) |
| pSIM108 | 193 | 138 (71%) | 137 (71%) | NA |
| pSIM109 | 133 | 82 (62%) | 80 (60%) | NA |

NA: not applicable

TABLE 5

Backbone integration resulting from Russet Burbank transformation

| Binary vector | Total Nr. | IPT phenotype |
|---|---|---|
| PSIM108 | 79 | 49 (60%) |
| PSIM109 | 72 | 60 (84%) |

TABLE 6

Acrylamide levels in French fries derived from cold-stored pSIM320 minitubers

| Line | glucose mg/g (%-reduced) | acrylamide (PPB) |
|---|---|---|
| Untransformed | 10.2 | 469 |
| Vector control | 10.2 | NA |
| 320-2 | 5.4 (47%) | 95 |
| 320-4 | 5.8 (43%) | 107 |
| 320-7 | 8.7 (14%) | 353 |
| 320-9 | 7.4 (27%) | 137 |
| 320-17 | 6.0 (41%) | 506 |
| 320-21 | 8.5 (16%) | 428 |
| 320-33 | 6.6 (35%) | 516 |

NA: not available

TABLE 7

Acrylamide levels in French fries derived from untransformed mature tubers

|  | Stored at 18° C. (color id.*) | Stored at 4° C. (color id.*) |
|---|---|---|
| Glucose levels | <0.1 mg/g | 3.4 mg/g |
| 8-minute blanch | 53 PPB (78) | 603 PPB (56) |
| 12-minute blanch | 28 PPB (84) | 244 PPB (71) |

*a higher value indicates a lighter color of the finished Fry product

TABLE 8

Glucose levels in cold-stored pSIM332 minitubers

| Line | glucose mg/g (%-reduced) |
|---|---|
| Untransformed control | 11.6 ± 0.5 |
| Vector control | 11.5 ± 0.5 |
| 332-1 | 5.4 (53%) |
| 332-2 | 4.8 (58%) |
| 332-4 | 7.0 (39%) |
| 332-5 | 5.8 (50%) |
| 332-6 | 6.9 (40%) |
| 332-7 | 6.0 (48%) |
| 332-8 | 6.8 (41%) |
| 332-9 | 6.6 (43%) |
| 332-10 | 5.4 (53%) |
| 332-11 | 6.1 (47%) |
| 332-12 | 6.4 (44%) |
| 332-13 | 6.4 (44%) |
| 332-15 | 7.7 (33%) |
| 332-16 | 6.5 (43%) |
| 332-17 | 5.3 (54%) |
| 332-18 | 7.1 (38%) |
| 332-21 | 6.3 (46%) |
| 332-22 | 5.4 (53%) |
| 332-23 | 4.2 (63%) |
| 332-31 | 6.0 (48%) |
| 332-34 | 6.2 (48%) |
| 332-35 | 6.4 (44%) |
| 332-39 | 6.7 (41%) |
| 332-40 | 7.5 (35%) |
| 332-41 | 5.7 (50%) |

TABLE 9

Glucose levels in cold-stored pSIM216 minitubers

| Line | glucose mg/g (%-reduced) |
|---|---|
| Untransformed control | 11.6 ± 0.5 |
| Vector control | 11.5 ± 0.5 |
| 216-2 | 5.5 (52%) |
| 216-3 | 8.8 (23%) |
| 216-4 | 7.4 (36%) |
| 216-5 | 5.8 (50%) |
| 216-8 | 8.4 (27%) |
| 216-10 | 5.1 (56%) |
| 216-11 | 10.1 (19%) |
| 216-12 | 9.3 (19%) |
| 216-13 | 6.4 (44%) |
| 216-15 | 8.8 (23%) |
| 216-16 | 9.7 (16%) |
| 216-17 | 6.4 (44%) |
| 216-19 | 8.7 (24%) |
| 216-21 | 3.2 (72%) |
| 216-24 | 9.4 (18%) |
| 216-26 | 9.3 (19%) |
| 216-29 | 7.1 (38%) |
| 216-30 | 8.2 (29%) |
| 216-32 | 9.3 (19%) |

TABLE 9-continued

Glucose levels in cold-stored pSIM216 minitubers

| Line | glucose mg/g (%-reduced) |
|---|---|
| 216-34 | 7.1 (38%) |
| 216-35 | 7.8 (32%) |
| 216-38 | 7.1 (38%) |
| 216-42 | 8.1 (30%) |
| 216-44 | 9.4 (18%) |
| 216-45 | 10.2 (11%) |

TABLE 10

PPO activity in potato lines expressing a modified PPO gene

| | OD-410/gram | |
|---|---|---|
| Line | micro-tubers (%-reduced) | mini-tubers (%-reduced) |
| Untransformed controls | 24.59 ± 2.22 | 20.07 ± 1.21 |
| Vector controls | 22.59 ± 3.36 | 19.55 ± 1.43 |
| 314-1 | 2.36 (90%) | 17.8 (11%) |
| 314-2 | 41.52 (−76%) | 21.3 (−7%) |
| 314-4 | 18.40 (22%) | 5.4 (73%) |
| 314-5 | 8.49 (64%) | 19.1 (4%) |
| 314-7 | 16.04 (32%) | 16 (20%) |
| 314-8 | 14.86 (37%) | 17 (15%) |
| 314-9 | 5.43 (77%) | 4.3 (78%) |
| 314-12 | 19.35 (18%) | 19.6 (2%) |
| 314-13 | 18.17 (23%) | 15.4 (23%) |
| 314-14 | 18.64 (21%) | 17.32 (13%) |
| 314-16 | 13.92 (41%) | 18.2 (9%) |
| 314-17 | 5.19 (78%) | 2.4 (88%) |
| 314-20 | 26.66 (−13%) | 13.2 (34%) |
| 314-21 | 11.32 (52%) | 17.6 (12%) |
| 314-22 | 13.45 (43%) | 18.8 (6%) |
| 314-23 | 5.19 (78%) | 20.4 (−2%) |
| 314-24 | 15.10 (36%) | 19.6 (2%) |
| 314-25 | 23.12 (2%) | 19 (5%) |
| 314-26 | 13.45 (43%) | 17.8 (11%) |
| 314-27 | 26.42 (−12%) | 19.4 (3%) |
| 314-28 | 31.85 (−35%) | 19.4 (3%) |
| 314-29 | 3.77 (84%) | 14.8 (26%) |
| 314-31 | 23.83 (−1%) | 21.2 (−6%) |
| 314-32 | 28.78 (−22%) | 20 (0%) |

TABLE 11

PPO activity in potato minitubers expressing a modified trailer sequence associated with the PPO gene

| Line | OD-410/gram (%-reduced) |
|---|---|
| Untransformed controls | 20.6 ± 1.3 |
| Vector controls | 17.9 ± 2.1 |
| 217-1 | 12.5 (39.4%) |
| 217-4 | 12.6 (38.6%) |
| 217-5 | 11.3 (45.0%) |
| 217-6 | 6.1 (70.4%) |
| 217-7 | 5.7 (72.5%) |
| 217-9 | 10.4 (49.6%) |
| 217-10 | 15.2 (26.3%) |
| 217-11 | 15.2 (26.3%) |
| 217-12 | 6.6 (67.9%) |
| 217-14 | 15.4 (25.4%) |
| 217-15 | 13.5 (34.6%) |
| 217-16 | 6.0 (71.0%) |
| 217-17 | 9.7 (53.0%) |
| 217-19 | 8.6 (58.4%) |
| 217-21 | 14.2 (31.1%) |
| 217-22 | 9.7 (53.0%) |

TABLE 11-continued

PPO activity in potato minitubers expressing a modified trailer sequence associated with the PPO gene

| Line | OD-410/gram (%-reduced) |
|---|---|
| 217-23 | 15.2 (26.3%) |
| 217-24 | 8.2 (60.1%) |
| 217-25 | 11.9 (42.2%) |
| 217-26 | 3.1 (84.8%) |
| 217-27 | 6.2 (69.9%) |
| 217-29 | 7.2 (65.1%) |

TABLE 12

Marker-free transformation with the LifeSupport vector + pSIM011

| Plant | Co-transformed | Marker only | Gene-of-interest only | Untransformed |
|---|---|---|---|---|
| Potato | 0% | 33% | 11% | 56% |
| Tobacco | 20% | 26% | 18% | 36% |

Co-transformed: PCR-positive for both GUS and NPT
Gene-of-interest only: PCR-positive for GUS
Untransformed: Plants are PCR-negative for both GUS and NPT

TABLE 13

Sequential potato transformation with the LifeSupport vector and pSIM011

| Time window | Co-transformed | Marker only | Gene-of-interest only | Untransformed |
|---|---|---|---|---|
| 0 hrs | 9% | 36% | 9% | 46% |
| 4 hrs | 20% | 30% | 20% | 30% |

Untransformed: Plants are PCR-negative for marker and gene-of-interest

TABLE 14

Marker-free transformation with the P-DNA vector pSIM340 + LifeSupport

| Plant | Co-transformed | Marker only | Gene-of-interest only | Untransformed |
|---|---|---|---|---|
| Potato | 17% | 52.8% | 1.2% | 29% |

Co-transformed: PCR-positive for both the PPO gene of pSIM340 and the NPT gene from LifeSupport
Untransformed: Plants are PCR-negative for PPO and NPTII

TABLE 15

Marker-free potato transformation with pSIM340 + improved LifeSupport vectors

| LifeSupport vector | Co-transformed | Marker only | Gene-of-interest only | Untransformed |
|---|---|---|---|---|
| PSIM346 | 0% | 0% | 4% | 96% |
| PSIM350 | 10% | 10% | 29% | 51% |
| PSIM401Ω | 6% | 34% | 5% | 55% |
| pSIM341Ω | 16% | 23% | 7% | 54% |

Co-transformed: PCR-positive for both the PPO gene of pSIM340 and the NPT gene from LifeSupport
Untransformed: Plants are PCR-negative for PPO and NPTII

TABLE 16

Marker-free potato transformation with a single *Agrobacterium* strain carrying both pSIM356 and pSIM363

| Plant | Co-transformed | Marker only | Gene-of-interest only | Untransformed |
|---|---|---|---|---|
| Tobacco | 50% | 15% | 19% | 16% |
| Potato | 22% | 5% | 15% | 58% |

Co-transformed: PCR-positive for both the GUS gene of pSIM356 and the NPT gene from LifeSupport
Untransformed: Plants are PCR-negative for PPO and NPTII SEQ ID NOs.

| | |
|---|---|
| SEQ ID NO.: 1: | Potato P-DNA. The bold underlined portions of SEQ ID NO. 1 represent the left (5') and right (3') border-like sequences of the P-DNA respectively. |
| SEQ ID NO.: 2: | Wheat P-DNA |
| SEQ ID NO.: 3: | Expression cassette for the IPT gene |
| SEQ ID NO.: 4: | Binary vectors pSIM111 |
| SEQ ID NO.: 5: | Potato invertase inhibitor gene |
| SEQ ID NO.: 6: | Potato GBSS promoter |
| SEQ ID NO.: 7: | Potato Ubiquitin-3 gene terminator |
| SEQ ID NO.: 8: | Potato leader associated with the R1 gene |
| SEQ ID NO.: 9: | Potato Ubiquitin intron |
| SEQ ID NO.: 10: | Expression cassette for a sense and antisense copy of the leader associated with the R1 gene |
| SEQ ID NO.: 11: | Spacer |
| SEQ ID NO.: 12: | Alternative expression cassette for a sense and antisense copy of the leader associated with the R1 gene |
| SEQ ID NO.: 13: | Longer potato GBSS promoter |
| SEQ ID NO.: 14: | Alternative expression cassette for a sense and antisense copy of the leader associated with the R1 gene |
| SEQ ID NO.: 15: | Alternative expression cassette for a sense and antisense copy of the leader associated with the R1 gene |
| SEQ ID NO.: 16: | Potato trailer associated with the R1 gene |
| SEQ ID NO.: 17: | Expression cassette for a sense and antisense copy of the trailer associated with the R1 gene |
| SEQ ID NO.: 18: | Expression cassette for a sense and antisense copy of the trailer associated with the R1 gene |
| SEQ ID NO.: 19: | Expression cassette for a sense and antisense copy of the trailer associated with the R1 gene |
| SEQ ID NO.: 20: | Expression cassette for a sense and antisense copy of the trailer associated with the R1 gene |
| SEQ ID NO.: 21: | Potato leader associated with the L glucan phosphorylase gene |
| SEQ ID NO.: 22: | Potato trailer associated with the L glucan phosphorylase gene |
| SEQ ID NO.: 23: | Expression cassette for a sense and antisense copy of the leader associated with the L glucan phosphorylase gene |
| SEQ ID NO.: 24: | Alternative expression cassette for a sense and antisense copy of the leader associated with the L glucan phosphorylase gene |
| SEQ ID NO.: 25: | Alternative expression cassette for a sense and antisense copy of the leader associated with the L glucan phosphorylase gene |
| SEQ ID NO.: 26: | Alternative expression cassette for a sense and antisense copy of the leader associated with the L glucan phosphorylase gene |
| SEQ ID NO.: 27: | Potato PPO gene |
| SEQ ID NO.: 28: | Modified inactive potato PPO gene |
| SEQ ID NO.: 29: | Potato trailer associated with a PPO gene |
| SEQ ID NO.: 30: | Expression cassette for a sense and antisense copy of the trailor associated with a PPO gene |
| SEQ ID NO.: 31: | Alternative expression cassette for a sense and antisense copy of the trailor associated with a PPO gene |

-continued

| SEQ ID NOs. | |
|---|---|
| SEQ ID NO.: 32: | Alternative expression cassette for a sense and antisense copy of the trailer associated with a PPO gene |
| SEQ ID NO.: 33: | Alternative expression cassette for a sense and antisense copy of the trailer associated with a PPO gene |
| SEQ ID NO.: 34: | Potato trailer associated with a starch branching enzyme gene |
| SEQ ID NO.: 35: | Potato trailer associated with a starch branching enzyme gene |

-continued

| SEQ ID NOs. | |
|---|---|
| SEQ ID NO.: 36: | Expression cassette for an omega-mutated virD2 gene |
| SEQ ID NO.: 37: | Potato salt tolerance gene Pst1 |
| SEQ ID NO.: 38: | Potato salt tolerance gene Pst2 |
| SEQ ID NO.: 39: | Potato salt tolerance gene Pst3 |
| SEQ ID NO.: 40: | Potato tuber specific promoter |
| SEQ ID NO.: 56: | Yeast ADH terminator |
| SEQ ID NO. 94: | Wheat left border-like sequence |
| SEQ ID NO. 95: | Wheat right border-like sequence |

```
SEQ ID NO: 1
GTTTACAGTACCATATATCCTGTCAGAGGTATAGAGGCATGACTGGCATGATCACTAAATTGATGCCCACAGAGGAGACTTATAAC

CTACAGGGGCACGTAGTTCTAGGACTTGAAAGTGACTGACCGTAGTCCAACTCGGTATAAAGCCTACTCCCAACTAAATATATGAA

ATTTATAGCATAACTGCAGATGAGCTCGATTCTAGAGTAGGTACCGAGCTCGAATTCCTTACTCCTCCACAAAGCCGTAACTGAAG

CGACTTCTATTTTTCTCAACCTTCGGACCTGACGATCAAGAATCTCAATAGGTAGTTCTTCATAAGTGAGACTATCCTTCATAGCT

ACACTTTCTAAAGGTACGATAGATTTTGGATCAACCACACACACTTCGTTTACACCGGTATATATCCTGCCA

SEQ ID NO: 2
TGGCAGGATATATGAGTGTGTAAACAACCATAATCAGGCTGTAATTATCAAGAGAACTAATGACAAGAAGCAGAGCTTATCAAGTG

TTTCGTCCAGCTGTAACATGGGCACAAAAGCTTGCTTGATGCATGTCTGGCTTTTCAAAGAGCAATGTATTCTCAGGTACCTGCAC

GTTTGATCCCCTACCACGTACAAGACGAGCAGAAAGGACATGTCTGCAGAAACTTAGACACATCCATTGCAGACTCGTTCCGAAGC

ATCAGGAGAGTAGTCAGCAATGGTCATCTGCTGATGTAAATTAATTGATTGTTGGTAATCAAATTTTAACAGCAATATATATAATA

TATCAATAGTATATTGAACTATGAAAGACTGTAATCATATATAACAGCATACAAATTGTCGTGGAAACAAGAGGAGCTCATCAAGT

GTTTAGTTCAGAAATAGCTAACCAAGAATGCAATATAATAGGGGTACTGAGCTCCCTTCAAAATTACTAACTTCAGAAATAGCTAA

CCAAGAATGCAATGGCATTGCATAATTTAAACAACTGTCAGCACCAATCTCTGACTGAAGGCAGTTTACCCATTCAGAAGAGCACA

CATTTTCTGAACGACAACTCTGAGCGGGATTGTTGACAGCAGCAATTAATCTGGCCTCAAGATGGTTTCCAACAACATAGATCAG

ATACAGCACTCAAGCACCCAATAATCAGCCAGTACTGATCTGGTTACCACTGCAATTGATTAACAGATGAACTGTGAAATTAAGAT

TTAACTGACAGTAATATATACCAGTTGGCAGGATATATCCCTCTGTAAAC

SEQ ID NO. 3
CTGCAGCCAAAGCACATACTTATCGATTTAAATTTCATCGAAGAGATTAATATCGAATAATCATATACATACTTTAAATACATAAC

AAATTTTAAATACATATATCTGGTATATAATTAATTTTTTAAAGTCATGAAGTATGTATCAAATACACATATGGAAAAAATTAACT

ATTCATAATTTAAAAAATAGAAAAGATACATCTAGTGAAATTAGGTGCATGTATCAAATACATTAGGAAAAGGGCATATATCTTGA

TCTAGATAATTAACGATTTTGATTTATGTATAATTTCCAAATGAAGGTTTATATCTACTTCAGAAATAACAATATACTTTTATCAG

AACATTCAACAAAGTAACAACCAACTAGAGTGAAAAATACACATTGTTCTCTAAACATACAAAATTGAGAAAAGAATCTCAAAATT

TAGAGAAACAAATCTGAATTTCTAGAAGAAAAAAATAATTATGCACTTTGCTATTGCTCGAAAAATAAATGAAAGAAATTAGACTT

TTTTAAAAGATGTTAGACTAGATATACTCAAAAGCTATCAAAGGAGTAATATTCTTCTTACATTAAGTATTTTAGTTACAGTCCTG

TAATTAAAGACACATTTTAGATTGTATCTAAACTTAAATGTATCTAGAATACATATATTTGAATGCATCATATACATGTATCCGAC

ACACCAATTCTCATAAAAAGCGTAATATCCTAAACTAATTTATCCTTCAAGTCAACTTAAGCCCAATATACATTTTCATCTCTAAA

GGCCCAAGTGGCACAAAATGTCAGGCCCAATTACGAAGAAAAGGGCTTGTAAAACCCTAATAAAGTGGCACTGGCAGAGCTTACAC

TCTCATTCCATCAACAAAGAAACCCTAAAAGCCGCAGCGCCACTGATTTCTCTCCTCCAGGCGAAGATGCAGATCTTCGTGAAGAC

CCTAACGGGGAAGACGATCACCCTAGAGGTTGAGTCTTCCGACACCATCGACAATGTCAAAGCCAAGATCCAGGACAAGGAAGGGA

TTCCCCCAGACCAGCAGCGTTTGATTTTCGCCGGAAAGCAGCTTGAGGATGGTCGTACTCTTGCCGACTACAACATCCAGAAGGAG

TCAACTCTCCATCTCGTGCTCCGTCTCCGTGGTGGTGGATCCATGGACCTGCATCTAATTTTCGGTCCAACTTGCACAGGAAAGAC

GACGACCGCGATAGCTCTTGCCCAGCAGACAGGGCTTCCAGTCCTTTCGCTTGATCGGGTCCAATGCTGTCCTCAACTATCAACCG
```

-continued

GAAGCGGACGACCAACAGTGGAAGAACTGAAAGGAACGACGCGTCTCTACCTTGATGATCGGCCTCTGGTGGAGGGTATCATCGCA
GCCAAGCAAGCTCATCATAGGCTGATCGAGGAGGTGTATAATCATGAGGCCAACGGCGGGCTTATTCTTGAGGGAGGATCCACCTC
GTTGCTCAACTGCATGGCGCGAAACAGCTATTGGAGTGCAGATTTTCGTTGGCATATTATTCGCCACAAGTTACCCGACCAAGAGA
CCTTCATGAAAGCGGCCAAGGCCAGAGTTAAGCAGATGTTGCACCCCGCTGCAGGCCATTCTATTATTCAAGAGTTGGTTTATCTT
TGGAATGAACCTCGGCTGAGGCCCATTCTGAAAGAGATCGATGGATATCGATATGCCATGTTGTTTGCTAGCCAGAACCAGATCAC
GGCAGATATGCTATTGCAGCTTGACGCAAATATGGAAGGTAAGTTGATTAATGGGATCGCTCAGGAGTATTTCATCCATGCGCGCC
AACAGGAACAGAAATTCCCCCAAGTTAACGCAGCCGCTTTCGACGGATTCGAAGGTCATCCGTTCGGAATGTATTAGGTTACGCCA
GCCCTGCGTCGCACCTGTCTTCATCTGGATAAGATGTTCGTAATTGTTTTTGGCTTTGTCCTGTTGTGGCAGGGCGGCAAATACTT
CCGACAATCCATCGTGTCTTCAAACTTTATGCTGGTGAACAAGTCTTAGTTTCCACGAAAGTATTATGTTAAATTTTAAAATTTCG
ATGTATAATGTGGCTATAATTGTAAAAATAAACTATCGTAAGTGTGCGTGTTATGTATAATTTGTCTAAATGTTTAATATATATCA
TAGAACGCAATAAATATTAAATATAGCGCTTTTATGAAATATAAATACATCATTACAAGTTGTTTATATTTCGGGTGGACTAGTTT
TTAATGTTTAGCAAATGTCCTATCAGTTTTCTCTTTTTGTCGAACGGTAATTTAGAGTTTTTTTGCTATATGGATTTTCGTTTTT
GATGTATGTGACAACCCTCGGGATTGTTGATTTATTTCAAAACTAAGAGTTTTTGCTTATTGTTCTCGTCTATTTTGGATATCAAT
CTTAGTTTTATATCTTTTCTAGTTCTCTACGTGTTAAATGTTCAACACACTAGCAATTTGGCTGCAGCGTATGGATTATGGAACTA
TCAAGTCTGTGGGATCGATAAATATGCTTCTCAGGAATTTGAGATTTTACAGTCTTTATGCTCATTGGGTTGAGTATAATATAGTA
AAAAAATAGGAATTC

SEQ ID NO: 4
AGCTTTGGCAGGATATATACCGGTGTAAACGAAGTGTGTGTGGTTGATCCAAAATCTATCGTACCTTTAGAAAGTGTAGCTATGAA
GGATAGTCTCACTTATGAAGAACTACCTATTGAGATTCTTGATCGTCAGGTCCGAAGGTTGAGAAAAATAGAAGTCGCTTCAGTTA
CGGCTTTGTGGAGGAGTAAGGGTACCTACTCTAGAATCGAGCTCATCGTTATGCTATAAATTTCATATATTTAGTTGGGAGTAGGC
TTTATACCGAGTTGGACTACGGTCAGTCACTTTCAAGTCCTAGAACTACGTGCCCCTGTAGGTTATAAGTCTCCTCTGTGGGCATC
AATTTAGTGATCATGCCAGTCATGCCTCTATACCTCTGACAGGATATATGGTACTGTAAACACTAGTTGTGAATAAGTCGCTGTGT
ATGTTTGTTTGAGATCTCTAAGAGAAAAGAGCGTTTATTAGAATAACGGATATTTAAAAGGGCGTGAAAAGGTTTATCCGTTCGTC
CATTTGTATGTGGTCACCTATCTCGAGCATGCCAACCACAGGGTTCCCCTCGGGATCAAAGTACTTTGATCCAACCCCTCCGCTGC
TATAGTGCAGTCGGCTTCTGACGTTCAGTGCAGCCGTCTTCTGAAAACGACATGTCGCACAAGTCCTAAGTTACGCGACAGGCTGC
CGCCCTGCCCTTTTCCTGGCGTTTTCTTGTCGCGTGTTTTAGTCGCATAAAGTAGAATACTTGCGACTAGAACCGGAGACATTACG
CCATGAACAAGAGCGCCGCCGCTGGCCTGCTGGGCTATGCCCGCGTCAGCACCGACGACCAGGACTTGACCAACCAACGGGCCGAA
CTGCACGCGGCCGGCTGCACCAAGCTGTTTTCCGAGAAGATCACCGGCACCAGGCGCGACCGCCCGGAGCTGGCCAGGATGCTTGA
CCACCTACGCCCTGGCGACGTTGTGACAGTGACCAGGCTAGACCGCCTGGCCCGCAGCACCCGCGACCTACTGGACATTGCCGAGC
GCATCCAGCAGGCCGGCGCGGGCCTGCGTAGCCTGGCAGAGCCGTGGGCCGACACCACCACGCCGGCCGGCCGCATGGTGTTGACC
GTGTTCGCCGGCATTGCCGAGTTCGAGCGTTCCCTAATCATCGACCGCACCCGGAGCGGGCGCGAGGCCGCCAAGGCCCGAGGCGT
GAAGTTTGGCCCCCGCCCTACCCTCACCCCGGCACAGATCGCGCACGCCCGCGAGCTGATCGACCAGGAAGGCCGCACCGTGAAAG
AGGCGGCTGCACTGCTTGGCGTGCATCGCTCGACCCTGTACCGCGCACTTGAGCGCAGCGAGGAAGTGACGCCCACCGAGGCCAGG
CGGCGCGGTGCCTTCCGTGAGGACGCATTGACCGAGGCCGACGCCCTGGCGGCCGCCGAGAATGAACGCCAAGAGGAACAAGCATG
AAACCGCACCAGGACGGCCAGGACGAACCGTTTTTCATTACCGAAGAGATCGAGGCGGAGATGATCGCGGCCGGGTACGTGTTCGA
GCCGCCCGCGCACGTCTCAACCGTGCGGCTGCATGAAATCCTGGCCGGTTTGTCTGATGCCAAGCTGGCGGCCTGGCCGGCCAGCT
TGGCCGCTGAAGAAACCGAGCGCCGCCGTCTAAAAAGGTGATGTGTATTTGAGTAAAACAGCTTGCGTCATGCGGTCGCTGCGTAT
ATGATGCGATGAGTAAATAAACAAATACGCAAGGGGAACGCATGAAGGTTATCGCTGTACTTAACCAGAAAGGCGGGTCAGGCAAG
ACGACCATCGCAACCCATCTAGCCCGCGCCCTGCAACTCGCCGGGGCCGATGTTCTGTTAGTCGATTCCGATCCCCAGGGCAGTGC
CCGCGATTGGGCGGCCGTGCGGGAAGATCAACCGCTAACCGTTGTCGGCATCGACCGCCCGACGATTGACCGCGACGTGAAGGCCA

-continued

```
TCGGCCGGCGCGACTTCGTAGTGATCGACGGAGCGCCCCAGGCGGCGGACTTGGCTGTGTCCGCGATCAAGGCAGCCGACTTCGTG
CTGATTCCGGTGCAGCCAAGCCCTTACGACATATGGGCCACCGCCGACCTGGTGGAGCTGGTTAAGCAGCGCATTGAGGTCACGGA
TGGAAGGCTACAAGCGGCCTTTGTCGTGTCGCGGGCGATCAAAGGCACGCGCATCGGCGGTGAGGTTGCCGAGGCGCTGGCCGGGT
ACGAGCTGCCCATTCTTGAGTCCCGTATCACGCAGCGCGTGAGCTACCCAGGCACTGCCGCCGCCGGCACAACCGTTCTTGAATCA
GAACCCGAGGGCGACGCTGCCCGCGAGGTCCAGGCGCTGGCCGCTGAAATTAAATCAAAACTCATTTGAGTTAATGAGGTAAAGAG
AAAATGAGCAAAAGCACAAACACGCTAAGTGCCGGCCGTCCGAGCGCACGCAGCAGCAAGGCTGCAACGTTGGCCAGCCTGGCAGA
CACGCCAGCCATGAAGCGGGTCAACTTTCAGTTGCCGGCGGAGGATCACACCAAGCTGAAGATGTACGCGGTACGCCAAGGCAAGA
CCATTACCGAGCTGCTATCTGAATACATCGCGCAGCTACCAGAGTAAATGAGCAAATGAATAAATGAGTAGATGAATTTTAGCGGC
TAAAGGAGGCGGCATGGAAAATCAAGAACAACCAGGCACCGACGCCGTGGAATGCCCCATGTGTGGAGGAACGGGCGGTTGGCCAG
GCGTAAGCGGCTGGGTTGTCTGCCGGCCCTGCAATGGCACTGGAACCCCCAAGCCCGAGGAATCGGCGTGACGGTCGCAAACCATC
CGGCCCGGTACAAATCGGCGCGGCGCTGGGTGATGACCTGGTGGAGAAGTTGAAGGCCGCGCAGGCCGCCCAGCGGCAACGCATCG
AGGCAGAAGCACGCCCCGGTGAATCGTGGCAAGCGGCCGCTGATCGAATCCGCAAAGAATCCCGGCAACCGCCGGCAGCCGGTGCG
CCGTCGATTAGGAAGCCGCCCAAGGGCGACGAGCAACCAGATTTTTTCGTTCCGATGCTCTATGACGTGGGCACCCGCGATAGTCG
CAGCATCATGGACGTGGCCGTTTTCCGTCTGTCGAAGCGTGACCGACGAGCTGGCGAGGTGATCCGCTACGAGCTTCCAGACGGGC
ACGTAGAGGTTTCCGCAGGGCCGGCCGGCATGGCCAGTGTGTGGGATTACGACCTGGTACTGATGGCGGTTTCCCATCTAACCGAA
TCCATGAACCGATACCGGGAAGGGAAGGGAGACAAGCCCGGCCGCGTGTTCCGTCCACACGTTGCGGACGTACTCAAGTTCTGCCG
GCGAGCCGATGGCGGAAAGCAGAAAGACGACCTGGTAGAAACCTGCATTCGGTTAAACACCACGCACGTTGCCATGCAGCGTACGA
AGAAGGCCAAGAACGGCCGCCTGGTGACGGTATCCGAGGGTGAAGCCTTGATTAGCCGCTACAAGATCGTAAAGAGCGAAACCGGG
CGGCCGGAGTACATCGAGATCGAGCTAGCTGATTGGATGTACCGCGAGATCACAGAAGGCAAGAACCCGGACGTGCTGACGGTTCA
CCCCGATTACTTTTTGATCGATCCCGGCATCGGCCGTTTTCTCTACCGCCTGGCACGCCGCGCCGCAGGCAAGGCAGAAGCCAGAT
GGTTGTTCAAGACGATCTACGAACGCAGTGGCAGCGCCGAGAGTTCAAGAAGTTCTGTTTCACCGTGCGCAAGCTGATCGGGTCA
AATGACCTGCCGGAGTACGATTTGAAGGAGGAGGCGGGGCAGGCTGGCCCGATCCTAGTCATGCGCTACCGCAACCTGATCGAGGG
CGAAGCATCCGCCGGTTCCTAATGTACGGAGCAGATGCTAGGGCAAATTGCCCTAGCAGGGGAAAAAGGTCGAAAAGGTCTCTTTC
CTGTGGATAGCACGTACATTGGGAACCCAAAGCCGTACATTGGGAACCGGAACCCGTACATTGGGAACCCAAAGCCGTACATTGGG
AACCGGTCACACATGTAAGTGACTGATATAAAAGAGAAAAAAGGCGATTTTTCCGCCTAAAACTCTTTAAAACTTATTAAAACTCT
TAAAACCCGCCTGGCCTGTGCATAACTGTCTGGCCAGCGCACAGCCGAAGAGCTGCAAAAAGCGCCTACCCTTCGGTCGCTGCGCT
CCCTACGCCCCGCCGCTTCGCGTCGGCCTATCGCGGCCGCTGGCCGCTCAAAAATGGCTGGCCTACGGCCAGGCAATCTACCAGGG
CGCGGACAAGCCGCGCCGTCGCCACTCGACCGCCGGCGCCCACATCAAGGCACCCTGCCTCGCGCGTTTCGGTGATGACGGTGAAA
ACCTCTGACACATGCAGCTCCCGGAGACGGTCACAGCTTGTCTGTAAGCGGATGCCGGGAGCAGACAAGCCCGTCAGGGCGCGTCA
GCGGGTGTTGGCGGGTGTCGGGGCGCAGCCATGACCCAGTCACGTAGCGATAGCGGAGTGTATACTGGCTTAACTATGCGGCATCA
GAGCAGATTGTACTGAGAGTGCACCATATGCGGTGTGAAATACCGCACAGATGCGTAAGGAGAAAATACCGCATCAGGCGCTCTTC
CGCTTCCTCGCTCACTGACTCGCTGCGCTCGGTCGTTCGGCTGCGGCGAGCGGTATCAGCTCACTCAAAGGCGGTAATACGGTTAT
CCACAGAATCAGGGGATAACGCAGGAAAGAACATGTGAGCAAAAGGCCAGCAAAAGGCCAGGAACCGTAAAAAGGCCGCGTTGCTG
GCGTTTTTCCATAGGCTCCGCCCCCTGACGAGCATCACAAAAATCGACGCTCAAGTCAGAGGTGGCGAAACCCGACAGGACTATA
AAGATACCAGGCGTTTCCCCCTGGAAGCTCCCTCGTGCGCTCTCCTGTTCCGACCCTGCCGCTTACCGGATACCTGTCCGCCTTTC
TCCCTTCGGGAAGCGTGGCGCTTTCTCATAGCTCACGCTGTAGGTATCTCAGTTCGGTGTAGGTCGTTCGCTCCAAGCTGGGCTGT
GTGCACGAACCCCCCGTTCAGCCCGACCGCTGCGCCTTATCCGGTAACTATCGTCTTGAGTCCAACCCGGTAAGACACGACTTATC
GCCACTGGCAGCAGCCACTGGTAACAGGATTAGCAGAGCGAGGTATGTAGGCGGTGCTACAGAGTTCTTGAAGTGGTGGCCTAACT
ACGGCTACACTAGAAGGACAGTATTTGGTATCTGCGCTCTGCTGAAGCCAGTTACCTTCGGAAAAAGAGTTGGTAGCTCTTGATCC
GGCAAAGAAACCAGGGGTGGTAGGGGTGGTTTTTTTGTTTGGAAGGAGCAGATTAGGCGGAGAAAAAAACGATCTCAAGAAGATCG
```

-continued

```
TTTGATCTTTTGTACGGGGTGTGAGGGTGAGTGGAACGAAAAGTCACGTTAAGGGATTTTGGTCATGGATTGTAGGTAGTAAAACA
ATTGATGCAGTAAAATATAATATTTTATTTTCTGGGAATGAGGGTTGATCCCGAGTAAGTCAAAAAATAGCTGGACATACTGTTGT
TCCGCGATATGCTCCCTGATGGACGGGAGGGAGAAGGGAATGTCATACCAGTTGTGGGGGCTGGGGCTTGTGGGAAGATCAATAAA
GCCACTTACTTTGCCATGTTTCACAAAGATGTTGGTGTGTGGCAGGTGGCGGTGGGAAAAGAGAAGTTCGTCTTCGGGCTTTTCGG
TCTTTAAAAAATGATACAGGTCGCGCGGATGTTTAAATGGAGTGTGTTCTTCGCAGTTTTCGGAATCCAGATCGGGCAGATCGTTA
TTCAGTAAGTAATCGAATTGGGGTAAGGGGGTGTCTAAGCTATTCGTATAGGGAGAATCCGATATGTCGATGGAGTGAAAGAGCGT
GATGGACTCGGGATACAGCTCGATAATGTTTTCAGGGCTTTGTTCATGTTGATAGTCTTCCGAGCAAAGGAGGCGATCGGCGTGAG
TCATGAGCAGATTGGTGGAGCGATCATGCGGTTGAAAGTGGAGGAGGTTTGGAACAGGCAGGTTTGGTTGGAGGGATAGCATGATG
TCCTTTTCCCGTTCGAGATCATAGGTGGTCCCTTTATAGGGGCTGTCCGTGATTTTTAAATATAGGTTTTGATTTTGTCCGACCAG
CTTATATACCTTAGCAGGAGACATTGGTTGCGTATGTTTTACGGAGCGGTATTTTTGGATCAGTTTTTTCAATTGGGGTGATATTG
TCATTTTAGCCATTTATTATTTGGTTGGTGTTTTGTAGAGTATTTAAAGATAGGGCAAGAAGGTAATTATAACAAGAGGAAGTGGA
ATTCACTGTTGGTTGCATTGTAAAACGTTAAATAGGAGAAAAGAGGTTTTTGAAAGTTGTTTTGAAAGTTGGGGTATAACATAGTA
TCGACGGAGCCGATTTTGAAACGGGGGATGGTGGAGGGAAAGGAGATAGTTATGGATTTAAATTTGATGGAAGAGATTAATATGGA
ATAATCATATACATACTTTAAATACATAACAAATTTTAAATAGATATATGTGGTATATAATTAATTTTTTAAAGTGATGAAGTATG
TATCAAATAGAGATATGGAAAAAATTAAGTATTGATAATTTAAAAAATAGAAAAGATAGATGTAGTGAAATTAGGTGGATGTATGA
AATACATTAGGAAAAGGGGATATATCTTGATGTAGATAATTAAGGATTTTGATTTATGTATAATTTGGAAATGAAGGTTTATATCT
ACTTCAGAAATAAGAATATAGTTTTATGAGAAGATTGAAGAAAGTAAGAAGGAAGTAGAGTGAAAAATAGAGATTGTTGTGTAAAC
ATACAAAATTGAGAAAAGAATGTGAAAATTTAGAGAAAGAAATGTGAATTTGTAGAAGAAAAAAATAATTATGGAGTTTGGTATTG
CTCGAAAATAAATGAAAGAAATTAGACTTTTTTAAAAGATGTTAGACTAGATATACTGAAAAGGTATCAAAGGAGTAATATTGTT
CTTACATTAAGTATTTTAGTTAGAGTGGTGTAATTAAAGACAGATTTTAGATTGTATGTAAAGTTAAATGTATGTAGAATAGATAT
ATTTGAATGCATCATATAGATGTATGGGAGAGACCAATTCTGATAAAAAGGGTAATATGGTAAAGTAATTTATGCTTCAAGTCAAG
TTAAGCGGAATATACATTTTGATCTGTAAAGGGCGAAGTGGGAGAAAATGTGAGGGCGAATTACGAAGAAAAGGGGTTGTAAAAGG
CTAATAAAGTGGGAGTGGCAGAGCTTAGACTCTCATTGCATGAAGAAAGAAAGGCTAAAAGCGGGAGGGGGAGTGATTTGTGTGGT
CCAGGGGAAGATGGAGATGTTGGTGAAGAGGCTAACGGGGAAGACGATCACCCTAGAGGTTGAGTGTTCGGAGAGGATGGAGAATG
TCAAAGGGAAGATGCAGGACAAGGAAGGGATTGGGGGAGACGAGGAGGGTTTGATTTTGGGGGGAAAGCAGCTTGAGGATGGTGGT
ACTCTTGCGGACTACAACATGCAGAAGGAGTCAAGTGTGGATGTGGTGGTGGGTGTGGGTGGTGGTGGATCGATGGAGGTGGATGT
AATTTTGGGTCCAACTTGGAGAGGAAAGAGGACGAGGGGGATAGGTCTTGGCGAGGAGACAGGGCTTGCAGTGCTTTGGGTTGATG
GGGTCGAATGCTGTCCTCAAGTATGAAGCGGAAGGGGAGGAGCAAGAGTGGAAGAAGTGAAAGGAACGACGGGTGTGTAGGTTGAT
GATCGGCCTCTGGTGGAGGGTATCATGGCAGCGAAGGAAGGTGATGATAGGCTGATCGAGGAGGTGTATAATGATGAGGCCAAGGG
CGGGCTTATTGTTGAGGGAGGATGGAGGTGGTTGGTGAAGTGGATGGGGCGAAACAGGTATTGGAGTGCAGATTTTGGTTGGCATA
TTATTCGCCACAAGTTAGCGGAGGAAGAGAGGTTGATGAAAGGGGCGAAGGGAGAGTTAAGGAGATGTTGGAGGGCGCTGGAGGG
CATTCTATTATTCAAGAGTTGGTTTATGTTTGGAATGAAGCTGGGCTGAGGGGATTGTGAAAGAGATGGATGGATATCGATATGC
CATGTTGTTTGGTAGCGAGAACAGATGAGGGCAGATATGCTATTGGAGCTTGACGGAAATATGGAAGGTAAGTTGATTAATGGGA
TCGCTGAGGAGTATTTCATCCATGGGCGCGAACAGGAACAGAAATTGCGCGAAGTTAAGGGAGCGGCTTTGGAGGGATTCGAAGGT
CATCCGTTGGGAATGTATTAGGTTAGGGCAGGGGTGGGTGGGACGTGTGTTGATCTGGATAAGATGTTGGTAATTGTTTTTGGCTT
TGTCCTGTTGTGGGAGGGCGGGAAATAGTTGGGACAATGGATCGTGTGTTGAAACTTTATGGTGGTGAACAAGTGTTAGTTTCGAC
GAAAGTATTATGTTAAATTTTAAAATTTGGATGTATAATGTGGGTATAATTGTAAAAATAAAGTATCGTAAGTGTGGGTGTTATGT
ATAAATTTGTCTAAATGTTTAATATATATCATAGAACGGAATAAATATTAAATATAGGGGTTTTATGAAATATAAATAGATGATTAC
AAGTTGTTTATATTTGGGGTGGAGTAGTTTTTAATGTTTAGGAAATGTCCTATGAGTTTTGTGTTTTTGTGGAAGGGTAATTTAGA
GTTTTTTTTGCTATATGGATTTTCGTTTTTGATGTATGTGACAAGGGTGGGGATTGTTGATTTATTTGAAAAGTAAGAGTTTTTGG
```

```
TTATTGTTGTGGTGTATTTTGGATATGAATCTTAGTTTTATATGTTTTGTAGTTGTGTACGTGTTAAATGTTGAAGAGAGTAGCAA

TTTGGCTGGAGGGTATGGATTATGGAACTATGAAGTCTGTGGGATCGATAAATATGCTTCTGAGGAATTTGAGATTTTAGAGTGTT

TATGCTCATTGGGTTGAGTATAATATAGTAAAAAAATAGGAATTGTATGGGGGTGATGACAGGGAGGAAGGGTGTGTGATGGTTA

CAATGAACATGGTACGCTGCGCGAGATCATCCGTGTTTGAAAGGGGGCAGGTTAGTTGGGGTTGTTCGGAATAGCATGGGTAAGAT

GAGGAAAGTGTGGGGGGTTAGAAGGGCTCTGCGGCTGAGGGCGTCGCGGAGTGATGGGGTGCGTGTATGGAGTGGTGATTTTGTGG

CGAGCTGCGGGTCGGGGAGCTGTTGGCTGGCTGGA

SEQ ID NO: 5
ATGAGAAATTTATTCCGCATATTGATGCTAATCACCAATTTGGGACTGAACAAGGATAAGAAGAAGAAGAACAACAACAAGAATAA

TTATAATGTCATAGAGGCAAGGTGTAGGGAGAGGGGATATTAGTCGGTATGTCTCAGGACCGTACAATGGGGTGGACGTAGTAAGG

AGGTTGAGGGTGGTGATGGCATCAGGAGGGTAGGGGTGATGATGGTGGAGGCGGTGAAATCAAAGTGCATAGAAATAATGGAAAAA

ATAAAAGAGCTAGAGAAATCGAAGGCTGAGTGGGGGGCCGCACTTAGGGAGTGTTAGGTGGGGTATAATGGGGTCCTACGAGGGGA

TGTAACGGTAGGGGTTGAAGCGTTAAAGAAGGGTGCCGCGAAATTTGGTGAAGATGGTATGGATGATGTTGTTGCTGAAGCAGAAA

CTTGTGAGTATAGTTTTAATTATTATAATAAATTGGATTTTGCAATTTGTAATTTGAGTAGGGAAATAATTGAACTATCAAAAGTT

GCTAAATCCATAATTAGAATGTTATTATGA

SEQ ID NO: 6
GAACCATGCATCTCAATCTTAATACTAAAAAATGCAACAAAATTGTAGTGGAGGGAGCAGTAGGAGTAGATTAGATATTATGTTTT

ATTACTATAATAATATTTTAATTAACACGAGAGATAGGAATGTGAAGTGGTAGGGGTAGGAGGGAGTTGGTTCAGTTTTTTAGATA

CTAGGAGACAGAACGGGAGGGGGGGATTGCAAGGCGCAAGTTGAAGTGGAGGGGTGAATGAACAAAGAGAGGGGGATAATAGTGT

CGATGAGGATTTGCCTATAATACAGTGTGCACAGTTGGGTTGCGGTAAGGGATAGGCACGCGCTATTCTCTTGAGAGGTGTCACTG

AAACCTGCTAGAAATAAGGGAGGCACGTCCTCATTCTCACAGTGACTGAGTCACAGAGGTCAAGAAGTGGTAAGTTTTAGTGATGT

CCTCCAATTATTTGTGATTTCATGCATGTTTGGGTACATTCTATTATGAATGGTGTTATGGTGTATAAAGGTTGTTTGATATCTGA

TCTCATCTATTGTGATTTTGATTGTGTTGCGTACTGAATTTGACGGTACTGTAATGGGTGATAAATGTGAATGGTTCGTGTTGTTG

TTCTTCTTCTGAGAAATCAATTTGTGTTTTGTTTTTGTTGATGTGTAGGTTGGTAG

SEQ ID NO: 7
TTTTAATGTTTAGGAAATGTGGTATGAGTTTTCTCTTTTTGTGGAAGGGTAATTTAGAGTTTTTTTGGTATATGGATTTTGGTTT

TTGATGTATGTGAGAACGGTGGGGATTGTTGATTTATTTGAAAAGTAAGAGTTTTTGGTTATTGTTGTGGTCTATTTTGGATATGA

ATCTTAGTTTTATATCTTTTCTAGTTCTGTAGGTGTTAAATGTTCAAGAGAGTAGCAATTTGGCTGGAGGGTATGGATTATGGAAG

TATCAAGTCTGTGGGATCGATAAATATGCTTCTCAGGAATTTGAGATTTTACAGTCTTTATGCTCATTGGGTTGAGTATAATATAG

TAAAAAAATAG

SEQ ID NO: 8
ACCTTATTTCACTACCACTTTCCACTCTCCAATCCCCATACTCTCTGCTCCAATCTTCATTTTGCTTCGTGAATTCATCTTCATCG

AATTTCTCGACGCTTCTTCGCTAATTTCCTCGTTACTTCACTAAAAATCGACGTTTCTACCTGAACTTGAGTGAATTAAGCCAGTG

GGAGGAT

SEQ ID NO: 9
GTTAGAAATCTTCTCTATTTTCCTTTTTCTCTGTTTACATTCTCGAATTACCTAATGACCTCCTCTTATACCCCTTAATTTTCAG

TTTTTTTCGGTTCTTTTGATGCAAAAGGCCTAAAATTTCACTTTTTTTACCTTCCTTTCATCGAAAACGCCTACAATTGCACTTT

TCCCCGTTGTTTTCATGAAAAAGCCCCTACTTTCAGATTTTTTTCTCTCCATTCCATTCTAAACCTTTAAAATTAGACTTTTTAC

ATTTCTTTCATCAAAAACCCCTTAAATTTCACTTTTTCCCGTTGATTTGATCAAAAACCCCTACAATTTCTCTTTTTTCCTCCGTT

TCATTCTCAACCCCTAAAATTTGACTTTCTCCCGCTCTTTTCATCAAAAACCCCTAAATTTCACTTTCTCCCCCTGTTTTGATCAA

AAAGCCCTAAATTTCACTTTTTTCCCCCTCTTTTAGATTCTTTCCTTTTAATTCTCCAATCACCTAATCACGCAGTGTCAAAACCC

CTAAAATTTCACTTTTTTTCCTTCTTCTCATTCTTCTTTTTATCAATTTCCAC

SEQ ID NO: 10
CCTACCGAACCATCCATCTCAATCTTAATACTAAAAAATGCAACAAAATTCTAGTCCACCCACCACTACCAGTACATTACATATTA
```

TCTTTTATTACTATAATAATATTTTAATTAACACCAGACATACCAATCTCAACTCCTAGCCCTACCACCCAGTTGCTTCAGTTTTT

TACATACTACCACACACAACCCCACCCCCCCATTCCAAGGCCCAACTTCAACTCCACCCCTCAATCAACAAACAGACCGCCCATAA

TACTGTCGATCACCATTTCCCTATAATACACTGTCCACACTTCCCTTCCGCTAACCCATACCCACCCGCTATTCTCTTGACACCTC

TCACTCAAACCTCCTACAAATAAGGCACCCACCTCCTCATTCTCACACTCACTCACTCACACACCTCAACAACCATCCACCTTATT

TCACTACCACTTTCCACTCTCCAATCCCCATACTCTCTCCTCCAATCTTCATTTTCCTTCCTCAATTCATCTTCATCCAATTTCTC

CACCCTTCTTCCCTAATTTCCTCCTTACTTCACTACAAATCCACCTTTCTACCTCAACTTCACTCAATTAACCCACTCGCAGGATC

AATTCAACCTTACAAATCTTCTCTATTTTTGCTTTTTGTCTGTTTACATTCTCCAATTACCTAATCAGCTCCTCTTATACCCCTTA

ATTTTCACTTTTTTTCCCTTCTTTTGATGGAAAAGCCCTAAAATTTCACTTTTTTTACGTTCCTTTCATGCAAAACCCCTACAAT

TCCACTTTTCCCCCTTCTTTTCATCAAAAAGCCCCTACTTTCACATTTTTTTCTCTCCATTCCATTCTAAACCTTTAAAATTACA

CTTTTTACATTTCTTTCATGAAAAACCCCTTAAATTTCACTTTTTCCCCTTCATTTGATCAAAAACCCCTACAATTTCTCTTTTTT

CCTCCCTTTCATTCTCAACCCCTAAAATTTCACTTTCTCCCCCTCTTTTCATCAAAAACCCCTAAATTTCACTTTCTCCCCCTCTT

TTCATCAAAAACCCCTAAATTTCACTTTTTTCCCCCTCTTTTACATTCTTTCCTTTTAATTCTCCAATCACCTAATCACCCACTGT

CAAAACCCCTAAAATTTCACTTTTTTTCCTTCTTCTCATTCTTCTTTTTATCAATTTCCACATCCATATCATCCTCCCACTCCCTT

AATTCACTCAACTTCACCTACAAACCTCCATTTCTACTCAACTAACCACCAAATTACCCAACAACCCTCCACAAATTCCATCAACA

TCAATTCACCAACCAAAATCAACATTCCACCACACACTATCCCCATTCCACACTCCAAACTCCTACTCAAATAACCTAACCTTTTC

ATTTTAATCTTTACCAAATGTCCTATCACTTTTCTCTTTTTCTCCAACCCTAATTTACACTTTTTTTTCCTATATCCATTTTCCTT

TTTCATCTATCTCACAACCCTCCCCATTCTTCATTTATTTCAAAACTAACACTTTTTCCTTATTCTTCTCCTCTATTTTCCATATC

AATCTTACTTTTATATCTTTTCTACTTCTCTACCTCTTAAATCTTCAACACACTACCAATTTCCCTCCACCCTATCCATTATCCAA

CTATCAACTCTCTCCCATCCATAAATATCCTTCTCACCAATTTCACATTTTACACTCTTTATCCTCATTCCCTTCACTATAATATA

CTAAAAAATACTCTACA

SEQ ID NO: 11
CTAACTTTTACTCATCTCCTCCAATTATTTCTCATTTCATCCATCTTTCCCTACATTCTATTATCAATCCTCTTATCCTCTATAAA

CCTTGTTTCATATCTCATCTCATCTATTCTCATTTTCATTCTCTTCCCTACTCAATTTCACCCTACTCTAATCCCTCATAAATCTC

AATCCTTCCTCTTCTTCTTCTTCTCACAAATCAATTTCTCTTTTCTTTTTCTTCATCTCTAC

SEQ ID NO: 12
GCTACCCAACCATCCATCTCAATCTTAATACTAAAAAATCCAACAAAATTCTACTCCAGCCACCACTACCACTACATTACATATTA

TCTTTTATTACTATAATAATATTTTAATTAACACCACACATACCAATCTCAACTCCTACCCCTACCACCCAGTTCCTTCACTTTTT

TACATACTACCACACACAACCCCACCCCCCCATTCCAACCCCCAACTTGAACTCCACCCCTCAATCAACAAACACACCCCCCATAA

TACTCTCCATCACCATTTCCCTATAATACACTCTCCACACTTCCCTTCCCCTAACCCATACCCACCCCCTATTCTCTTCACACCTC

TCACTCAAACCTGCTACAAATAACCCACCCACCTCCTCATTCTCACACTCACTCACTCACACACCTCAACAACCATCCACCTTATT

TCACTACCACTTTCCACTCTCCAATCCCCATACTCTCTCCTCCAATCTTCATTTTCCTTCCTCAATTCATCTTCATCCAATTTCTC

CACGCTTCTTCCCTAATTTCCTCCTTACTTCACTACAAATCCACCTTTCTACCTCAACTTCAGTCAATTAACCCACTCCCACCATC

AATTCGTGCTAACTTTTACTCATCTCCTCCAATTATTTCTCATTTCATCCATCTTTCCCTACATTCTATTATCAATCCTCTTATCC

TCTATAAACCTTCTTTCATATCTCATCTCATCTATTCTCATTTTCATTCTCTTCCCTACTCAATTTCACCCTACTCTAATCCCTCA

TAAATCTCAATCCTTCCTCTTCTTCTTCTTCTTCTCACAAATCAATTTCTCTTTTCTTTTTGTTCATCTCTACCTTCATATCATCC

TCCCACTCCCTTAATTCACTCAACTTCACCTACAAACCTCCATTTCTACTCAACTAACCACCAAATTACCCAACAACCCTCGACAA

ATTCCATCAACATCAATTCACCAACCAAAATGAACATTCCACCACACACTATCCCCATTCCACACTCGAAACTCCTACTCAAATAA

GGTAACCTTTTCATTTAATCTTTACCAAATCTCCTATCACTTTTCTCTTTTTCTCCAACCCTAATTTACACTTTTTTTTCCTATA

TGGATTTTCCTTTTTCATCTATCTCACAACCCTCCCCATTCTTCATTTATTTCAAAACTAACACTTTTTCCTTATTCTTCTCCTCT

ATTTTCCATATCAATCTTACTTTTATATCTTTTCTACTTCTCTACCTCTTAAATCTTCAACACACTACCAATTTCCCTCCACCCTA

TGGATTATCCAACTATCAACTCTCTCCCATCCATAAATATGCTTCTCACCAATTTCACATTTTACACTCTTTATCCTCATTCCCTT

```
GAGTATAATATACTAAAAAAATACTCTACA

SEQ ID NO: 13
GAACCATCCATCTCAATCTTAATACTAAAAAATCCAACAAAATTCTACTCCACCCACCACTACCACTACATTACATATTATCTTTT

ATTACTATAATAATATTTTAATTAACACCACACATACCAATCTCAACTCCTACCCCTACCACCCACTTCCTTCACTTTTTTACATA

CTAGGAGACACAACCCCACCCCCCCATTCCAACCCCCAACTTCAACTCCACCCCTCAATCAACAAACACAGCCCCCATAATACTCT

CGATCACCATTTCCCTATAATACACTCTCCACACTTCCCTTCCCCTAACCCATACCCACCCCCTATTCTCTTCACACCTCTCACTC

AAACCTCCTACAAATAAGGCAGGCACCTCCTCATTCTCACACTCACTCACTCACACAGCTCAACAACTGGTAACTTTTAGTCATCT

CCTCCAATTATTTCTCATTTCATCCATCTTTCCCTACATTCTATTATGAATCGTGTTATCCTGTATAAACGTTGTTTCATATCTCA

TCTCATCTATTCTGATTTTGATTCTCTTGCCTACTGAATTTGACCCTACTGTAATCGGTGATAAATGTGAATGCTTCCTCTTCTTC

TTCTTCTTCTCAGAAATCAATTTCTGTTTTGTTTTTGTTCATCTGTAGCTTGGTAGATTCCCCTTTTTGTAGACCACACATCAC

SEQ ID NO: 14
GGTACCGAACCATGCATCTCAATCTTAATACTAAAAAATGCAACAAAATTCTAGTGGAGGGACCAGTACCAGTACATTAGATATTA

TCTTTTATTACTATAATAATATTTTAATTAACACGAGACATAGGAATGTGAAGTGGTACCGGTAGGAGGGAGTTGGTTGAGTTTTT

TAGATACTAGGAGACAGAACCGGAGGGGCCCATTGCAAGGCCCAAGTTGAAGTCCAGCCGTGAATCAACAAAGAGAGGGCCCATAA

TACTGTCGATGAGCATTTCCCTATAATACAGTGTCCACAGTTGCCTTCCGCTAAGGGATAGCCACCCGCTATTCTCTTGACACGTG

TCACTGAAACCTGCTACAAATAAGGCAGGCACCTCCTCATTCTCACACTCACTCACTCACACAGCTCAAGAAGGATCCTCATATTC

TAGTTGTATGTTGTTCAGAGAAGACCACAGATGTGATCATATTCTCATTGTATCAGATCTGTGACCACTTACCTGATACCTCCCAT

GAAGTTACCTGTATGATTATACGTGATCCAAAGCCATCACATCATGTTCACCTTCAGCTATTGGAGGAGAAGTGAGAAGTAGGAAT

TGCAATATGAGGAATAATAAGAAAAACTTTGTAAAAGCTAAATTAGCTGGGTATGATATAGGGAGAAATGTGTAAACATTGTACTA

TATATAGTATATACACACGCATTATGTATTGCATTATGCACTGAATAATACCGCAGCATCAAAGAAGGAATTCAAGGTTAGAAATC

TTCTCTATTTTTGGTTTTTGTCTGTTTAGATTCTCGAATTAGCTAATCAGGTGCTGTTATAGCCCTTAATTTTGAGTTTTTTTCG

GTTGTTTTGATGGAAAAGGCCTAAAATTTGAGTTTTTTTACGTTGGTTTGATGGAAAAGGCCTACAATTGGAGTTTTCCCCGTTGT

TTTGATGAAAAAGCCCCTAGTTTGAGATTTTTTTTCTGTCGATTCGATTCTAAAGGTTTAAAATTAGAGTTTTTACATTTGTTTGA

TGAAAAAGGCCTTAAATTTGAGTTTTTCCGGTTGATTTGATGAAAAAGCCCTAGAATTTGTGTTTTTCGTCGGTTTGATTCTGAA

GGCCTAAAATTTGAGTTTCTCCGGCTGTTTTGATGAAAAAGCCCTAAATTTGAGTTTCTCCGGCTGTTTTGATGAAAAAGCCCTAA

ATTTGAGTTTTTTCCCCGTGTTTTAGATTGTTTGGTTTTAATTCTCGAATCAGCTAATCAGGGAGTGTGAAAAGCCCTAAAATTTG

AGTTTTTTTCGTTGTTCTGATTGTTGTTTTATGAATTTGCAGATGGATATCCTTCTTTGATGCTGCGGTATTATTCAGTGCATAA

TGGAATAGATAATGGGTGTGTATATAGTATATATAGTAGAATGTTTAGAGATTTGTGGGTATATGATAGGGAGGTAATTTAGGTTT

TAGAAAGTTTTTGTTATTATTGGTGATATTGGAATTGGTAGTTGTGAGTTGTGGTGGAATAGGTGAAGGTGAAGATGATGTGATGG

GTTTGGATGAGGTATAATGATAGAGGTAAGTTGATGGGAGGTATGAGGTAAGTGGTGAGAGATGTGATAGAATGAGAATATGATGA

GATGTGTGGTGTTGTGTGAAGAAGATAGAAGTAGAATATGAAAGGTTTTGATTTTAATGTTTAGGAAATGTGGTATGAGTTTTGTG

TTTTTGTGGAAGGGTAATTTAGAGTTTTTTTGGTATATGGATTTTGGTTTTGATGTATGTGAGAAGGGTGGGGATTGTTGATTT

ATTTGAAAAGTAAGAGTTTTTGCTTATTGTTGTGGTGTATTTTGGATATGAATGTTAGTTTTATATGTTTTGTAGTTGTGTAGGTG

TTAAATGTTGAAGAGACTAGGAATTTGGCTGGAGGGTATGGATTATGGAAGTATGAAGTGTGTGGGATGGATAAATATGGTTGTGA

GGAATTTGAGATTTTAGAGTGTTTATGGTGATTGGGTTGAGTATAATATAGTAAAAAAATAGTGTAGA

SEQ ID NO: 15
GGTAGGGAAGGATGGATGTCAATGTTAATAGTAAAAAATGGAAGAAAATTGTAGTGGAGGGAGGAGTAGGAGTAGATTAGATATTA

TGTTTTATTAGTATAATAATATTTTAATTAAGAGGAGAGATAGGAATGTGAAGTGGTAGGGGTAGGAGGGAGTTGGTTGAGTTTTT

TAGATAGTAGGAGAGAGAAGGGGAGGGGGGATTGGAAGGGGAAGTTGAAGTGGAGGGGTGAATGAAGAAAGAGAGGGGGGATAA

TAGTGTGGATGAGGATTTGGGTATAATAGAGTGTGGAGAGTTGGGTTGGGGTAAGGGATAGGGAGCGGGTATTGTGTTGAGAGGTG

TGAGTGAAAGGTGGTAGAAATAAGGGAGGGAGGTGGTGATTGTGAGAGTGAGTGAGTGAGAGAGGTGAAGAAGGATGGTGATATTG

TAGTTGTATGTTGTTGAGAGAAGAGGAGAGATGTGATGATATTGTGATTGTATGAGATGTGTGAGGAGTTAGGTGATAGGTGGGAT
```

-continued

GAAGTTAGGTGTATGATTATAGGTGATGGAAAGGGATGAGATGATGTTGAGGTTGAGGTATTGGAGGAGAAGTGAGAAGTAGGAAT
TGGAATATGAGGAATAATAAGAAAAAGTTTGTAAAAGGTAAATTAGGTGGGTATGATATAGGGAGAAATGTGTAAAGATTGTAGTA
TATATAGTATATAGAGAGGGATTATGTATTGGATTATGGAGTGAATAATAGGGGAGGATGAAAGAAGGAATTGGTGGTAAGTTTTA
GTGATGTGGTGGAATTATTTGTGATTTGATGGATGTTTGGGTAGATTGTATTATGAATGGTGTTATGGTGTATAAAGGTTGTTTGA
TATGTGATGTGATGTATTGTGATTTTGATTGTGTTGCGTAGTGAATTTGAGGGTAGTGTAATGGGTGATAAATGTGAATGGTTGGT
GTTGTTGTTGTTGTGAGAAATGAATTTGTGTTTTGTTTTTGTTGATGTGTAGGTTGATATGGTTGTTTGATGGTGGGGTATTA
TTGAGTGGATAATGGAATAGATAATGGGTGTGTATATAGTATATATAGTAGAATGTTTAGAGATTTGTGGGTATATGATAGGGAGG
TAATTTAGGTTTTAGAAAGTTTTTGTTATTATTGGTGATATTGGAATTGGTAGTTGTGAGTTGTGGTGGAATAGGTGAAGGTGAAG
ATGATGTGATGGCTTTGGATGAGGTATAATCATACAGGTAAGTTCATGGGAGGTATCAGGTAAGTGGTGAGAGATCTGATAGAATG
AGAATATGATGAGATGTGTGGTCTTCTGTGAACAACATAGAACTAGAATATGAAAGGTTTTGATTTTAATGTTTAGGAAATGTCGT
ATGAGTTTTGTGTTTTTGTGGAAGGGTAATTTAGAGTTTTTTTTGCTATATGGATTTTCGTTTTTGATGTATGTGAGAAGGGTCGG
GATTGTTGATTTATTTGAAAAGTAAGAGTTTTTGGTTATTGTTGTGGTGTATTTTGGATATGAATGTTAGTTTTATATGTTTTGTA
GTTGTGTAGGTGTTAAATGTTGAAGAGAGTAGGAATTTGGGTGGAGGGTATGGATTATGGAAGTATGAAGTGTGTGGGATGGATAA
ATATGGTTGTGAGGAATTTGAGATTTTAGAGTGTTTATGGTGATTGGGTTGAGTATAATATAGTAAAAAAATAGTGTAGA

SEQ ID NO: 16
TCATATTGTAGTTGTATGTTGTTGAGAGAAGACCACAGATGTGATGATATTGTGATTGTATCAGATGTGTGAGGACTTACCTGATA
GCTGGGATGAAGTTAGGTGTATGATTATAGGTGATGGAAAGGGATGAGATGATGTTGAGGTTGAGGTATTGGAGGAGAAGTGAGAA
GTAGGAATTGGAATATGAGGAATAATAAGAAAAAGTTTGTAAAAGGTAAATTAGGTGGGTATGATATAGGGAGAAATGTGTAAAGA
TTGTAGTATATATAGTATATAGAGAGGGATTATGTATTGGATTATGGAGTGAATAATAGGGGAGGATGAAAGAAG

SEQ ID NO: 17
GGTAGGGAACGATGCATCTCAATCTTAATACTAAAAAATGGAAGAAAATTCTAGTGGAGGGAGGAGTACCAGTACATTAGATATTA
TGTTTTATTAGTATAATAATATTTTAATTAAGAGGAGAGATAGGAATGTGAAGTGGTAGGGGTAGGAGGGAGTTGGTTGAGTTTTT
TAGATACTAGGAGACAGAACCGGAGGGGCCCATTGGAAGGGCGAAGTTGAAGTCGAGGGGTGAATGAACAAAGAGAGGGGCCATAA
TAGTGTGGATGAGGATTTGGGTATAATAGAGTGTGGAGAGTTGGGTTGGGGTAAGGGATAGGGAGGGGGTATTGTGTTGAGAGGTG
TCAGTGAAAGGTGCTAGAAATAAGGCAGGCACCTCGTCATTGTGACACTCACTGACTGACAGAGGTGAAGAAGGATCCTCATATTG
TAGTTGTATGTTGTTCAGAGAAGACCACAGATGTGATGATATTCTCATTGTATGAGATGTGTGAGGAGTTACGTGATACGTGGGAT
GAAGTTAGGTGTATGATTATAGGTGATGGAAAGGGATGAGATGATGTTGAGGTTGAGGTATTGGAGGAGAAGTGAGAAGTAGGAAT
TGGAATATGAGGAATAATAAGAAAAAGTTTGTAAAAGGTAAATTAGGTGGGTATGATATAGGGAGAAATGTGTAAAGATTGTAGTA
TATATAGTATATAGAGAGGGATTATGTATTGGATTATGGAGTGAATAATAGGGGAGGATGAAAGAAGGAATTGAAGGTTAGAAATG
TTGTGTATTTTGGTTTTTGTGTGTTTAGATTGTGGAATTAGGTAATGAGGTGGTGTTATAGGGGTTAATTTTGAGTTTTTTTGG
GTTGTTTTGATGGAAAAGGGGTAAATTTGAGTTTTTTTAGGTTGGTTTGATGGAAAAGGGGTAGAATTGGAGTTTTGGGGGTTGT
TTTGATGAAAAAGGGGGTAGTTTGAGATTTTTTTGTGTGGATTGGATTGTAAAGGTTTAAAATTAGAGTTTTTAGATTTGTTTGA
TGAAAAAGGGGTTAAATTTGAGTTTTTGGGGTTGATTTGATGAAAAGGGGTAGAATTTGTGTTTTTGGTGGGTTTGATTGTGAA
GGGGTAAATTTGAGTTTGTGGGGGTGTTTTGATGAAAAGGGGTAAATTTGAGTTTGTGGGGTGTTTTGATGAAAAGGGGTAA
ATTTGAGTTTTTTCCCCGTGTTTTAGATTGTTTGGTTTTAATTCTCGAATCAGCTAATCAGGGAGTGTGAAAAGCCCTAAAATTTG
AGTTTTTTTCGTTGTTCTGATTGTTGTTTTTATGAATTTGCAGATGGATATCCTTCTTTGATGCTGCGGTATTATTCAGTGCATAA
TGCAATACATAATGCGTGTGTATATACTATATATAGTACAATGTTTACACATTTCTCCCTATATCATACCCAGCTAATTTAGCTTT
TACAAAGTTTTTCTTATTATTCCTCATATTGCAATTCCTACTTCTCACTTCTCCTCCAATAGCTGAAGGTGAACATGATGTGATGG
CTTTGGATCACGTATAATCATACAGGTAACTTCATGGGAGGTATCAGGTAAGTGGTCACAGATCTGATACAATGAGAATATGATCA
CATCTGTGGTCTTCTCTGAACAACATACAACTAGAATATGAAAGCTTTTGATTTAATGTTTAGCAAATGTCCTATCAGTTTTCTC
TTTTTGTCGAACGGTAATTTAGAGTTTTTTTTGCTATATGGATTTTCGTTTTTGATGTATGTGACAACCCTCGGGATTGTTGATTT

-continued

ATTTCAAAACTAAGAGTTTTTGCTTATTGTTCTCGTCTATTTTGGATATCAATCTTAGTTTTATATCTTTTCTAGTTCTCTACGTG

TTAAATGTTCAACACACTAGCAATTTGGCTGCAGCGTATGGATTATGGAACTATCAAGTCTGTGGGATCGATAAATATGCTTCTCA

GGAATTTGAGATTTTACAGTCTTTATGCTCATTGGGTTGAGTATAATATAGTAAAAAAATAGTCTAGA

SEQ ID NO: 18
GGTACCGAACCATGCATCTCAATCTTAATACTAAAAAATGCAACAAAATTCTAGTGGAGGGACCAGTACCAGTACATTAGATATTA

TCTTTTATTACTATAATAATATTTTAATTAACACGAGACATAGGAATGTCAAGTGGTAGCGGTAGGAGGGAGTTGGTTCAGTTTTT

TAGATACTAGGAGACAGAACCGGAGGGGCCCATTGCAAGGCCCAAGTTGAAGTCCAGCCGTGAATCAACAAAGAGAGGGCCCATAA

TACTGTCGATGAGCATTTCCCTATAATACAGTGTCCACAGTTGCCTTCCGCTAAGGGATAGCCACCCGCTATTCTCTTGACACGTG

TCACTGAAACCTGCTACAAATAAGGCAGGCACCTCCTCATTCTCACACTCACTCACTCACACAGCTCAAGAAGGATCCTCATATTC

TAGTTGTATGTTGTTCAGAGAAGACCACAGATGTGATCATATTCTCATTGTATCAGATCTGTGACCACTTACCTGATACCTCCCAT

GAAGTTACCTGTATGATTATACGTGATCCAAAGCCATCACATCATGTTCACCTTCAGCTATTGGAGGAGAAGTGAGAAGTAGGAAT

TGCAATATGAGGAATAATAAGAAAAACTTTGTAAAAGCTAAATTAGCTGGGTATGATATAGGGAGAAATGTGTAAACATTGTACTA

TATATAGTATATACACACGCATTATGTATTGCATTATGCACTGAATAATACCGCAGCATCAAAGAAGGAATTCGTGGTAACTTTTA

CTCATCTCCTCCAATTATTTCTGATTTCATGCATGTTTCCCTACATTCTATTATGAATCGTGTTATGGTGTATAAACGTTGTTTCA

TATCTCATCTCATCTATTCTGATTTTGATTCTCTTGCCTACTGAATTTGACCCTACTGTAATCGGTGATAAATGTGAATGCTTCCT

CTTCTTCTTCTTCTCAGAAATCAATTTCTGTTTTGTTTTTGTTCATCTGTAGCTTGATATCCTTCTTTGATGCTGCGGTATTA

TTCAGTGCATAATGCAATACATAATGCGTGTGTATATACTATATATAGTACAATGTTTACACATTTCTCCCTATATCATACCCAGC

TAATTTAGCTTTTACAAAGTTTTTCTTATTATTCCTCATATTGCAATTCCTACTTCTCACTTCTCCTCCAATAGCTGAAGGTGAAC

ATGATGTGATGGCTTTGGATCACGTATAATCATACAGGTAACTTCATGGGAGGTATCAGGTAAGTGGTCACAGATCTGATACAATG

AGAATATGATCACATCTGTGGTCTTCTCTGAACAACATACAACTAGAATATGAAAGCTTTTGATTTTAATGTTTAGCAAATCTCCT

ATCAGTTTTCTCTTTTTGTCGAACGGTAATTTAGAGTTTTTTTGCTATATGGATTTTCGTTTTGATGTATGTGACAACCCTCGG

GATTGTTGATTTATTTCAAAACTAAGAGTTTTTGCTTATTGTTCTCGTCTATTTTGGATATCAATCTTAGTTTTATATCTTTTCTA

GTTCTCTACGTGTTAAATGTTCAACACACTAGCAATTTGGCTGCAGCGTATGGATTATGGAACTATCAAGTCTGTGGGATCGATAA

ATATGCTTCTCAGGAATTTGAGATTTTACAGTCTTTATGCTCATTGGGTTGAGTATAATATAGTAAAAAAATAGTCTAGA

SEQ ID NO: 19
GGTACCGAACCATGCATCTCAATCTTAATACTAAAAAATGCAACAAAATTCTAGTGGAGGGACCAGTACCAGTACATTAGATATTA

TCTTTTATTACTATAATAATATTTTAATTAACACGAGACATAGGAATGTCAAGTGGTAGCGGTAGGAGGGAGTTGGTTCAGTTTTT

TAGATACTAGGAGACAGAACCGGAGGGGCCCATTGCAAGGCCCAAGTTGAAGTCCAGCCGTGAATCAACAAAGAGAGGGCCCATAA

TACTGTCGATGAGCATTTCCCTATAATACAGTGTCCACAGTTGCCTTCCGCTAAGGGATAGCCACCCGCTATTCTCTTGACACGTG

TCACTGAAACCTGCTACAAATAAGGCAGGCACCTCCTCATTCTCACACTCACTCACTCACACAGCTCAACAAGTGGTAACTTTTAC

TCATCTCCTCCAATTATTTCTGATTTCATGCATGTTTCCCTACATTCTATTATGAATCGTGTTATGGTGTATAAACGTTGTTTCAT

ATCTCATCTCATCTATTCTGATTTTGATTCTCTTGCCTACTGAATTTGACCCTACTGTAATCGGTGATAAATGTGAATGCTTCCTC

TTCTTCTTCTTCTCAGAAATCAATTTCTGTTTTGTTTTTGTTCATCTGTAGCTTGGTAGATTCCCCTTTTTGTAGACCACACA

TCACGGATCCTCATATTCTAGTTGTATGTTGTTCAGAGAAGACCACAGATGTGATCATATTCTCATTGTATCAGATCTGTGACCAC

TTACCTGATACCTCCCATGAAGTTACCTGTATGATTATACGTGATCCAAAGCCATCACATCATGTTCACCTTCAGCTATTGGAGGA

GAAGTGAGAAGTAGGAATTGCAATATGAGGAATAATAAGAAAAACTTTGTAAAAGCTAAATTAGCTGGGTATGATATAGGGAGAAA

TGTGTAAACATTGTACTATATATAGTATATACACACGCATTATGTATTGCATTATGCACTGAATAATACCGCAGCATCAAAGAAGG

AATTCAAGGTTAGAAATCTTCTCTATTTTGGTTTTTGTCTGTTTAGATTCTCGAATTAGCTAATCAGGTGCTCTTATAGCCCTTA

ATTTTGAGTTTTTTTTCGGTTGTTTTGATGGAAAAGGCCTAAAATTTGAGTTTTTTACGTTGGTTTGATGGAAAAGGCCTACAAT

TGGAGTTTTCCCCGTTGTTTTGATGAAAAAGCCCCTAGTTTGAGATTTTTTTCTGTCGATTCGATTCTAAAGGTTTAAAATTAGA

GTTTTTACATTTGTTTGATGAAAAAGGCCTTAAATTTGAGTTTTTCCGGTTGATTTGATGAAAAAGCCCTAGAATTTGTGTTTTTT

-continued

CGTCGGTTTGATTCTGAAGGCCTAAAATTTGAGTTTCTCCGGCTGTTTTGATGAAAAGCCCTAAATTTGAGTTTCTCCGGCTGTT

TTGATGAAAAGCCCTAAATTTGAGTTTTTTCCCCGTGTTTTAGATTGTTTGGTTTTAATTCTCGAATCAGCTAATCAGGGAGTGT

GAAAAGCCCTAAAATTTGAGTTTTTTTCGTTGTTCTGATTGTTGTTTTTATGAATTTGCAGATGGATATCCTTCTTTGATGCTGCG

GTATTATTCAGTGCATAATGCAATACATAATGCGTGTGTATATACTATATATAGTACAATGTTTACACATTTCTCCCTATATCATA

CCCAGCTAATTTAGCTTTTACAAAGTTTTTCTTATTATTCCTCATATTGCAATTCCTACTTCTCACTTCTCCTCCAATAGCTCAAG

GTGAACATGATGTGATGGCTTTGGATCACGTATAATCATACAGGTAACTTCATGGGAGGTATCAGGTAAGTGGTCACAGATCTGAT

ACAATGAGAATATGATCACATCTGTGGTCTTCTCTGAACAACATACAACTAGAATATGAAAGCTTTTGATTTTAATGTTTAGCAAA

TGTCCTATCAGTTTTCTCTTTTTGTCGAACGGTAATTTAGAGTTTTTTTGCTATATGGATTTTCGTTTTTGATGTATGTGACAAC

CCTCGGGATTGTTGATTTATTTCAAAACTAAGAGTTTTTGCTTATTGTTCTCGTCTATTTTGGATATCAATCTTAGTTTTATATCT

TTTCTAGTTCTCTACGTGTTAAATGTTCAACACACTAGCAATTTGGCTGCAGCGTATGGATTATGGAACTATCAAGTCTGTGGGAT

CGATAAATATGCTTCTCAGGAATTTGAGATTTTACAGTCTTTATGCTCATTGGGTTGAGTATAATATAGTAAAAAATAGTCTAGA

SEQ ID NO: 20
GGTACCGAACCATGCATCTCAATCTTAATACTAAAAAATGCAACAAAATTCTAGTGGAGGGACCAGTACCAGTACATTAGATATTA

TCTTTTATTACTATAATAATATTTTAATTAACACGAGACATAGGAATGTCAAGTGGTAGCGGTAGGAGGGAGTTGGTTCAGTTTTT

TAGATACTAGGAGACAGAACCGGAGGGGCCCATTGCAAGGCCCAAGTTGAAGTCCAGCCGTGAATCAACAAAGAGAGGGCCCATAA

TACTGTCGATGAGCATTTCCCTATAATACAGTGTCCACAGTTGCCTTCCGCTAAGGGATAGCCACCCGCTATTCTCTTGACACGTG

TCACTGAAACCTGCTACAAATAAGGCAGGCACCTCCTCATTCTCACACTCACTCACTCACACAGCTCAAGAAGGATCCTCATATTC

TAGTTGTATGTTGTTCAGAGAAGACCACAGATGTGATCATATTCTCATTGTATCAGATCTGTGACCACTTACCTGATACCTCCCAT

GAAGTTACCTGTATGATTATACGTGATCCAAAGCCATCACATCATGTTCACCTTCAGCTATTGGAGGAGAAGTGAGAAGTAGGAAT

TGCAATATGAGGAATAATAAGAAAAACTTTGTAAAAGCTAAATTAGCTGGGTATGATATAGGGAGAAATGTGTAAACATTGTACTA

TATATAGTATATACACACGCATTATGTATTGCATTATGCACTGAATAATACCGCAGCATCAAAGAAGGAATTCGTGGTAACTTTTA

CTCATCTCCTCCAATTATTTCTGATTTCATGCATGTTTCCCTACATTCTATTATGAATCGTGTTATGGTGTATAAACGTTGTTTCA

TATCTCATCTCATCTATTCTGATTTTGATTCTCTTGCCTACTGAATTTGACCCTACTGTAATCGGTGATAAATGTGAATGCTTCCT

CTTCTTCTTCTTCTTCTCAGAAATCAATTTCTGTTTTGTTTTTGTTCATCTGTAGCTTGATATCCTTCTTTGATGCTGCGGTATTA

TTCAGTGCATAATGCAATACATAATGCGTGTGTATATACTATATATAGTACAATGTTTACACATTTCTCCCTATATCATACCCAGC

TAATTTAGCTTTTACAAAGTTTTTCTTATTATTCCTCATATTGCAATTCCTACTTCTCACTTCTCCTCCAATAGCTGAAGGTGAAC

ATGATGTGATGGCTTTGGATCACGTATAATCATACAGGTAACTTCATGGGAGGTATCAGGTAAGTGGTCACAGATCTGATACAATG

AGAATATGATCACATCTGTGGTCTTCTCTGAACAACATACAACTAGAATATGAAAGCTTTTGATTTAATGTTTAGCAAATGTCCT

ATCAGTTTTCTCTTTTTGTCGAACGGTAATTTAGAGTTTTTTTGCTATATGGATTTTCGTTTTTGATGTATGTGACAACCCTCGG

GATTGTTGATTTATTTCAAAACTAAGAGTTTTTGCTTATTGTTCTCGTCTATTTTGGATATCAATCTTAGTTTTATATCTTTTCTA

GTTCTCTACGTGTTAAATGTTCAACACACTAGCAATTTGGCTGCAGCGTATGGATTATGAACTATCAAGTCTGTGGGATCGATAA

ATATGCTTCTCAGGAATTTGAGATTTTACAGTCTTTATGCTCATTGGGTTGAGTATAATATAGTAAAAAATAGTCTAGA

SEQ ID NO: 21
TTAGAGTGTGGGTAAGTAATTAAGTTAGGGATTTGTGGGAAATGGACAAATATAAGAGAGTGCAGGGGAGTAGTGCAGGAGATTTT

CGTGCTTTTATTGATAAATAAAAAAAGGGTGACATTTAATTTCCACAAGAGGACGCAACACAACACACTTAATTCCTGTGTGTGAA

TCAATAATTGACTTCTCCAATCTTCATCAATAAAATAATTCACAATCCTCACTCTCTTATCACTCTCATTCGAAAAGCTAGATTTG

CATAGAGAGCACAAA

SEQ ID NO: 22
GAGGGGGAAGTGAATGAAAAATAACAAAGGCACAGTAAGTAGTTTCTCTTTTTATCATGTGATGAAGGTATATAATGTATGTGTAA

GAGGATGATGTTATTACCACATAATAAGAGATGAAGAGTCTCATTTTCTGCTTAAAAAAACAATTCACTGGC

SEQ ID NO: 23
GGTACCGAACCATGCATCTCAATCTTAATACTAAAAAATGCAACAAAATTCTAGTGGAGGGACCAGTACCAGTACATTAGATATTA

```
TCTTTTATTAGTATAATAATATTTTAATTAACACGAGACATAGGAATGTCAAGTGGTAGCGGTAGGAGGGAGTTGGTTCAGTTTTT
TAGATACTAGGAGACAGAACCGGAGGGGCCCATTGCAAGGCCCAAGTTGAAGTCCAGCCGTGAATCAACAAAGAGAGGGCCCATAA
TACTGTCGATGAGCATTTCCCTATAATACAGTGTCCACAGTTGCCTTCCGCTAAGGGATAGCCACCCGCTATTCTCTTGACACGTG
TCACTGAAACCTGCTACAAATAAGGCAGGCACCTCCTCATTCTCACACTCACTCACTCACACAGCTCAAGAAGGATCCGAGTGTGG
GTAAGTAATTAAGTTAGGGATTTGTGGGAAATGGACAAATATAAGAGAGTGCAGGGGAGTAGTGCAGGAGATTTTCGTGCTTTTAT
TGATAAATAAAAAAAGGGTGACATTTAATTTCCACAAGAGGACGCAACACAACACACTTAATTCCTGTGTGTGAATCAATAATTGA
CTTCTCCAATCTTCATCAATAAAATAATTCACAATCCTCACTCTCTTATCACTCTCATTCGAAAAGCTAGATTTGCATAGAGAGCA
CAGAATTCAAGGTTAGAAATCTTCTCTATTTTTGGTTTTTGTCTGTTTAGATTCTCGAATTAGCTAATCAGGTGCTGTTATAGCCC
TTAATTTTGAGTTTTTTTCGGTTGTTTTGATGGAAAAGGCCTAAAATTTGAGTTTTTTTACGTTGGTTTGATGGAAAAGGCCTAC
AATTGGAGTTTTCCCCGTTGTTTTGATGAAAAAGCCCCTAGTTTGAGATTTTTTTCTGTCGATTCGATTCTAAAGGTTTAAAATT
AGAGTTTTTACATTTGTTTGATGAAAAAGGCCTTAAATTTGAGTTTTTCCGGTTGATTTGATGAAAAAGCCCTAGAATTTGTGTTT
TTTCGTCGGTTTGATTCTGAAGGCCTAAAATTTGAGTTTCTCCGGCTGTTTTGATGAAAAAGCCCTAAATTTGAGTTTCTCCGGCT
GTTTTGATGAAAAAGCCCTAAATTTGAGTTTTTTCCCCGTGTTTTAGATTGTTTGGTTTTAATTCTCGAATCAGCTAATCAGGGAG
TGTGAAAAGCCCTAAAATTTGAGTTTTTTTCGTTGTTCTGATTGTTGTTTTTATGAATTTGCAGATGGATATCTGTGCTCTCTATG
CAAATCTAGCTTTTCGAATGAGAGTGATAAGAGAGTGAGGATTGTGAATTATTTTATTGATGAAGATTGGAGAAGTCAATTATTGA
TTCACACACAGGAATTAAGTGTGTTGTGTTGCGTCCTCTTGTGGAAATTAAATGTCACCCTTTTTTTATTTATCAATAAAAGCACG
AAAATCTCCTGCACTACTCCCCTGCACTCTCTTATATTTGTCCATTTCCCACAAATCCCTAACTTAATTACTTACCCACACTCTAA
GCTTTTGATTTAATGTTTAGCAAATGTCCTATCAGTTTTCTCTTTTTGTCGAACGGTAATTTAGAGTTTTTTTGCTATATGGAT
TTTCGTTTTTGATGTATGTGACAACCCTCGGGATTGTTGATTTATTTCAAAACTAAGAGTTTTTGCTTATTGTTCTCGTCTATTTT
GGATATCAATCTTAGTTTTATATCTTTTCTAGTTCTCTACGTGTTAAATGTTCAACACACTAGCAATTTGGCTGCAGCGTATGGAT
TATGGAACTATCAAGTCTGTGGGATCGATAAATATGCTTCTCAGGAATTTGAGATTTTACAGTCTTTATGCTCATTGGGTTGAGTA
TAATATAGTAAAAAAATAGTCTAGA
```

SEQ ID NO: 24
```
GGTACCGAACCATGCATCTCAATCTTAATACTAAAAAATGCAACAAAATTCTAGTGGAGGGACCAGTACCAGTACATTAGATATTA
TCTTTTATTACTATAATAATATTTTAATTAACACGAGACATAGGAATGTCAAGTGGTAGCGGTAGGAGGGAGTTGGTTCAGTTTTT
TAGATACTAGGAGACAGAACCGGAGGGGCCCATTGCAAGGCCCAAGTTGAAGTCCAGCCGTGAATCAACAAAGAGAGGGCCCATAA
TACTGTCGATGAGCATTTCCCTATAATACAGTGTCCACAGTTGCCTTCCGCTAAGGGATAGCCACCCGCTATTCTCTTGACACGTG
TCACTGAAACCTGCTACAAATAAGGCAGGCACCTCCTCATTCTCACACTCACTCACTCACACAGCTCAAGAAGGATCCGAGTGTGG
GTAAGTAATTAAGTTAGGGATTTGTGGGAAATGGACAAATATAAGAGAGTGCAGGGGAGTAGTGCAGGAGATTTTCGTGCTTTTAT
TGATAAATAAAAAAAGGGTGACATTTAATTTCCACAAGAGGACGCAACACAACACACTTAATTCCTGTGTGTGAATCAATAATTGA
CTTCTCCAATCTTCATCAATAAAATAATTCACAATCCTCACTCTCTTATCACTCTCATTCGAAAAGCTAGATTTGCATAGAGAGCA
CAGAATTCGTGGTAACTTTTACTCATCTCCTCCAATTATTTCTGATTTCATGCATGTTTCCCTACATTCTATTATGAATCGTGTTA
TGGTGTATAAACGTTGTTTCATATCTCATCTCATCTATTCTGATTTTGATTCTCTTGCCTACTGAATTTGACCCTACTGTAATCGG
TGATAAATGTGAATGCTTCCTCTTCTTCTTCTTCTCAGAAATCAATTTCTGTTTTGTTTTGTTCATCTGTAGCTTGATATCT
GTGCTCTCTATGCAAATCTAGCTTTTCGAATGAGAGTGATAAGAGAGTGAGGATTGTGAATTATTTTATTGATGAAGATTGGAGAA
GTCAATTATTGATTCACACACAGGAATTAAGTGTGTTGTGTTGCGTCCTCTTGTGGAAATTAAATGTCACCCTTTTTTTATTTATC
AATAAAAGCACGAAAATCTCCTGCACTACTCCCCTGCACTCTCTTATATTTGTCCATTTCCCACAAATCCCTAACTTAATTACTTA
CCCACACTCTAAGCTTTTGATTTAATGTTTAGCAAATGTCCTATCAGTTTTCTCTTTTTGTCGAACGGTAATTTAGAGTTTTTTT
TGCTATATGGATTTTCGTTTTTGATGTATGTGACAACCCTCGGGATTGTTGATTTATTTCAAAACTAAGAGTTTTTGCTTATTGTT
CTCGTCTATTTTGGATATCAATCTTAGTTTTATATCTTTTCTAGTTCTCTACGTGTTAAATGTTCAACACACTAGCAATTTGGCTG
```

-continued

CAGCGTATGGATTATGGAACTATCAAGTCTGTGGGATCGATAAATATGCTTCTCAGGAATTTGAGATTTTACAGTCTTTATGCTCA

TTGGGTTGAGTATAATATAGTAAAAAAATAGTCTAGA

SEQ ID NO: 25
GGTACCGAACCATGCATCTCAATCTTAATACTAAAAAATGCAACAAAATTCTAGTGGAGGGACCAGTACCAGTACATTAGATATTA

TCTTTTATTACTATAATAATATTTTAATTAACACGAGACATAGGAATGTCAAGTGGTAGCGGTAGGAGGGAGTTGGTTCAGTTTTT

TAGATACTAGGAGACAGAACCGGAGGGGCCCATTGCAAGGCCCAAGTTGAAGTCCAGCCGTGAATCAACAAAGAGAGGGCCCATAA

TACTGTCGATGAGCATTTCCCTATAATACAGTGTCCACAGTTGCCTTCCGCTAAGGGATAGCCACCCGCTATTCTCTTGACACGTG

TCACTGAAACCTGCTACAAATAAGGCAGGCACCTCCTCATTCTCACACTCACTCACTCACACAGCTCAACAAGTGGTAACTTTTAC

TCATCTCCTCCAATTATTTCTGATTTCATGCATGTTTCCCTACATTCTATTATGAATCGTGTTATGGTGTATAAACGTTGTTTCAT

ATCTCATCTCATCTATTCTGATTTTGATTCTCTTGCCTACTGAATTTGACCCTACTGTAATCGGTGATAAATGTGAATGCTTCCTC

TTCTTCTTCTTCTTCTCAGAAATCAATTTCTGTTTTGTTTTGTTCATCTGTAGCTTGGTAGATTCCCCTTTTTGTAGACCACACA

TCACGGATCCGAGTGTGGGTAAGTAATTAAGTTAGGGATTTGTGGGAAATGGACAAATATAAGAGAGTGCAGGGGAGTAGTGCAGG

AGATTTTCGTGCTTTTATTGATAAATAAAAAAAGGGTGACATTTAATTTCCACAAGAGGACGCAACACAACACACTTAATTCCTGT

GTGTGAATCAATAATTGACTTCTCCAATCTTCATCAATAAAATAATTCACAATCCTCACTCTCTTATCACTCTCATTCGAAAAGCT

AGATTTGCATAGAGAGCACAGAATTCAAGGTTAGAAATCTTCTCTATTTTTGGTTTTTGTCGTTTAGATTCTCGAATTAGCTAAT

CAGGTGCTGTTATAGCCCTTAATTTTGAGTTTTTTTTCGGTTGTTTTGATGGAAAAGGCCTAAAATTTGAGTTTTTTTACGTTGGT

TTGATGGAAAAGGCCTACAATTGGAGTTTTCCCCGTTGTTTTGATGAAAAAGCCCCTAGTTTGAGATTTTTTTCTGTCGATTCGA

TTCTAAAGGTTTAAAATTAGAGTTTTTACATTTGTTTGATGAAAAACGCCTTAAATTTGAGTTTTTCCGGTTGATTTGATGAAAA

GCCCTAGAATTTGTGTTTTTCGTCGGTTTGATTCTGAAGGCCTAAAATTTGAGTTTCTCCGGCTGTTTTGATGAAAAAGCCCTAA

ATTTGAGTTTCTCCGGCTCTTTTGATGAAAAAGCCCTAAATTTGAGTTTTTTCCCCGTGTTTTAGATTGTTTGGTTTTAATTCTCG

AATCAGCTAATCAGGGAGTGTGAAAAGCCCTAAAATTTGAGTTTTTTTCGTTGTTCTGATTGTTGTTTTATGAATTTGCAGATCG

ATATCTGTGCTCTCTATGCAAATCTAGCTTTTCGAATGAGAGTGATAAGAGAGTGAGGATTGTGAATTATTTTATTGATGAAGATT

GGAGAAGTCAATTATTGATTCACACACAGGAATTAAGTGTGTTGTGTTGCGTCCTCTTGTGGAAATTAAATGTCACCCTTTTTTA

TTTATCAATAAAAGCACGAAAATCTCCTGCACTACTCCCCTGCACTCTCTTATATTTGTCCATTTCCCACAAATCCCTAACTTAAT

TACTTACCCACACTCTAAGCTTTTGATTTTAATGTTTAGCAAATGTCCTATCAGTTTTCTCTTTTTGTCGAACGGTAATTTAGAGT

TTTTTTTGCTATATGGATTTTCGTTTTTGATGTATGTGACAACCCTCGGGATTGTTGATTTATTTCAAAACTAAGAGTTTTTGCTT

ATTGTTCTCGTCTATTTTGGATATCAATCTTAGTTTTATATCTTTTCTAGTTCTCTACGTGTTAAATGTTCAACACACTAGCAATT

TGGCTGCAGCGTATGGATTATGGAACTATCAAGTCTGTGGGATCGATAAATATGCTTCTCAGGAATTTGAGATTTTACAGTCTTTA

TGCTCATTGGGTTGAGTATAATATAGTAAAAAAATAGTCTAGA

SEQ ID NO: 26
GGTACCGAACCATGCATCTCAATCTTAATACTAAAAAATGCAACAAAATTCTAGTGGAGGGACCAGTACCAGTACATTAGATATTA

TCTTTTATTACTATAATAATATTTTAATTAACACGAGACATAGGAATGTCAAGTGGTAGCGGTAGGAGGGAGTTGGTTCAGTTTTT

TAGATACTAGGAGACAGAACCGGAGGGGCCCATTGCAAGGCCCAAGTTGAAGTCCAGCCGTGAATCAACAAAGAGAGGGCCCATAA

TACTGTCGATGAGCATTTCCCTATAATACAGTGTCCACAGTTGCCTTCCGCTAAGGGATAGCCACCCGCTATTCTCTTGACACGTG

TCACTGAAACCTGCTACAAATAAGGCAGGCACCTCCTCATTCTCACACTCACTCACTCACACAGCTCAACAAGTGGTAACTTTTAC

TCATCTCCTCCAATTATTTCTGATTTCATGCATGTTTCCCTACATTCTATTATGAATCGTGTTATGGTGTATAAACGTTGTTTCAT

ATCTCATCTCATCTATTCTGATTTTGATTCTCTTGCCTACTGAATTTGACCCTACTGTAATCGGTGATAAATGTGAATGCTTCCTC

TTCTTCTTCTTCTTCTCAGAAATCAATTTCTGTTTTGTTTTGTTCATCTGTAGCTTGGTAGATTCCCCTTTTTGTAGACCACACA

TCACGGATCCGAGTGTGGGTAAGTAATTAAGTTAGGGATTTGTGGGAAATGGACAAATATAAGAGAGTGCAGGGGAGTAGTGCAGG

AGATTTTCGTGCTTTTATTGATAAATAAAAAAAGGGTGACATTTAATTTCCACAAGAGGACGCAACACAACACACTTAATTCCTGT

GTGTGAATCAATAATTGACTTCTCCAATCTTCATCAATAAAATAATTCACAATCCTCACTCTCTTATCACTCTCATTCGAAAAGCT

-continued

AGATTTGCATAGAGAGCACAGAATTCGTGGTAACTTTTACTCATCTCCTCCAATTATTTCTGATTTCATGCATGTTTCCCTACATT
CTATTATGAATCGTGTTATGGTGTATAAACGTTGTTTCATATCTCATCTCATCTATTCTGATTTTGATTCTCTTGCCTACTGAATT
TGACCCTACTGTAATCGGTGATAAATGTGAATGCTTCCTCTTCTTCTTCTTCTCAGAAATCAATTTCTGTTTTGTTTTTGTTC
ATCTGTAGCTTGATATCTGTGCTCTCTATGCAAATCTAGCTTTTCGAATGAGAGTGATAAGAGAGTGAGGATTGTGAATTATTTTA
TTGATGAAGATTGGAGAAGTCAATTATTGATTCACACACAGGAATTAAGTGTGTTGTGTTGCGTCCTCTTGTGGAAATTAAATGTC
ACCCTTTTTTATTTATCAATAAAAGCACGAAAATCTCCTGCACTACTCCCCTGCACTCTCTTATATTTGTCCATTTCCCACAAAT
CCCTAACTTAATTACTTACCCACACTCTAAGCTTTTGATTTTAATGTTTAGCAAATGTCCTATCAGTTTTCTCTTTTGTCGAACG
GTAATTTAGAGTTTTTTTTGCTATATGGATTTTCGTTTTTGATGTATGTGACAACCCTCGGGATTGTGATTTATTTCAAAACTAA
GAGTTTTTGCTTATTGTTCTCGTCTATTTTGGATATCAATCTTAGTTTTATATCTTTTCTAGTTCTCTACGTGTTAAATGTTCAAC
ACACTAGCAATTTGGCTGCAGCGTATGGATTATGGAACTATCAAGTCTGTGGGATCGATAAATATGCTTCTCAGGAATTTGAGATT
TTACAGTCTTTATGCTCATTGGGTTGAGTATAATATAGTAAAAAAATAGTCTAGA
SEQ ID NO: 27
ATGGCAAGCTTGTGCAATAGTAGTAGTACATCTCTCAAAACTCCTTTTACTTCTTCCTCCACTTCTTTATCTTCCACTCCTAAGCC
CTCTCAACTTTTCATCCATGGAAAACGTAACCAAATGTTCAAAGTTTCATGCAAGGTTATCAATAATAACGGTGACCAAAACGTTG
AAACGAATTCTGTTGATCGAAGAAATGTTCTTCTTGGCTTAGGTGGTCTTTATGGTGTTGCTAATGCTATACCATTAGCTGCATCC
GCTGCTCCAACTCCACCTCCTGATCTCTCGTCTTGTAGTATAGCCAGGATTAACGAAAATCAGGTGGTGCCGTACAGTTGTTGCGC
GCCTAAGCCTGATGATATGGAGAAAGTTCCGTATTACAAGTTCCCTTCTATGACTAAGCTCCGTGTCCGTCAGCCTGCTCATGAAG
CTAATGAGGAGTATATTGCCAAGTACAATCTGGCGATTAGTCGAATGAGAGATCTTGATAAGACACAACCTTTAAACCCTATTGGT
TTTAAGCAACAAGCTAATATACATTGTGCTTATTGTAATGGTGCTTATAGAATTGGTGGCAAAGAGTTACAAGTTCATAATTCTTG
GCTTTTCTTCCCGTTCCATAGATGGTACTTGTACTTCCACGAGAGAATCGTGGGAAAATTCATTGATGATCCAACTTTCGCTTTGC
CATATTGGAATTGGGACCATCCAAAGGGTATGCGTTTTCCTGCCATGTATGATCGTGAAGGGACTTCCCTTTTCGATGTAACACGT
GACCAAAGTCACCGAAATGGAGCAGTAATCGATCTTGGTTTTTTCGGCAATGAAGTCGAAACAACTCAACTCCAGTTGATGAGCAA
TAATTTAACACTAATGTACCGTCAAATGGTAACTAATGCTCCATGTCCTCGGATGTTCTTTGGTGGGCCTTATGATCTCGGGATTA
ACACTGAACTCCCGGGAACTATAGAAAACATTCCTCACGGTCCTGTCCACATCTGGTCTGGTACAGTGAGAGGTTCAACTTTGCCC
AATGGTGCAATATCAAACGGTGAGAATATGGGTCATTTTTACTCAGCTGCTTTGGACCCGGTTTTCTTTTGCCATCACAGCAATGT
GGATCGGATGTGGAGCGAATGGAAAGCGACAGGAGGGAAAAGAACAGATATCACACATAAAGGTTGGTTGAACTCCGAGTTCTTTT
TCTATGATGAAAATGAAAACCCTTACCGTGTGAAAGTCCGAGACTGTTTGGACACGAAGAAGATGGGGTATGATTATGCACCAATG
GCCACCCCGTGGCGTAACTTCAAGCCAATAACAAAAACTACAGCTGGGAAAGTGAATACAGCTTCTCTTCCGCCAGCTAGCAATGT
ATTCCCAGTGGCTAAACTCGACAAAGCAATTTCGTTTTCCATCAATAGGCCGACTTCGTCAAGGACTCAACAAGAGAAAATGCAC
AAGAGGAGATGTTGACATTCAGTAGCATAAGATATGATAACAGAGGGTACATAAGGTTCGATGTGTTCCTGAACGTGGACAATAAT
GTGAATGCGAATGAGCTTGACAAGGCGGAGTTTGCGGGAGTTTATACTAGTTTGCCACATGTTCATAGAGCTGGTGAGACTAATCA
TATCGCGACTGTTGATTTCCAGCTGGCGATAACGGAACTGTTGGAGGATATTGGTTTGGAAGATGAAGATACTATTGCGGTGACTC
TGGTGCCAAAGAGAGGTGGTGAAGGTATCTCCATTGAAAGTGCGACGATCAGTCTTGCAGATTGTTAA
SEQ ID NO: 28
ATGGCAAGCTTGTGCAATAGTAGTAGTACATCTCTCAAAACTCCTTTTACTTCTTCCTCCACTTCTTTATCTTCCACTCCTAAGCC
CTCTCAACTTTTCATCCATGGAAAACGTAACCAAATGTTCAAAGTTTCATGCAAGGTTATCAATAATAACGGTGACCAAAACGTTG
AAACGAATTCTGTTGATCGAAGAAATGTTCTTCTTGGCTTAGGTGGTCTTTATGGTGTTGCTAATGCTATACCATTAGCTGCATCC
GCTGCTCCAACTCCACCTCCTGATCTCTCGTCTTGTAGTATAGCCAGGATTAACGAAAATCAGGTGGTGCCGTACAGTTGTTGCGC
GCCTAAGCCTGATGATATGGAGAAAGTTCCGTATTACAAGTTCCCTTCTATGACTAAGCTCCGTGTCCGTCAGCCTGCTCATGAAG
CTAATGAGGAGTATATTGCCAAGTACAATCTGGCGATTAGTCGAATGAGAGATCTTGATAAGACACAACCTTTAAACCCTATTGGT
TTTAAGCAACAAGCTAATATACAGTGGGCTTATGGTAATGGTGCTTATAGAATTGGTGGCAAAGAGTTACAAGTTCATAATTCTTG

```
GCTTTTCTTCCCGTTCCATAGATGGTACTTGTACTTCCACGAGAGAATCGTGGGAAAATTCATTGATGATCCAACTTTCGCTTTGC

CATATTGGAATTGGGACCATCCAAAGGGTATGCGTTTTCCTGCCATGTATGATCGTGAAGGGACTTCCCTTTTCGATGTAACACGT

GACCAAAGTCACCGAAATGGAGCAGTAATCGATCTTGGTTTTTTCGGCAATGAAGTCGAAACAACTCAACTCCAGTTGATGAGCAA

TAATTTAACACTAATGTACCGTCAAATGGTAACTAATGCTCCATGTCCTCGGATGTTCTTTGGTGGGCCTTATGATCTCGGGATTA

ACACTGAACTCCCGGGAACTATAGGAAACATTCCTCTCGGTCCTGTCCACATCTGGTCTGGTACAGTGAGAGGTTCAACTTTGCCC

AATGGTGCAATATCAAACGGTCAGAATATGGGTCATTTTTACTCAGCTGCTTTGGACCCGGTTTTCTTTTGCCATCACAGCAATGT

GGATCGGATGTCGAGCGAATGGAAAGCGACAGGAGGGAAAAGAACAGATATCACACATAAAGGTTGGTTGAACTCCGAGTTCTTTT

TCTATGATGAAAATGAAAACCCTTACCGTGTGAAAGTCCGAGACTGTTTGGACACGAAGAAGATGGGGTATGATTATGCACCAATG

GCCACCCCGTGGCGTAACTTCAAGCCAATAACAAAAACTACAGCTGGGAAAGTCAATACAGCTTCTCTTCCGCCAGCTAGCAATGT

ATTCCCAGTGGCTAAACTCGACAAAGCAATTTCGTTTTCCATCAATAGGCCGACTTCGTCAAGGACTCAACAAGAGAAAATGCAC

AAGAGGAGATGTTGACATTCAGTAGCATAAGATATGATAACAGAGGGTACATAAGGTTCGATGTGTTCCTGAACGTGGACAATAAT

GTGAATGCGAATGAGCTTGACAAGGCGGAGTTTGCGGGGAGTTATACTAGTTTGCCACATGTTCATAGAGCTGGTGAGACTAATCA

TATCGCGACTGTTGATTTCCAGCTGGCGATAACGGAACTGTTGGAGGATATTGGTTTGGAAGATGAAGATACTATTGCGGTGACTC

TGGTGCCAAAGAGAGGTGGTCAAGGTATCTCCATTGAAAGTGCGACGATCAGTCTTGCAGATTGTTAA

SEQ ID NO: 29
TTAGTCTCTATTGAATCTGCTGAGATTACACTTTGATGGATGATGCTCTGTTTTTGTTTTCTTGTTCTGTTTTTTCCTCTGTTGAA

ATCAGCTTTGTTGCTTGATTTCATTGAAGTTGTTATTCAAGAATAAATCAGTTACAATTATGTTTGGG

SEQ ID NO: 30
GGTACCGAACCATGCATCTCAATCTTAATACTAAAAAATGCAACAAAATTCTAGTGGACGCACCAGTACCAGTACATTAGATATTA

TCTTTTATTACTATAATAATATTTTAATTAACACGAGACATAGGAATGTCAAGTGGTAGCGGTAGGAGGGAGTTGGTTCAGTTTTT

TAGATACTAGGAGACAGAACCGGAGGGGCCCATTGCAACGCCCAAGTTCAAGTCCACCCGTGAATCAACAAAGACAGCGCCCATAA

TACTGTCGATGAGCATTTCCCTATAATACAGTGTCCACAGTTGCCTTCCGCTAAGGCATAGCCACCCGCTATTCTCTTGACACGTG

TCACTGAAACCTGCTACAAATAAGGCACGCACCTCCTCATTCTCACACTCACTCACTCACACAGCTCAAGAAGGATCCTTAGTCTC

TATTCAATCTGCTCAGATTACACTTTGATGGATCATGCTCTGTTTTTGTTTTCTTGTTCTGTTTTTTCCTCTGTTGAAATCAGCTT

TGTTGCTTGATTTCATTGAAGTTGTTATTCAAGAATAAATCAGTTACAATTATGGAATTCAAGCTTAGAAATCTTCTCTATTTTTG

GTTTTTGTCTGTTTAGATTCTCGAATTAGCTAATCAGGTGCTGTTATAGCCCTTAATTTTCACTTTTTTTCGGTTGTTTTGATCG

AAAAGGCCTAAAATTTGAGTTTTTTTACGTTGGTTTCATGGAAAACGCCTACAATTGGAGTTTTCCCCGTTGTTTTGATGAAAAAG

CCCCTAGTTTGAGATTTTTTTCTGTCGATTCGATTCTAAAGGTTTAAAATTAGAGTTTTTACATTTCTTTGATGAAAAAGCCCTT

AAATTTCAGTTTTTCCGGTTGATTTGATGAAAAAGCCCTAGAATTTGTGTTTTTTCCTCCCTTTGATTCTGAACCCCTAAAATTTG

AGTTTCTCCGCCTGTTTTGATGAAAAAGCCCTAAATTTGAGTTTCTCCGGCTGTTTTGATGAAAAAGCCCTAAATTTCAGTTTTTT

CCCCGTGTTTTAGATTGTTTGGTTTTAATTCTCGAATCACCTAATCAGGGAGTGTGAAAAGCCCTAAAATTTGAGTTTTTTTCGTT

GTTCTGATTGTTCTTTTTATGAATTTGCAGATGGATATCCTTCTTTGATGCTGATCCATAATTGTAACTGATTTATTCTTGAATAA

CAACTTCAATGAAATCAAGCAACAAACCTGATTTCAACACAGCAAAAAACAGAACAACAAAACAAAAACAGAGCATCATCCATCAA

ACTGTAATCTCAGCAGATTCAATAGAGACTAAGCTTTTGATTTTAATGTTTAGCAAATGTCCTATCACTTTTCTCTTTTTGTCGAA

CGGTAATTTAGAGTTTTTTTGCTATATCGATTTTCGTTTTGATGTATGTGACAACCCTCGGGATTGTTGATTTATTTCAAAACT

AAGAGTTTTTGCTTATTGTTCTCGTCTATTTTCGATATCAATCTTAGTTTTATATCTTTTCTAGTTCTCTACGTGTTAAATGTTCA

ACACACTAGCAATTTGGCTGCAGCGTATCGATTATGGAACTATCAAGTCTGTGGGATCGATAAATATCCTTCTCAGGAATTTGAGA

TTTTACAGTCTTTATGCTCATTGGGTTGAGTATAATATAGTAAAAAAATAGTCTAGA

SEQ ID NO: 31
GGTACCGAACCATGCATCTCAATCTTAATACTAAAAAATGCAACAAAATTCTAGTGGAGGGACCAGTACCAGTACATTAGATATTA

TCTTTTATTACTATAATAATATTTTAATTAACACGACACATAGGAATGTCAAGTGGTAGCCGTAGGAGGGAGTTGGTTCAGTTTTT

TAGATACTAGGAGACACAACCGGAGGCGCCCATTGCAAGGCCCAAGTTGAAGTCCAGCCGTGAATCAACAAAGAGAGCGCCCATAA
```

-continued

```
TACTGTCGATGAGCATTTCCCTATAATACAGTGTCCACACTTGCCTTCCGCTAAGGGATAGCCACCCGCTATTCTCTTGACACGTC
TCACTCAAACCTGCTACAAATAAGGCAGGCACCTCCTCATTCTCACACTCACTCACTCACACAGCTCAACAACGATCCTTAGTCTC
TATTGAATCTCCTCAGATTACACTTTCATGGATGATGCTCTGTTTTTCTTTTCTTGTTCTGTTTTTTCCTCTGTTGAAATCAGCTT
TCTTGCTTCATTTCATTGAAGTTGTTATTCAAGAATAAATCACTTACAATTATGGAATTCGTGGTAACTTTTACTCATCTCCTCCA
ATTATTTCTGATTTCATCCATGTTTCCCTACATTCTATTATGAATCGTGTTATGGTGTATAAACGTTGTTTCATATCTCATCTCAT
CTATTCTGATTTTGATTCTCTTGCCTACTGAATTTGACCCTACTGTAATCGCTGATAAATGTGAATGCTTCCTCTTCTTCTTCTTC
TTCTCAGAAATCAATTTCTGTTTTGTTTTTGTTCATCTGTACCTTGATATCCTTCTTTGATGCTGATCCATAATTGTAACTGATTT
ATTCTTCAATAACAACTTCAATGAAATCAAGCAACAAAGCTGATTTCAACAGAGGAAAAAACAGAACAAGAAAACAAAAACAGAGC
ATCATCCATCAAACTGTAATCTCAGCAGATTCAATAGAGACTAAGCTTTTGATTTTAATGTTTAGCAAATGTCCTATCAGTTTTCT
CTTTTTGTCGAACGGTAATTTAGAGTTTTTTTGCTATATGGATTTTCGTTTTTGATGTATGTGACAACCCTCGGGATTGTTGATT
TATTTCAAAACTAAGAGTTTTTGCTTATTGTTCTCGTCTATTTTGGATATCAATCTTAGTTTTATATCTTTTCTAGTTCTCTACGT
GTTAAATGTTCAACACACTAGCAATTTGGCTGCAGCCTATGGATTATGGAACTATCAAGTCTCTCGGATCGATAAATATGCTTCTC
AGGAATTTGAGATTTTACAGTCTTTATGCTCATTGGGTTGAGTATAATATAGTAAAAAAATAGTCTACA
SEQ ID NO: 32
GGTACCCAACCATCCATCTCAATCTTAATACTAAAAAATGCAACAAAATTCTACTGCACGGACCAGTACCACTACATTACATATTA
TCTTTTATTACTATAATAATATTTTAATTAACACCACACATAGGAATCTCAAGTGCTACCGCTACCACCCACTTGGTTCACTTTTT
TAGATACTACCAGACAGAACCCCACCGCCCCATTGCAACCCCCAACTTCAACTCCACCCCTCAATCAACAAAGACACCGCCCATAA
TACTCTCGATCACCATTTCCCTATAATACAGTGTCCACAGTTCCCTTCCGCTAACCGATAGCCACCCCCTATTCTCTTGACACCTC
TCACTCAAACCTCCTACAAATAACGCAGGCACCTCCTCATTCTCACACTCACTCACTCACACACCTCAACAACTCGTAACTTTTAC
TCATCTCCTCCAATTATTTCTGATTTCATGCATGTTTCCCTACATTCTATTATGAATCGTGTTATGGTGTATAAACGTTGTTTCAT
ATCTCATCTCATCTATTCTGATTTTGATTCTCTTGCCTACTGAATTTGACCCTACTGTAATCGGTGATAAATGTGAATGCTTCCTC
TTCTTCTTCTTCTCAGAAATCAATTTCTGTTTTGTTTTTGTTCATCTGTAGCTTGGTAGATTCCCCTTTTTGTAGACCACACA
TCACGGATCCTTAGTCTCTATTGAATCTGCTGAGATTACACTTTGATGGATGATGCTCTGTTTTTGTTTCTTGTTCTGTTTTTC
CTCTGTTGAAATCAGCTTTGTTGCTTGATTTCATTGAAGTTGTTATTCAAGAATAAATCAGTTACAATTATGGAATTCAAGGTTAG
AAATCTTCTCTATTTTTGGTTTTTCTCTGTTTAGATTCTCGAATTAGCTAATCAGGTGCTGTTATAGCCCTTAATTTTGAGTTTTT
TTTCGGTTGTTTTCATGGAAAAGGCCTAAAATTTCACTTTTTTTACGTTGGTTTGATGGAAAAGGCCTACAATTGGAGTTTTCCCC
GTTGTTTTGATGAAAAAGCCCCTAGTTTGAGATTTTTTTTCTGTCGATTCGATTCTAAAGGTTTAAAATTAGAGTTTTTACATTTG
TTTGATGAAAAAGGCCTTAAATTTGAGTTTTTCCGGTTGATTTGATGAAAAAGCCCTAGAATTTGTGTTTTTTCGTCGGTTTGATT
CTGAAGGCCTAAAATTTGAGTTTCTCCGGCTGTTTTGATGAAAAAGCCCTAAATTTGAGTTTCTCCGGCTGTTTTGATGAAAAAGC
CCTAAATTTGAGTTTTTTCCCCGTGTTTAGATTGTTTGGTTTAATTCTCGAATCAGCTAATCAGGGAGTGTGAAAAGCCCTAAA
ATTTGAGTTTTTTCGTTGTTCTGATTGTTGTTTTTATGAATTTGCAGATGGATATCCTTCTTTGATGCTGATCCATAATTGTAAC
TGATTTATTCTTGAATAACAACTTCAATGAAATCAAGCAACAAAGCTGATTTCAACAGAGGAAAAAACAGAACAAGAAAACAAAA
CAGAGCATCATCCATCAAAGTGTAATCTCAGCAGATTCAATAGAGACTAAGCTTTTGATTTTAATGTTTAGCAAATGTCCTATCAG
TTTTCTCTTTTTGTCGAACGGTAATTTAGAGTTTTTTTGCTATATGGATTTTCGTTTTTGATGTATGTGACAACCCTCGGGATTG
TTGATTTATTTCAAAACTAAGAGTTTTTGCTTATTGTTCTCGTCTATTTTGGATATCAATCTTAGTTTTATATCTTTTCTAGTTCT
CTACGTGTTAAATGTTCAACACACTAGCAATTTGGCTGCAGCGTATGGATTATGGAACTATCAAGTCTGTGGGATCGATAAATATG
CTTCTCAGGAATTTGAGATTTACAGTCTTTATGCTCATTGGGTTGAGTATAATATAGTAAAAAAATAGTCTAGA
SEQ ID NO: 33
GGTACCGAACCATGCATCTCAATCTTAATACTAAAAAATGCAACAAAATTCTAGTGGAGGGACCAGTACCAGTACATTAGATATTA
TCTTTTATTACTATAATAATATTTTAATTAACACGAGACATAGGAATGTCAAGTGGTAGCGGTAGGAGGGAGTTGGTTCAGTTTTT
TAGATACTAGGAGACAGAACCGGAGGGGCCCATTGCAAGGCCCAAGTTGAAGTCCAGCCGTGAATCAACAAAGAGAGGGCCCATAA
```

-continued

TACTGTCGATGAGCATTTCCCTATAATACAGTGTCCACAGTTGCCTTCCGCTAAGGGATAGCCACCCGCTATTCTCTTGACACGTG
TCACTGAAACCTGCTACAAATAAGGCAGGCACCTCCTCATTCTCACACTCACTCACTCACACAGCTCAACAAGTGGTAACTTTTAC
TCATCTCCTCCAATTATTTCTGATTTCATGCATGTTTCCCTACATTCTATTATGAATCGTGTTATGGTGTATAAACGTTGTTTCAT
ATCTCATCTCATCTATTCTGATTTTGATTCTCTTGCCTACTGAATTTGACCCTACTGTAATCGGTGATAAATGTGAATGCTTCCTC
TTCTTCTTCTTCTTCTCAGAAATCAATTTCTGTTTTGTTTTTGTTCATCTGTAGCTTGGTAGATTCCCCTTTTTGTAGACCACACA
TCACGGATCCTTAGTCTCTATTGAATCTGCTGAGATTACACTTTGATGGATGATGCTCTGTTTTTGTTTTCTTGTTCTGTTTTTTC
CTCTGTTGAAATCAGCTTTGTTGCTTGATTTCATTGAAGTTGTTATTCAAGAATAAATCAGTTACAATTATGGAATTCGTGGTAAC
TTTTACTCATCTCCTCCAATTATTTCTCATTTCATGCATGTTTCCCTACATTCTATTATGAATCGTGTTATGGTGTATAAACGTTG
TTTCATATCTCATCTCATCTATTCTGATTTTGATTCTCTTGCCTACTGAATTTGACCCTACTGTAATCGGTGATAAATGTGAATGC
TTCCTCTTCTTCTTCTTCTTCTCAGAAATCAATTTCTGTTTTGTTTTTGTTCATCTGTAGCTTGATATCCTTCTTTGATGCTGATC
CATAATTGTAACTGATTTATTCTTGAATAACAACTTCAATGAAATCAAGCAACAAAGCTGATTTCAACAGAGGAAAAAACAGAACA
AGAAAACAAAAACAGAGCATCATCCATCAAAGTGTAATCTCAGCAGATTCAATAGAGACTAAGCTTTTGATTTTAATGTTTAGCAA
ATGTCCTATCAGTTTTCTCTTTTTGTCGAACGGTAATTTAGAGTTTTTTTGCTATATGGATTTTCGTTTTTGATGTATGTGACAA
CCCTCGGGATTGTTGATTTATTTCAAAACTAAGAGTTTTTGCTTATTGTTCTCGTCTATTTTGGATATCAATGTTAGTTTTATATC
TTTTCTAGTTCTCTACGTGTTAAATGTTCAACACACTAGCAATTTGGCTGCAGCGTATGGATTATGGAACTATCAAGTCTGTGGGA
TCGATAAATATGCTTCTCAGGAATTTGAGATTTTACAGTCTTTATGCTCATTGGGTTGAGTATAATATAGTAAAAAATAGTCTAG
A

SEQ ID NO: 34
GTCCATGATGTCTTCACGGTGGTAGCATTGACTGATGGCATCATAGTTTTTTTTTAAAAGTATTTCCTCTATGCATATTATTAGT
ATCCAATAAATTTACTGGTTGTTGTACATAGAAAAAGTGCATTTGCATGTATGTGTTTCTCTGAAATTTTCCCCAGTTTTTGGTGC
TTTGCCTTTGGAGCCAAGTCTCTATATGTATAAGAAAACTAAGAACAATCACATATATCAAATATTAG

SEQ ID NO: 35
ACGAACTTGTGATCGCGTTGAAAGATTTGAACGCTACATAGAGCTTCTTGACGTATCTGGCAATATTGCATCAGTCTTGGCGGAAT
TTCATGTGACAACAAGGTTTGCAATTCTTTCCACTATTAGTAGTGCAACGATATACGCAGAGATGAAGTGCTGAACAAACATATGT
AAAATCGATGAATTTATGTCGAATGCTGGGACGGGCTTCAGCAGGTTTTGCTTAGT

SEQ ID NO: 36
CCGCGGTTTTCTCTCCATCGCGTCAGAGGCCGGTTTTCGTCGGCATCGAAGAGGGCCACTCGTTTACCGTCATTTGCCAAAGCAGC
GCAAAGGCCCATGAGTGCGGTGGTTTTGCCAGCACCCCCTTTGAAAGAGCAAAACGTCAAAAGTTGCATATTCTGATCCCGCCTGT
CCTGTGAAACGGAGTGCATTTGTATTTTTGTTCGTATAAATGTTTTTGTGATTATCGATGAGTAAAAGCGTTGTTACACTATTTTT
TATTTCAAATTCGTTATAATTAAATTGCAATTGTAGCAATTATATTCGGTTTTTCCTGTAAATATACTGTTGATTTCATATCGAGT
AGGGCTAGACTTTAATCTGTCTACCCGGGCACATTTCGTGCTGGAGTATTCAGACCTTCCGCTTTTTTGGAGGAAGCTATGTCAA
AACACACCAGAGTCACGTCGAGTGAGACTGCCATCAACCAGCATCGATCCCTGAACGTTGAAGGGTTTAAGGTCGTGAGTGCCCGT
CTGCGATCGGCCGAGTATGAAACCTTTTCCTATCAAGCGCGCCTGCTGGGACTTTCGGATAGTATGGCAATTCGCGTTGCGGTGCG
TCGCATCGGGGCTTTCTCGAAATAGATGCACACACCCGAGAAAAGATGGAAGCCATACTTCAGTCCATCGGAATACTCTCAAGTA
ATGTATCCATGCTTGTATCTGCCTACGCCGAAGACCCTCGATCGGATCTGGAGGCTGTGCGAGATGAACGTATTGCTTTTGGTGAG
GCTTTCGCCGCCCTCGATGGCCTACTCCGCTCCATTTTGTCCGTATCCCGGCGACGGATCGACGGTTGCTCGCTATTGAAAGGTGC
CTTGTAGCACTTGACCACGCACCTGACGGGAGAAAATTGGATGCCCGATCGCGCTCAAGTAATCATTCGCATTGTGCCAGGAGGTG
GAACCAAGACCCTTCAGCAGATAATCAATCAGTTGGAGTACCTGTCCCGTAAGGGAAAGCTGGAACTGCAGCGTTCACCCCGGCAT
CTCGATATTCCCGTTCCGCCGGATCAAATCCGTGAGCTTGCCCAAAGCTGGGTTACGGAGGCCGGGATTTATGACGAAAGTCAGTC
AGACGATGATAGGCAACAAGACTTAACAACACACATTATTGTAAGCTTCCCCGCAGGTACCGACCAAACCGCAGCTTATGAAGCCA
GCCGGGAATGGGCAGCCGAGATGTTTGGGTCAGGATACGGGGGTGGCCGCTATAACTATCTGACAGCCTACCACGTCGACCGCGAT

-continued

CATCCACATTTACATGTCGTGGTCAATCGTCGGGAACTTCTGGGGCACGGGTGGCTGAAAATATCCAGGCGCCATCCCCAGCTGAA
TTATGACGGCTTACGGAAAAAGATGGCAGAGATTTCACTTCGTCACGGCATAGTCCTGGATGCGACTTCGCGAGCAGAAGGGGAA
TAGCAGAGCGACCAATCACATATGCTGAACATCGCCGCCTTGAGCGGATGCAGGCTCAAAAGATTCAATTCGAAGATACAGATTTT
GATGAGACCTCGCCTGAGGAAGATCGTCGGGACCTCAGTCAATCGTTCGATCCATTTCGATCGGACCCATCTACCGGCGAACCGGA
CCGTGCAACCCGACATGACAAACAACCGCTTGAACAGCACGCCCGTTTCCAGGAGTCCGCCGGCTCCAGCATCAAAGCCGACGCAC
GGATCCGCGTATCATTGGAGAGCGAGCGGAGTGCCCAACCATCCGCGTCCAAAATCCCTGTAATTGGGCATTTCGGGATTGAGACT
TCCTATGTCGCTGAAGCCAGCGTGCGCAAACGAAGCGGCATTTTCGGTACTTCTCGCCCGGTGACTGACGTTGCCATGCACACAGT
CAAGCGCCAGCAGCGATCAAAACGACGTAATGACGAGGAGGCAGGTCCGAGCGGAGCAAACCGTAAAGGATTGAAGGCTGCGCAAG
TTGATTCCGAGGCAAATGTCGGTGAGCAAGACACTCGCGATGACAGCAACAAGGCGGCTGATCCGGTGTCTGCTTCCATCGGTACC
GAGCAACCGGAAGCTTCTCCAAAGCGTCCGCGTGACCGTCACGATGGAGAATTGGGTGGACGCAAACGTGCAAGAGGTAATCGTCG
CTCGAGCTCGAGCCGGCGGACCTAGAGACAGGAAGGACCGAATAATGGCCGCGG

SEQ ID NO: 37
ATGGCTTCTGTGCTGGCTTCTCTGTTTCCAAAACTGGGCTCTTTGGGTACTTCAGATCATGCTTCTGTTGTATCCATCAACCTCTT
TGTGGCACTCCTTTGTGCTTGCATCATCATTGGTCATCTCTTGGAGGAGAACCGCTGGGTTAATGAGTCCATTACTGCCCTCATAA
TTGGTTTGTGTACAGGAGTGGTTATCTTGCTCGTAAGTGGTGGAAAGAGCTCACACCTTCTGGTTTTCAGTGAAGATCTCTTTTTC
ATATATGTACTTCCTCCAATCATATTTAATGCAGGGTTTCAGGTAAAAAAGAAGCAATTTTTCGTAAACTTCATTACTATAATGAT
GTTCGGAGCCATTGGTACCCTGGTCTCATGTGCCATTATATCATTAGGTGCCATTCAAACTTTCAAGAAGTTGGACATTGAATTTC
TAGATATTGGGGATTATCTTGCAATTGGAGCAATATTTGCTGCCACAGATTCCGTCTGCACATTGCAGGTCCTACATCAGGATGAG
ACACCCCTCCTTTACAGTCTTGTATTTGGAGAAGGAGTTGTAAATGATGCTACATCGGTGGTGCTTTTCAATGCTATTCAAAACTT
CGACCTTACGAGCATGAATCCCAGTATAGCCCTCAGTTTCCTTGGCAACTTCTTCTATCTGTTCCTTGCTAGCACTTTACTGGGAG
CAGGAACTGGTCTTCTTAGTGCTTACATTATCAAGAAGCTATATTTTGGCAGGCACTCCACAGATCGTGAGGTTGCCCTTATGATG
CTCATGGCTTACTTATCATACTTGCTGGCCGAATTATTCTATTTGAGTGGGATTCTCACCGTCTTTTTCTGTGGTATTGTAATGTC
TCACTACACTTGGCACAATGTGACCGAGAGTTCAAGAGTCACTACAAGGCACACTTTTGCAACTTTGTCATTTCTTGCAGAGACTT
TCCTCTTCCTCTATGTCGGCATGGATGCTTTGGATATCGAGAAGTGGAAATTTGTTGGTGACAGGCCTGGATTATCAATTTCCGTG
AGTTCAATACTGATGGGACTAATCTTGCTTGGGAGAGCTGCCTTTGTTTTTCCATTATCATTCTTATCCAACTTAATGAAGAAATC
CTCGGAGCAAAAAATTACCTTTAGGCAGCAAGTGATAATATGGTGGGCAGGTTTGATGAGAGGCGCAGTGTCCATGGCACTGGCAT
ATAATAAGTTCACTCGTGGGGGACACACTCAACTGCAGGACAATGCAATAATGATTACCAGCACGATAACCATTGTTCTATTCAGC
ACAATGGTATTCGGTTTAATGACAAAACCCCTTATAAGTCTCCTGCTGCCACCACAGAGGCAATTGAGTACAGTGTCATCAGGCGC
AAATACTCCAAAGTCTCTAACAGCCCCACTCCTAGGCAGTCGAGAGGACTCTGAAGTTGATTTAAATGTTCCAGATCTTCCTCACC
CACCAAGTTTGAGGATGCTACTTACCGCACCAAGTCATAAAGTGCATCGGTACTGGCGCAAGTTTGACGATGCATTCATGCGCCCT
ATGTTTGGTGGTCGGGGATTTGCTCCTCCTGCCCCTGGTTCTCCAACGGAACAGGGTCCATGAGGTACCAATC

SEQ ID NO: 38
ATGGCTTCTGTGCTGGCTTCTCTGTTTCCAAAACTGGGCTCTTTGGGTACTTCAGATCATGCTTCTGTTGTATCCATCAACCTCTT
TGTGGCACTCCTTTGTGCTTGCATCATCATTGGTCATCTCTTGGAGGAGAACCGCTGGGTTAATGAGTCCATTACTGCCCTCATAA
TTGGTTTGTGTACAGGAGTGGTTATCTTGCTCGTAAGTGGTGGAAAGAACTCACACCTTCTGGTTTTCAGTGAAGATCTCTTTTTC
ATATATGTACTTCCTCCAATCATATTTAATGCAGGGTTTCAGGTAAAAAGAAGCAATTTTTCGTGAACTTCATTACTATAATGAT
GTTCGGAGCCATTGGTACCCTGGTCTCATGTGCCATTATATCATTAGGTGCAATTCAAACTTTCAAGAAGTTGGACATTGAATTTC
TAGATATTGGGGATTATCTTGCAATTGGAGCAATATTTGCTGCCACAGATTCCGTCTGCACATTGCAGGTCCTACATCAGGATGAG
ACACCCCTCCTTTACAGTCTTGTATTTGGAGAAGGAGTTGTAAATGATGCTACATCGGTGGTGCTTTTCAATGCTATTCAAAACTT
TGACCTTACGAGCGTGAATCCCAGTATAGCCCTCAGTTTCCTTGGCAACTTCTTCTATCTGTTCCTTGCTAGCACTTTACTGGGAG
CAGGAACTGGTCTTCTTAGTGCTTACATTATCAAGAAGCTGTATTTTGGCAGGCACTCCACAGATCGTGAGGTTGCCCTTATGATG

```
                                                            -continued
CTCATGGCTTACTTATCATACATGCTGGCTGAACTATTCTATTTGAGTGGGATTCTCACTGTATTTTTCTGTGGTATTGTAATGTC TCATTACACTTGGCACAATGTGACCGAGAGTTCAAGAGTCACTACAAGGCACGCTTTTGCAACTTTGTCATTTCTTGCAGAGACTT TCCTCTTCCTCTATGTCGGCATGGATGCTTTGGATATCGAGAAGTGGAAATTTGTTGGTGACAGGCCTGGATTATCAATTTCCGTG AGTTCAATACTGATGGGATTAATCTTGCTGGGGAGAGCTGCCTTTGTTTTTCCATTATCATTCTTCTCCAACTTAATGAAGAAATC CTCGGAGCAAAAAATTACCTTTAGGCAGCAAGTGATAATATGGTGGGCAGGTTTGATGAGAGGCGCAGTGTCCATGGCACTGGCAT ATAATAAGTTCACTCGTGGGGACACACTCAACTGCAGGACAATGCAATAATGATTACCAGCACGATAACCATTGTTCTATTCAGC ACAATGGTATTCGGTTTAATGACAAAACCCCTTATAAGTCTCCTGCTGCCACCACAGAGGCAATTGAGTACAGTGTCATCAGGTGC AAATACTCCAAAGTCTCTAACAGCCCCACTCCTAGGCAGTCGAGAGGACTCTGAAGTTGATTTAAATGTTCCAGATCTTCCTCACC CACCAAGTTTGAGGATGCTACTTACCGCACCAAGTCATAAAGTGCATCGGTACTGGCGCAAGTTTGACGATGCATTCATGCGCCCT

ATGTTTGGTGGTCGGGGATTTGCTCCTCCTGCCCCTGGTTCTCCAACGGAACAGGGTCCATGAGGTACAATC

SEQ ID NO: 39
ATGGAAAATTCGGTACCCAGGACTGTAGAAGAAGTATTCAACGATTTCAAAGGTCGTAGAGCTGGTTTAATCAAAGCACTAACTAC

AGATGTCGAGAAGTTTTATCAATCGTGTGATCCTGAAAAGGAGAACTTGTGTCTCTATGGGCTTCCTAATGAAACATGGGAAGTAA

ACCTCCCTGTAGAGGAGGTGCCTCCAGAACTTCCGGAGCCAGCATTGGGCATAAACTTCGCACGTGATGGAATGCAAGAGAAAGAC

TGGTTATCACTTGTTGCTGTTCACAGTGATTCATGGCTGCTTTCTGTTGCATTTTACTTTGGTGCAAGGTTTGGGTTCGGCAAGAG

TGAAAGGAAGAGGCTTTTCCAAATGATAAATGATCTCCCAACAGTGTTTGAAGTTGTTACCGGAGCTGCTAAACAGACACGTGATC

CCCCTCACAACAATAGCAACAAAAGCAAATCAAGTGGAAAGCCTCGACAGCCAGAGTCCCAACTCAAGGCAGTAAAGGTGTCTCCA

CCTAAAATGGAGAACGACAGTGGGGAGGAGGAAGAAGAAGAAGAGGATGAACAAGGAGCAACTCTCTGTGGAGCTTGTGGTGATAA

TTATGCCACTGATGAATTCTGGATTTGCTGTGATATTTGTGAGAGATGGTTCCATGGCAAATGTGTGAAGATTACCCCAGCAAAAG

CTGAGCATATCAAGCAGTACAAGTGTCCTAGTTGCAGTAGCAAGAGAGCTAGAGTTTAA

SEQ ID NO: 40
TGACATCTGCCAATAAAGCCAAGAATAATTGGCATTAACATGACCAAAAAAATGGTTTGGCAGCATTAAGTCAAATAAAAAAGCTA

CTTTAATATAAAATAATATTAAAATGCTTAATAACCAACAGTTTATAAGAAGGTTAATGTTAACATGGATGAGGAATGACCAAAAG

GGGAATTATATATTAACCTTTAAATCAATCTAATTCTCTCTTTTTGTTTCTAGCTATATTTACTCGATAGATAAACTCTCTTACTT

GACGAATTTTTTGATACAAGAAGACATATTTCATCATGATTTTAATTCGTCGTGTCAAATTTATTAAATAGTTTAATTTTAATCGT

AAATTTAGATATGAAATTTAAAAAAAAATAAATATATACATATTTGAAGAATACATAAAAAGTACATATAAATCACAAATATTTAA

TAATTCAAGATATTAAAACACATAGAAAAATAATTACTTACAAAGAAATTCTTATTTGAATCCTCTAAATTCGAGAAGTGCAACAC

AAACTGAGACGAAGAAAATGAATAATATTTGATAAGAAATTTATTATAATTGAATGACCATTTAAGTAATTACGGGTAATAACAAC

ACAATAAGGAACTGTAGTCATTTTTAATACATGGCAAGGAATATGAGAGTGTGATGAGTCTATAAATACAAGGCTTCATTAGTGTA

GAGGAGTCACAAACAAGCAATACACAAATAAAATTAGTAGCTTAAACAAGATG

SEQ ID NO: 56
TTCTTCGCCAGAGGTTTGGTCAAGTCTCCAATCAAGGTTGTCGGCTTGTCTACCTTGCCAGAAATTTACGAAAGATGGAAAAGGG

TCAAATCGTTGGTAGATACGTTGTTGACACTTCTAAATAAGCGAATTTCTTATGATTTATGATTTTTATTATTAAATAAGTTATAA

AAAAAATAAGTGTATACAAATTTTAAAGTGACTCTTAGGTTTTAAAACGAAAATTCTTATTCTTGAGTAACTCTTTCCTGTAGGTC

AGGTTGCTTTCTCAGGTATAGCATGAGGTCGCTC

SEQ ID NO: 94
TGGCAGGATATATGAGTGTGTAAAC

SEQ ID NO: 95
TTGGCAGGATATATCCCTCTGTAAAC
```

What is claimed is:

1. A method of transforming a plant cell with a desired polynucleotide, comprising (A) contacting a plant cell with an *Agrobacterium* strain that comprises a first plasmid, wherein the first plasmid comprises (i) nucleic acid sequences obtained from at least one plant genome that facilitate enzymatic nicking of the plasmid in *Agrobacterium*, wherein a nucleic acid sequence that facilitates enzymatic nicking comprises a 5'YGRYAGGATATATWSNVBKGTAAWY-3' (SEQ ID NO: 47), consensus sequence, wherein Y is C or T; R is A or G; K is C or T; M is A or C; W is A or T; S is C or G; V is A, C, or G; and B is C, G, or T, and (ii) a desired polynucleotide, wherein any plant nucleic acid that facilitates enzymatic nicking of the plasmid is not an *Agrobacterium* T-DNA or an *Agrobacterium* T-DNA border sequence, and (B) obtaining a transformed plant cell that comprises the desired polynucleotide in its genome.

2. The method of claim 1, wherein (i) the nucleic acid sequences that are obtained from at least one plant genome and facilitate enzymatic nicking are obtained from one or more genomes of the same or different plant species as the species of the plant cell to be transformed.

3. The method of claim 1, wherein the nucleic acid sequence that facilitates enzymatic nicking is a T-DNA border-like sequence that shares no more than 96% nucleotide sequence identity with an *Agrobacterium* T-DNA border sequence.

4. The method of claim 3, wherein the plasmid comprises two T-DNA border-like sequences.

5. The method of claim 4, wherein the desired polynucleotide is positioned between the two T-DNA border-like sequences.

6. The method of claim 5, wherein the desired polynucleotide is operably linked to elements that are capable of expressing it in a plant cell, wherein expression of the desired polynucleotide alters the expression of a gene in the plant cell.

7. The method of claim 6, wherein the desired polynucleotide comprises (i) a sequence that comprises all or part of a coding or non-coding region of a gene that is native to the plant cell or (ii) a regulatory sequence associated with a gene.

8. The method of claim 1, wherein the plasmid further comprises a backbone integration marker gene.

9. The method of claim 8, wherein the backbone integration marker gene is a cytokinin gene.

10. The method of claim 9, wherein the cytokinin gene encodes isopentyl transferase.

11. The method of claim 1, further comprising contacting the plant cell with an *Agrobacterium* strain that contains a second plasmid that comprises a selectable marker gene positioned within a transfer-DNA in the second plasmid.

12. The method of claim 11, wherein the selectable marker gene encodes antibiotic resistance and is operably linked to an upstream promoter and downstream terminator that is derived from a gene that is not naturally expressed in a plant cell, and wherein the transformed plant cell is subjected to the corresponding antibiotic.

13. The method of claim 11, wherein the second plasmid further comprises a negative selectable marker within its transfer-DNA.

14. The method of claim 13, wherein the negative selectable marker gene encodes cytosine deaminase and wherein the transformed plant cell is subjected to 5-fluorocytosine.

15. The method of claim 11, wherein the second plasmid is in an *Agrobacterium* strain that is the same or different as the strain containing the first plasmid.

16. The method of claim 1, wherein the plant cell is a cell in a plant tissue or cell culture.

17. The method of claim 16, wherein the plant tissue is an explant, stem, seed, seedling, shoot, root, leaf cutting, stem cutting, root cutting, tuber eye, stolon, flower, pollen, or callus.

18. The method of claim 1, wherein the plant cell is from a monocotyledonous plant or dicotyledonous plant.

19. The method of claim 18, wherein (a) the monocotyledonous plant is selected from the group consisting of wheat, turf grass, cereal, maize, rice, oat, barley, sorghum, orchid, iris, lily, onion, banana, sugarcane, sorghum, and palm; and (b) the dicotyledonous plant is selected from the group consisting of avocado, potato, tobacco, tomato, sugarbeet, broccoli, cassava, sweet potato, pepper, cotton, poinsettia, legumes, alfalfa, soybean, carrot, strawberry, lettuce, oak, maple, walnut, rose, mint, squash, daisy, and cactus.

20. A method for producing a transformed plant, comprising growing a plant from the plant cell of claim 1 or from plant tissue comprising the plant cell of claim 1.

21. The method of claim 1, further comprising growing a plant from the transformed plant cell.

22. The method of claim 7, wherein the desired polynucleotide comprises (i) a part of the 5'- or 3'-untranslated region sequences of at least one of the R1 gene, polyphenol oxidase gene, and phosphorylase gene and (ii) the complementary sequence thereof.

23. The method of claim 22, wherein the expression of the desired polynucleotide modifies a trait in a plant obtained from the transformed plant cell, wherein the trait is at least one of (i) lower levels of processing-induced acrylamide, (ii) reduced black-spot bruising, (iii) reduced cold-induced sweetening, and (iv) reduced starch phosphate levels in comparison to a plant that does not comprise a cell that expresses the desired polynucleotide.

24. The method of claim 23, wherein the trait is a lower level of acrylamide.

25. An isolated nucleic acid sequence with a 5'-end and a 3'-end, wherein (a) the 5'-end comprises the consensus sequence of (i) 5'-YGRYAGGATATATWSNVBKGTAAWY-3' (SEQ ID NO: 47) and (b) the 3'-end comprises the consensus sequence of (i) 5'-YGRYAGGATATATWSNVBKG-TAAWY-3' (SEQ ID NO: 47), wherein Y is C or T; R is A or G; K is G or T; M is A or C; W is A or T; S is C or G; V is A, C, or G; and B is C, G, or T and the nucleic acid sequence does not comprise an *Agrobacterium* T-DNA border, wherein at least one consensus sequence facilitates enzymatic nicking of the nucleic acid sequence.

26. The nucleic acid sequence of claim 25, further comprising an expression cassette between its 5'-end and 3'-end, wherein the expression cassette is located between the two consensus sequences.

27. The nucleic acid sequence of claim 26, wherein the expression cassette comprises at least one regulatory element for expressing a desired polynucleotide to which it is operably linked.

28. The nucleic acid sequence of claim 25, wherein the nucleic acid sequence is from plants.

29. The nucleic acid sequence of claim 28, wherein the nucleic acid sequence is from the genome of one plant species or from genomes of plants that are sexually interfertile with one another.

30. The nucleic acid sequence of claim 27, wherein the desired polynucleotide sequence is a sequence that is upstream or downstream of the coding region of a gene, wherein the upstream sequence is a leader sequence or a promoter sequence, and wherein the downstream sequence is a trailer sequence.

31. The nucleic acid sequence of claim 30, wherein the desired polynucleotide comprises a part of the 5'- or 3'-untranslated region sequences of a gene.

32. The nucleic acid sequence of claim 30, wherein the 5'- or 3'-untranslated region is from a gene that is selected from the group consisting of a PPO gene, an R1 gene, an L-type phosphorylase gene, HOS1 gene, a S-adenosylhomocysteine hydrolase gene, a class II cinnamate 4-hydroxylase gene, a cinnamoyl-coenzyme A reductase gene, a cinnamoyl alcohol dehydrogenase gene, a caffeoyl coenzyme A O-methyltransferase gene, an actin depolymerizing factor gene, a Nin88 gene, a Lol p 5 gene, an allergen gene, a P450 hydroxylase gene, an ADP-glucose pyrophosphorylase gene, a proline dehydrogenase gene, an endo-1,4-beta-glucanase gene, a zeaxanthin epoxidase gene, and a 1-aminocyclopropane-1-carboxylate synthase gene.

33. A vector comprising the nucleic acid sequence of claim 27.

* * * * *

UNITED STATES PATENT AND TRADEMARK OFFICE
CERTIFICATE OF CORRECTION

| | | |
|---|---|---|
| PATENT NO. | : 7,619,138 B2 | Page 1 of 1 |
| APPLICATION NO. | : 11/375095 | |
| DATED | : November 17, 2009 | |
| INVENTOR(S) | : Rommens et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 392 days.

Signed and Sealed this

Ninth Day of November, 2010

David J. Kappos
*Director of the United States Patent and Trademark Office*

SEQUENCE LISTING

<160> NUMBER OF SEQ ID NOS: 124

<210> SEQ ID NO 1
<211> LENGTH: 416
<212> TYPE: DNA
<213> ORGANISM: Solanum tuberosum

<400> SEQUENCE: 1

```
gtttacagta ccatatatcc tgtcagaggt atagaggcat gactggcatg atcactaaat      60
tgatgcccac agaggagact tataacctac aggggcacga agttctagga cttgaaagtg     120
actgaccgta gtccaactcg gtataaagcc tactcccaac taaatatatg aaatttatag     180
cataactgca gatgagctcg attctagagt aggtaccgag ctcgaattcc ttactcctcc     240
acaaagccgt aactgaagcg acttctatt  ttctcaacct tcggacctga cgatcaagaa     300
tctcaatagg tagttcttca taagtgagac tatccttcat agctcacctt tctaaaggta     360
cgatagattt tggatcaacc acacacactt cgtttacacc ggtatatatc ctgcca         416
```

<210> SEQ ID NO 2
<211> LENGTH: 824
<212> TYPE: DNA
<213> ORGANISM: Triticum sp.

<400> SEQUENCE: 2

```
tggcaggata tatgagtgtg taaacaacca taatcaggct gtaattatca agagaactaa      60
tgacaagaag cagagcttat caagtgtttc gtccagctgt aacatgggca caaaagcttg     120
cttgatgcat gtctggcttt tcaaagagca atgtattctc aggtacctgc acgtttgatc     180
ccctaccacg tacaagacga gcagaaagga catgtctgca gaaacttaga cacatccatt     240
gcagactcgt tccgaagcat caggagagta gtcagcaatg gtcatctgct gatgtaaatt     300
aattgattgt tggtaatcaa attttaacag caatatatat aatatatcaa tagtatattg     360
aactatgaaa gactgtaatc atatataaca gcatacaaat tgtcgtggaa acaagaggag     420
ctcatcaagt gtttagttca gaaatagcta accaagaatg caatataata ggggtactga     480
gctcccttca aaattactaa cttcagaaat agctaaccaa gaatgcaatg gcattgcata     540
atttaaacaa ctgtcagcac caatctctga ctgaaggcag tttacccatt cagaagagca     600
cacattttct gaacgacaac tctgagcggg gattgttgac agcagcaatt aatctggcct     660
caagatggtt tccaacaaca tagatcagat acagcactca agcacccaat aatcagccag     720
tactgatctg gttaccactg caattgatta acagatgaac tgtgaaatta agatttaact     780
gacagtaata taccagtt  ggcaggatat atccctctgt aaac                       824
```

<210> SEQ ID NO 3
<211> LENGTH: 2595
<212> TYPE: DNA
<213> ORGANISM: Artificial Sequence
<220> FEATURE:
<223> OTHER INFORMATION: Description of Artificial Sequence: Expression
      cassette for the IPT gene

<400> SEQUENCE: 3

```
ctgcagccaa agcacatact tatcgattta aatttcatcg aagagattaa tatcgaataa      60
tcatatacat actttaaata cataacaaat tttaaataca tatatctggt atataattaa     120
tttttttaaag tcatgaagta tgtatcaaat acacatatgg aaaaaattaa ctattcataa     180
```

-continued

| | |
|---|---|
| tttaaaaaat agaaaagata catctagtga aattaggtgc atgtatcaaa tacattagga | 240 |
| aaagggcata tatcttgatc tagataatta acgattttga tttatgtata atttccaaat | 300 |
| gaaggtttat atctacttca gaaataacaa tatacttttta tcagaacatt caacaaagta | 360 |
| acaaccaact agagtgaaaa atacacattg ttctctaaac atacaaaatt gagaaaagaa | 420 |
| tctcaaaatt tagagaaaca aatctgaatt tctagaagaa aaaaataatt atgcactttg | 480 |
| ctattgctcg aaaataaaat gaaagaaatt agactttttt aaaagatgtt agactagata | 540 |
| tactcaaaag ctatcaaagg agtaatattc ttcttacatt aagtatttta gttacagtcc | 600 |
| tgtaattaaa gacacatttt agattgtatc taaacttaaa tgtatctaga atacatatat | 660 |
| ttgaatgcat catatacatg tatccgacac accaattctc ataaaaagcg taatatccta | 720 |
| aactaattta tccttcaagt caacttaagc ccaatataca ttttcatctc taaaggccca | 780 |
| agtggcacaa aatgtcaggc ccaattacga agaaagggc ttgtaaaacc ctaataaagt | 840 |
| ggcactggca gagcttacac tctcattcca tcaacaaaga aaccctaaaa gccgcagcgc | 900 |
| cactgatttc tctcctccag gcgaagatgc agatcttcgt gaagaccta acggggaaga | 960 |
| cgatcaccct agaggttgag tcttccgaca ccatcgacaa tgtcaaagcc aagatccagg | 1020 |
| acaaggaagg gattcccccca gaccagcagc gtttgatttt cgccggaaag cagcttgagg | 1080 |
| atggtcgtac tcttgccgac tacaacatcc agaaggagtc aactctccat ctcgtgctcc | 1140 |
| gtctccgtgg tggtggatcc atggacctgc atctaatttt cggtccaact tgcacaggaa | 1200 |
| agacgacgac cgcgatagct cttgcccagc agacagggct tccagtcctt tcgcttgatc | 1260 |
| gggtccaatg ctgtcctcaa ctatcaaccg gaagcggacg accaacagtg gaagaactga | 1320 |
| aaggaacgac gcgtctctac cttgatgatc ggcctctggt ggagggtatc atcgcagcca | 1380 |
| agcaagctca tcataggctg atcgaggagg tgtataatca tgaggccaac ggcgggctta | 1440 |
| ttcttgaggg aggatccacc tcgttgctca actgcatggc gcgaaacagc tattggagtg | 1500 |
| cagattttcg ttggcatatt attcgccaca gttacccga ccaagagacc ttcatgaaag | 1560 |
| cggccaaggc cagagttaag cagatgttgc accccgctgc aggccattct attattcaag | 1620 |
| agttggttta tctttggaat gaacctcggc tgaggcccat tctgaaagag atcgatggat | 1680 |
| atcgatatgc catgttgttt gctagccaga accagatcac ggcagatatg ctattgcagc | 1740 |
| ttgacgcaaa tatggaaggt aagttgatta atgggatcgc tcaggagtat ttcatccatg | 1800 |
| cgcgccaaca ggaacagaaa ttccccccaag ttaacgcagc cgctttcgac ggattcgaag | 1860 |
| gtcatccgtt cggaatgtat taggttacgc cagccctgcg tcgcacctgt cttcatctgg | 1920 |
| ataagatgtt cgtaattgtt tttggctttg tcctgttgtg gcagggcggc aaatacttcc | 1980 |
| gacaatccat cgtgtcttca aactttatgc tggtgaacaa gtcttagttt ccacgaaagt | 2040 |
| attatgttaa attttaaaat ttcgatgtat aatgtggcta taattgtaaa aataaactat | 2100 |
| cgtaagtgtg cgtgttatgt ataatttgtc taaatgttta atatatatca tagaacgcaa | 2160 |
| taaatattaa atatagcgct tttatgaaat ataaatacat cattacaagt tgtttatatt | 2220 |
| tcgggtggac tagtttttaa tgtttagcaa atgtcctatc agttttctct ttttgtcgaa | 2280 |
| cggtaattta gagttttttt tgctatatgg attttcgttt ttgatgtatg tgacaaccct | 2340 |
| cgggattgtt gatttatttc aaaactaaga gttttttgctt attgttctcg tctattttgg | 2400 |
| atatcaatct tagttttata tcttttctag ttctctacgt gttaaatgtt caacacacta | 2460 |
| gcaatttggc tgcagcgtat ggattatgga actatcaagt ctgtgggatc gataaatatg | 2520 |
| cttctcagga atttgagatt ttacagtctt tatgctcatt gggttgagta taatatagta | 2580 | aaaaaatagg aattc 2595

<210> SEQ ID NO 4
<211> LENGTH: 9323
<212> TYPE: DNA
<213> ORGANISM: Artificial Sequence
<220> FEATURE:
<223> OTHER INFORMATION: Description of Artificial Sequence: pSIM111
nucleotide sequence

<400> SEQUENCE: 4

| | | | | | |
|---|---|---|---|---|---|
| agctttggca | ggatatatac | cggtgtaaac | gaagtgtgtg | tggttgatcc | aaaatctatc | 60 |
| gtacctttag | aaagtgtagc | tatgaaggat | agtctcactt | atgaagaact | acctattgag | 120 |
| attcttgatc | gtcaggtccg | aaggttgaga | aaaatagaag | tcgcttcagt | tacggctttg | 180 |
| tggaggagta | agggtaccta | ctctagaatc | gagctcatcg | ttatgctata | aatttcatat | 240 |
| atttagttgg | gagtaggctt | tataccgagt | tggactacgg | tcagtcactt | tcaagtccta | 300 |
| gaactacgtg | cccctgtagg | ttataagtct | cctctgtggg | catcaattta | gtgatcatgc | 360 |
| cagtcatgcc | tctatacctc | tgacaggata | tatggtactg | taaacactag | ttgtgaataa | 420 |
| gtcgctgtgt | atgtttgttt | gagatctcta | agagaaaaga | gcgtttatta | gaataacgga | 480 |
| tatttaaaag | ggcgtgaaaa | ggtttatccg | ttcgtccatt | tgtatgtggt | cacctatctc | 540 |
| gagcatgcca | accacagggt | tcccctcggg | atcaaagtac | tttgatccaa | cccctccgct | 600 |
| gctatagtgc | agtcggcttc | tgacgttcag | tgcagccgtc | ttctgaaaac | gacatgtcgc | 660 |
| acaagtccta | agttacgcga | caggctgccg | ccctgccctt | ttcctggcgt | tttcttgtcg | 720 |
| cgtgttttag | tcgcataaag | tagaatactt | gcgactagaa | ccggagacat | acgccatga | 780 |
| acaagagcgc | cgccgctggc | ctgctgggct | atgcccgcgt | cagcaccgac | gaccaggact | 840 |
| tgaccaacca | acgggccgaa | ctgcacgcgg | ccggctgcac | caagctgttt | tccgagaaga | 900 |
| tcaccggcac | caggcgcgac | cgcccggagc | tggccaggat | gcttgaccac | ctacgccctg | 960 |
| gcgacgttgt | gacagtgacc | aggctagacc | gcctggcccg | cagcacccgc | gacctactgg | 1020 |
| acattgccga | gcgcatccag | gaggccggcg | cgggcctgcg | tagcctggca | gagccgtggg | 1080 |
| ccgacaccac | cacgccggcc | ggccgcatgg | tgttgaccgt | gttcgccggc | attgccgagt | 1140 |
| tcgagcgttc | cctaatcatc | gaccgcaccc | ggagcgggcg | cgaggccgcc | aaggcccgag | 1200 |
| gcgtgaagtt | tggcccccgc | cctaccctca | ccccggcaca | gatcgcgcac | gcccgcgagc | 1260 |
| tgatcgacca | ggaaggccgc | accgtgaaag | aggcggctgc | actgcttggc | gtgcatcgct | 1320 |
| cgaccctgta | ccgcgcactt | gagcgcagcg | aggaagtgac | gcccaccgag | gccaggcggc | 1380 |
| gcggtgcctt | ccgtgaggac | gcattgaccg | aggccgacgc | cctggcggcc | gccgagaatg | 1440 |
| aacgccaaga | ggaacaagca | tgaaaccgca | ccaggacggc | caggacgaac | cgtttttcat | 1500 |
| taccgaagag | atcgaggcgg | agatgatcgc | ggccgggtac | gtgttcgagc | cgcccgcgca | 1560 |
| cgtctcaacc | gtgcggctgc | atgaaatcct | ggccggtttg | tctgatgcca | agctggcggc | 1620 |
| ctggccggcc | agcttggccg | ctgaagaaac | cgagcgccgc | cgtctaaaaa | ggtgatgtgt | 1680 |
| atttgagtaa | aacagcttgc | gtcatgcggt | cgctgcgtat | atgatgcgat | gagtaaataa | 1740 |
| acaaatacgc | aaggggaacg | catgaaggtt | atcgctgtac | ttaaccagaa | aggcgggtca | 1800 |
| ggcaagacga | ccatcgcaac | ccatctagcc | cgcgccctgc | aactcgccgg | ggccgatgtt | 1860 |
| ctgttagtcg | attccgatcc | ccagggcagt | gcccgcgatt | gggcggccgt | gcgggaagat | 1920 |
| caaccgctaa | ccgttgtcgg | catcgaccgc | ccgacgattg | accgcgacgt | gaaggccatc | 1980 |

```
ggccggcgcg acttcgtagt gatcgacgga gcgccccagg cggcggactt ggctgtgtcc    2040
gcgatcaagg cagccgactt cgtgctgatt ccggtgcagc caagccctta cgacatatgg    2100
gccaccgccg acctggtgga gctggttaag cagcgcattg aggtcacgga tggaaggcta    2160
caagcggcct ttgtcgtgtc gcgggcgatc aaaggcacgc gcatcggcgg tgaggttgcc    2220
gaggcgctgg ccgggtacga gctgcccatt cttgagtccc gtatcacgca gcgcgtgagc    2280
tacccaggca ctgccgccgc cggcacaacc gttcttgaat cagaacccga gggcgacgct    2340
gcccgcgagg tccaggcgct ggccgctgaa attaaatcaa aactcatttg agttaatgag    2400
gtaaagagaa aatgagcaaa agcacaaaca cgctaagtgc cggccgtccg agcgcacgca    2460
gcagcaaggc tgcaacgttg gccagcctgg cagacacgcc agccatgaag cgggtcaact    2520
ttcagttgcc ggcggaggat cacaccaagc tgaagatgta cgcggtacgc caaggcaaga    2580
ccattaccga gctgctatct gaatacatcg cgcagctacc agagtaaatg agcaaatgaa    2640
taaatgagta gatgaatttt agcggctaaa ggaggcggca tggaaaatca agaacaacca    2700
ggcaccgacg ccgtggaatg ccccatgtgt ggaggaacgg gcggttggcc aggcgtaagc    2760
ggctgggttg tctgccggcc ctgcaatggc actggaaccc ccaagcccga ggaatcggcg    2820
tgacggtcgc aaaccatccg gcccggtaca aatcggcgcg cgctgggtg atgacctggt    2880 ggagaagttg aaggccgcgc aggccgccca gcggcaacgc atcgaggcag aagcacgccc    2940
cggtgaatcg tggcaagcgg ccgctgatcg aatccgcaaa gaatcccggc aaccgccggc    3000
agccggtgcg ccgtcgatta ggaagccgcc caagggcgac gagcaaccag atttttccgt    3060
tccgatgctc tatgacgtgg gcacccgcga tagtcgcagc atcatggacg tggccgtttt    3120
ccgtctgtcg aagcgtgacc gacgagctgg cgaggtgatc cgctacgagc ttccagacgg    3180
gcacgtagag gtttccgcag ggccggccgg catggccagt gtgtgggatt acgacctggt    3240
actgatggcg gtttcccatc taaccgaatc catgaaccga taccgggaag ggaagggaga    3300
caagcccggc cgcgtgttcc gtccacacgt tgcggacgta ctcaagttct gccggcgagc    3360
cgatggcgga aagcagaaag acgacctggt agaaacctgc attcggttaa acaccacgca    3420
cgttgccatg cagcgtacga agaaggccaa gaacggccgc ctggtgacgg tatccgaggg    3480
tgaagccttg attagccgct acaagatcgt aaagagcgaa accgggcggc cggagtacat    3540
cgagatcgag ctagctgatt ggatgtaccg cgagatcaca gaaggcaaga acccggacgt    3600
gctgacggtt caccccgatt acttttttgat cgatcccggc atcggccgtt ttctctaccg    3660
cctggcacgc cgcgccgcag gcaaggcaga agccagatgg ttgttcaaga cgatctacga    3720
acgcagtggc agcgccggag agttcaagaa gttctgtttc accgtgcgca agctgatcgg    3780
gtcaaatgac ctgccggagt acgatttgaa ggaggaggcg gggcaggctg cccgatcct    3840 agtcatgcgc taccgcaacc tgatcgaggg cgaagcatcc gccggttcct aatgtacgga    3900
gcagatgcta gggcaaattg ccctagcagg ggaaaaaggt cgaaaaggtc tctttcctgt    3960
ggatagcacg tacattggga acccaaagcc gtacattggg aaccggaacc cgtacattgg    4020
gaacccaaag ccgtacattg gaaccggtc acacatgtaa gtgactgata taaaagagaa    4080
aaaaggcgat ttttccgcct aaaactcttt aaaacttatt aaaactctta aacccgcct    4140 ggcctgtgca taactgtctg gccagcgcac agccgaagag ctgcaaaaag cgcctaccct    4200
tcggtcgctg cgctccctac gccccgccgc ttcgcgtcgg cctatcgcgg ccgctggccg    4260
ctcaaaaatg gctggcctac ggccaggcaa tctaccaggg cgcggacaag ccgcgccgtc    4320
```

```
gccactcgac cgccggcgcc cacatcaagg caccctgcct cgcgcgtttc ggtgatgacg   4380
gtgaaaacct ctgacacatg cagctcccgg agacggtcac agcttgtctg taagcggatg   4440
ccgggagcag acaagcccgt cagggcgcgt cagcgggtgt tggcgggtgt cggggcgcag   4500
ccatgaccca gtcacgtagc gatagcggag tgtatactgg cttaactatg cggcatcaga   4560
gcagattgta ctgagagtgc accatatgcg gtgtgaaata ccgcacagat gcgtaaggag   4620
aaaataccgc atcaggcgct cttccgcttc ctcgctcact gactcgctgc gctcggtcgt   4680
tcggctgcgg cgagcggtat cagctcactc aaaggcggta atacggttat ccacagaatc   4740
aggggataac gcaggaaaga acatgtgagc aaaaggccag caaaaggcca ggaaccgtaa   4800
aaaggccgcg ttgctggcgt ttttccatag gctccgcccc cctgacgagc atcacaaaaa   4860
tcgacgctca agtcagaggt ggcgaaaccc gacaggacta taaagatacc aggcgtttcc   4920
ccctggaagc tccctcgtgc gctctcctgt tccgaccctg ccgcttaccg gatacctgtc   4980
cgcctttctc ccttcgggaa gcgtggcgct ttctcatagc tcacgctgta ggtatctcag   5040
ttcggtgtag gtcgttcgct ccaagctggg ctgtgtgcac gaaccccccg ttcagcccga   5100
ccgctgcgcc ttatccggta actatcgtct tgagtccaac ccggtaagac acgacttatc   5160
gccactggca gcagccactg gtaacaggat tagcagagcg aggtatgtag gcggtgctac   5220
agagttcttg aagtggtggc ctaactacgg ctacactaga aggacagtat ttggtatctg   5280
cgctctgctg aagccagtta ccttcggaaa aagagttggt agctcttgat ccggcaaaca   5340
aaccaccgct ggtagcggtg gttttttttgt ttgcaagcag cagattacgc gcagaaaaaa   5400
aggatctcaa gaagatcctt tgatcttttc tacggggtct gacgctcagt ggaacgaaaa   5460
ctcacgttaa gggattttgg tcatgcattc taggtactaa acaattcat ccagtaaaat   5520 ataatatttt attttctccc aatcaggctt gatccccagt aagtcaaaaa atagctcgac   5580
atactgttct tccccgatat cctccctgat cgaccggacg cagaaggcaa tgtcatacca   5640
cttgtccgcc ctgccgcttc tcccaagatc aataaagcca cttactttgc catctttcac   5700
aaagatgttg ctgtctccca ggtcgccgtg ggaaaagaca agttcctctt cgggcttttc   5760
cgtctttaaa aaatcataca gctcgcgcgg atctttaaat ggagtgtctt cttcccagtt   5820
ttcgcaatcc acatcggcca gatcgttatt cagtaagtaa tccaattcgg ctaagcggct   5880
gtctaagcta ttcgtatagg gacaatccga tatgtcgatg gagtgaaaga gcctgatgca   5940
ctccgcatac agctcgataa tcttttcagg gctttgttca tcttcatact cttccgagca   6000
aaggacgcca tcggcctcac tcatgagcag attgctccag ccatcatgcc gttcaaagtg   6060
caggaccttt ggaacaggca gctttccttc cagccatagc atcatgtcct tttcccgttc   6120
cacatcatag gtggtccctt tataccggct gtccgtcatt tttaaatata ggttttcatt   6180
ttctcccacc agcttatata ccttagcagg agacattcct tccgtatctt ttacgcagcg   6240 gtattttttcg atcagttttt tcaattccgg tgatattctc attttagcca tttattattt   6300
ccttcctctt ttctacagta tttaaagata ccccaagaag ctaattataa caagacgaac   6360
tccaattcac tgttccttgc attctaaaac cttaaatacc agaaacagc tttttcaaag   6420 ttgttttcaa agttggcgta taacatagta tcgacggagc cgattttgaa accgcggatc   6480
ctgcagccaa agcacatact tatcgattta aatttcatcg aagagattaa tatcgaataa   6540
tcatatacat actttaaata cataacaaat tttaaataca tatatctggt atataattaa   6600
ttttttaaag tcatgaagta tgtatcaaat acacatatgg aaaaaattaa ctattcataa   6660
tttaaaaaat agaaaagata catctagtga aattaggtgc atgtatcaaa tacattagga   6720
```

```
aaagggcata tatcttgatc tagataatta acgattttga tttatgtata atttccaaat    6780
gaaggtttat atctacttca gaaataacaa tactttta tcagaacatt caacaaagta      6840
acaaccaact agagtgaaaa atacacattg ttctctaaac atacaaaatt gagaaaagaa    6900
tctcaaaatt tagagaaaca aatctgaatt tctagaagaa aaaataatt atgcactttg     6960 ctattgctcg aaaaataaat gaaagaaatt agactttttt aaaagatgtt agactagata    7020
tactcaaaag ctatcaaagg agtaatattc ttcttacatt aagtatttta gttacagtcc    7080
tgtaattaaa gacacatttt agattgtatc taaacttaaa tgtatctaga atacatatat    7140
ttgaatgcat catatacatg tatccgacac accaattctc ataaaaagcg taatatccta    7200
aactaattta tccttcaagt caacttaagc ccaatataca ttttcatctc taaaggccca    7260
agtggcacaa aatgtcaggc ccaattacga agaaagggc ttgtaaaacc ctaataaagt     7320
ggcactggca gagcttacac tctcattcca tcaacaaaga aaccctaaaa gccgcagcgc    7380
cactgatttc tctcctccag gcgaagatgc agatcttcgt gaagaccta acggggaaga    7440 cgatcaccct agaggttgag tcttccgaca ccatcgacaa tgtcaaagcc aagatccagg    7500
acaaggaagg gattcccca gaccagcagc gtttgatttt cgccggaaag cagcttgagg    7560
atggtcgtac tcttgccgac tacaacatcc agaaggagtc aactctccat ctcgtgctcc    7620
gtctccgtgg tggtggatcc atggacctgc atctaatttt cggtccaact tgcacaggaa    7680
agacgacgac cgcgatagct cttgcccagc agacagggct tccagtcctt tcgcttgatc    7740
gggtccaatg ctgtcctcaa ctatcaaccg gaagcggacg accaacagtg gaagaactga    7800
aaggaacgac gcgtctctac cttgatgatc ggcctctggt ggagggtatc atcgcagcca    7860
agcaagctca tcataggctg atcgaggagg tgtataatca tgaggccaac ggcgggctta    7920
ttcttgaggg aggatccacc tcgttgctca actgcatggc gcgaaacagc tattggagtg    7980
cagattttcg ttggcatatt attcgccaca agttacccga ccaagagacc ttcatgaaag    8040
cggccaaggc cagagttaag cagatgttgc accccgctgc aggccattct attattcaag    8100
agttggttta tctttggaat gaacctcggc tgaggcccat tctgaaagag atcgatggat    8160
atcgatatgc catgttgttt gctagccaga accagatcac ggcagatatg ctattgcagc    8220
ttgacgcaaa tatggaaggt aagttgatta atggatcgc tcaggagtat ttcatccatg    8280
cgcgccaaca ggaacagaaa ttcccccaag ttaacgcagc cgctttcgac ggattcgaag    8340
gtcatccgtt cggaatgtat taggttacgc cagccctgcg tcgcacctgt cttcatctgg    8400
ataagatgtt cgtaattgtt tttggctttg tcctgttgtg gcagggcggc aaatacttcc    8460
gacaatccat cgtgtcttca aactttatgc tggtgaacaa gtcttagttt ccacgaaagt    8520
attatgttaa attttaaaat ttcgatgtat aatgtggcta taattgtaaa aataaactat    8580
cgtaagtgtg cgtgttatgt ataatttgtc taaatgttta atatatatca tagaacgcaa    8640
taaatattaa atatagcgct tttatgaaat ataaatacat cattacaagt tgtttatatt    8700
tcgggtggac tagttttaa tgtttagcaa atgtcctatc agtttctct ttttgtcgaa      8760 cggtaattta gagtttttt tgctatatgg atttttcgttt ttgatgtatg tgacaaccct    8820
cgggattgtt gatttattc aaaactaaga gtttttgctt attgttctcg tctattttgg     8880
atatcaatct tagttttata tcttttctag ttctctacgt gttaaatgtt caacacacta    8940
gcaatttggc tgcagcgtat ggattatgga actatcaagt ctgtgggatc gataaatatg    9000
cttctcagga atttgagatt ttacagtctt tatgctcatt gggttgagta taatatagta    9060
```

| aaaaaatagg aattctatcc gcggtgatca caggcagcaa cgctctgtca tcgttacaat | 9120 |
|---|---|
| caacatgcta ccctccgcga gatcatccgt gtttcaaacc cggcagctta gttgccgttc | 9180 |
| ttccgaatag catcggtaac atgagcaaag tctgccgcct acaacggct ctcccgctga | 9240 |
| cgccgtcccg gactgatggg ctgcctgtat cgagtggtga ttttgtgccg agctgccggt | 9300 |
| cggggagctg ttggctggct gga | 9323 |

<210> SEQ ID NO 5
<211> LENGTH: 546
<212> TYPE: DNA
<213> ORGANISM: Solanum tuberosum

<400> SEQUENCE: 5

| atgagaaatt tattccccat attgatgcta atcaccaatt tggcactcaa caacgataac | 60 |
|---|---|
| aacaacaaca caacaacaa caataattat aatctcatac acgcaacgtg tagggagacc | 120 |
| ccatattact ccctatgtct caccacccta caatccggtc cacgtagtaa cgaggttgag | 180 |
| ggtggtgatg ccatcaccac cctaggcctc atcatggtgg acgcggtgaa atcaaagtcc | 240 |
| atagaaataa tggaaaaaat aaaagagcta gagaaatcga accctgagtg gcgggcccca | 300 |
| cttagccagt gttacgtggc gtataatgcc gtcctacgag ccgatgtaac ggtagccgtt | 360 |
| gaagccttaa agaagggtgc ccccaaattt gctgaagatg gtatggatga tgttgttgct | 420 |
| gaagcacaaa cttgtgagta tagttttaat tattataata aattggattt tccaatttct | 480 |
| aatttgagta gggaaataat tgaactatca aaagttgcta atccataat tagaatgtta | 540 |
| ttatga | 546 |

<210> SEQ ID NO 6
<211> LENGTH: 658
<212> TYPE: DNA
<213> ORGANISM: Solanum tuberosum

<400> SEQUENCE: 6

| gaaccatgca tctcaatctt aatactaaaa aatgcaacaa aattctagtg gagggaccag | 60 |
|---|---|
| taccagtaca ttagatatta tcttttatta ctataataat attttaatta acacgagaca | 120 |
| taggaatgtc aagtggtagc ggtaggaggg agttggttca gttttttaga tactaggaga | 180 |
| cagaaccgga ggggcccatt gcaaggccca agttgaagtc cagccgtgaa tcaacaaaga | 240 |
| gagggcccat aatactgtcg atgagcattt ccctataata cagtgtccac agttgccttc | 300 |
| cgctaaggga tagccacccg ctattctctt gacacgtgtc actgaaacct gctacaaata | 360 |
| aggcaggcac ctcctcattc tcacactcac tcactcacac agctcaacaa gtggtaactt | 420 |
| ttactcatct cctccaatta tttctgattt catgcatgtt ccctacatt ctattatgaa | 480 |
| tcgtgttatg gtgtataaac gttgtttcat atctcatctc atctattctg attttgattc | 540 |
| tcttgcctac tgaattgac cctactgtaa tcggtgataa atgtgaatgc ttcctcttct | 600 |
| tcttcttctt ctcagaaatc aatttctgtt ttgttttgt tcatctgtag cttggtag | 658 |

<210> SEQ ID NO 7
<211> LENGTH: 355
<212> TYPE: DNA
<213> ORGANISM: Solanum tuberosum

<400> SEQUENCE: 7

| ttttaatgtt tagcaaatgt cctatcagtt ttctctttt gtcgaacggt aatttagagt | 60 |
|---|---|
| ttttttttgct atatggattt tcgttttga tgtatgtgac aaccctcggg attgttgatt | 120 |

```
tatttcaaaa ctaagagttt ttgcttattg ttctcgtcta ttttggatat caatcttagt      180
tttatatctt ttctagttct ctacgtgtta aatgttcaac acactagcaa tttggctgca      240
gcgtatggat tatggaacta tcaagtctgt gggatcgata aatatgcttc tcaggaattt      300
gagattttac agtctttatg ctcattgggt tgagtataat atagtaaaaa aatag           355

<210> SEQ ID NO 8
<211> LENGTH: 179
<212> TYPE: DNA
<213> ORGANISM: Solanum tuberosum

<400> SEQUENCE: 8
accttatttc actaccactt tccactctcc aatccccata ctctctgctc caatcttcat       60
tttgcttcgt gaattcatct tcatcgaatt tctcgacgct tcttcgctaa tttcctcgtt      120
acttcactaa aaatcgacgt ttctagctga acttgagtga attaagccag tgggaggat       179

<210> SEQ ID NO 9
<211> LENGTH: 569
<212> TYPE: DNA
<213> ORGANISM: Solanum tuberosum

<400> SEQUENCE: 9
gttagaaatc ttctctattt ttggtttttg tctgtttaga ttctcgaatt agctaatcag       60
gtgctgttat agcccttaat tttgagtttt ttttcggttg ttttgatgga aaaggcctaa      120
aatttgagtt tttttacgtt ggtttgatgg aaaaggccta caattggagt tttccccgtt      180
gttttgatga aaaagcccct agtttgagat ttttttttctg tcgattcgat tctaaaggtt     240
taaaattaga gttttttacat ttgtttgatg aaaaaggcct taaatttgag ttttttccggt    300 tgatttgatg aaaaagccct agaatttgtg ttttttcgtc ggtttgattc tgaaggccta      360
aaatttgagt ttctccggct gttttgatga aaaagcccta aatttgagtt tctccggctg      420
ttttgatgaa aaagccctaa atttgagttt ttccccgtg ttttagattg tttggtttta       480
attctcgaat cagctaatca gggagtgtga aaagccctaa aatttgagtt tttttcgttg      540
ttctgattgt tgttttatg aatttgcag                                         569

<210> SEQ ID NO 10
<211> LENGTH: 1738
<212> TYPE: DNA
<213> ORGANISM: Artificial Sequence
<220> FEATURE:
<223> OTHER INFORMATION: Description of Artificial Sequence: Expression
      cassette for a sense and antisense copy of the
      leader associated with the R1 gene

<400> SEQUENCE: 10
ggtaccgaac catgcatctc aatcttaata ctaaaaaatg caacaaaatt ctagtggagg       60
gaccagtacc agtacattag atattatctt ttattactat aataatattt taattaacac      120
gagacatagg aatgtcaagt ggtagcggta ggagggagtt ggttcagttt tttagatact      180
aggagacaga accggagggg cccattgcaa ggcccaagtt gaagtccagc cgtgaatcaa      240
caaagagagg gcccataata ctgtcgatga gcatttccct ataatacagt gtccacagtt      300
gccttccgct aagggatagc caccgctat tctcttgaca cgtgtcactg aaacctgcta      360
caaataaggc aggcacctcc tcattctcac actcactcac tcacacagct caagaaggat      420
ccaccttatt tcactaccac tttccactct ccaatcccca tactctctgc tccaatcttc      480
```

-continued

```
attttgcttc gtgaattcat cttcatcgaa tttctcgacg cttcttcgct aatttcctcg    540
ttacttcact agaaatcgac gtttctagct gaacttgagt gaattaagcc agtgggagga    600
tgaattcaag gttagaaatc ttctctattt ttggttttg tctgtttaga ttctcgaatt    660
agctaatcag gtgctgttat agcccttaat tttgagtttt ttttcggttg ttttgatgga    720
aaaggcctaa aatttgagtt tttttacgtt ggtttgatgg aaaaggccta caattggagt    780
tttccccgtt gttttgatga aaaagcccct agtttgagat tttttttctg tcgattcgat    840
tctaaaggtt taaaattaga gtttttacat ttgtttgatg aaaaaggcct taaatttgag    900
tttttccggt tgatttgatg aaaaagcccct agaatttgtg tttttcgtc ggtttgattc    960 tgaaggccta aaatttgagt ttctccggct gttttgatga aaaagcccta aatttgagtt   1020
tctccggctg ttttgatgaa aaagcccctaa atttgagttt tttccccgtg ttttagattg   1080
tttggtttta attctcgaat cagctaatca gggagtgtga aaagcccctaa aatttgagtt   1140 tttctcgttg ttctgattgt tgtttttatg aatttgcaga tggatatcat cctcccactg   1200
gcttaattca ctcaagttca gctagaaacg tcgatttcta gtgaagtaac gaggaaatta   1260
gcgaagaagc gtcgagaaat tcgatgaaga tgaattcacg aagcaaaatg aagattggag   1320
cagagagtat ggggattgga gagtggaaag tggtagtgaa ataaggtaag cttttgattt   1380
taatgtttag caaatgtcct atcagttttc tcttttttgtc gaacggtaat ttagagtttt   1440
ttttgctata tggattttcg ttttttgatgt atgtgacaac cctcgggatt gttgatttat   1500
ttcaaaacta agagttttg cttattgttc tcgtctattt tggatatcaa tcttagtttt   1560
atatcttttc tagttctcta cgtgttaaat gttcaacaca ctagcaattt ggctgcagcg   1620
tatggattat ggaactatca agtctgtggg atcgataaat atgcttctca ggaatttgag   1680
attttacagt ctttatgctc attgggttga gtataatata gtaaaaaaat agtctaga    1738
```

<210> SEQ ID NO 11  
<211> LENGTH: 237  
<212> TYPE: DNA  
<213> ORGANISM: Artificial Sequence  
<220> FEATURE:  
<223> OTHER INFORMATION: Description of Artificial Sequence: Synthetic spacer sequence

<400> SEQUENCE: 11

```
gtaacttta ctcatctcct ccaattattt ctgatttcat gcatgtttcc ctacattcta    60
ttatgaatcg tgttatggtg tataaacgtt gtttcatatc tcatctcatc tattctgatt   120
ttgattctct tgcctactga atttgaccct actgtaatcg gtgataaatg tgaatgcttc   180
ctcttcttct tcttcttctc agaaatcaat ttctgttttg ttttgttca tctgtag      237
```

<210> SEQ ID NO 12  
<211> LENGTH: 1406  
<212> TYPE: DNA  
<213> ORGANISM: Artificial Sequence  
<220> FEATURE:  
<223> OTHER INFORMATION: Description of Artificial Sequence: Alternative expression cassette for a sense and antisense coopy of the leader associated with the R1 gene

<400> SEQUENCE: 12

```
ggtaccgaac catgcatctc aatcttaata ctaaaaaatg caacaaaatt ctagtggagg    60
gaccagtacc agtacattag atattatctt ttattactat aataatatttt taattaacac   120 gagacatagg aatgtcaagt ggtagcggta ggagggagtt ggttcagttt tttagatact   180
```

| aggagacaga | accggagggg | cccattgcaa | ggcccaagtt | gaagtccagc | cgtgaatcaa | 240 |
| caaagagagg | gcccataata | ctgtcgatga | gcatttccct | ataatacagt | gtccacagtt | 300 |
| gccttccgct | aagggatagc | cacccgctat | tctcttgaca | cgtgtcactg | aaacctgcta | 360 |
| caaataaggc | aggcacctcc | tcattctcac | actcactcac | tcacacagct | caagaaggat | 420 |
| ccaccttatt | tcactaccac | tttccactct | ccaatcccca | tactctctgc | tccaatcttc | 480 |
| attttgcttc | gtgaattcat | cttcatcgaa | tttctcgacg | cttcttcgct | aatttcctcg | 540 |
| ttacttcact | agaaatcgac | gtttctagct | gaacttgagt | gaattaagcc | agtgggagga | 600 |
| tgaattcgtg | gtaacttta | ctcatctcct | ccaattattt | ctgatttcat | gcatgtttcc | 660 |
| ctacattcta | ttatgaatcg | tgttatggtg | tataaacgtt | gtttcatatc | tcatctcatc | 720 |
| tattctgatt | ttgattctct | tgcctactga | atttgaccct | actgtaatcg | gtgataaatg | 780 |
| tgaatgcttc | ctcttcttct | tcttcttctc | agaaatcaat | ttctgttttg | tttttgttca | 840 |
| tctgtagctt | gatatcatcc | tcccactggc | ttaattcact | caagttcagc | tagaaacgtc | 900 |
| gatttctagt | gaagtaacga | ggaaattagc | gaagaagcgt | cgagaaattc | gatgaagatg | 960 |
| aattcacgaa | gcaaaatgaa | gattggagca | gagagtatgg | ggattggaga | gtggaaagtg | 1020 |
| gtagtgaaat | aaggtaagct | tttgatttta | atgtttagca | aatgtcctat | cagttttctc | 1080 |
| tttttgtcga | acgtaatttt | agagtttttt | ttgctatatg | gattttcgtt | tttgatgtat | 1140 |
| gtgacaaccc | tcgggattgt | tgatttattt | caaaactaag | agtttttgct | tattgttctc | 1200 |
| gtctattttg | gatatcaatc | ttagttttat | atcttttcta | gttctctacg | tgttaaatgt | 1260 |
| tcaacacact | agcaatttgg | ctgcagcgta | tggattatgg | aactatcaag | tctgtgggat | 1320 |
| cgataaaatat | gcttctcagg | aatttgagat | tttacagtct | ttatgctcat | tgggttgagt | 1380 |
| ataatatagt | aaaaaaatag | tctaga |  |  |  | 1406 |

<210> SEQ ID NO 13
<211> LENGTH: 686
<212> TYPE: DNA
<213> ORGANISM: Solanum tuberosum

<400> SEQUENCE: 13

| gaaccatgca | tctcaatctt | aatactaaaa | aatgcaacaa | aattctagtg | gagggaccag | 60 |
| taccagtaca | ttagatatta | tctttttatta | ctataataat | atttaattta | acacgagaca | 120 |
| taggaatgtc | aagtggtagc | ggtaggaggg | agttggttca | gttttttaga | tactaggaga | 180 |
| cagaaccgga | ggggcccatt | gcaaggccca | agttgaagtc | cagccgtgaa | tcaacaaaga | 240 |
| gagggcccat | aatactgtcg | atgagcattt | ccctataata | cagtgtccac | agttgccttc | 300 |
| cgctaaggga | tagccacccg | ctattctctt | gacacgtgtc | actgaaacct | gctacaaata | 360 |
| aggcaggcac | ctcctcattc | tcacactcac | tcactcacac | agctcaacaa | gtggtaactt | 420 |
| ttactcatct | cctccaatta | tttctgatt | catgcatgtt | tccctacatt | ctattatgaa | 480 |
| tcgtgttatg | gtgtataaac | gttgtttcat | atctcatctc | atctattctg | attttgattc | 540 |
| tcttgcctac | tgaatttgac | cctactgtaa | tcggtgataa | atgtgaatgc | ttcctcttct | 600 |
| tcttcttctt | ctcagaaatc | aatttctgtt | ttgttttttgt | tcatctgtag | cttggtagat | 660 |
| tccccttttt | gtagaccaca | catcac |  |  |  | 686 |

<210> SEQ ID NO 14
<211> LENGTH: 2046
<212> TYPE: DNA
<213> ORGANISM: Artificial Sequence
<220> FEATURE:
<223> OTHER INFORMATION: Description of Artificial Sequence: Alternative
expression cassette for a sense and antisense copy
of the leader associated with the R1 gene

<400> SEQUENCE: 14

```
ggtaccgaac catgcatctc aatcttaata ctaaaaaatg caacaaaatt ctagtggagg      60
gaccagtacc agtacattag atattatctt ttattactat aataatattt taattaacac     120
gagacatagg aatgtcaagt ggtagcggta ggagggagtt ggttcagttt tttagatact     180
aggagacaga accggagggg cccattgcaa ggcccaagtt gaagtccagc cgtgaatcaa     240
caaagagagg gcccataata ctgtcgatga gcatttccct ataatacagt gtccacagtt     300
gccttccgct aagggatagc cacccgctat tctcttgaca cgtgtcactg aaacctgcta     360
caaataaggc aggcacctcc tcattctcac actcactcac tcacacagct caagaaggat     420
cctcatattc tagttgtatg ttgttcagag aagaccacag atgtgatcat attctcattg     480
tatcagatct gtgaccactt acctgatacc tcccatgaag ttacctgtat gattatacgt     540
gatccaaagc catcacatca tgttcacctt cagctattgg aggagaagtg agaagtagga     600
attgcaatat gaggaataat aagaaaaact ttgtaaaagc taaattagct gggtatgata     660
tagggagaaa tgtgtaaaca ttgtactata tatagtatat acacacgcat tatgtattgc     720
attatgcact gaataatacc gcagcatcaa agaaggaatt caaggttaga aatcttctct     780
atttttggtt tttgtctgtt tagattctcg aattagctaa tcaggtgctg ttatagccct     840
taattttgag ttttttttcg gttgtttttga tggaaaaggc ctaaaatttg agttttttta     900
cgttggtttg atggaaaagg cctacaattg gagttttccc cgttgttttg atgaaaaagc     960
ccctagtttg agattttttt tctgtcgatt cgattctaaa ggtttaaaat tagagttttt    1020
acatttgttt gatgaaaaag gccttaaatt tgagtttttc cggttgattt gatgaaaaag    1080
ccctagaatt tgtgtttttt cgtcggtttg attctgaagg cctaaaattt gagtttctcc    1140
ggctgttttg atgaaaaagc cctaaatttg agtttctccg gctgttttga tgaaaaagcc    1200
ctaaatttga gttttttccc cgtgttttag attgtttggt tttaattctc gaatcagcta    1260
atcagggagt gtgaaaagcc ctaaaatttg agtttttttc gttgttctga ttgttgtttt    1320
tatgaatttg cagatggata tccttctttg atgctgcggt attattcagt gcataatgca    1380
atacataatg cgtgtgtata tactatatat agtacaatgt ttacacattt ctccctatat    1440
catacccagc taatttagct tttacaaagt ttttcttatt attcctcata ttgcaattcc    1500
tacttctcac ttctcctcca atagctgaag gtgaacatga tgtgatggct ttggatcacg    1560
tataatcata caggtaactt catgggaggt atcaggtaag tggtcacaga tctgatacaa    1620
tgagaatatg atcacatctg tggtcttctc tgaacaacat acaactagaa tatgaaagct    1680
tttgatttta atgtttagca aatgtccgtat cagttttctc tttttgtcga acggtaattt    1740
agagttttttt ttgctatatg gattttcgtt tttgatgtat gtgacaaccc tcgggattgt    1800
tgatttattt caaaactaag agttttttgct tattgttctc gtctattttg gatatcaatc    1860
ttagttttat atcttttcta gttctctacg tgttaaatgt tcaacacact agcaatttgg    1920
ctgcagcgta tggattatgg aactatcaag tctgtgggat cgataaatat gcttctcagg    1980
aatttgagat tttacagtct ttatgctcat tgggttgagt ataatatagt aaaaaaatag    2040
tctaga                                                               2046
```

<210> SEQ ID NO 15

<211> LENGTH: 1714
<212> TYPE: DNA
<213> ORGANISM: Artificial Sequence
<220> FEATURE:
<223> OTHER INFORMATION: Description of Artificial Sequence: Alternative
    expression cassette for a sense and antisense copy
    of the leader associated with the R1 gene

<400> SEQUENCE: 15

```
ggtaccgaac catgcatctc aatcttaata ctaaaaaatg caacaaaatt ctagtggagg      60
gaccagtacc agtacattag atattatctt ttattactat aataatattt taattaacac     120
gagacatagg aatgtcaagt ggtagcggta ggagggagtg ggttcagttt tttagatact     180
aggagacaga accggagggg cccattgcaa ggcccaagtt gaagtccagc cgtgaatcaa     240
caaagagagg gcccataata ctgtcgatga gcatttccct ataatacagt gtccacagtt     300
gccttccgct aagggatagc cacccgctat tctcttgaca cgtgtcactg aaacctgcta     360
caaataaggc aggcacctcc tcattctcac actcactcac tcacacagct caagaaggat     420
cctcatattc tagttgtatg ttgttcagag aagaccacag atgtgatcat attctcattg     480
tatcagatct gtgaccactt acctgatacc tccatgaag ttacctgtat gattatacgt      540
gatccaaagc catcacatca tgttcacctt cagctattgg aggagaagtg agaagtagga     600
attgcaatat gaggaataat aagaaaaact tgtaaaagc taaattagct gggtatgata      660
tagggagaaa tgtgtaaaca ttgtactata tatagtatat acacacgcat tatgtattgc     720
attatgcact gaataatacc gcagcatcaa agaaggaatt cgtggtaact tttactcatc     780
tcctccaatt atttctgatt tcatgcatgt ttccctacat tctattatga atcgtgttat     840
ggtgtataaa cgttgtttca tatctcatct catctattct gattttgatt ctcttgccta     900
ctgaatttga ccctactgta atcggtgata aatgtgaatg cttcctcttc ttcttcttct     960
tctcagaaat caatttctgt tttgttttg ttcatctgta gcttgatatc cttctttgat     1020
gctgcggtat tattcagtgc ataatgcaat acataatgcg tgtgtatata ctatatatag    1080
tacaatgttt acacatttct ccctatatca tacccagcta atttagcttt tacaaagttt    1140
ttcttattat tcctcatatt gcaattccta cttctcactt ctcctccaat agctgaaggt    1200
gaacatgatg tgatggcttt ggatcacgta taatcataca ggtaacttca tgggaggtat    1260
caggtaagtg gtcacagatc tgatacaatg agaatatgat cacatctgtg gtcttctctg    1320
aacaacatac aactagaata tgaaagcttt tgattttaat gtttagcaaa tgtcctatca    1380
gttttctctt tttgtcgaac ggtaatttag agttttttt gctatatgga ttttcgtttt     1440
tgatgtatgt gacaaccctc gggattgttg atttatttca aaactaagag tttttgctta    1500
ttgttctcgt ctattttgga tatcaatctt agttttatat cttttctagt tctctacgtg    1560
ttaaatgttc aacacactag caatttggct gcagcgtatg gattatggaa ctatcaagtc    1620
tgtgggatcg ataaatatgc ttctcaggaa tttgagattt tacagtcttt atgctcattg    1680
ggttgagtat aatatagtaa aaaaatagtc taga                                1714
```

<210> SEQ ID NO 16
<211> LENGTH: 333
<212> TYPE: DNA
<213> ORGANISM: Solanum tuberosum

<400> SEQUENCE: 16

```
tcatattcta gttgtatgtt gttcagagaa gaccacagat gtgatcatat tctcattgta      60
tcagatctgt gaccacttac ctgatacctc ccatgaagtt acctgtatga ttatacgtga     120
```

-continued

```
tccaaagcca tcacatcatg ttcaccttca gctattggag gagaagtgag aagtaggaat    180
tgcaatatga ggaataataa gaaaaacttt gtaaaagcta aattagctgg gtatgatata    240
gggagaaatg tgtaaacatt gtactatata tagtatatac acacgcatta tgtattgcat    300
tatgcactga ataataccgc agcatcaaag aag                                 333
```

<210> SEQ ID NO 17
<211> LENGTH: 2046
<212> TYPE: DNA
<213> ORGANISM: Artificial Sequence
<220> FEATURE:
<223> OTHER INFORMATION: Description of Artificial Sequence: Alternative
      expression cassette for a sense and antisense copy
      of the trailer associated with the R1 gene

<400> SEQUENCE: 17

```
ggtaccgaac catgcatctc aatcttaata ctaaaaaatg caacaaaatt ctagtggagg    60
gaccagtacc agtacattag atattatctt ttattactat aataatatt taattaacac    120 gagacatagg aatgtcaagt ggtagcggta ggagggagtt ggttcagttt tttagatact   180
aggagacaga accggagggg cccattgcaa ggcccaagtt gaagtccagc cgtgaatcaa   240
caaagagagg gcccataata ctgtcgatga gcatttccct ataatacagt gtccacagtt   300
gccttccgct aagggatagc cacccgctat tctcttgaca cgtgtcactg aaacctgcta   360
caaataaggc aggcacctcc tcattctcac actcactcac tcacacagct caagaaggat   420
cctcatattc tagttgtatg ttgttcagag aagaccacag atgtgatcat attctcattg   480
tatcagatct gtgaccactt acctgatacc tcccatgaag ttacctgtat gattatacgt   540
gatccaaagc catcacatca tgttcacctt cagctattgg aggagaagtg agaagtagga   600
attgcaatat gaggaataat aagaaaaact ttgtaaaagc taaattagct gggtatgata   660
tagggagaaa tgtgtaaaca ttgtactata tatagtatat acacacgcat tatgtattgc   720
attatgcact gaataatacc gcagcatcaa agaaggaatt caaggttaga aatcttctct   780
atttttggtt tttgtctgtt tagattctcg aattagctaa tcaggtgctg ttatagccct   840
taattttgag ttttttttcg gttgttttga tggaaaaggc ctaaaatttg agttttttta   900
cgttggtttg atggaaaagg cctacaattg gagttttccc cgttgttttg atgaaaaagc   960
ccctagtttg agatttttt tctgtcgatt cgattctaaa ggtttaaaat tagagttttt   1020
acatttgttt gatgaaaaag gccttaaatt tgagttttc cggttgattt gatgaaaaag   1080
ccctagaatt tgtgtttttt cgtcggtttg attctgaagg cctaaaattt gagtttctcc   1140
ggctgttttg atgaaaaagc cctaaatttg agtttctccg gctgttttga tgaaaaagcc   1200
ctaaatttga gttttttccc cgtgttttag attgtttggt tttaattctc gaatcagcta   1260
atcagggagt gtgaaaagcc ctaaaatttg agtttttttc gttgttctga ttgttgtttt   1320
tatgaatttg cagatggata tccttctttg atgctgcggt attattcagt gcataatgca   1380
atacataatg cgtgtgtata tactatatat agtacaatgt ttacacattt ctccctatat   1440
catacccagc taatttagct tttacaaagt ttttcttatt attcctcata ttgcaattcc   1500
tacttctcac ttctcctcca atagctgaag gtgaacatga tgtgatggct ttggatcacg   1560
tataatcata caggtaactt catgggaggt atcaggtaag tggtcacaga tctgatacaa   1620
tgagaatatg atcacatctg tggtcttctc tgaacaacat acaactagaa tatgaaagct   1680
tttgatttta atgtttagca aatgtcctat cagttttctc tttttgtcga acggtaattt   1740
```

```
agagttttttt ttgctatatg gattttcgtt tttgatgtat gtgacaaccc tcgggattgt    1800
tgatttattt caaaactaag agttttgct tattgttctc gtctattttg gatatcaatc     1860
ttagttttat atcttttcta gttctctacg tgttaaatgt tcaacacact agcaatttgg    1920
ctgcagcgta tggattatgg aactatcaag tctgtgggat cgataaatat gcttctcagg    1980
aatttgagat tttacagtct ttatgctcat tgggttgagt ataatatagt aaaaaaatag    2040
tctaga                                                                2046
```

<210> SEQ ID NO 18
<211> LENGTH: 1714
<212> TYPE: DNA
<213> ORGANISM: Artificial Sequence
<220> FEATURE:
<223> OTHER INFORMATION: Description of Artificial Sequence: Alternative
      expression cassette for a sense and antisense copy
      of the trailer associated with the R1 gene

<400> SEQUENCE: 18

```
ggtaccgaac catgcatctc aatcttaata ctaaaaaatg caacaaaatt ctagtggagg     60
gaccagtacc agtacattag atattatctt ttattactat aataatattt taattaacac    120
gagacatagg aatgtcaagt ggtagcggta ggagggagtt ggttcagttt tttagatact    180
aggagacaga accggagggg cccattgcaa ggcccaagtt gaagtccagc cgtgaatcaa    240
caaagagagg gcccataata ctgtcgatga gcatttccct ataatacagt gtccacagtt    300
gccttccgct aagggatagc cacccgctat tctcttgaca cgtgtcactg aaacctgcta    360
caaataaggc aggcacctcc tcattctcac actcactcac tcacacagct caagaaggat    420
cctcatattc tagttgtatg ttgttcagag aagaccacag atgtgatcat attctcattg    480
tatcagatct gtgaccactt acctgatacc tcccatgaag ttacctgtat gattatacgt    540
gatccaaagc catcacatca tgttcacctt cagctattgg aggagaagtg agaagtagga    600
attgcaatat gaggaataat aagaaaaact tgtaaaagc taaattagct gggtatgata    660
tagggagaaa tgtgtaaaca ttgtactata tatagtatat acacacgcat tatgtattgc    720
attatgcact gaataatacc gcagcatcaa agaaggaatt cgtggtaact tttactcatc    780
tcctccaatt atttctgatt tcatgcatgt ttccctacat tctattatga atcgtgttat    840
ggtgtataaa cgttgtttca tatctcatct catctattct gattttgatt ctcttgccta    900
ctgaatttga ccctactgta atcggtgata aatgtgaatg cttcctcttc ttcttcttct    960
tctcagaaat caatttctgt tttgtttttg ttcatctgta gcttgatatc cttctttgat    1020
gctgcggtat tattcagtgc ataatgcaat acataatgcg tgtgtatata ctatatatag    1080
tacaatgttt acacatttct ccctatatca tacccagcta atttagcttt tacaaagttt    1140
ttcttattat tcctcatatt gcaattccta cttctcactt ctcctccaat agctgaaggt    1200
gaacatgatg tgatggcttt ggatcacgta taatcataca ggtaacttca tgggaggtat    1260
caggtaagtg gtcacagatc tgatacaatg agaatatgat cacatctgtg gtcttctctg    1320
aacaacatac aactagaata tgaaagcttt tgatttaat gtttagcaaa tgtcctatca    1380
gttttctctt tttgtcgaac ggtaatttag agtttttttt gctatatgga ttttcgtttt    1440
tgatgtatgt gacaaccctc gggattgttg atttatttca aaactaagag ttttttgctta   1500 ttgttctcgt ctattttgga tatcaatctt agttttatat cttttctagt tctctacgtg    1560
ttaaatgttc aacacactag caatttggct gcagcgtatg gattatgaa ctatcaagtc    1620 tgtgggatcg ataaatatgc ttctcaggaa tttgagattt tacagtcttt atgctcattg    1680
```

```
ggttgagtat aatatagtaa aaaaatagtc taga                              1714

<210> SEQ ID NO 19
<211> LENGTH: 2322
<212> TYPE: DNA
<213> ORGANISM: Artificial Sequence
<220> FEATURE:
<223> OTHER INFORMATION: Description of Artificial Sequence: Alternative
      expression cassette for a sense and antisense copy
      of the trailer associated with the R1 gene

<400> SEQUENCE: 19
ggtaccgaac catgcatctc aatcttaata ctaaaaaatg caacaaaatt ctagtggagg     60
gaccagtacc agtacattag atattatctt ttattactat aataatattt taattaacac    120
gagacatagg aatgtcaagt ggtagcggta ggagggagtt ggttcagttt tttagatact    180
aggagacaga accggagggg cccattgcaa ggcccaagtt gaagtccagc cgtgaatcaa    240
caaagagagg gcccataata ctgtcgatga gcatttccct ataatacagt gtccacagtt    300
gccttccgct aagggatagc cacccgctat tctcttgaca cgtgtcactg aaacctgcta    360
caaataaggc aggcacctcc tcattctcac actcactcac tcacacagct caacaagtgg    420
taacttttac tcatctcctc caattatttc tgatttcatg catgtttccc tacattctat    480
tatgaatcgt gttatggtgt ataaacgttg tttcatatct catctcatct attctgattt    540
tgattctctt gcctactgaa tttgacccta ctgtaatcgg tgataaatgt gaatgcttcc    600
tcttcttctt cttcttctca gaaatcaatt tctgttttgt ttttgttcat ctgtagcttg    660
gtagattccc cttttttgtag accacacatc acggatcctc atattctagt tgtatgttgt    720
tcagagaaga ccacagatgt gatcatattc tcattgtatc agatctgtga ccacttacct    780
gatacctccc atgaagttac ctgtatgatt atacgtgatc caaagccatc acatcatgtt    840
caccttcagc tattggagga gaagtgagaa gtaggaattg caatatgagg aataataaga    900
aaaactttgt aaaagctaaa ttagctgggt atgatatagg gagaaatgtg taaacattgt    960
actatatata gtatatacac acgcattatg tattgcatta tgcactgaat aataccgcag   1020
catcaaagaa ggaattcaag gttagaaatc ttctctatttt ttggtttttg tctgtttaga   1080
ttctcgaatt agctaatcag gtgctgttat agcccttaat tttgagtttt ttttcggttg   1140
ttttgatgga aaaggcctaa aatttgagtt tttttacgtt ggtttgatgg aaaaggccta   1200
caattggagt tttccccgtt gttttgatga aaaagcccct agtttgagat tttttttctg   1260
tcgattcgat tctaaaggtt taaaattaga gttttttacat ttgtttgatg aaaaaggcct   1320
taaatttgag ttttttccggt tgatttgatg aaaaagccct agaatttgtg tttttttcgtc   1380 ggtttgattc tgaaggccta aaatttgagt ttctccggct gttttgatga aaaagcccta   1440
aatttgagtt tctccggctg ttttgatgaa aaagccctaa atttgagttt tttccccgtg   1500
ttttagattg tttggtttta attctcgaat cagctaatca gggagtgtga aaagcccctaa   1560 aatttgagtt tttttcgttg ttctgattgt tgttttatg aatttgcaga tggatatcct   1620
tctttgatgc tgcggtatta ttcagtgcat aatgcaatac ataatgcgtg tgtatatact   1680
atatatagta caatgtttac acatttctcc ctatatcata cccagctaat ttagcttttta   1740 caaagttttt cttattattc ctcatattgc aattcctact tctcacttct cctccaatag   1800
ctgaaggtga acatgatgtg atggctttgg atcacgtata atcatacagg taacttcatg   1860
ggaggtatca ggtaagtggt cacagatctg atacaatgag aatatgatca catctgtggt   1920
```

```
cttctctgaa caacatacaa ctagaatatg aaagcttttg attttaatgt ttagcaaatg      1980
tcctatcagt tttctctttt tgtcgaacgg taatttagag ttttttttgc tatatggatt      2040 ttcgttttg atgtatgtga caaccctcgg gattgttgat ttatttcaaa actaagagtt       2100
tttgcttatt gttctcgtct attttggata tcaatcttag ttttatatct tttctagttc      2160
tctacgtgtt aaatgttcaa cacactagca atttggctgc agcgtatgga ttatggaact      2220
atcaagtctg tgggatcgat aaatatgctt ctcaggaatt tgagatttta cagtctttat      2280
gctcattggg ttgagtataa tatagtaaaa aaatagtcta ga                          2322
```

<210> SEQ ID NO 20
<211> LENGTH: 1714
<212> TYPE: DNA
<213> ORGANISM: Artificial Sequence
<220> FEATURE:
<223> OTHER INFORMATION: Description of Artificial Sequence: Alternative
      expression cassette for a sense and antisense copy
      of the trailer associated with the R1 gene

<400> SEQUENCE: 20

```
ggtaccgaac catgcatctc aatcttaata ctaaaaaatg caacaaaatt ctagtggagg        60
gaccagtacc agtacattag atattatctt ttattactat aataatattt taattaacac       120
gagacatagg aatgtcaagt ggtagcggta ggagggagtt ggttcagttt tttagatact       180
aggagacaga accggagggg cccattgcaa ggcccaagtt gaagtccagc cgtgaatcaa       240
caaagagagg gcccataata ctgtcgatga gcatttccct ataatacagt gtccacagtt       300
gccttccgct aagggatagc cacccgctat tctcttgaca cgtgtcactg aaacctgcta       360
caaataaggc aggcacctcc tcattctcac actcactcac tcacacagct caagaaggat       420
cctcatattc tagttgtatg ttgttcagag aagaccacag atgtgatcat attctcattg       480
tatcagatct gtgaccactt acctgatacc tcccatgaag ttacctgtat gattatacgt       540
gatccaaagc catcacatca tgttcacctt cagctattgg aggagaagtg agaagtagga       600
attgcaatat gaggaataat aagaaaaact ttgtaaaagc taaattagct gggtatgata       660
tagggagaaa tgtgtaaaca ttgtactata tatagtatat acacacgcat tatgtattgc       720
attatgcact gaataatacc gcagcatcaa agaaggaatt cgtggtaact tttactcatc       780
tcctccaatt atttctgatt tcatgcatgt ttccctacat tctattatga atcgtgttat       840
ggtgtataaa cgttgtttca tatctcatct catctattct gattttgatt ctcttgccta       900
ctgaatttga ccctactgta atcggtgata aatgtgaatg cttcctcttc ttcttcttct       960
tctcagaaat caatttctgt tttgttttttg ttcatctgta gcttgatatc cttctttgat     1020
gctgcggtat tattcagtgc ataatgcaat acataatgcg tgtgtatata ctatatatag      1080
tacaatgttt acacatttct ccctatatca tacccagcta atttagcttt tacaaagttt     1140
ttcttattat tcctcatatt gcaattccta cttctcactt ctcctccaat agctgaaggt     1200
gaacatgatg tgatggcttt ggatcacgta taatcataca ggtaacttca tgggaggtat     1260
caggtaagtg gtcacagatc tgatacaatg agaatatgat cacatctgtg gtcttctctg    1320
aacaacatac aactagaata tgaaagcttt tgattttaat gtttagcaaa tgtcctatca    1380
gttttctctt tttgtcgaac ggtaatttag agttttttttt gctatatgga tttttcgtttt 1440 tgatgtatgt gacaaccctc gggattgttg atttatttca aaactaagag tttttgctta    1500
ttgttctcgt ctattttgga tatcaatctt agttttatat cttttctagt tctctacgtg    1560
ttaaatgttc aacacactag caatttggct gcagcgtatg gattatggaa ctatcaagtc    1620
```

```
tgtgggatcg ataaatatgc ttctcaggaa tttgagattt tacagtctt  atgctcattg    1680 ggttgagtat aatatagtaa aaaaatagtc taga                                1714

<210> SEQ ID NO 21
<211> LENGTH: 273
<212> TYPE: DNA
<213> ORGANISM: Solanum tuberosum

<400> SEQUENCE: 21
ttagagtgtg ggtaagtaat taagttaggg atttgtggga aatggacaaa tataagagag     60
tgcaggggag tagtgcagga gattttcgtg cttttattga taaataaaaa aagggtgaca    120
tttaatttcc acaagaggac gcaacacaac acacttaatt cctgtgtgtg aatcaataat    180
tgacttctcc aatcttcatc aataaaataa ttcacaatcc tcactctctt atcactctca    240
ttcgaaaagc tagatttgca tagagagcac aaa                                 273

<210> SEQ ID NO 22
<211> LENGTH: 158
<212> TYPE: DNA
<213> ORGANISM: Solanum tuberosum

<400> SEQUENCE: 22
gagggggaag tgaatgaaaa ataacaaagg cacagtaagt agtttctctt tttatcatgt     60
gatgaaggta tataatgtat gtgtaagagg atgatgttat taccacataa taagagatga    120
agagtctcat tttctgctta aaaaaacaat tcactggc                            158

<210> SEQ ID NO 23
<211> LENGTH: 1917
<212> TYPE: DNA
<213> ORGANISM: Artificial Sequence
<220> FEATURE:
<223> OTHER INFORMATION: Description of Artificial Sequence: Expression
      cassette for a sense and antisense copy of the
      leader associated with the L glucan phosphorylase gene

<400> SEQUENCE: 23
ggtaccgaac catgcatctc aatcttaata ctaaaaaatg caacaaaatt ctagtggagg     60
gaccagtacc agtacattag atattatctt ttattactat aataatattt taattaacac    120
gagacatagg aatgtcaagt ggtagcggta ggagggagtt ggttcagttt tttagatact    180
aggagacaga accggagggg cccattgcaa ggcccaagtt gaagtccagc cgtgaatcaa    240
caaagagagg gcccataata ctgtcgatga gcatttccct ataatacagt gtccacagtt    300
gccttccgct aagggatagc cacccgctat tctcttgaca cgtgtcactg aaacctgcta    360
caaataaggc aggcacctcc tcattctcac actcactcac tcacacagct caagaaggat    420
ccgagtgtgg gtaagtaatt aagttaggga tttgtgggaa atggacaaat ataagagagt    480 gcagggagt agtgcaggag attttcgtgc ttttattgat aaataaaaaa agggtgacat    540
ttaatttcca agaggacg caacacaaca cacttaattc ctgtgtgtga atcaataatt    600
gacttctcca atcttcatca ataaaataat tcacaatcct cactctctta tcactctcat    660
tcgaaaagct agatttgcat agagagcaca gaattcaagg ttagaaatct tctctatttt    720 tggttttgt ctgtttagat tctcgaatta gctaatcagg tgctgttata gcccttaatt    780
ttgagttttt tttcggttgt tttgatgaa aaggcctaaa atttgagttt ttttacgttg    840
gtttgatgga aaggcctac aattggagtt tccccgttg ttttgatgaa aaagccccta    900
```

```
gtttgagatt tttttctgt cgattcgatt ctaaaggttt aaaattagag tttttacatt      960
tgtttgatga aaaggcctt aaatttgagt ttttccggtt gatttgatga aaaagcccta     1020
gaatttgtgt ttttcgtcg gtttgattct gaaggcctaa aatttgagtt tctccggctg     1080
ttttgatgaa aaagccctaa atttgagttt ctccggctgt tttgatgaaa aagccctaaa    1140
tttgagtttt ttccccgtgt tttagattgt ttggttttaa ttctcgaatc agctaatcag    1200
ggagtgtgaa aagccctaaa atttgagttt ttttcgttgt tctgattgtt gttttatga     1260 atttgcagat ggatatctgt gctctctatg caaatctagc ttttcgaatg agagtgataa    1320
gagagtgagg attgtgaatt attttattga tgaagattgg agaagtcaat tattgattca    1380
cacacaggaa ttaagtgtgt tgtgttgcgt cctcttgtgg aaattaaatg tcacccttt     1440 tttatttatc aataaaagca cgaaaatctc ctgcactact cccctgcact ctcttatatt    1500
tgtccatttc ccacaaatcc ctaacttaat tacttaccca cactctaagc ttttgattt     1560 aatgtttagc aaatgtccta tcagttttct cttttgtcg aacggtaatt tagagtttt     1620 tttgctatat ggattttcgt ttttgatgta tgtgacaacc ctcgggattg ttgatttatt    1680
tcaaaactaa gagtttttgc ttattgttct cgtctatttt ggatatcaat cttagtttta   1740
tatcttttct agttctctac gtgttaaatg ttcaacacac tagcaatttg gctgcagcgt    1800
atggattatg gaactatcaa gtctgtggga tcgataaata tgcttctcag gaatttgaga   1860
ttttacagtc tttatgctca ttgggttgag tataatatag taaaaaaata gtctaga      1917
```

<210> SEQ ID NO 24
<211> LENGTH: 1585
<212> TYPE: DNA
<213> ORGANISM: Artificial Sequence
<220> FEATURE:
<223> OTHER INFORMATION: Description of Artificial Sequence: Alternative
      expression cassette for a sense and antisense copy of the leader
      associated with the L glucan phosphorylase gene

<400> SEQUENCE: 24

```
ggtaccgaac catgcatctc aatcttaata ctaaaaaatg caacaaaatt ctagtggagg      60
gaccagtacc agtacattag atattatctt ttattactat aataatattt taattaacac     120
gagacatagg aatgtcaagt ggtagcggta ggagggagtt ggttcagttt tttagatact     180
aggagacaga accggagggg cccattgcaa ggcccaagtt gaagtccagc cgtgaatcaa     240
caaagagagg gcccataata ctgtcgatga gcatttccct ataatacagt gtccacagtt     300
gccttccgct aagggatagc cacccgctat tctcttgaca cgtgtcactg aaacctgcta     360
caaataaggc aggcacctcc tcattctcac actcactcac tcacacagct caagaaggat     420
ccgagtgtgg gtaagtaatt aagttaggga tttgtgggaa atggacaaat ataagagagt     480 gcagggagt agtgcaggag attttcgtgc ttttattgat aaataaaaaa agggtgacat      540
ttaattccaa caagaggacg caacacaaca cacttaattc ctgtgtgtga atcaataatt     600
gacttctcca atcttcatca ataaaataat tcacaatcct cactctctta tcactctcat    660
tcgaaaagct agatttgcat agagagcaca gaattcgtgg taactttac tcatctcctc     720 caattatttc tgatttcatg catgtttccc tacattctat tatgaatcgt gttatggtgt    780
ataaacgttg tttcatatct catctcatct attctgattt tgattctctt gcctactgaa    840
tttgacccta ctgtaatcgg tgataaatgt gaatgcttcc tcttcttctt cttcttctca   900
gaaatcaatt tctgttttgt ttttgttcat ctgtagcttg atatctgtgc tctctatgca    960
aatctagctt ttcgaatgag agtgataaga gagtgaggat tgtgaattat tttattgatg   1020
```

-continued

```
aagattggag aagtcaatta ttgattcaca cacaggaatt aagtgtgttg tgttgcgtcc      1080
tcttgtggaa attaaatgtc acccttttt tatttatcaa taaaagcacg aaaatctcct      1140
gcactactcc cctgcactct cttatatttg tccatttccc acaaatccct aacttaatta      1200
cttacccaca ctctaagctt ttgatttaa tgtttagcaa atgtcctatc agttttctct      1260
ttttgtcgaa cggtaattta gagttttttt tgctatatgg attttcgttt ttgatgtatg      1320
tgacaaccct cgggattgtt gatttatttc aaaactaaga gtttttgctt attgttctcg      1380
tctattttgg atatcaatct tagttttata tcttttctag ttctctacgt gttaaatgtt      1440
caacacacta gcaatttggc tgcagcgtat ggattatgga actatcaagt ctgtgggatc      1500
gataaatatg cttctcagga atttgagatt ttacagtctt tatgctcatt gggttgagta      1560
taatatagta aaaaaatagt ctaga                                            1585

<210> SEQ ID NO 25
<211> LENGTH: 2193
<212> TYPE: DNA
<213> ORGANISM: Artificial Sequence
<220> FEATURE:
<223> OTHER INFORMATION: Description of Artificial Sequence: Alternative
      expression cassette for a sense and antisense copy of the leader
      associated with the L glucan phosphorylase gene

<400> SEQUENCE: 25
ggtaccgaac catgcatctc aatcttaata ctaaaaatg caacaaaatt ctagtggagg       60
gaccagtacc agtacattag atattatctt ttattactat aataatattt taattaacac     120
gagacatagg aatgtcaagt ggtagcggta ggagggagtt ggttcagttt tttagatact     180
aggagacaga accggagggg cccattgcaa ggcccaagtt gaagtccagc cgtgaatcaa     240
caaagagagg gcccataata ctgtcgatga gcatttccct ataatacagt gtccacagtt     300
gccttccgct aagggatagc cacccgctat tctcttgaca cgtgtcactg aaacctgcta     360
caaataaggc aggcacctcc tcattctcac actcactcac tcacacagct caacaagtgg     420 taactttttac tcatctcctc caattatttc tgatttcatg catgtttccc tacattctat     480
tatgaatcgt gttatggtgt ataaacgttg tttcatatct catctcatct attctgattt     540
tgattctctt gcctactgaa tttgacccta ctgtaatcgg tgataaatgt gaatgcttcc     600
tcttcttctt cttcttctca gaaatcaatt tctgttttgt ttttgttcat ctgtagcttg     660
gtagattccc cttttttgtag accacacatc acgatccga gtgtgggtaa gtaattaagt    720
tagggatttg tgggaaatgg acaaatataa gagagtgcag gggagtagtg caggagattt     780
tcgtgctttt attgataaat aaaaaaaggg tgacatttaa tttccacaag aggacgcaac     840
acaacacact taattcctgt gtgtgaatca ataattgact tctccaatct tcatcaataa     900
aataattcac aatcctcact ctcttatcac tctcattcga aaagctagat ttgcatagag     960
agcacagaat tcaaggttag aaatcttctc tattttggt ttttgtctgt ttagattctc     1020
gaattagcta atcaggtgct gttatagccc ttaatttga gttttttttc ggttgttttg     1080
atggaaaagg cctaaaattt gagttttttt acgttggttt gatggaaaag gcctacaatt     1140 ggagtttttcc ccgttgtttt gatgaaaaag cccctagttt gagatttttt ttctgtcgat     1200
tcgattctaa aggtttaaaa ttgagttttt tacatttgtt tgatgaaaaa ggccttaaat     1260
ttgagttttt ccggttgatt tgatgaaaaa gccctagaat ttgtgttttt tcgtcggttt     1320
gattctgaag gcctaaaatt tgagtttctc cggctgtttt gatgaaaaag ccctaaattt     1380
```

```
gagtttctcc ggctgttttg atgaaaaagc cctaaatttg agttttttcc ccgtgtttta    1440
gattgtttgg ttttaattct cgaatcagct aatcagggag tgtgaaaagc cctaaaattt    1500
gagttttttt cgttgttctg attgttgttt ttatgaattt gcagatggat atctgtgctc    1560
tctatgcaaa tctagctttt cgaatgagag tgataagaga gtgaggattg tgaattattt    1620
tattgatgaa gattggagaa gtcaattatt gattcacaca caggaattaa gtgtgttgtg    1680
ttgcgtcctc ttgtggaaat taaatgtcac cctttttta tttatcaata aaagcacgaa     1740
aatctcctgc actactcccc tgcactctct tatatttgtc catttcccac aaatccctaa    1800
cttaattact tacccacact ctaagctttt gattttaatg tttagcaaat gtcctatcag    1860
ttttctcttt ttgtcgaacg gtaatttaga gttttttttg ctatatggat tttcgttttt    1920
gatgtatgtg acaaccctcg ggattgttga tttatttcaa aactaagagt ttttgcttat    1980
tgttctcgtc tattttggat atcaatctta gttttatatc ttttctagtt ctctacgtgt    2040
taaatgttca acacactagc aatttggctg cagcgtatgg attatggaac tatcaagtct    2100
gtgggatcga taaatatgct tctcaggaat ttgagatttt acagtcttta tgctcattgg    2160
gttgagtata atatagtaaa aaaatagtct aga                                 2193

<210> SEQ ID NO 26
<211> LENGTH: 1861
<212> TYPE: DNA
<213> ORGANISM: Artificial Sequence
<220> FEATURE:
<223> OTHER INFORMATION: Description of Artificial Sequence: Alternative
      expression cassette for a sense and antisense copy of the leader
      associated with the L glucan phosphorylase gene

<400> SEQUENCE: 26
ggtaccgaac catgcatctc aatcttaata ctaaaaaatg caacaaaatt ctagtggagg      60
gaccagtacc agtacattag atattatctt ttattactat aataatattt taattaacac     120
gagacatagg aatgtcaagt ggtagcggta ggagggagtt ggttcagttt tttagatact     180
aggagacaga accggagggg cccattgcaa ggcccaagtt gaagtccagc cgtgaatcaa     240
caaagagagg gcccataata ctgtcgatga gcatttccct ataatacagt gtccacagtt     300
gccttccgct aagggatagc cacccgctat tctcttgaca cgtgtcactg aaacctgcta     360
caaataaggc aggcacctcc tcattctcac actcactcac tcacacagct caacaagtgg     420
taacttttac tcatctcctc caattattt tgatttcatg catgtttccc tacattctat      480
tatgaatcgt gttatggtgt ataaacgttg tttcatatct catctcatct attctgattt     540
tgattctctt gcctactgaa tttgacccta ctgtaatcgg tgataaatgt gaatgcttcc     600
tcttcttctt cttcttctca gaaatcaatt tctgttttgt ttttgttcat ctgtagcttg     660
gtagattccc cttttttgtag accacacatc acggatccga gtgtgggtaa gtaattaagt     720
tagggatttg tgggaaatgg acaaatataa gagagtgcag gggagtagtg caggagattt     780
tcgtgctttt attgataaat aaaaaaaggg tgacatttaa tttccacaag aggacgcaac    840
acaacacact taattcctgt gtgtgaatca ataattgact tctccaatct tcatcaataa    900
aataattcac aatcctcact ctcttatcac tctcattcga aaagctagat ttgcatagag    960
agcacagaat tcgtggtaac ttttactcat ctcctccaat tatttctgat ttcatgcatg   1020
tttccctaca ttctattatg aatcgtgtta tggtgtataa acgttgtttc atatctcatc   1080
tcatctattc tgattttgat tctcttgcct actgaatttg accctactgt aatcggtgat   1140
aaatgtgaat gcttcctctt cttcttcttc ttctcagaaa tcaatttctg ttttgttttt   1200
```

```
gttcatctgt agcttgatat ctgtgctctc tatgcaaatc tagcttttcg aatgagagtg    1260
ataagagagt gaggattgtg aattatttta ttgatgaaga ttggagaagt caattattga    1320
ttcacacaca ggaattaagt gtgttgtgtt gcgtcctctt gtggaaatta aatgtcaccc    1380
tttttttatt tatcaataaa agcacgaaaa tctcctgcac tactccctg cactctctta    1440 tatttgtcca tttcccacaa atccctaact taattactta cccacactct aagcttttga    1500
ttttaatgtt tagcaaatgt cctatcagtt ttctcttttt gtcgaacggt aatttagagt    1560 ttttttgct atatggattt tcgtttttga tgtatgtgac aaccctcggg attgttgatt     1620
tatttcaaaa ctaagagttt ttgcttattg ttctcgtcta ttttggatat caatcttagt    1680
tttatatctt ttctagttct ctacgtgtta aatgttcaac acactagcaa tttggctgca    1740
gcgtatggat tatggaacta tcaagtctgt gggatcgata aatatgcttc tcaggaattt    1800
gagattttac agtctttatg ctcattgggt tgagtataat atagtaaaaa aatagtctag    1860
a                                                                    1861

<210> SEQ ID NO 27
<211> LENGTH: 1788
<212> TYPE: DNA
<213> ORGANISM: Solanum tuberosum

<400> SEQUENCE: 27
atggcaagct gtgcaatag tagtagtaca tctctcaaaa ctccttttac ttcttcctcc      60
acttctttat cttccactcc taagccctct caacttttca tccatggaaa acgtaaccaa    120
atgttcaaag tttcatgcaa ggttatcaat aataacggtg accaaaacgt tgaaacgaat    180
tctgttgatc gaagaaatgt tcttcttggc ttaggtggtc tttatggtgt tgctaatgct    240
ataccattag ctgcatccgc tgctccaact ccacctcctg atctctcgtc ttgtagtata    300
gccaggatta acgaaaatca ggtggtgccg tacagttgtt gcgcgcctaa gcctgatgat    360
atggagaaag ttccgtatta caagttccct tctatgacta agctccgtgt ccgtcagcct    420
gctcatgaag ctaatgagga gtatattgcc aagtacaatc tggcgattag tcgaatgaga    480
gatcttgata agacacaacc tttaaaccct attggtttta agcaacaagc taatatacat    540
tgtgcttatt gtaatggtgc ttatagaatt ggtggcaaag agttacaagt tcataattct    600
tggcttttct tcccgttcca tagatggtac ttgtacttcc acgagagaat cgtgggaaaa    660
ttcattgatg atccaacttt cgctttgcca tattggaatt gggaccatcc aaagggtatg    720
cgttttcctg ccatgtatga tcgtgaaggg acttcccttt tcgatgtaac acgtgaccaa    780
agtcaccgaa atggagcagt aatcgatctt ggttttttcg gcaatgaagt cgaaacaact    840
caactccagt tgatgagcaa taatttaaca ctaatgtacc gtcaaatggt aactaatgct    900
ccatgtcctc ggatgttctt tggtgggcct tatgatctcg ggattaacac tgaactcccg    960
ggaactatag aaaacattcc tcacggtcct gtccacatct ggtctggtac agtgagaggt   1020
tcaactttgc ccaatggtgc aatatcaaac ggtgagaata tgggtcatt ttactcagct    1080 gctttggacc cggttttctt tgccatcac agcaatgtgg atcggatgtg gagcgaatgg    1140
aaagcgacag gagggaaaag aacagatatc acacataaag gttggttgaa ctccgagttc   1200 ttttctatg atgaaaatga aaacccttac cgtgtgaaag tccgagactg tttggacacg    1260
aagaagatgg ggtatgatta tgcaccaatg gccaccccgt ggcgtaactt caagccaata   1320
acaaaaacta cagctgggaa agtgaataca gcttctcttc cgccagctag caatgtattc    1380
```

```
ccagtggcta aactcgacaa agcaatttcg ttttccatca ataggccgac ttcgtcaagg    1440
actcaacaag agaaaaatgc acaagaggag atgttgacat tcagtagcat aagatatgat    1500
aacagagggt acataaggtt cgatgtgttc ctgaacgtgg acaataatgt gaatgcgaat    1560
gagcttgaca aggcggagtt tgcggggagt tatactagtt tgccacatgt tcatagagct    1620
ggtgagacta atcatatcgc gactgttgat ttccagctgg cgataacgga actgttggag    1680
gatattggtt tggaagatga agatactatt gcggtgactc tggtgccaaa gagaggtggt    1740
gaaggtatct ccattgaaag tgcgacgatc agtcttgcag attgttaa                 1788
```

<210> SEQ ID NO 28
<211> LENGTH: 1788
<212> TYPE: DNA
<213> ORGANISM: Solanum tuberosum

<400> SEQUENCE: 28

```
atggcaagct gtgcaatag tagtagtaca tctctcaaaa ctccttttac ttcttcctcc      60
acttctttat cttccactcc taagccctct caacttttca tccatggaaa acgtaaccaa     120
atgttcaaag tttcatgcaa ggttatcaat aataacggtg accaaaacgt tgaaacgaat     180
tctgttgatc gaagaaatgt tcttcttggc ttaggtggtc tttatggtgt tgctaatgct     240
ataccattag ctgcatccgc tgctccaact ccacctcctg atctctcgtc ttgtagtata     300
gccaggatta acgaaaatca ggtggtgccg tacagttgtt gcgcgcctaa gcctgatgat     360
atggagaaag ttccgtatta caagttccct tctatgacta agctccgtgt ccgtcagcct     420
gctcatgaag ctaatgagga gtatattgcc aagtacaatc tggcgattag tcgaatgaga     480
gatcttgata agacacaacc tttaaaccct attggtttta agcaacaagc taatatacag     540
tgggcttatg gtaatggtgc ttatagaatt ggtggcaaag agttacaagt tcataattct     600 tggctttttct tcccgttcca tagatggtac ttgtacttcc acgagagaat cgtgggaaaa     660
ttcattgatg atccaacttt cgctttgcca tattggaatt gggaccatcc aaagggtatg     720
cgttttcctg ccatgtatga tcgtgaaggg acttcccttt tcgatgtaac acgtgaccaa     780
agtcaccgaa atggagcagt aatcgatctt ggttttttcg gcaatgaagt cgaaacaact     840
caactccagt tgatgagcaa taatttaaca ctaatgtacc gtcaaatggt aactaatgct     900
ccatgtcctc ggatgttctt tggtgggcct tatgatctcg ggattaacac tgaactcccg     960
ggaactatag gaaacattcc tctcggtcct gtccacatct ggtctggtac agtgagaggt    1020
tcaactttgc ccaatggtgc aatatcaaac ggtgagaata tgggtcatct ttactcagct    1080
gctttggacc cggttttctt ttgccatcac agcaatgtgg atcggatgtg agcgaatgg     1140 aaagcgacag gagggaaaag aacagatatc acacataaag gttggttgaa ctccgagttc    1200 ttttctatg atgaaaatga aaacccttac cgtgtgaaag tccgagactg tttggacacg     1260
aagaagatgg ggtatgatta tgcaccaatg gccaccccgt ggcgtaactt caagccaata    1320
acaaaaacta cagctgggaa agtgaataca gcttctcttc cgccagctag caatgtattc    1380
ccagtggcta aactcgacaa agcaatttcg ttttccatca ataggccgac ttcgtcaagg    1440
actcaacaag agaaaaatgc acaagaggag atgttgacat tcagtagcat aagatatgat    1500
aacagagggt acataaggtt cgatgtgttc ctgaacgtgg acaataatgt gaatgcgaat    1560
gagcttgaca aggcggagtt tgcggggagt tatactagtt tgccacatgt tcatagagct    1620
ggtgagacta atcatatcgc gactgttgat ttccagctgg cgataacgga actgttggag    1680
gatattggtt tggaagatga agatactatt gcggtgactc tggtgccaaa gagaggtggt    1740
```
gaaggtatct ccattgaaag tgcgacgatc agtcttgcag attgttaa         1788

<210> SEQ ID NO 29
<211> LENGTH: 154
<212> TYPE: DNA
<213> ORGANISM: Solanum tuberosum

<400> SEQUENCE: 29
ttagtctcta ttgaatctgc tgagattaca ctttgatgga tgatgctctg ttttttgtttt    60 cttgttctgt ttttcctct gttgaaatca gctttgttgc ttgatttcat tgaagttgtt    120
attcaagaat aaatcagtta caattatgtt tggg                                154

<210> SEQ ID NO 30
<211> LENGTH: 1691
<212> TYPE: DNA
<213> ORGANISM: Artificial Sequence
<220> FEATURE:
<223> OTHER INFORMATION: Description of Artificial Sequence: Expression
      cassette for a sense and antisense copy of the trailer
      associated with a PPO gene

<400> SEQUENCE: 30
ggtaccgaac catgcatctc aatcttaata ctaaaaaatg caacaaaatt ctagtggagg      60
gaccagtacc agtacattag atattatctt ttattactat aataatattt taattaacac    120
gagacatagg aatgtcaagt ggtagcggta ggagggagtt ggttcagttt tttagatact    180
aggagacaga accggagggg cccattgcaa ggcccaagtt gaagtccagc cgtgaatcaa    240
caaagagagg gcccataata ctgtcgatga gcatttccct ataatacagt gtccacagtt    300
gccttccgct aagggatagc cacccgctat tctcttgaca cgtgtcactg aaacctgcta    360
caaataaggc aggcacctcc tcattctcac actcactcac tcacacagct caagaaggat    420
ccttagtctc tattgaatct gctgagatta cactttgatg gatgatgctc tgttttttgtt    480 ttcttgttct gttttttcct ctgttgaaat cagctttgtt gcttgatttc attgaagttg    540
ttattcaaga ataaatcagt tacaattatg gaattcaagg ttagaaatct tctctatttt    600 tggttttttgt ctgtttagat tctcgaatta gctaatcagg tgctgttata gcccttaatt    660
ttgagttttt tttcggttgt tttgatggaa aaggcctaaa atttgagttt ttttacgttg    720
gtttgatgga aaaggcctac aattggagtt ttccccgttg ttttgatgaa aaagccccta    780
gtttgagatt ttttttctgt cgattcgatt ctaaaggttt aaaattagag tttttacatt    840
tgtttgatga aaaaggcctt aaatttgagt ttttccggtt gatttgatga aaaagcccta    900
gaatttgtgt tttttcgtcg gtttgattct gaaggcctaa aatttgagtt tctccggctg    960
ttttgatgaa aaagccctaa atttgagttt ctccggctgt tttgatgaaa aagccctaaa    1020 tttgagttttt ttccccgtgt tttagattgt ttggttttaa ttctcgaatc agctaatcag    1080
ggagtgtgaa aagccctaaa atttgagttt ttttcgttgt tctgattgtt gtttttatga    1140
atttgcagat ggatatcctt ctttgatgct gatccataat tgtaactgat ttattcttga    1200
ataacaactt caatgaaatc aagcaacaaa gctgatttca acagaggaaa aaacagaaca    1260
agaaaacaaa aacagagcat catccatcaa agtgtaatct cagcagattc aatagagact    1320
aagcttttga ttttaatgtt tagcaaatgt cctatcagtt ttctcttttt gtcgaacggt    1380
aatttagagt tttttttgct atatggattt tcgttttttga tgtatgtgac aaccctcggg    1440
attgttgatt tatttcaaaa ctaagagttt ttgcttattg ttctcgtcta ttttggatat    1500

```
caatcttagt tttatatctt ttctagttct ctacgtgtta aatgttcaac acactagcaa    1560
tttggctgca gcgtatggat tatggaacta tcaagtctgt gggatcgata aatatgcttc    1620
tcaggaattt gagattttac agtctttatg ctcattgggt tgagtataat atagtaaaaa    1680
aatagtctag a                                                         1691

<210> SEQ ID NO 31
<211> LENGTH: 1359
<212> TYPE: DNA
<213> ORGANISM: Artificial Sequence
<220> FEATURE:
<223> OTHER INFORMATION: Description of Artificial Sequence: Expression
      cassette for a sense and antisense copy of the trailer
      associated with a PPO gene

<400> SEQUENCE: 31
ggtaccgaac catgcatctc aatcttaata ctaaaaaatg caacaaaatt ctagtggagg      60
gaccagtacc agtacattag atattatctt ttattactat aataatattt taattaacac     120
gagacatagg aatgtcaagt ggtagcggta ggagggagtt ggttcagttt tttagatact     180
aggagacaga accggagggg cccattgcaa ggcccaagtt gaagtccagc cgtgaatcaa     240
caaagagagg gcccataata ctgtcgatga gcatttccct ataatacagt gtccacagtt     300
gccttccgct aagggatagc cacccgctat tctcttgaca cgtgtcactg aaacctgcta     360
caaataaggc aggcacctcc tcattctcac actcactcac tcacacagct caagaaggat     420
ccttagtctc tattgaatct gctgagatta cactttgatg gatgatgctc tgttttttgtt     480 ttcttgttct gttttttcct ctgttgaaat cagctttgtt gcttgatttc attgaagttg     540
ttattcaaga ataaatcagt tacaattatg gaattcgtgg taactttttac tcatctcctc     600 caattatttc tgatttcatg catgtttccc tacattctat tatgaatcgt gttatggtgt     660
ataaacgttg tttcatatct catctcatct attctgattt tgattctctt gcctactgaa     720
tttgacccta ctgtaatcgg tgataaatgt gaatgcttcc tcttcttctt cttcttctca     780
gaaatcaatt tctgttttgt ttttgttcat ctgtagcttg atatccttct ttgatgctga     840
tccataattg taactgattt attcttgaat aacaacttca atgaaatcaa gcaacaaagc     900
tgatttcaac agaggaaaaa acagaacaag aaaacaaaaa cagagcatca tccatcaaag     960
tgtaatctca gcagattcaa tagagactaa gcttttgatt ttaatgttta gcaaatgtcc    1020
tatcagtttt ctcttttttgt cgaacggtaa tttagagttt ttttttgctat atggattttc    1080 gttttttgatg tatgtgacaa ccctcgggat tgttgattta tttcaaaact aagagttttt    1140
gcttattgtt ctcgtctatt ttggatatca atcttagttt tatatctttt ctagttctct    1200
acgtgttaaa tgttcaacac actagcaatt tggctgcagc gtatggatta tggaactatc    1260
aagtctgtgg gatcgataaa tatgcttctc aggaatttga gattttacag tctttatgct    1320
cattgggttg agtataatat agtaaaaaaa tagtctaga                           1359

<210> SEQ ID NO 32
<211> LENGTH: 1967
<212> TYPE: DNA
<213> ORGANISM: Artificial Sequence
<220> FEATURE:
<223> OTHER INFORMATION: Description of Artificial Sequence: Expression
      cassette for a sense and antisense copy of the trailer
      associated with a PPO gene

<400> SEQUENCE: 32
ggtaccgaac catgcatctc aatcttaata ctaaaaaatg caacaaaatt ctagtggagg      60
```

```
gaccagtacc agtacattag atattatctt ttattactat aataatatttt taattaacac      120 gagacatagg aatgtcaagt ggtagcggta ggagggagtt ggttcagttt tttagatact      180
aggagacaga accggagggg cccattgcaa ggcccaagtt gaagtccagc cgtgaatcaa      240
caaagagagg gcccataata ctgtcgatga gcatttccct ataatacagt gtccacagtt      300
gccttccgct aagggatagc cacccgctat tctcttgaca cgtgtcactg aaacctgcta      360
caaataaggc aggcacctcc tcattctcac actcactcac tcacacagct caacaagtgg      420
taacttttac tcatctcctc caattatttc tgatttcatg catgtttccc tacattctat      480
tatgaatcgt gttatggtgt ataaacgttg tttcatatct catctcatct attctgattt      540
tgattctctt gcctactgaa tttgacccta ctgtaatcgg tgataaatgt gaatgcttcc      600
tcttcttctt cttcttctca gaaatcaatt tctgttttgt ttttgttcat ctgtagcttg      660
gtagattccc cttttttgtag accacacatc acggatcctt agtctctatt gaatctgctg      720
agattacact ttgatggatg atgctctgtt tttgttttct tgttctgttt tttcctctgt      780
tgaaatcagc tttgttgctt gatttcattg aagttgttat tcaagaataa atcagttaca      840
attatggaat tcaaggttag aaatcttctc tattttggt ttttgtctgt ttagattctc        900
gaattagcta atcaggtgct gttatagccc ttaattttga gttttttttc ggttgttttg      960
atggaaaagg cctaaaattt gagtttttt acgttggttt gatggaaaag gcctacaatt      1020
ggagttttcc ccgttgtttt gatgaaaaag cccctagttt gagattttt ttctgtcgat      1080 tcgattctaa aggtttaaaa ttagagtttt tacatttgtt tgatgaaaaa ggccttaaat      1140
ttgagttttt ccggttgatt tgatgaaaaa gccctagaat ttgtgttttt tcgtcggttt      1200
gattctgaag gcctaaaatt tgagtttctc cggctgtttt gatgaaaaag ccctaaattt      1260
gagtttctcc ggctgttttg atgaaaaagc cctaaatttg agtttttcc ccgtgtttta       1320 gattgtttgg ttttaattct cgaatcagct aatcagggag tgtgaaaagc cctaaaattt      1380 gagtttttt cgttgttctg attgttgttt ttatgaattt gcagatggat atccttcttt       1440
gatgctgatc cataattgta actgatttat tcttgaataa caacttcaat gaaatcaagc      1500
aacaaagctg atttcaacag aggaaaaaac agaacaagaa aacaaaaaca gagcatcatc      1560
catcaaagtg taatctccagc agattcaata gagactaagc ttttgatttt aatgtttagc     1620
aaatgtccta tcagttttct cttttttgtcg aacggtaatt tagagttttt tttgctatat     1680
ggattttcgt ttttgatgta tgtgacaacc ctcgggattg ttgatttatt tcaaaactaa     1740 gagttttgc ttattgttct cgtctatttt ggatatcaat cttagttta tatctttct        1800 agttctctac gtgttaaatg ttcaacacac tagcaatttg gctgcagcgt atggattatg      1860
gaactatcaa gtctgtggga tcgataaata tgcttctcag gaatttgaga ttttacagtc      1920
tttatgctca ttgggttgag tataatatag taaaaaaata gtctaga                   1967
```

<210> SEQ ID NO 33
<211> LENGTH: 1635
<212> TYPE: DNA
<213> ORGANISM: Artificial Sequence
<220> FEATURE:
<223> OTHER INFORMATION: Description of Artificial Sequence: Expression
      cassette for a sense and antisense copy of the trailer
      associated with a PPO gene

<400> SEQUENCE: 33

```
ggtaccgaac catgcatctc aatcttaata ctaaaaaatg caacaaaatt ctagtggagg       60
```

```
gaccagtacc agtacattag atattatctt ttattactat aataatattt taattaacac      120
gagacatagg aatgtcaagt ggtagcggta ggagggagtt ggttcagttt tttagatact      180
aggagacaga accggagggg cccattgcaa ggcccaagtt gaagtccagc cgtgaatcaa      240
caaagagagg gcccataata ctgtcgatga gcatttccct ataatacagt gtccacagtt      300
gccttccgct aagggatagc cacccgctat tctcttgaca cgtgtcactg aaacctgcta      360
caaataaggc aggcacctcc tcattctcac actcactcac tcacacagct caacaagtgg      420
taacttttac tcatctcctc caattatttc tgatttcatg catgtttccc tacattctat      480
tatgaatcgt gttatggtgt ataaacgttg tttcatatct catctcatct attctgattt      540
tgattctctt gcctactgaa tttgacccta ctgtaatcgg tgataaatgt gaatgcttcc      600
tcttcttctt cttcttctca gaaatcaatt tctgttttgt ttttgttcat ctgtagcttg      660
gtagattccc cttttttgtag accacacatc acggatcctt agtctctatt gaatctgctg      720
agattacact ttgatggatg atgctctgtt tttgttttct tgttctgttt tttcctctgt      780
tgaaatcagc tttgttgctt gatttcattg aagttgttat tcaagaataa atcagttaca      840
attatggaat tcgtggtaac ttttactcat ctcctccaat tatttctgat tcatgcatg      900 tttccctaca ttctattatg aatcgtgtta tggtgtataa acgttgtttc atatctcatc     960
tcatctattc tgattttgat tctcttgcct actgaatttg accctactgt aatcggtgat     1020
aaatgtgaat gcttcctctt cttcttcttc ttctcagaaa tcaatttctg ttttgttttt     1080
gttcatctgt agcttgatat ccttctttga tgctgatcca taattgtaac tgatttattc     1140
ttgaataaca acttcaatga aatcaagcaa caaagctgat ttcaacagag gaaaaaacag     1200
aacaagaaaa caaaaacaga gcatcatcca tcaaagtgta atctcagcag attcaataga     1260
gactaagctt ttgattttaa tgtttagcaa atgtcctatc agttttctct ttttgtcgaa     1320
cggtaattta gagttttttt tgctatatgg attttcgttt ttgatgtatg tgacaaccct     1380
cgggattgtt gatttatttc aaaactaaga gttttttgctt attgttctcg tctatttttgg    1440 atatcaatct tagttttata tcttttctag ttctctacgt gttaaatgtt caacacacta     1500
gcaatttggc tgcagcgtat ggattatgga actatcaagt ctgtgggatc gataaatatg     1560
cttctcagga atttgagatt ttacagtctt tatgctcatt gggttgagta taatatagta     1620
aaaaaatagt ctaga                                                      1635

<210> SEQ ID NO 34
<211> LENGTH: 240
<212> TYPE: DNA
<213> ORGANISM: Solanum tuberosum

<400> SEQUENCE: 34
gtccatgatg tcttcagggt ggtagcattg actgatggca tcatagtttt ttttttaaaa       60
gtatttcctc tatgcatatt attagtatcc aataaattta ctggttgttg tacatagaaa      120
aagtgcattt gcatgtatgt gtttctctga aattttcccc agttttttggt gctttgcctt     180 tggagccaag tctctatatg tataagaaaa ctaagaacaa tcacatatat caaatattag     240

<210> SEQ ID NO 35
<211> LENGTH: 228
<212> TYPE: DNA
<213> ORGANISM: Solanum tuberosum

<400> SEQUENCE: 35
acgaacttgt gatcgcgttg aaagatttga acgctacata gagcttcttg acgtatctgg      60
```

```
caatattgca tcagtcttgg cggaatttca tgtgacaaca aggtttgcaa ttctttccac    120
tattagtagt gcaacgatat acgcagagat gaagtgctga acaaacatat gtaaaatcga    180
tgaatttatg tcgaatgctg ggacgggctt cagcaggttt tgcttagt                228
```

<210> SEQ ID NO 36
<211> LENGTH: 2204
<212> TYPE: DNA
<213> ORGANISM: Artificial Sequence
<220> FEATURE:
<223> OTHER INFORMATION: Description of Artificial Sequence: Expression
      cassette for an omega-mutated virD2 gene

<400> SEQUENCE: 36

```
ccgcggtttt ctctccatcg cgtcagaggc cggttttcgt cggcatcgaa gagggccact     60
cgtttaccgt catttgccaa agcagcgcaa aggcccatga gtgcggtggt tttgccagca    120 cccccttttga aagagcaaaa cgtcaaaagt tgcatattct gatcccgcct gtcctgtgaa   180
acggagtgca tttgtatttt tgttcgtata aatgttttg tgattatcga tgagtaaaag    240
cgttgttaca ctattttta tttcaaattc gttataatta aattgcaatt gtagcaatta    300
tattcggttt ttcctgtaaa tatactgttg atttcatatc gagtagggct agactttaat    360
ctgtctaccc gggcacattt cgtgctgag tattcagacc ttccgctttt tttggaggaa     420
gctatgtcaa aacacaccag agtcacgtcg agtgagactg ccatcaacca gcatcgatcc    480
ctgaacgttg aagggtttaa ggtcgtgagt gcccgtctgc gatcggccga gtatgaaacc    540
ttttcctatc aagcgcgcct gctgggactt tcggatagta tggcaattcg cgttgcggtg    600
cgtcgcatcg ggggctttct cgaaatagat gcacacaccc gagaaaagat ggaagccata    660
cttcagtcca tcggaatact ctcaagtaat gtatccatgc ttctatctgc ctacgccgaa    720
gaccctcgat cggatctgga ggctgtgcga gatgaacgta ttgcttttgg tgaggctttc    780
gccgccctcg atggcctact ccgctccatt ttgtccgtat cccggcgacg gatcgacggt    840
tgctcgctat tgaaaggtgc cttgtagcac ttgaccacgc acctgacggg agaaaattgg    900
atgcccgatc gcgctcaagt aatcattcgc attgtgccag gaggtggaac caagacccct    960
cagcagataa tcaatcagtt ggagtacctg tcccgtaagg gaaagctgga actgcagcgt   1020
tcagcccggc atctcgatat tcccgttccg ccggatcaaa tccgtgagct tgcccaaagc   1080
tgggttacgg aggccgggat ttatgacgaa agtcagtcag acgatgatag gcaacaagac   1140
ttaacaacac acattattgt aagcttcccc gcaggtaccg accaaccgc agcttatgaa    1200 gccagccggg aatgggcagc cgagatgttt gggtcaggat acggggtgg ccgctataac    1260 tatctgacag cctaccacgt cgaccgcgat catccacatt tacatgtcgt ggtcaatcgt   1320
cgggaacttc tggggcacgg gtggctgaaa atatccaggc gccatcccca gctgaattat   1380
gacggcttac ggaaaaagat ggcagagatt tcacttcgtc acggcatagt cctggatgcg   1440
acttcgcgag cagaaagggg aatagcagag cgaccaatca catatgctga acatcgccgc   1500
cttgagcgga tgcaggctca aaagattcaa ttcgaagata cagattttga tgagacctcg   1560
cctgaggaag atcgtcggga cctcagtcaa tcgttcgatc catttcgatc ggacccatct   1620
accggcgaac cggaccgtgc aacccgacat gacaaacaac cgcttgaaca gcacgcccgt   1680
ttccaggagt ccgccggctc cagcatcaaa gccgacgcac ggatccgcgt atcattggag   1740
agcgagcgga gtgcccaacc atccgcgtcc aaaatccctg taattgggca tttcgggatt   1800
gagacttcct atgtcgctga agccagcgtg cgcaaacgaa gcggcatttt cggtacttct   1860
```

| | |
|---|---|
| cgcccggtga ctgacgttgc catgcacaca gtcaagcgcc agcagcgatc aaaacgacgt | 1920 |
| aatgacgagg aggcaggtcc gagcggagca aaccgtaaag gattgaaggc tgcgcaagtt | 1980 |
| gattccgagg caaatgtcgg tgagcaagac actcgcgatg acagcaacaa ggcggctgat | 2040 |
| ccggtgtctg cttccatcgg taccgagcaa ccggaagctt ctccaaagcg tccgcgtgac | 2100 |
| cgtcacgatg gagaattggg tggacgcaaa cgtgcaagag gtaatcgtcg ctcgagctcg | 2160 |
| agcgggggga cctagagaca ggaaggaccg aataatggcc gcgg | 2204 |

<210> SEQ ID NO 37
<211> LENGTH: 1621
<212> TYPE: DNA
<213> ORGANISM: Solanum tuberosum

<400> SEQUENCE: 37

| | |
|---|---|
| atggcttctg tgctggcttc tctgtttcca aaactgggct ctttgggtac ttcagatcat | 60 |
| gcttctgttg tatccatcaa cctctttgtg gcactccttt gtgcttgcat catcattggt | 120 |
| catctcttgg aggagaaccg ctgggttaat gagtccatta ctgccctcat aattggtttg | 180 |
| tgtacaggag tggttatctt gctcgtaagt ggtggaaaga gctcacacct tctggttttc | 240 |
| agtgaagatc tcttttttcat atatgtactt cctccaatca tatttaatgc agggtttcag | 300 |
| gtaaaaaaga agcaattttt cgtaaacttc attactataa tgatgttcgg agccattggt | 360 |
| accctggtct catgtgccat tatatcatta ggtgccattc aaactttcaa gaagttggac | 420 |
| attgaatttc tagatattgg ggattatctt gcaattggag caatatttgc tgccacagat | 480 |
| tccgtctgca cattgcaggt cctacatcag gatgagacac ccctccttta cagtcttgta | 540 |
| tttgagaag gagttgtaaa tgatgctaca tcggtggtgc ttttcaatgc tattcaaaac | 600 |
| ttcgaccttta cgagcatgaa tcccagtata gccctcagtt ccttggcaa cttcttctat | 660 |
| ctgttccttg ctagcacttt actgggagca ggaactggtc ttcttagtgc ttacattatc | 720 |
| aagaagctat attttggcag gcactccaca gatcgtgagg ttgcccttat gatgctcatg | 780 |
| gcttacttat catacttgct ggccgaatta ttctatttga gtgggattct caccgtcttt | 840 |
| ttctgtggta ttgtaatgtc tcactacact tggcacaatg tgaccgagag ttcaagagtc | 900 |
| actacaaggc acacttttgc aactttgtca tttcttgcag agactttcct cttcctctat | 960 |
| gtcggcatgg atgctttgga tatcgagaag tggaaatttg ttggtgacag gcctggatta | 1020 |
| tcaatttccg tgagttcaat actgatggga ctaatcttgc ttgggagagc tgcctttgtt | 1080 |
| tttccattat cattcttatc caacttaatg aagaaatcct cggagcaaaa aattacccttt | 1140 |
| aggcagcaag tgataaatatg gtgggcaggt ttgatgagag cgcagtgtc catggcactg | 1200 |
| gcatataata agttcactcg tgggggacac actcaactgc aggacaatgc aataatgatt | 1260 |
| accagcacga taaccattgt tctattcagc acaatggtat tcggtttaat gacaaaaccc | 1320 |
| cttataagtc tcctgctgcc accacagagg caattgagta cagtgtcatc aggcgcaaat | 1380 |
| actccaaagt ctctaacagc cccactccta ggcagtcgag aggactctga agttgattta | 1440 |
| aatgttccag atcttcctca cccaccaagt ttgaggatgc tacttaccgc accaagtcat | 1500 |
| aaagtgcatc ggtactggcg caagtttgac gatgcattca tgcgccctat gtttggtggt | 1560 |
| cggggatttg ctcctcctgc ccctggttct ccaacggaac agggtccatg aggtaccaat | 1620 |
| c | 1621 |

<210> SEQ ID NO 38

<211> LENGTH: 1620
<212> TYPE: DNA
<213> ORGANISM: Solanum tuberosum

<400> SEQUENCE: 38

```
atggcttctg tgctggcttc tctgtttcca aaactgggct ctttgggtac ttcagatcat      60
gcttctgttg tatccatcaa cctctttgtg gcactccttt gtgcttgcat catcattggt     120
catctcttgg aggagaaccg ctgggttaat gagtccatta ctgccctcat aattggtttg     180
tgtacaggag tggttatctt gctcgtaagt ggtggaaaga actcacacct tctggttttc     240
agtgaagatc tcttttttcat atatgtactt cctccaatca tatttaatgc agggtttcag    300
gtaaaaaaga agcaattttt cgtgaacttc attactataa tgatgttcgg agccattggt     360
accctggtct catgtgccat tatatcatta ggtgcaattc aaactttcaa gaagttggac     420
attgaatttc tagatattgg ggattatctt gcaattggag caatatttgc tgccacagat     480
tccgtctgca cattgcaggt cctacatcag gatgagacac ccctccttta cagtcttgta     540
tttggagaag gagttgtaaa tgatgctaca tcggtggtgc ttttcaatgc tattcaaaac     600
tttgacctta cgagcgtgaa tcccagtata gccctcagtt tccttggcaa cttcttctat     660
ctgttccttg ctagcacttt actgggagca ggaactggtc ttcttagtgc ttacattatc     720
aagaagctgt attttggcag gcactccaca gatcgtgagg ttgcccttat gatgctcatg     780
gcttacttat catacatgct ggctgaacta ttctatttga gtgggattct cactgtattt     840
ttctgtggta ttgtaatgtc tcattacact tggcacaatg tgaccgagag ttcaagagtc     900
actacaaggc acgcttttgc aactttgtca tttcttgcag agactttcct cttcctctat     960
gtcggcatgg atgctttgga tatcgagaag tggaaatttg ttggtgacag gcctggatta    1020
tcaatttccg tgagttcaat actgatggga ttaatcttgc tggggagagc tgcctttgtt    1080
tttccattat cattcttctc caacttaatg aagaaatcct cggagcaaaa aattaccttt    1140
aggcagcaag tgataatatg gtgggcaggt ttgatgagag gcgcagtgtc catggcactg    1200
gcatataata agttcactcg tgggggacac actcaactgc aggacaatgc aataatgatt    1260
accagcacga taaccattgt tctattcagc acaatggtat tcggtttaat gacaaaaccc    1320
cttataagtc tcctgctgcc accacagagg caattgagta cagtgtcatc aggtgcaaat    1380
actccaaagt ctctaacagc cccactccta ggcagtcgag aggactctga agttgattta    1440
aatgttccag atcttcctca cccaccaagt ttgaggatgc tacttaccgc accaagtcat    1500
aaagtgcatc ggtactggcg caagtttgac gatgcattca tgcgccctat gtttggtggt    1560
cggggatttg ctcctcctgc ccctggttct ccaacggaac agggtccatg aggtacaatc    1620
```

<210> SEQ ID NO 39
<211> LENGTH: 747
<212> TYPE: DNA
<213> ORGANISM: Solanum tuberosum

<400> SEQUENCE: 39

```
atggaaaatt cggtacccag gactgtagaa gaagtattca cgatttcaa aggtcgtaga       60
gctggtttaa tcaaagcact aactacagat gtcgagaagt tttatcaatc gtgtgatcct    120
gaaaaggaga acttgtgtct ctatgggctt cctaatgaaa catgggaagt aaacctccct    180
gtagaggagg tgcctccaga acttccggag ccagcattgg gcataaactt cgcacgtgat    240
ggaatgcaag agaagactg gttatcactt gttgctgttc acagtgattc atggctgctt    300
tctgttgcat tttactttgg tgcaaggttt gggttcggca agagtgaaag gaagaggctt    360
```

```
ttccaaatga taaatgatct cccaacagtg tttgaagttg ttaccggagc tgctaaacag    420
acacgtgatc cccctcacaa caatagcaac aaaagcaaat caagtggaaa gcctcgacag    480
ccagagtccc aactcaaggc agtaaaggtg tctccaccta aatggagaa cgacagtggg     540 gaggaggaag aagaagaaga ggatgaacaa ggagcaactc tctgtggagc ttgtggtgat    600
aattatgcca ctgatgaatt ctggatttgc tgtgatattt gtgagagatg gttccatggc    660
aaatgtgtga agattacccc agcaaaagct gagcatatca agcagtacaa gtgtcctagt    720
tgcagtagca agagagctag agtttaa                                        747

<210> SEQ ID NO 40
<211> LENGTH: 741
<212> TYPE: DNA
<213> ORGANISM: Solanum tuberosum

<400> SEQUENCE: 40
tgacatctgc caataaagcc aagaataatt ggcattaaca tgaccaaaaa aatggtttgg     60
cagcattaag tcaaataaaa aagctacttt aatataaaat aatattaaaa tgcttaataa    120
ccaacagttt ataagaaggt taatgttaac atggatgagg aatgaccaaa aggggaatta    180
tatattaacc tttaaatcaa tctaattctc tcttttgtt tctagctata tttactcgat     240
agataaactc tcttacttga cgaattttt gatacaagaa gacatatttc atcatgattt     300
taattcgtcg tgtcaaattt attaaatagt ttaattttaa tcgtaaattt agatatgaaa    360
tttaaaaaaa aataaaatata tacatatttg aagaatacat aaaaagtaca tataaatcac    420
aaatatttaa taattcaaga tattaaaaca catagaaaaa taattactta caagaaatt     480 cttatttgaa tcctctaaat tcgagaagtg caacacaaac tgagacgaag aaaatgaata    540
atatttgata agaaatttat tataattgaa tgaccattta agtaattacg ggtaataaca    600
acacaataag gaactgtagt catttttaat acatggcaag gaatatgaga gtgtgatgag    660
tctataaata gaaggcttca ttagtgtaga ggagtcacaa acaagcaata cacaaataaa    720
attagtagct taaacaagat g                                              741

<210> SEQ ID NO 41
<211> LENGTH: 25
<212> TYPE: DNA
<213> ORGANISM: Agrobacterium sp.

<400> SEQUENCE: 41
tgacaggata tattggcggg taaac                                           25

<210> SEQ ID NO 42
<211> LENGTH: 25
<212> TYPE: DNA
<213> ORGANISM: Agrobacterium sp.

<400> SEQUENCE: 42
tggcaggata tattgtggtg taaac                                           25

<210> SEQ ID NO 43
<211> LENGTH: 25
<212> TYPE: DNA
<213> ORGANISM: Agrobacterium sp.

<400> SEQUENCE: 43
tggcaggata tataccgttg taatt                                           25
```

<210> SEQ ID NO 44
<211> LENGTH: 25
<212> TYPE: DNA
<213> ORGANISM: Agrobacterium sp.

<400> SEQUENCE: 44
cggcaggata tattcaattg taatt                    25

<210> SEQ ID NO 45
<211> LENGTH: 25
<212> TYPE: DNA
<213> ORGANISM: Agrobacterium sp.

<400> SEQUENCE: 45
tggtaggata tataccgttg taatt                    25

<210> SEQ ID NO 46
<211> LENGTH: 25
<212> TYPE: DNA
<213> ORGANISM: Agrobacterium sp.

<400> SEQUENCE: 46
tggcaggata tatggtactg taatt                    25

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Consensus
      sequence
<220> FEATURE:
<221> NAME/KEY: modified_base
<222> LOCATION: (16)
<223> OTHER INFORMATION: a, t, c or g

<400> SEQUENCE: 47
ygryaggata tatwsnvbkg taawy                    25

<210> SEQ ID NO 48
<211> LENGTH: 25
<212> TYPE: DNA
<213> ORGANISM: Rhizobium leguminosarum

<400> SEQUENCE: 48
cggcaggata tatcctgatg taaat                    25

<210> SEQ ID NO 49
<211> LENGTH: 25
<212> TYPE: DNA
<213> ORGANISM: Thermoanaerobacter tengcongensis

<400> SEQUENCE: 49
tggcaggagt tattcgaggg taaac                    25

<210> SEQ ID NO 50
<211> LENGTH: 25
<212> TYPE: DNA
<213> ORGANISM: Arabidopsis thaliana

<400> SEQUENCE: 50
tgacaggata tatcgtgatg tcaac                    25

<210> SEQ ID NO 51

-continued

```
<211> LENGTH: 25
<212> TYPE: DNA
<213> ORGANISM: Arabidopsis thaliana

<400> SEQUENCE: 51
gggaagtaca tattggcggg taaac                                              25

<210> SEQ ID NO 52
<211> LENGTH: 25
<212> TYPE: DNA
<213> ORGANISM: Oryza sativa

<400> SEQUENCE: 52
ttacaggata tattaatatg tatga                                              25

<210> SEQ ID NO 53
<211> LENGTH: 25
<212> TYPE: DNA
<213> ORGANISM: Homo sapiens

<400> SEQUENCE: 53
taacatgata tattcccttg taaat                                              25

<210> SEQ ID NO 54
<211> LENGTH: 25
<212> TYPE: DNA
<213> ORGANISM: Solanum tuberosum

<400> SEQUENCE: 54
tgacaggata tatggtaatg taaac                                              25

<210> SEQ ID NO 55
<211> LENGTH: 25
<212> TYPE: DNA
<213> ORGANISM: Solanum tuberosum

<400> SEQUENCE: 55
tggcaggata tataccgatg taaac                                              25

<210> SEQ ID NO 56
<211> LENGTH: 292
<212> TYPE: DNA
<213> ORGANISM: Saccharomyces cerevisiae

<400> SEQUENCE: 56
ttcttcgcca gaggtttggt caagtctcca atcaaggttg tcggcttgtc taccttgcca       60
gaaatttacg aaaagatgga aagggtcaa atcgttggta gatacgttgt tgacacttct       120
aaataagcga atttcttatg atttatgatt tttattatta aataagttat aaaaaaaata      180
agtgtataca aattttaaag tgactcttag gttttaaaac gaaaattctt attcttgagt      240
aactctttcc tgtaggtcag gttgctttct caggtatagc atgaggtcgc tc              292

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (14)
<223> OTHER INFORMATION: a, t, c or g
<220> FEATURE:
<221> NAME/KEY: modified_base
```

```
<222> LOCATION: (16)
<223> OTHER INFORMATION: a, t, c or g
<220> FEATURE:
<221> NAME/KEY: modified_base
<222> LOCATION: (18)
<223> OTHER INFORMATION: a, t, c or g

<400> SEQUENCE: 57
tgrcaggata tatnvndntg taaac                                              25

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 58
ccgcggtgat cacaggcagc aac                                                23

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 59
aagcttccag ccagccaaca gctccccgac                                         30

<210> SEQ ID NO 60
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 60
aagcttggct actagtgcga gatctctaag agaaaagagc gttta                        45

<210> SEQ ID NO 61
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 61
gcatgctcga gataggtgac cacatacaaa tggacgaacg g                            41

<210> SEQ ID NO 62
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 62
actagtgttt acccgccaat atatcctgtc agag                                    34

<210> SEQ ID NO 63
<211> LENGTH: 35
<212> TYPE: DNA
<213> ORGANISM: Artificial Sequence
<220> FEATURE:
<223> OTHER INFORMATION: Description of Artificial Sequence: Primer
```

<400> SEQUENCE: 63
aagctttggc aggatatatt gtggtgtaaa cgaag                                    35

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 64
cggtgtaagt gaactgcagt tgccatg                                            27

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 65
catcggcctc actcatgagc agattg                                             26

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cacgctaagt gccggccgtc cgag                                               24

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tcctaatcga cggcgcaccg gctg                                               24

<210> SEQ ID NO 68
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 68
aaagttgaat tcaaatgaga aatttattc                                          29

<210> SEQ ID NO 69
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 69
ttttaagctt tcataataac attctaat                                           28

```
<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 70
gaaccatgca tctcaatc                                              18

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 71
gtcaggatcc ctaccaagct acagatgaac                                 30

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 72
ggatccgagt gtgggtaagt aattaag                                    27

<210> SEQ ID NO 73
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 73
gaattctgtg ctctctatgc aaatctagc                                  29

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 74
ggaacattga agctgtgg                                              18

<210> SEQ ID NO 75
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 75
cgaattcatg gcaagcttgt gcaatag                                    27

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Primer
```

```
<400> SEQUENCE: 76
cgaattctta acaatctgca agactgatcg                                    30

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 77
gagagatctt gataagacac aacc                                          24

<210> SEQ ID NO 78
<211> LENGTH: 35
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (7)
<223> OTHER INFORMATION: "a" to "c" mutation
<220> FEATURE:
<221> NAME/KEY: misc_feature
<222> LOCATION: (14)
<223> OTHER INFORMATION: "a" to "c" mutation
<220> FEATURE:
<221> NAME/KEY: misc_feature
<222> LOCATION: (17)
<223> OTHER INFORMATION: "a" to "c" mutation

<400> SEQUENCE: 78
cattaccata agcccactgt atattagctt gttgc                              35

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 79
gtgcttatag aattggtggc                                               20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 80
tagttcccgg gagttcagtg                                               20

<210> SEQ ID NO 81
<211> LENGTH: 50
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (17)
<223> OTHER INFORMATION: "a" to "g" mutation
<220> FEATURE:
<221> NAME/KEY: misc_feature
<222> LOCATION: (29)
<223> OTHER INFORMATION: "a" to "t" mutation
```

<400> SEQUENCE: 81
ctcccgggaa ctataggaaa cattcctctc ggtcctgtcc acatctggtc　　　　　　50

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 82
gtgtgatatc tgttctttc c　　　　　　21

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 83
gaatgagctt gacaaggcgg ag　　　　　　22

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 84
ctggcgataa cggaactgtt g　　　　　　21

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 85
gtccatgatg tcttcagggt ggta　　　　　　24

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 86
ctaatatttg atatatgtga ttgt　　　　　　24

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 87
acgaacttgt gatcgcgttg aaag　　　　　　24

<210> SEQ ID NO 88

```
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 88
actaagcaaa acctgctgaa gccc                                              24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 89
cccgggatgg cttctgtgct ggct                                              24

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 90
ggtacctcat ggaccctgtt ccgt                                              24

<210> SEQ ID NO 91
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 91
cccgggtatg gaaaattcgg tacccaggac tg                                     32

<210> SEQ ID NO 92
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 92
actagttaaa ctctagctct cttgc                                             25

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (2)
<223> OTHER INFORMATION: a, t, c or g
<220> FEATURE:
<221> NAME/KEY: modified_base
<222> LOCATION: (6)
<223> OTHER INFORMATION: a, t, c or g
<220> FEATURE:
<221> NAME/KEY: modified_base
<222> LOCATION: (10)..(15)
<223> OTHER INFORMATION: a, t, c or g

<400> SEQUENCE: 93
```
angatntatn nnnnntgt 18

<210> SEQ ID NO 94
<211> LENGTH: 25
<212> TYPE: DNA
<213> ORGANISM: Triticum sp.

<400> SEQUENCE: 94
tggcaggata tatgagtgtg taaac 25

<210> SEQ ID NO 95
<211> LENGTH: 26
<212> TYPE: DNA
<213> ORGANISM: Triticum sp.

<400> SEQUENCE: 95
ttggcaggat atatccctct gtaaac 26

<210> SEQ ID NO 96
<211> LENGTH: 74
<212> TYPE: PRT
<213> ORGANISM: Solanum tuberosum

<400> SEQUENCE: 96

Met Ser Ser Thr Ser Asn Val Gly Gln Asp Cys Leu Ala Glu Val Thr
1               5                   10                  15

Ile Ser Tyr Gln Trp Val Gly Arg Val Ile Asn Tyr Asn Phe Phe Leu
            20                  25                  30

Leu Ile His Trp Tyr Thr Val Val Glu Ala Ser Thr Gly Ile Thr Phe
        35                  40                  45

Gln Ile Phe Pro Ile Gly Ile Arg Ser Glu Asp Asp Arg Ser Phe Tyr
    50                  55                  60

Glu Lys Ala Asp Arg Phe Ala Trp Val Thr
65                  70

<210> SEQ ID NO 97
<211> LENGTH: 51
<212> TYPE: PRT
<213> ORGANISM: Solanum tuberosum

<400> SEQUENCE: 97

Met Ser Ser Glu Ser Thr Phe Ser Lys Thr Pro Asn Gly Arg Ala Thr
1               5                   10                  15

Asp Val Gly Ile Pro Thr Glu Glu Gly Thr Phe Pro Phe Arg Tyr Ala
            20                  25                  30

Ile Leu Arg Asp Leu Ala Pro Thr Ile Ser Leu Val Asn Ser Ser Ala
        35                  40                  45

Asp Ile Ala
    50

<210> SEQ ID NO 98
<211> LENGTH: 76
<212> TYPE: PRT
<213> ORGANISM: Solanum tuberosum

<400> SEQUENCE: 98

Met Ser Glu Gly Val Gly Phe Lys Ser Lys Ile Leu Pro Ser Phe Ala
1               5                   10                  15

Trp Arg Ser Ala Asn Ile Leu Gly Ser Lys His Val Ala Lys Gln Thr
            20                  25                  30

```
Phe Pro Phe Leu Ala Arg Thr Glu Thr Cys Glu Arg Thr Ser Gly Met
        35                  40                  45

Ser Gly Val Ile Arg Ala Thr Ala Pro Ser Gly Ile Ser Ser Ser Pro
    50                  55                  60

Leu Thr Asp Phe Ala Thr Lys Ile Val Gly Phe Ser
65                  70                  75

<210> SEQ ID NO 99
<211> LENGTH: 62
<212> TYPE: PRT
<213> ORGANISM: Solanum tuberosum

<400> SEQUENCE: 99

Val Cys Ser Pro Ala Leu Lys Ala Asp Lys Ser Lys Ser Ala Asp Gly
1               5                   10                  15

Thr Cys Val Asp His Ser Arg Arg Leu Ile Val Val Leu Val Leu Tyr
            20                  25                  30

Pro Gly Met Gly Thr Ser Tyr Ala Thr Ala Phe Ile Ser Ser Pro Pro
        35                  40                  45

Ile Gln Tyr Leu Phe Pro Ser Asp Pro Val Glu Thr Phe Pro
    50                  55                  60

<210> SEQ ID NO 100
<211> LENGTH: 50
<212> TYPE: PRT
<213> ORGANISM: Solanum tuberosum

<400> SEQUENCE: 100

Met Leu Gly Ser Leu Val Leu Pro Lys Ser Pro Glu Asn Arg Lys Gln
1               5                   10                  15

Ala Val Pro Asn Pro His Phe Gln Glu Gln His Leu Val Pro Glu Lys
            20                  25                  30

Pro His Phe Leu Asp Cys Gly Gln Gly Phe Ser Lys Leu Pro Gln Met
        35                  40                  45

His Gln
    50

<210> SEQ ID NO 101
<211> LENGTH: 65
<212> TYPE: PRT
<213> ORGANISM: Solanum tuberosum

<400> SEQUENCE: 101

Met Val Asn Phe Leu Thr Gln Gly Ile Val Asp Met Glu Thr Ala Phe
1               5                   10                  15

Gly Ser Pro Lys Met Gly Gly Phe Gly Lys Glu Gln Phe Gly Ala Cys
            20                  25                  30

Val Ser Arg Ser Glu Met Asp Glu Ser Gly Ile Gly Ala Val Met Val
        35                  40                  45

Glu Gln Val Cys Ser Ile Cys Ser Arg His Phe Val Leu Ser Met Gln
    50                  55                  60

Ile
65

<210> SEQ ID NO 102
<211> LENGTH: 77
<212> TYPE: PRT
<213> ORGANISM: Solanum tuberosum
```

```
<400> SEQUENCE: 102

Met Leu Glu Gly Ser Met Trp Pro Trp Asn Gln Glu Ser Met Lys Arg
 1               5                  10                  15

Ala Phe Leu Asn His His Phe Leu Met Leu His Leu Phe Pro Ala Gln
             20                  25                  30

Arg Pro Pro Gln Ala Ala Asp Pro Val Cys Leu Lys His Gln His Met
         35                  40                  45

His Cys Gly Cys Leu Ser Phe Gln Leu His Leu Ser Lys Leu Ala Pro
     50                  55                  60

Gly Asp Thr Pro Leu Ile Ser Ser Met Phe Ala Leu Asp
 65                  70                  75

<210> SEQ ID NO 103
<211> LENGTH: 49
<212> TYPE: PRT
<213> ORGANISM: Solanum tuberosum

<400> SEQUENCE: 103

Met Lys Leu Cys Ser Ser Ile Ile Leu Ser Ile Ile Lys Gln Lys Gln
 1               5                  10                  15

Val Glu Ile Leu Arg Ala Cys Phe Gly Phe Pro Glu Thr Lys Thr Ile
             20                  25                  30

Ser Val Phe Ser Ser Val Ser Trp Asn Trp His Ile Ile Cys Lys Ser
         35                  40                  45

Leu

<210> SEQ ID NO 104
<211> LENGTH: 64
<212> TYPE: PRT
<213> ORGANISM: Solanum tuberosum

<400> SEQUENCE: 104

Met Thr Lys Lys Pro Asp Arg Lys Asp Asn Ile Met Pro Tyr Asn Phe
 1               5                  10                  15

Pro Gly Thr Lys Phe Leu Gln Pro Ile Phe Arg Asn Phe Phe Leu Pro
             20                  25                  30

Ser Leu Cys Asp Lys Leu Leu Lys Lys Ser Ile Ser Val Pro Gln Ala
         35                  40                  45

Ile Thr Pro Cys Trp Lys Val Gln Cys Gly His Gly Ile Lys Lys Ala
     50                  55                  60

<210> SEQ ID NO 105
<211> LENGTH: 115
<212> TYPE: PRT
<213> ORGANISM: Solanum tuberosum

<400> SEQUENCE: 105

Thr Ile Leu Lys Leu Asp Leu His Thr Phe Asn Gly His Phe Phe Thr
 1               5                  10                  15

Ala Ser Phe Trp Asn Gln Ser His Arg Asn Ser Ile Phe Ile Phe Gln
             20                  25                  30

Ser Asn Ile Leu Gln Gln Phe Ser Tyr Arg Gln Leu Glu Ser Asn Thr
         35                  40                  45

Gly Asn Met Ile Ser Ile Thr Ser Met Asn Met Arg Gln Ala Ser Ile
     50                  55                  60

Thr Pro Cys Lys Leu Arg Leu Ile Lys Leu Ile Cys Ile His Ser Leu
 65                  70                  75                  80
```

```
Val His Val Gln Lys His Ile Glu Pro Tyr Ile Val Pro Ile Ile Ile
            85                  90                  95

Arg Tyr Phe Ile Glu Cys Gln Tyr Leu Leu Leu Ile Phe Leu Leu
            100                 105                 110

Cys Cys Pro
        115

<210> SEQ ID NO 106
<211> LENGTH: 122
<212> TYPE: PRT
<213> ORGANISM: Solanum tuberosum

<400> SEQUENCE: 106

Met Lys Gly Lys Glu Lys Pro Arg Glu Met Asn Leu Gln Phe Phe Thr
  1               5                  10                  15

Thr Asn Phe Val Ser Thr Val Ala Ile Ser Thr Met Asn Ile Ser Leu
                20                  25                  30

Leu Phe Lys Ala Lys Arg Val Lys Gly Val Phe Ile Lys Phe Pro His
            35                  40                  45

Ser Thr Arg Ser Gln Leu Ile Leu Gly Tyr Val Leu Leu Ile Arg Arg
        50                  55                  60

Met Ser Arg Gly Ala Asp Ala Glu Phe Ser His Arg Arg Glu Leu Val
 65                  70                  75                  80

Val Arg Asn Thr Ile Asp Leu Ile Gly Tyr Arg Arg Ala Thr Thr Val
                85                  90                  95

Tyr Tyr Ile Asn Thr Phe Phe Tyr Met Gly Ser Thr Arg Leu Glu
            100                 105                 110

Ile Arg Arg Trp Tyr Arg Cys Ser Ser Arg
        115                 120

<210> SEQ ID NO 107
<211> LENGTH: 104
<212> TYPE: PRT
<213> ORGANISM: Solanum tuberosum

<400> SEQUENCE: 107

Met Glu Trp Ala Leu Ala Arg Asn Arg Ile Pro Phe Phe Tyr Cys Pro
  1               5                  10                  15

Asn Ser Leu Arg Thr Ser His Gly Lys Gly Tyr Asp Phe His Arg Arg
                20                  25                  30

Lys Arg Ile Gln Ser Ser Thr Asn Leu Tyr Leu Leu Asn Pro Phe Phe
            35                  40                  45

Ser Arg Gln Leu Ile Ser Ile His Ser Thr Ser Cys Pro His Trp His
        50                  55                  60

Gly Gly Ser Lys Lys Ser Asp Leu Asn Arg Val Ser Arg Asn Tyr Pro
 65                  70                  75                  80

Cys Leu His Arg Phe Phe Asp Glu Val Cys His Arg Ser Arg Cys Glu
                85                  90                  95

Pro Glu Tyr Glu Gly Cys Phe Gln
            100

<210> SEQ ID NO 108
<211> LENGTH: 92
<212> TYPE: PRT
<213> ORGANISM: Solanum tuberosum

<400> SEQUENCE: 108

Met Asn Asn Ile Thr His Ser Pro Ile Leu Ile Pro Phe Leu Glu Gln
  1               5                  10                  15
```

```
                1               5                  10                 15
Leu Asn Pro Phe Ile Ser Asn Cys His Met Gln Pro Ile Val Lys Ala
                20                 25                 30

Asn Thr Pro Ile Leu Asn Gly Asn Thr Lys Cys Arg His Ser Ala Asn
            35                 40                 45

Ile Phe Thr Asn Gly Asn Cys Ile Trp Glu Lys Pro Met Asn Lys Ile
            50                 55                 60

Val Asp Gln His Gln Ile His Asn Ser Ile His Ile Ser Cys Glu Ser
 65                 70                 75                 80

Lys Val Phe Leu Val Val Pro Ser Glu Ser His Arg
                85                 90

<210> SEQ ID NO 109
<211> LENGTH: 57
<212> TYPE: PRT
<213> ORGANISM: Solanum tuberosum

<400> SEQUENCE: 109

Met Lys Phe Arg Tyr Pro Ser Pro Pro Asn Pro Ile Val Thr Ser Leu
 1               5                  10                 15

Ile Ile Leu Cys Asn Ala Ile Pro Arg Ser Ile Asn Asp Val Asp Gly
                20                 25                 30

Leu Ser Arg Ala Ile Lys Ser Tyr Ile Ser Leu Ser Ile Ser Gln Asn
            35                 40                 45

Ala Ile Val Leu Ser Pro Thr Arg Ala
        50                 55

<210> SEQ ID NO 110
<211> LENGTH: 70
<212> TYPE: PRT
<213> ORGANISM: Solanum tuberosum

<400> SEQUENCE: 110

Met Val Asn Ile Met Thr Ser Ser Met Ala Thr Lys Phe Pro Ser
 1               5                  10                 15

Ile Thr Val Gln Cys Asn Ser Val Leu Pro Trp Gln Val Thr Ser Asn
                20                 25                 30

Phe Ile Pro Phe Val Cys Val Leu Trp Val Glu Val Glu Tyr Lys Tyr
            35                 40                 45

Gln Val Thr Thr Phe Lys His Asn Asn Leu Ile Ile Ile Ile His Ala
        50                 55                 60

Ala Tyr Tyr Leu Phe Ser
 65              70

<210> SEQ ID NO 111
<211> LENGTH: 51
<212> TYPE: PRT
<213> ORGANISM: Solanum tuberosum

<400> SEQUENCE: 111

Met Ala Lys Leu Val Thr His Glu Ile Glu Val Pro Leu Ser Ser Gln
 1               5                  10                 15

Gly His Cys Glu Lys Met Asp His Leu Val Lys Arg Asn Ser Ser Ile
                20                 25                 30

Asn Asn Arg Arg Ser Ile Cys Gln Ala Arg His Ala Arg Ile His Leu
            35                 40                 45

Phe Val His
        50
```

```
<210> SEQ ID NO 112
<211> LENGTH: 72
<212> TYPE: PRT
<213> ORGANISM: Solanum tuberosum

<400> SEQUENCE: 112

Met Phe Glu Thr Lys Leu Asn Ser Gly Val Val Trp Asn Asp Trp Leu
1               5                   10                  15

Thr Val Asn Ile Arg Asn Ser Asn Thr Pro Asn Thr Lys Leu Val Leu
            20                  25                  30

Leu His His Val Val Arg Thr Val Pro Ser Ile Glu Ile Ala Asn Asn
        35                  40                  45

Phe Val Phe Leu Ser Ser Arg Ser Pro Phe Thr Ile Asp Tyr Ala Thr
    50                  55                  60

Ile Phe Pro Val Glu Ser Lys Phe
65                  70

<210> SEQ ID NO 113
<211> LENGTH: 66
<212> TYPE: PRT
<213> ORGANISM: Solanum tuberosum

<400> SEQUENCE: 113

Met Leu Tyr Thr Ser Leu Tyr Ile Ser Tyr Leu Ser Asn Ser Met Leu
1               5                   10                  15

Leu Pro Ser Trp Thr Asn Leu His His Ser Tyr Ser Leu Asn Asn Leu
            20                  25                  30

Ser Thr Tyr Leu Gly Leu Pro Leu Pro Gly Gly Asn Gln Asn Gln Phe
        35                  40                  45

Leu Pro Gln Lys Gln Ala Gly Gln Gly Pro Ala Tyr Gln Lys His Leu
    50                  55                  60

Arg Gln
65

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 114
gttcagacaa gaccacagat gtga                                              24

<210> SEQ ID NO 115
<211> LENGTH: 181
<212> TYPE: PRT
<213> ORGANISM: Solanum tuberosum

<400> SEQUENCE: 115

Met Arg Asn Leu Phe Pro Ile Leu Met Leu Ile Thr Asn Leu Ala Leu
1               5                   10                  15

Asn Asn Asp Asn Asn Asn Asn Asn Asn Asn Asn Asn Tyr Asn Leu
            20                  25                  30

Ile His Ala Thr Cys Arg Glu Thr Pro Tyr Tyr Ser Leu Cys Leu Thr
        35                  40                  45

Thr Leu Gln Ser Gly Pro Arg Ser Asn Glu Val Glu Gly Gly Asp Ala
    50                  55                  60
```

```
Ile Thr Thr Leu Gly Leu Ile Met Val Asp Ala Val Lys Ser Lys Ser
 65                  70                  75                  80

Ile Glu Ile Met Glu Lys Ile Lys Glu Leu Glu Lys Ser Asn Pro Glu
                 85                  90                  95

Trp Arg Ala Pro Leu Ser Gln Cys Tyr Val Ala Tyr Asn Ala Val Leu
            100                 105                 110

Arg Ala Asp Val Thr Val Ala Val Glu Ala Leu Lys Lys Gly Ala Pro
        115                 120                 125

Lys Phe Ala Glu Asp Gly Met Asp Asp Val Val Ala Glu Ala Gln Thr
    130                 135                 140

Cys Glu Tyr Ser Phe Asn Tyr Tyr Asn Lys Leu Asp Phe Pro Ile Ser
145                 150                 155                 160

Asn Leu Ser Arg Glu Ile Ile Glu Leu Ser Lys Val Ala Lys Ser Ile
                165                 170                 175

Ile Arg Met Leu Leu
            180

<210> SEQ ID NO 116
<211> LENGTH: 172
<212> TYPE: PRT
<213> ORGANISM: Nicotiana tabacum

<400> SEQUENCE: 116

Met Arg Asn Leu Phe Pro Ile Phe Met Leu Ile Thr Asn Leu Ala Phe
  1               5                  10                  15

Asn Asp Asn Asn Asn Ser Asn Asn Ile Ile Asn Thr Thr Cys Arg Ala
                 20                  25                  30

Thr Thr Asn Tyr Pro Leu Cys Leu Thr Thr Leu His Ser Asp Pro Arg
             35                  40                  45

Thr Ser Glu Ala Glu Gly Ala Asp Leu Thr Thr Leu Gly Leu Val Met
         50                  55                  60

Val Asp Ala Val Lys Leu Lys Ser Ile Glu Ile Met Lys Ser Ile Lys
 65                  70                  75                  80

Lys Leu Glu Lys Ser Asn Pro Glu Leu Arg Leu Pro Leu Ser Gln Cys
                 85                  90                  95

Tyr Ile Val Tyr Tyr Ala Val Leu His Ala Asp Val Thr Val Ala Val
            100                 105                 110

Glu Ala Leu Lys Arg Gly Val Pro Lys Phe Ala Glu Asn Gly Met Val
        115                 120                 125

Asp Val Ala Val Glu Ala Glu Thr Cys Glu Phe Ser Phe Lys Tyr Asn
    130                 135                 140

Gly Leu Val Ser Pro Val Ser Asp Met Asn Lys Glu Ile Ile Glu Leu
145                 150                 155                 160

Ser Ser Val Ala Lys Ser Ile Ile Arg Met Leu Leu
                165                 170

<210> SEQ ID NO 117
<211> LENGTH: 181
<212> TYPE: PRT
<213> ORGANISM: Solanum tuberosum

<400> SEQUENCE: 117

Met Arg Asn Leu Phe Pro Ile Leu Met Leu Ile Thr Asn Leu Ala Leu
  1               5                  10                  15

Asn Asn Asp Asn Asn Asn Asn Asn Asn Asn Asn Asn Tyr Asn Leu
                 20                  25                  30
```

```
Ile His Ala Thr Cys Arg Glu Thr Pro Tyr Tyr Ser Leu Cys Leu Thr
            35                  40                  45

Thr Leu Gln Ser Gly Pro Arg Ser Asn Glu Val Glu Gly Gly Asp Ala
 50                  55                  60

Ile Thr Thr Leu Gly Leu Ile Met Val Asp Ala Val Lys Ser Lys Ser
 65                  70                  75                  80

Ile Glu Ile Met Glu Lys Ile Lys Glu Leu Glu Lys Ser Asn Pro Glu
                 85                  90                  95

Trp Arg Ala Pro Leu Ser Gln Cys Tyr Val Ala Tyr Asn Ala Val Leu
                100                 105                 110

Arg Ala Asp Val Thr Val Ala Val Glu Ala Leu Lys Lys Gly Ala Pro
                115                 120                 125

Lys Phe Ala Glu Asp Gly Met Asp Val Val Ala Glu Ala Gln Thr
130                 135                 140

Cys Glu Tyr Ser Phe Asn Tyr Tyr Asn Lys Leu Asp Phe Pro Ile Ser
145                 150                 155                 160

Asn Leu Ser Arg Glu Ile Ile Glu Leu Ser Lys Val Ala Lys Ser Ile
                165                 170                 175

Ile Arg Met Leu Leu
            180

<210> SEQ ID NO 118
<211> LENGTH: 166
<212> TYPE: PRT
<213> ORGANISM: Nicotiana tabacum

<400> SEQUENCE: 118

Met Lys Asn Leu Ile Phe Leu Thr Met Phe Leu Thr Ile Leu Leu Gln
 1               5                  10                  15

Thr Asn Ala Asn Asn Leu Val Glu Thr Thr Cys Lys Asn Thr Pro Asn
                 20                  25                  30

Tyr Gln Leu Cys Leu Lys Thr Leu Leu Ser Asp Lys Arg Ser Ala Thr
            35                  40                  45

Gly Asp Ile Thr Thr Leu Ala Leu Ile Met Val Asp Ala Ile Lys Ala
 50                  55                  60

Lys Ala Asn Gln Ala Ala Val Thr Ile Ser Lys Leu Arg His Ser Asn
 65                  70                  75                  80

Pro Pro Ala Ala Trp Lys Gly Pro Leu Lys Asn Cys Ala Phe Ser Tyr
                 85                  90                  95

Lys Val Ile Leu Thr Ala Ser Leu Pro Glu Ala Ile Glu Ala Leu Thr
                100                 105                 110

Lys Gly Asp Pro Lys Phe Ala Glu Asp Gly Met Val Gly Ser Ser Gly
                115                 120                 125

Asp Ala Gln Glu Cys Glu Glu Tyr Phe Lys Gly Ser Lys Ser Pro Phe
130                 135                 140

Ser Ala Leu Asn Ile Ala Val His Glu Leu Ser Asp Val Gly Arg Ala
145                 150                 155                 160

Ile Val Arg Asn Leu Leu
                165

<210> SEQ ID NO 119
<211> LENGTH: 277
<212> TYPE: DNA
<213> ORGANISM: Unknown Organism
<220> FEATURE:
<223> OTHER INFORMATION: Description of Unknown Organism: P-PPO3
      nucleotide sequence
```

```
<400> SEQUENCE: 119
ctggcgataa cggaactgtt ggaggatatt ggtttggaag atgaagatac tattgcggtg      60
actctggtgc caaagagagg tggtgaaggt atctccattg aaagtgcgac gatcagtctt     120
gcagattgtt aattagtctc tattgaatct gctgagatta cactttgatg gatgatgctc     180
tgtttttgtt ttcttgttct gttttttcct ctgttgaaat cagctttgtt gcttgatttc     240
attgaagttg ttattcaaga ataaatcagt tacaatt                              277

<210> SEQ ID NO 120
<211> LENGTH: 300
<212> TYPE: DNA
<213> ORGANISM: Unknown Organism
<220> FEATURE:
<223> OTHER INFORMATION: Description of Unknown Organism: PPOM-41
      nucleotide sequence

<400> SEQUENCE: 120
ctggcgataa cggaactgtt ggaggatatt ggattggaag atgaagatac tattgcggta      60
actttggttc caaaagtagg tggtgaaggt gtatccattg aaagtgtgga gatcaagctt     120
gaggattgtt aagtcctcat gagttggtgg ctacggtacc aaattttatg tttaattagt     180
attaatgtgt gtatgtgttt gattatgttt cggttaaaat gtatcagctg atagctgat     240 tactagcctt gccagttgtt aatgctatgt atgaaataaa taaataaatg gttgtcttct     300

<210> SEQ ID NO 121
<211> LENGTH: 296
<212> TYPE: DNA
<213> ORGANISM: Unknown Organism
<220> FEATURE:
<223> OTHER INFORMATION: Description of Unknown Organism: PPOM-44
      nucleotide sequence
<220> FEATURE:
<221> NAME/KEY: modified_base
<222> LOCATION: (54)
<223> OTHER INFORMATION: a, t, c or g
<220> FEATURE:
<221> NAME/KEY: modified_base
<222> LOCATION: (166)
<223> OTHER INFORMATION: a, t, c or g
<220> FEATURE:
<221> NAME/KEY: modified_base
<222> LOCATION: (223)
<223> OTHER INFORMATION: a, t, c or g

<400> SEQUENCE: 121
ctggcgataa cggaactgtt ggaggataat ggattggaag atgaaggtac tatngcggta      60
actttggttc caaaagttgg tggtgaaggt gtatccattg aaagtgcgga gatcaagctt     120
gaggattgtt aagtcctcat gagttggtgg ctatggtacc aaattntatg tttaattagt     180
attaatgtgt gtgtttgatt atgtttcggt taaaatgtat canctggata gctgattact     240
agccttccca gttgttaatg ctatgtatga aatacataaa taaatggttg tcttcc         296

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 122
gtccaacttg cacaggaaag ac                                               22
```

-continued

```
<210> SEQ ID NO 123
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
catggatgaa atactcctga gc                                                  22

<210> SEQ ID NO 124
<211> LENGTH: 25
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (8)
<223> OTHER INFORMATION: a, t, c or g
<220> FEATURE:
<221> NAME/KEY: modified_base
<222> LOCATION: (10)
<223> OTHER INFORMATION: a, t, c or g
<220> FEATURE:
<221> NAME/KEY: modified_base
<222> LOCATION: (12)
<223> OTHER INFORMATION: a, t, c or g

<400> SEQUENCE: 124
gtttacanhn bnatatatcc tgyca                                               25
```